United States Patent
Rotter et al.

(10) Patent No.: US 12,084,722 B2
(45) Date of Patent: *Sep. 10, 2024

(54) METHODS OF DETERMINING RESPONSIVENESS TO ANTI-TNFα THERAPY IN INFLAMMATORY BOWEL DISEASE

(71) Applicant: CEDARS-SINAI MEDICAL CENTER, Los Angeles, CA (US)

(72) Inventors: Jerome I. Rotter, Los Angeles, CA (US); Marla Dubinsky, Los Angeles, CA (US); Stephan R. Targan, Santa Monica, CA (US); Kent D. Taylor, Ventura, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/551,028

(22) Filed: Dec. 14, 2021

(65) Prior Publication Data

US 2022/0251656 A1    Aug. 11, 2022

Related U.S. Application Data

(63) Continuation of application No. 16/025,769, filed on Jul. 2, 2018, now Pat. No. 11,236,393, which is a continuation of application No. 13/130,998, filed as application No. PCT/US2009/065928 on Nov. 25, 2009, now abandoned.

(60) Provisional application No. 61/182,552, filed on May 29, 2009, provisional application No. 61/142,307, filed on Jan. 2, 2009, provisional application No. 61/118,290, filed on Nov. 26, 2008.

(51) Int. Cl.
    *C12Q 1/68*     (2018.01)
    *C12P 19/34*    (2006.01)
    *C12Q 1/6883*   (2018.01)

(52) U.S. Cl.
    CPC ..... *C12Q 1/6883* (2013.01); *C12Q 2600/106* (2013.01); *C12Q 2600/156* (2013.01); *C12Q 2600/172* (2013.01)

(58) Field of Classification Search
    CPC ............ C12Q 1/6883; C12Q 2600/172; C12Q 2600/156; C12Q 2600/106
    See application file for complete search history.

(56) References Cited

U.S. PATENT DOCUMENTS

| | | |
|---|---|---|
| 3,654,090 A | 4/1972 | Antonius et al. |
| 3,850,752 A | 11/1974 | Schuurs et al. |
| 4,016,043 A | 4/1977 | Schuurs et al. |
| 4,265,823 A | 5/1981 | Nobile |
| 4,518,584 A | 5/1985 | Mark et al. |
| 4,698,195 A | 10/1987 | Okumura et al. |
| 4,699,880 A | 10/1987 | Goldstein |
| 4,704,692 A | 11/1987 | Ladner |
| 4,737,462 A | 4/1988 | Mark et al. |
| 4,800,159 A | 1/1989 | Mullis et al. |
| 4,880,548 A | 11/1989 | Pall et al. |
| 4,925,572 A | 5/1990 | Pall |
| 4,935,234 A | 6/1990 | Todd, III et al. |
| 4,946,778 A | 8/1990 | Ladner et al. |
| 5,002,873 A | 3/1991 | St. John et al. |
| 5,085,318 A | 2/1992 | Leverick |
| 5,091,302 A | 2/1992 | Newman et al. |
| 5,114,842 A | 5/1992 | Plow et al. |
| 5,137,806 A | 8/1992 | Lemaistre et al. |
| 5,147,637 A | 9/1992 | Wright et al. |
| 5,210,015 A | 5/1993 | Gelfand et al. |
| 5,219,997 A | 6/1993 | Schlossman et al. |
| 5,225,539 A | 7/1993 | Winter |
| 5,227,369 A | 7/1993 | Rosen et al. |
| 5,234,810 A | 8/1993 | Kehrli, Jr. et al. |
| 5,235,049 A | 8/1993 | McClelland et al. |
| 5,236,081 A | 8/1993 | Fitzsimmons et al. |
| 5,263,743 A | 11/1993 | Jones |
| 5,264,554 A | 11/1993 | Newman |
| 5,272,263 A | 12/1993 | Hession et al. |
| 5,284,931 A | 2/1994 | Springer et al. |
| 5,411,842 A | 5/1995 | Ridgway et al. |
| 5,491,063 A | 2/1996 | Fisher et al. |
| 5,494,920 A | 2/1996 | Glasebrook et al. |
| 5,518,488 A | 5/1996 | Schluger |
| 5,545,806 A | 8/1996 | Lonberg et al. |

(Continued)

FOREIGN PATENT DOCUMENTS

| AU | 698604 B2 | 11/1998 |
|---|---|---|
| AU | 2014317991 A1 | 3/2016 |

(Continued)

OTHER PUBLICATIONS

Reference SNP (rs) report for rs35693, Sep. 21, 2022, from https://www.ncbi.nlm.nih.gov/snp/rs35693 (Year: 2022).*

(Continued)

*Primary Examiner* — Stephen T Kapushoc
(74) *Attorney, Agent, or Firm* — Wilson Sonsini Goodrich & Rosati

(57) ABSTRACT

The present invention relates to methods of prognosing responsiveness to anti-TNFα therapy by determining the presence or absence of risk factors in the individual. In one embodiment, the risk factors are genetic markers, serological markers and/or clinical phenotypes associated with non-responsiveness to treatment with anti-TNFα therapy in an individual diagnosed with IBD.

8 Claims, 20 Drawing Sheets
Specification includes a Sequence Listing.

(56) References Cited

U.S. PATENT DOCUMENTS

| | | |
|---|---|---|
| 5,545,807 A | 8/1996 | Surani et al. |
| 5,569,825 A | 10/1996 | Lonberg et al. |
| 5,585,089 A | 12/1996 | Queen et al. |
| 5,590,769 A | 1/1997 | Lin |
| 5,607,879 A | 3/1997 | Wuu et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,683,698 A | 11/1997 | Chavali et al. |
| 5,691,151 A | 11/1997 | Braun et al. |
| 5,713,061 A | 1/1998 | Yoshioka |
| 5,750,355 A | 5/1998 | Targan et al. |
| 5,830,675 A | 11/1998 | Targan et al. |
| 5,840,300 A | 11/1998 | Williams et al. |
| 5,861,155 A | 1/1999 | Lin |
| 5,874,233 A | 2/1999 | Targan et al. |
| 5,885,793 A | 3/1999 | Griffiths et al. |
| 5,905,827 A | 5/1999 | Naganuma et al. |
| 5,916,748 A | 6/1999 | Targan et al. |
| 5,937,862 A | 8/1999 | Targan et al. |
| 5,942,390 A | 8/1999 | Cominelli et al. |
| 5,947,281 A | 9/1999 | Kaneff |
| 5,968,741 A | 10/1999 | Plevy et al. |
| 5,969,108 A | 10/1999 | McCafferty et al. |
| 6,034,102 A | 3/2000 | Aiello |
| 6,074,835 A | 6/2000 | Braun et al. |
| 6,114,395 A | 9/2000 | Aiello |
| 6,172,197 B1 | 1/2001 | McCafferty et al. |
| 6,183,951 B1 | 2/2001 | Plevy et al. |
| 6,215,040 B1 | 4/2001 | Lee et al. |
| 6,297,367 B1 | 10/2001 | Tribouley |
| 6,300,064 B1 | 10/2001 | Knappik et al. |
| 6,348,316 B1 | 2/2002 | Taylor et al. |
| 6,376,176 B1 | 4/2002 | Taylor et al. |
| 6,406,701 B1 | 6/2002 | Pulido-Cejudo |
| 6,407,213 B1 | 6/2002 | Carter et al. |
| 6,479,284 B1 | 11/2002 | Marasco et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,599,719 B2 | 7/2003 | Yu et al. |
| 6,607,879 B1 | 8/2003 | Cocks et al. |
| 6,632,976 B1 | 10/2003 | Tomizuka et al. |
| 6,653,068 B2 | 11/2003 | Frisch et al. |
| 6,692,916 B2 | 2/2004 | Bevilacqua et al. |
| 6,706,484 B1 | 3/2004 | Knappik et al. |
| 6,713,061 B1 | 3/2004 | Yu et al. |
| 6,762,042 B2 | 7/2004 | Liu et al. |
| 6,812,339 B1 | 11/2004 | Venter et al. |
| 6,824,767 B2 | 11/2004 | Yu et al. |
| 6,824,989 B1 | 11/2004 | Eisinger et al. |
| 6,835,823 B2 | 12/2004 | Le et al. |
| 6,858,391 B2 | 2/2005 | Nunez et al. |
| 6,869,762 B1 | 3/2005 | Daly et al. |
| 6,905,827 B2 | 6/2005 | Wohlgemuth et al. |
| 6,950,827 B2 | 9/2005 | Jung |
| 7,060,869 B2 | 6/2006 | Tsien et al. |
| 7,138,237 B1 | 11/2006 | Targan et al. |
| 7,186,800 B1 | 3/2007 | Gentz et al. |
| 7,252,971 B2 | 8/2007 | Benson et al. |
| 7,264,963 B1 | 9/2007 | Knappik et al. |
| 7,285,267 B2 | 10/2007 | Gentz et al. |
| 7,332,156 B2 | 2/2008 | Bowman et al. |
| 7,332,631 B2 | 2/2008 | Hogarth et al. |
| 7,361,491 B2 | 4/2008 | Liu et al. |
| 7,361,733 B2 | 4/2008 | Hershberg et al. |
| 7,368,527 B2 | 5/2008 | Rosen et al. |
| 7,534,428 B2 | 5/2009 | Gentz et al. |
| 7,597,886 B2 | 10/2009 | Yu et al. |
| 7,612,181 B2 | 11/2009 | Wu et al. |
| 7,708,996 B2 | 5/2010 | Yu et al. |
| 7,709,218 B2 | 5/2010 | Gentz et al. |
| 7,745,391 B2 | 6/2010 | Mintz et al. |
| 7,759,079 B2 | 7/2010 | Oh et al. |
| 7,820,447 B2 | 10/2010 | Morris et al. |
| 7,820,798 B2 | 10/2010 | Yu et al. |
| 7,838,239 B2 | 11/2010 | Mitsuhashi et al. |
| 7,892,730 B2 | 2/2011 | Morris et al. |
| 7,993,833 B2 | 8/2011 | Begovich et al. |
| 8,003,099 B2 | 8/2011 | Auer et al. |
| 8,003,386 B1 | 8/2011 | Gentz et al. |
| 8,017,122 B2 | 9/2011 | Siadak et al. |
| 8,093,363 B2 | 1/2012 | Yu et al. |
| 8,263,743 B2 | 9/2012 | Smith et al. |
| 8,409,577 B2 | 4/2013 | Thompson et al. |
| 8,524,869 B2 | 9/2013 | Smith et al. |
| 8,642,741 B2 | 2/2014 | Classon et al. |
| 8,715,943 B2 | 5/2014 | Princen et al. |
| 8,728,282 B2 | 5/2014 | Niu |
| 8,728,475 B2 | 5/2014 | Burkly et al. |
| 8,728,482 B2 | 5/2014 | Smith et al. |
| 8,766,034 B2 | 7/2014 | Shih et al. |
| 8,781,750 B2 | 7/2014 | Stuart et al. |
| 8,859,739 B2 | 10/2014 | Kontermann et al. |
| 8,883,975 B2 | 11/2014 | Brandt et al. |
| 8,975,022 B2 | 3/2015 | Begovich et al. |
| 9,017,679 B2 | 4/2015 | Podack et al. |
| 9,068,003 B2 | 6/2015 | Siegel et al. |
| 9,102,733 B2 | 8/2015 | Endl et al. |
| 9,290,576 B2 | 3/2016 | Attinger et al. |
| 9,305,137 B1 | 4/2016 | Targan et al. |
| 9,332,741 B2 | 5/2016 | Shih et al. |
| 9,371,565 B2 | 6/2016 | Begovich et al. |
| 9,416,185 B2 | 8/2016 | Smith et al. |
| 9,556,277 B2 | 1/2017 | Classon et al. |
| 9,580,752 B2 | 2/2017 | Rotter et al. |
| 9,683,998 B2 | 6/2017 | Arch et al. |
| 9,732,385 B2 | 8/2017 | Barken et al. |
| 9,834,606 B2 | 12/2017 | Li et al. |
| 9,839,670 B2 | 12/2017 | Podack et al. |
| 9,896,511 B2 | 2/2018 | Siegel et al. |
| 9,902,996 B2 | 2/2018 | Dubinsky |
| 10,316,083 B2 | 6/2019 | Michelsen et al. |
| 10,322,174 B2 | 6/2019 | Bilsborough et al. |
| 10,626,180 B2 | 4/2020 | McGovern et al. |
| 10,633,449 B2 | 4/2020 | Shih et al. |
| 11,186,872 B2 | 11/2021 | Gonsky et al. |
| 11,236,393 B2 | 2/2022 | Dubinsky et al. |
| 2001/0006789 A1 | 7/2001 | Maino et al. |
| 2002/0006613 A1 | 1/2002 | Shyjan et al. |
| 2002/0019837 A1 | 2/2002 | Balnaves |
| 2002/0048566 A1 | 4/2002 | El-Deiry et al. |
| 2002/0078757 A1 | 6/2002 | Hines et al. |
| 2002/0106684 A1 | 8/2002 | Kopreski |
| 2002/0150939 A1 | 10/2002 | Taylor et al. |
| 2002/0165137 A1 | 11/2002 | Ruben et al. |
| 2002/0198371 A1 | 12/2002 | Wang |
| 2003/0017518 A1 | 1/2003 | Lam et al. |
| 2003/0092019 A1 | 5/2003 | Meyer et al. |
| 2003/0129189 A1 | 7/2003 | Yu et al. |
| 2003/0129215 A1 | 7/2003 | Mollison et al. |
| 2003/0138781 A1 | 7/2003 | Whitehead |
| 2003/0148345 A1 | 8/2003 | Kopreski |
| 2003/0166871 A1 | 9/2003 | Barbas et al. |
| 2003/0176409 A1 | 9/2003 | Offner |
| 2003/0198640 A1 | 10/2003 | Yu et al. |
| 2003/0229455 A1 | 12/2003 | Bevilacqua et al. |
| 2004/0013655 A1 | 1/2004 | Shiozawa et al. |
| 2004/0053262 A1 | 3/2004 | Lu |
| 2004/0072154 A1 | 4/2004 | Morris et al. |
| 2004/0123343 A1 | 6/2004 | La Rosa et al. |
| 2004/0142325 A1 | 7/2004 | Mintz et al. |
| 2004/0181048 A1 | 9/2004 | Wang |
| 2004/0203076 A1 | 10/2004 | Targan et al. |
| 2004/0213761 A1 | 10/2004 | Bowman et al. |
| 2004/0219555 A1 | 11/2004 | Van Heel |
| 2004/0265864 A1 | 12/2004 | Mitsuhashi |
| 2005/0054021 A1 | 3/2005 | Targan et al. |
| 2005/0143333 A1 | 6/2005 | Richards et al. |
| 2005/0163764 A1 | 7/2005 | Medzhitov et al. |
| 2005/0182007 A1 | 8/2005 | McSwiggen et al. |

(56) References Cited

U.S. PATENT DOCUMENTS

| | | |
|---|---|---|
| 2005/0228172 A9 | 10/2005 | Wang |
| 2005/0260204 A1 | 11/2005 | Allan |
| 2005/0261219 A1 | 11/2005 | Richards et al. |
| 2006/0003392 A1 | 1/2006 | Oh et al. |
| 2006/0008819 A1 | 1/2006 | Curtis et al. |
| 2006/0067936 A1 | 3/2006 | Benson et al. |
| 2006/0100132 A1 | 5/2006 | Corneliussen et al. |
| 2006/0134663 A1 | 6/2006 | Harkin et al. |
| 2006/0141478 A1 | 6/2006 | Brant et al. |
| 2006/0154276 A1 | 7/2006 | Lois et al. |
| 2006/0211020 A1 | 9/2006 | Farrer et al. |
| 2006/0234285 A1 | 10/2006 | Gentz et al. |
| 2007/0015271 A1 | 1/2007 | Rosen et al. |
| 2007/0020268 A1 | 1/2007 | Ashkenazi et al. |
| 2007/0020637 A1 | 1/2007 | Isogai et al. |
| 2007/0037165 A1 | 2/2007 | Venter et al. |
| 2007/0054278 A1 | 3/2007 | Cargill |
| 2007/0054282 A1 | 3/2007 | Liew |
| 2007/0059758 A1 | 3/2007 | Levine |
| 2007/0072180 A1 | 3/2007 | Abreu |
| 2007/0083334 A1 | 4/2007 | Mintz et al. |
| 2007/0161031 A1 | 7/2007 | Trinklein et al. |
| 2007/0196835 A1 | 8/2007 | Bankaitis-Davis et al. |
| 2007/0237770 A1 | 10/2007 | Lai et al. |
| 2007/0254850 A1 | 11/2007 | Lieberman et al. |
| 2007/0275424 A1 | 11/2007 | Gewirtz et al. |
| 2008/0003221 A1 | 1/2008 | Podack |
| 2008/0038746 A1 | 2/2008 | Rosenberg et al. |
| 2008/0038831 A1 | 2/2008 | Benson et al. |
| 2008/0081822 A1 | 4/2008 | Berry et al. |
| 2008/0091471 A1 | 4/2008 | Michon et al. |
| 2008/0095775 A1 | 4/2008 | Lewis et al. |
| 2008/0103180 A1 | 5/2008 | Fleming et al. |
| 2008/0108713 A1 | 5/2008 | Begovich et al. |
| 2008/0131887 A1 | 6/2008 | Stephan et al. |
| 2008/0177048 A1 | 7/2008 | Gagnon |
| 2008/0206762 A1 | 8/2008 | Ferrer et al. |
| 2008/0261207 A1 | 10/2008 | Mitsuhashi |
| 2008/0274467 A1 | 11/2008 | Morris et al. |
| 2008/0293582 A1 | 11/2008 | Li et al. |
| 2009/0018031 A1 | 1/2009 | Trinklein et al. |
| 2009/0048119 A1 | 2/2009 | Krjutskov et al. |
| 2009/0099789 A1 | 4/2009 | Stephan et al. |
| 2009/0162350 A1 | 6/2009 | Abbas et al. |
| 2009/0180380 A1 | 7/2009 | Prabhakar et al. |
| 2009/0186034 A1 | 7/2009 | Abbas et al. |
| 2009/0187005 A1 | 7/2009 | Gagnon |
| 2009/0220417 A1 | 9/2009 | Siadak et al. |
| 2009/0221437 A1 | 9/2009 | Harkin et al. |
| 2009/0253133 A1 | 10/2009 | Mitsuhashi et al. |
| 2009/0258848 A1 | 10/2009 | Chakravarti et al. |
| 2009/0297563 A1 | 12/2009 | Borglum et al. |
| 2009/0317388 A1 | 12/2009 | Burkly et al. |
| 2010/0015156 A1 | 1/2010 | Dubinsky et al. |
| 2010/0019016 A1 | 1/2010 | Edoga et al. |
| 2010/0021455 A1 | 1/2010 | Targan et al. |
| 2010/0021917 A1 | 1/2010 | Rotter et al. |
| 2010/0041600 A1 | 2/2010 | Russel et al. |
| 2010/0055700 A1 | 3/2010 | Targan et al. |
| 2010/0099092 A1 | 4/2010 | Song et al. |
| 2010/0105044 A1 | 4/2010 | Fleshner et al. |
| 2010/0136543 A1 | 6/2010 | Georges et al. |
| 2010/0144903 A1 | 6/2010 | Taylor et al. |
| 2010/0184050 A1 | 7/2010 | Rotter et al. |
| 2010/0190162 A1 | 7/2010 | Rotter et al. |
| 2010/0240043 A1 | 9/2010 | Rotter et al. |
| 2010/0240077 A1 | 9/2010 | Targan et al. |
| 2010/0254971 A1 | 10/2010 | Dotan et al. |
| 2010/0266594 A1 | 10/2010 | Reed |
| 2010/0284999 A1 | 11/2010 | Taylor et al. |
| 2010/0291551 A1 | 11/2010 | Belouchi |
| 2010/0298232 A1 | 11/2010 | Liu |
| 2011/0003707 A1 | 1/2011 | Goix et al. |
| 2011/0033486 A1 | 2/2011 | Abbas et al. |
| 2011/0045476 A1 | 2/2011 | Barken et al. |
| 2011/0111418 A1 | 5/2011 | Rhodes et al. |
| 2011/0124644 A1 | 5/2011 | Targan et al. |
| 2011/0136113 A1 | 6/2011 | Uga et al. |
| 2011/0159011 A1 | 6/2011 | Carrier et al. |
| 2011/0160085 A1 | 6/2011 | Li et al. |
| 2011/0177502 A1 | 7/2011 | Hakonarson et al. |
| 2011/0177969 A1 | 7/2011 | Rotter et al. |
| 2011/0189685 A1 | 8/2011 | Taylor et al. |
| 2011/0217310 A1 | 9/2011 | Siegel et al. |
| 2011/0229471 A1 | 9/2011 | Rotter et al. |
| 2011/0243951 A1 | 10/2011 | Podack et al. |
| 2012/0014950 A1 | 1/2012 | Migone et al. |
| 2012/0026371 A1 | 2/2012 | Itano et al. |
| 2012/0041082 A1 | 2/2012 | Rotter et al. |
| 2012/0053131 A1 | 3/2012 | Rotter et al. |
| 2012/0073585 A1 | 3/2012 | Rotter et al. |
| 2012/0079611 A1 | 3/2012 | Shih et al. |
| 2012/0094934 A1 | 4/2012 | Collard et al. |
| 2012/0114654 A1 | 5/2012 | Classon et al. |
| 2012/0135011 A1 | 5/2012 | Podack et al. |
| 2012/0190698 A1 | 7/2012 | Dubinsky et al. |
| 2012/0208900 A1 | 8/2012 | Dubinsky et al. |
| 2012/0263718 A1 | 10/2012 | Siegel et al. |
| 2012/0315282 A1 | 12/2012 | Bedinger et al. |
| 2012/0328559 A1 | 12/2012 | Podack et al. |
| 2013/0012602 A1 | 1/2013 | Haritunians et al. |
| 2013/0012604 A1 | 1/2013 | Rotter et al. |
| 2013/0123117 A1 | 5/2013 | Xu et al. |
| 2013/0129668 A1 | 5/2013 | Firestein et al. |
| 2013/0136720 A1 | 5/2013 | Mcgovern et al. |
| 2013/0142809 A1 | 6/2013 | Welcher et al. |
| 2013/0216551 A1 | 8/2013 | Begovich et al. |
| 2013/0225439 A1 | 8/2013 | Princen et al. |
| 2013/0344621 A1 | 12/2013 | Wang et al. |
| 2014/0017711 A1 | 1/2014 | Taylor et al. |
| 2014/0018447 A1 | 1/2014 | Mcgovern et al. |
| 2014/0018448 A1 | 1/2014 | Gonsky |
| 2014/0037618 A1 | 2/2014 | Pidasheva et al. |
| 2014/0141983 A1 | 5/2014 | Singh et al. |
| 2014/0162894 A1 | 6/2014 | Hatchwell et al. |
| 2014/0255302 A1 | 9/2014 | Poulton et al. |
| 2015/0026831 A1 | 1/2015 | Shih et al. |
| 2015/0031972 A1 | 1/2015 | Freeman et al. |
| 2015/0072879 A1 | 3/2015 | Princen et al. |
| 2015/0086567 A1 | 3/2015 | Gonsky et al. |
| 2015/0132311 A1 | 5/2015 | Arch et al. |
| 2015/0259744 A1 | 9/2015 | Begovich et al. |
| 2015/0313904 A1 | 11/2015 | Kolatch et al. |
| 2015/0337378 A1 | 11/2015 | Targan |
| 2015/0376612 A1 | 12/2015 | Lee et al. |
| 2015/0376707 A1 | 12/2015 | Targan et al. |
| 2016/0053007 A1 | 2/2016 | Siegel et al. |
| 2016/0060330 A1 | 3/2016 | Presta |
| 2016/0090629 A1 | 3/2016 | Mcgovern |
| 2016/0096885 A1 | 4/2016 | Shih et al. |
| 2016/0200833 A1 | 7/2016 | Amann et al. |
| 2016/0208329 A1 | 7/2016 | Targan et al. |
| 2016/0215046 A1 | 7/2016 | Michelsen et al. |
| 2016/0222450 A1 | 8/2016 | Schrodi et al. |
| 2016/0333104 A1 | 11/2016 | Poulton et al. |
| 2017/0044615 A1 | 2/2017 | Rotter et al. |
| 2017/0081400 A1 | 3/2017 | Poulton et al. |
| 2017/0096491 A1 | 4/2017 | Classon et al. |
| 2017/0166967 A1 | 6/2017 | Rotter et al. |
| 2018/0021696 A1 | 1/2018 | Wang et al. |
| 2018/0051078 A1 | 2/2018 | Targan et al. |
| 2018/0052175 A1 | 2/2018 | Arch et al. |
| 2018/0078611 A1 | 3/2018 | Podack et al. |
| 2018/0086840 A1 | 3/2018 | Attinger et al. |
| 2018/0142302 A1 | 5/2018 | Dubinsky et al. |
| 2018/0156781 A1 | 6/2018 | Shih et al. |
| 2018/0208988 A1 | 7/2018 | Targan et al. |
| 2018/0230543 A1 | 8/2018 | Mcgovern |
| 2018/0305689 A1 | 10/2018 | Sætrom et al. |
| 2019/0060449 A1 | 2/2019 | Singh et al. |

(56) References Cited

U.S. PATENT DOCUMENTS

| | | | |
|---|---|---|---|
| 2019/0194754 A1 | 6/2019 | Mcgovern et al. | |
| 2020/0216526 A1 | 7/2020 | Michelsen et al. | |

FOREIGN PATENT DOCUMENTS

| | | |
|---|---|---|
| CA | 2468316 A1 | 6/2003 |
| CA | 2471840 A1 | 7/2003 |
| CA | 2668691 A1 | 6/2008 |
| CA | 2830351 A1 | 10/2012 |
| CA | 2830362 A1 | 10/2012 |
| CA | 2830365 A1 | 10/2012 |
| CA | 2922381 A1 | 3/2015 |
| CL | 2015002866 A1 | 8/2016 |
| CN | 101198624 A | 6/2008 |
| CN | 101903402 A | 12/2010 |
| CN | 202109170 U | 1/2012 |
| CN | 103149371 A | 6/2013 |
| CN | 105246501 A | 1/2016 |
| CN | 105358713 A | 2/2016 |
| CN | 105636648 A | 6/2016 |
| EP | 0760010 B1 | 10/2001 |
| EP | 1285271 B1 | 8/2005 |
| EP | 1716227 A2 | 11/2006 |
| EP | 1243274 B1 | 6/2008 |
| EP | 2005175 A2 | 12/2008 |
| EP | 2034030 A2 | 3/2009 |
| EP | 2064345 A2 | 6/2009 |
| EP | 2097540 A2 | 9/2009 |
| EP | 1819827 B1 | 8/2010 |
| EP | 2270512 A1 | 1/2011 |
| EP | 2565277 A1 | 3/2013 |
| EP | 2689034 A2 | 1/2014 |
| EP | 2689036 A2 | 1/2014 |
| EP | 2689246 A1 | 1/2014 |
| EP | 2978440 A1 | 2/2016 |
| EP | 2996717 A2 | 3/2016 |
| EP | 2997165 A2 | 3/2016 |
| EP | 2462165 B1 | 5/2016 |
| EP | 3022295 A1 | 5/2016 |
| EP | 3041580 A1 | 7/2016 |
| EP | 2638069 B1 | 1/2018 |
| EP | 3270964 A1 | 1/2018 |
| EP | 3294336 A1 | 3/2018 |
| JP | 2005510225 A | 4/2005 |
| JP | 2005514923 A | 5/2005 |
| JP | 2008518610 A | 6/2008 |
| JP | 2009526756 A | 7/2009 |
| JP | 2009195249 A | 9/2009 |
| JP | 2009535016 A | 10/2009 |
| JP | 2010088432 A | 4/2010 |
| JP | 2014515599 A | 7/2014 |
| JP | 2016522164 A | 7/2016 |
| JP | 2016526875 A | 9/2016 |
| JP | 2016536002 A | 11/2016 |
| JP | 2016198116 A | 12/2016 |
| KR | 20150134393 A | 12/2015 |
| KR | 20160009582 A | 1/2016 |
| KR | 20160052585 A | 5/2016 |
| WO | WO-9116928 A1 | 11/1991 |
| WO | WO-9202819 A2 | 2/1992 |
| WO | WO-9222323 A1 | 12/1992 |
| WO | WO-9307485 A1 | 4/1993 |
| WO | WO-9312248 A1 | 6/1993 |
| WO | WO-9404188 A1 | 3/1994 |
| WO | WO-9521941 A1 | 8/1995 |
| WO | WO-9531575 A1 | 11/1995 |
| WO | WO-9614328 A1 | 5/1996 |
| WO | WO-9725445 A1 | 7/1997 |
| WO | WO-9847004 A1 | 10/1998 |
| WO | WO-0066608 A1 | 11/2000 |
| WO | WO-0076492 A1 | 12/2000 |
| WO | WO-0120036 A2 | 3/2001 |
| WO | WO-0142511 A2 | 6/2001 |
| WO | WO-0157182 A2 | 8/2001 |
| WO | WO-0204643 A1 | 1/2002 |
| WO | WO-0157182 A3 | 3/2002 |
| WO | WO-0228999 A2 | 4/2002 |
| WO | WO-03008583 A2 | 1/2003 |
| WO | WO-03025148 A2 | 3/2003 |
| WO | WO-03040404 A1 | 5/2003 |
| WO | WO-03053220 A2 | 7/2003 |
| WO | WO-03057146 A2 | 7/2003 |
| WO | WO-03059333 A2 | 7/2003 |
| WO | WO-03090694 A2 | 11/2003 |
| WO | WO-03099312 A1 | 12/2003 |
| WO | WO-2004020968 A2 | 3/2004 |
| WO | WO-2004031159 A1 | 4/2004 |
| WO | WO-2004035537 A2 | 4/2004 |
| WO | WO-2004048600 A2 | 6/2004 |
| WO | WO-2004050836 A2 | 6/2004 |
| WO | WO-2005044792 A2 | 5/2005 |
| WO | WO-2005114469 A1 | 12/2005 |
| WO | WO-2005115115 A2 | 12/2005 |
| WO | WO-2005116251 A1 | 12/2005 |
| WO | WO-2006017173 A1 | 2/2006 |
| WO | WO-2006063093 A2 | 6/2006 |
| WO | WO-2006075254 A2 | 7/2006 |
| WO | WO-2006110091 A1 | 10/2006 |
| WO | WO-2006116721 A1 | 11/2006 |
| WO | WO-2006122079 A1 | 11/2006 |
| WO | WO-2007005608 A2 | 1/2007 |
| WO | WO-2007025989 A2 | 3/2007 |
| WO | WO-2007117611 A2 | 10/2007 |
| WO | WO-2007133816 A2 | 11/2007 |
| WO | WO-2007140625 A1 | 12/2007 |
| WO | WO-2008014400 A2 | 1/2008 |
| WO | WO-2008033239 A2 | 3/2008 |
| WO | WO-2008048902 A2 | 4/2008 |
| WO | WO-2008048984 A2 | 4/2008 |
| WO | WO-2008048986 A2 | 4/2008 |
| WO | WO-2008101133 A2 | 8/2008 |
| WO | WO-2008106451 A2 | 9/2008 |
| WO | WO-2008106579 A2 | 9/2008 |
| WO | WO-2008109782 A2 | 9/2008 |
| WO | WO-2008112990 A2 | 9/2008 |
| WO | WO-2008116150 A2 | 9/2008 |
| WO | WO-2008106451 A3 | 11/2008 |
| WO | WO-2008134569 A2 | 11/2008 |
| WO | WO-2008137762 A2 | 11/2008 |
| WO | WO-2008141148 A2 | 11/2008 |
| WO | WO-2009020403 A1 | 2/2009 |
| WO | WO-2009052512 A2 | 4/2009 |
| WO | WO-2009064854 A2 | 5/2009 |
| WO | WO-2009073628 A2 | 6/2009 |
| WO | WO-2009105590 A2 | 8/2009 |
| WO | WO-2009117122 A2 | 9/2009 |
| WO | WO-2009143278 A2 | 11/2009 |
| WO | WO-2009105590 A3 | 1/2010 |
| WO | WO-2010008858 A1 | 1/2010 |
| WO | WO-2010039931 A2 | 4/2010 |
| WO | WO-2010048415 A1 | 4/2010 |
| WO | WO-2010056682 A2 | 5/2010 |
| WO | WO-2010062960 A2 | 6/2010 |
| WO | WO-2010075579 A2 | 7/2010 |
| WO | WO-2010075584 A1 | 7/2010 |
| WO | WO-2010083234 A1 | 7/2010 |
| WO | WO-2010118210 A1 | 10/2010 |
| WO | WO-2010120814 A1 | 10/2010 |
| WO | WO-2011017120 A1 | 2/2011 |
| WO | WO-2011088237 A1 | 7/2011 |
| WO | WO-2011088306 A1 | 7/2011 |
| WO | WO-2011088380 A1 | 7/2011 |
| WO | WO-2011116111 A1 | 9/2011 |
| WO | WO-2012054532 A1 | 4/2012 |
| WO | WO-2012064682 A1 | 5/2012 |
| WO | WO-2012135142 A1 | 10/2012 |
| WO | WO-2012135144 A1 | 10/2012 |
| WO | WO-2012135146 A2 | 10/2012 |
| WO | WO-2012154253 A1 | 11/2012 |
| WO | WO-2012161856 A1 | 11/2012 |
| WO | WO-2012174338 A2 | 12/2012 |
| WO | WO-2013012604 A1 | 1/2013 |
| WO | WO-2013059732 A1 | 4/2013 |
| WO | WO-2014106602 A1 | 7/2014 |

(56) References Cited

FOREIGN PATENT DOCUMENTS

| | | |
|---|---|---|
| WO | WO-2014160463 A1 | 10/2014 |
| WO | WO-2014160883 A1 | 10/2014 |
| WO | WO-2014186665 A2 | 11/2014 |
| WO | WO-2014186750 A2 | 11/2014 |
| WO | WO-2015010108 A1 | 1/2015 |
| WO | WO-2015035261 A1 | 3/2015 |
| WO | WO-2015168699 A1 | 11/2015 |
| WO | WO-2016149282 A1 | 9/2016 |
| WO | WO-2016186972 A1 | 11/2016 |
| WO | WO-2017077715 A1 | 5/2017 |
| WO | WO-2017106383 A1 | 6/2017 |
| WO | WO-2017161342 A1 | 9/2017 |
| WO | WO-2017196663 A1 | 11/2017 |
| WO | WO-2018081074 A1 | 5/2018 |

OTHER PUBLICATIONS

Submitted SNP(ss) Details: ss66681084 (rs35693), Nov. 9, 2006, from https://www.ncbi.nlm.nih.gov (Year: 2006).*
Abraham et al.: Haplotypic polymorph isms of the TNFB gene. Immunogenetics 33:50-53 (1991).
Abreu et al.: Mutations in NOD2 are associated with fibrostenosing disease in patients with Crohn's disease. Gastroenterology 123:679-688 (2002).
Adam et al.: Immune response in cancer. Pharmacology & Therapeutics 99:113-132 (2003).
Adams et al.: 3400 new expressed sequence tags identify diversity of transcripts in the human brain. Nature Genetics 4:256-267 (1993).
Adams et al.: Two-stage genome-wide methylation profiling in childhood-onset Crohn's Disease implicates epigenetic alterations at the VMP1/MIR21 and HLA loci. Inflamm Bowel Dis. 20(10):1784-1793 (2014).
Adler et al. Anti-tumor necrosis factor [alpha] prevents bowel fibrosis assessed by messenger RNA, histology, and magnetization transfer MRI in rats with Crohn's disease. Inflamm Bowel Dis 19(4):683-690 (2013).
Aggarwal et al. The Role of TNF and its Family Members in Inflammation and Cancer: Lessons from Gene Deletion, CLUT. Drug Targets Inflamm. Allergy, 1(4):327-341, 2002.
Ahmad et al.: Clinical relevance of advances in genetics and pharmacogenetics of IBD. Gastroenterology, 126:1533-1549, 2004.
Ahmad et al. The molecular classification of the clinical manifestations of Crohn's disease. Gasterenterology 122:854-866 (2002).
Ahn et al.: The First Korean Genome Sequence and Analysis: Full Genome Sequencing for a Socio-Ethnic Group, Genome Res., 2009, vol. 19, pp. 1622-1629.
Aiba et al.: The role of TL1A and DR3 in autoimmune and inflammatory diseases. Mediators Inflamm. 2013:#258164, 9 pages.
Ajioka et al.: Haplotype analysis of hemochromatosis: evaluation of linkage-disequilibrium approaches and evolution of disease chromosome. Am J Hum Genet 60:1439-1447 (1997).
Akbas et al.: Screening for Mutations of the HFE Gene in Parkinson's Disease Patients with Hyperechogenicity of the Substantia Nigra, Neuroscience Letters, 2006, vol. 407, pp. 16-19.
Akolkar et al.: The IBD1 locus for susceptibility to Crohn's disease has a greater impact on Ashkenazi Jews with early onset diabetes. Am J Gastroenterol 96:1127-1132 (2001).
Al-Lazikani et al.: Standard conformations for the canonical structures of immunoglobulins. J. Molec. Biol. 273:927-948, 1997.
Alvarez-Lobos et al.: Crohn's Disease patients carrying Nod2/CARD15 gene variants have an increased and early need for first surgery due to stricturing disease and higher rate of surgical recurrence. Ann Surg, 242:693-700, 2005.
Ames et al.: Are vitamin and mineral deficiencies a major cancer risk? Nature 694-704 (2002).
An et al.: A tumor necrosis factor a-inducible promoter variant of interferon-g accelerates C04+ T cell depletion in human immunodeficiency virus-1 infected individuals. J Infectious Diseases 188:228-213 (2003).

Ando et al. Triplet repeat polymorphism within the NOTCH4 gene located near the junction of the HLA class II and class III regions in narcolepsy. Tissue Antigens 50:646-649 (1997).
Andoh et al.: Mucosal cytokine network in inflammatory bowel disease. World J Gastroenterol. 14(33):5154-5161 (2008).
Andus et al.: Measurement of TNFalpha mRNA in a small numbers of cells by quantitative polymerase chain reaction. (PCR) Regional Immunology 5:11-17 (1993).
Andus et al.: Measurement of TNFalpha mRNA in lamina propia lymphocytes (LPL) isolated from mucosal biopsies by quantitative polymerase chain reaction (PCR). Cytokines and cytokine receptor in mucosal immunity Abstract# 2742 p. A1409 (1992).
Annese et al.: Genetic analysis in Italian families with inflammatory bowel disease supports linkage to the IB01 locus—a GSIC study. Eur J Hum Genet 7:567-573 (1999).
Annese et al.: Variants of CARD15 are associated with an aggressive clinical course of Crohn's disease—an IG-IBD study. American Journal of Gastroenterology 100:84-92 (2005).
Aron et al.: Analysis of hsp70 gene polymorphism in allergic asthma Allergy 54:165-170 (1999).
Ausubel, F. M. et al.: Current protocols in Molecular Biology. Wiley Interscience, New York, 1987 1989. Book not included.
Babbage, A., Human DNA Sequence from Clone RP11-428F18 on Chromosome 9, Complete Sequence, GenBank: AL390240, Dec. 13, 2012, pp. 1-31.
Badger et al.: Idoxifene, a novel selective estrogen receptor modulator is effective in a rat model of adjuvant-induced arthritis. J Pharmacology and Experimental Therapeutics 291:1380-1386 (1999).
Ballantyne et al.: Short communication, assignment of the gene for intercellular adhesion molecule-1 (ICAM-1) to proximal mouse chromosome 9. Genomics 9:547-550 (1991).
Bamias et al. Circulating levels of TNF-like cytokine 1A (TL1A) and its decoy receptor 3 (DcR3) in rheumatoid arthritis. Clin Immunol 129:249-255, 2008.
Bamias et al.: Expression, localization, and functional activity of TL1A, a novel Th1-polarizing cytokine in inflammatory bowel disease. Journal of Immunology 171(9):4868-4874 (2003).
Bamias et al.: Proinflammatory Effects of Th2 Cytokines in a Murine Model of Chronic Small Intestinal Inflammation, Gastroenterol, 128:654-666, 2005.
Bamias et al.: Role of TL1A and its Receptor DR3 in Two Models of Chronic Murine Ileitis, PNAS, 103(22):8441-8446, 2006.
Bao et al.: Molecular mechanism for gender differences in susceptibility to T Cell mediated autoimmune diabetes in nonobese diabetic mice. J of Immunol 168:5269-5379 (2002).
Barrett et al.: Constitutive TL1A Expression under Colitogenic Condition Modulates the Severity and Location of Gut Mucosal Inflammation and Induces Fibrostenosis, American Journal of Pathology, 180(2):636-649 (2012).
Barrett et al.: Genome-wide association defines more than 30 distinct susceptibility loci for Crohn's disease. Nature Genetics, 40:955-962, 2008.
Barrett et al.: In Vivo constitutive expression of an IBD associated gene TNFSF15 causes severe inflammation and induces fibrostenotic disease in 2 marine models of chronic colitis. Gastroenterology, 140(5):Supplement 1, S-151, Abstract 925, 2011.
Bauer et al.: A genetic enrichment for mutations constructed by oligodeoxynucleotide-directed mutagenesis. Gene, 37:73-81, 1985.
Becker et al.: Clustering of non-major histocompatibility complex susceptibility candidate loci in human autoimmune disease. PNAS USA 95:9979-9984 (1998).
Benedict et al.: Immunoglobulin Kappa light chain variable region, Partial (Mus musculus). GenBank: AAD39789.1, Jul. 26, 2016, 1 page.
Benner et al.: Evolution, Language and Analogy in Functional Genomics, Trends in Genetics, 2001, vol. 17, pp. 414-418.
Benoit et al.: Presence of somatostatin-28-(1-12) in hypothalamus and pancreas. PNAS USA 79:917-921 (1982).
Beutler et al.: Control of cachectin (tumor necrosis factor) synthesis: mechanisms of endotoxin resistance. Science 232:977-980 (1986).
Biener-Ramanujan et al.: Functional signaling of membrane-bound TL 1A induces IFNgamma expression. FEBS Lett 11:2376-2380 (2010).

(56) References Cited

OTHER PUBLICATIONS

Bioque et al.: Further evidence for a genetic association of interleukin-1 receptor antagonist and ulcerative colitis in the Northern and Mediterranean population. Gastroenterology 108:a783 (1995) Abstract only.
Bird et al.: Single-chain antigen-binding proteins; Science, 242:423-42, 1988.
Birren et al.: GeneBank Accession No. AC021483 retrieved from: http://www.ncbi.nlm.nih.gov/nuccore/AC021483 on Aug. 30, 2012.
Birren et al.: GeneBank Accession No. AC026826 retrieved from: http://www.ncbi.nlm.nih.gov/nuccore/AC026826 on Aug. 30, 2012.
Birren et al.: GeneBank Accession No. AC105243 retrieved from: http://www.ncbi.nlm.nih.gov/nuccore/AC105243 on Aug. 30, 2012.
Boirivant et al.: Hypoproliferative human lamina propia T cells retain the capacity to secrete lymphokines when stimulated via CD2/CD28 pathways. Proceedings of the association of American physicians Abstract Only Proc Assoc Am Physicians 108:55-67 (1996).
Bomprezzi et al.: Gene Expression Profile in Multiple Sclerosis Patients and Healthy Controls: Identifying Pathways Relevant to Disease, Human Molecular Genetics, 12(17):2191- 2199, 2003.
Bossuyt et al.: Serologic markers in inflammatory bowel disease. Clinical Chemistry, 52(2):171-181, 2006.
Bourinbaiar et al.: Pregnancy hormones, estrogen and progesteron prevent HIV-1 synthesis in monocytes but not in lymphocytes. FEBS Letters 302:206-208 (1992).
Braasch et al.: Novel Antisense and Peptide Nucleic Acid Strategies for Controlling Gene Expression, Biochemistry, 41(14):4503-4509, 2002.
Brabin. Interactions of the female hormonal environment, susceptibility to viral infection and disease progression. A/OS Patient Care and STDs. 16:211-221 (2002).
Braegger et al.: Tumor necrosis factor alpha in stool as a marker of intestinal inflammation. The Lancet 339:89-91 (1992).
Brambs et al.: Inflammatory Bowel Disease: Radiographical diagnostics. (reprints available at the Department of Radiography, Albert Ludwigs University Hospital, Freiburg, Federal Republic of Germany 3-49 (2009).
Brand, Crohn's Disease: Th1, Th17 or both? The Change of a Paradigm: New Immunological and Genetic Insights implicate Th17 Cells in the Pathogenesis of Crohn's Disease, GUT, 58(8):1152-1167, 2009.
Brant et al.: American families with Crohn's disease have strong evidence for linkage to chromosomes 16 but not chromosome 12. Gastroentrol 115:1056-1061 (1998).
Braun et al.: Chapter 13: Multiparameter analysis of immunogenetic mechanisms in clinical diagnosis and management of inflammatory bowel disease. Immune mechanisms in inflammatory bowel disease edited by Richard S. Blumberg and Markus F. Neurath Mar. 10, 2006, Springer first edition: pp. 209-218.
Bream et al.: A single nucleotide polymorphism in the proximal IFN-gamma promoter alters control of gene transcription. Genes and Immunity 3:165-169 (2002).
Brennan et al. Preparation of bispecific antibodies by chemical recombination of monoclonal immunoglobulin G1 fragments. Science 229:81-83, 1985.
Brinar et al.: P217—Genetic Variants in Autophagy Related Genes and Granuloma Formation in Patients with Crohn's Disease, Journal of Crohn's and Colitis, 2009, vol. 3(1), p. S96.
Brummell et al. Probing the combining site of an anti-carbohydrate antibody by saturation-mutagenesis: Role of the heavy-chain CDR3 residues. Biochem. 32: 1180-1187, 1993.
Bull et al.: The death receptor 3-TNF-like protein 1A pathway drives adverse bone pathology in inflammatory arthritis. J.Exp. Med., 205(11):2457-2464, 2008.
Buning et al.: Heterozygosity for IL23R, p.Arg318 Gin confers a protective effect not only against Crohn's disease but also ulcerative colitis. Aliment. Pharmacal Ther. 26:1025-1033 (2007).
Burke et al.: Transcriptomic analysis of intestinal fibrosis-associated gene expression in response to medical therapy in Crohn's disease. Inflammatory Bowel Diseases. 14(9):1197-1204 (2008).
Burks et al.: GenBank Nucleic Acids Res (Suppl) 29:2065-2069 (1992).
Burks et al.: In vitro scanning saturation mutagenesis of an antibody binding pocket. Proc. Natl. Acad. Sci. USA 94:412-417, 1997.
Burstein et al.: Atrial fibrosis: mechanisms and clinical relevance in atrial fibrillation. J. Am. College Cardiol., 51(8), 8 pages, 2008.
Bush et al.: Cancer chemoresistance: the relationship between p53 and multidrug transporters Int. J Cancer 98:323-330 (2002).
Calemine et al.: Immunomodulation by diethylstillbestrol is dose and gender related: effects on thymocyte apoptosis and mitogen-induced proliferation. Toxicology 178:101-118 (2002).
Camoglio et al.: Altered expression of interfero-gamma and interleukin-4 in inflammatory bowel disease; Inflamm Bowel Dis., 4(4): 285-290; Abstract only (1998).
Cardullo, et al. Detection of nucleic acid hybridization by nonradiative fluorescence resonance energy transfer. Proc Natl Acad Sci U S A. Dec. 1988;85(23):8790-4.
Casini-Raggi et al.: Mucosal imbalance of IL-1 and IL-1 receptor antagonist in inflammatory bowel disease. J Immunol 154:2434-2440 (1995).
Cavanaugh et al.: Analysis of Australian Crohn's disease pedigrees refines the localization for susceptibility to inflammatory bowel disease on chromosome 16. Ann Hum Genet 62:291-298 (1998).
Cenci et al.: Estrogen deficiency induces bone loss by increasing T cell proliferation and lifespan through IFN-gamma induced class II transactivator. PNAS USA 100:10405-10410 (2003).
Chaudhary et al.: Prediction of response to infliximab in Crohn's disease. Digestive and Liver Disease 37:559-563 2005.
Chen et al.: Discordant protein and mRNA expression in lung adenocarcinomas. Mol. Cell. Proteomics, 4:304-313, 2002.
Chen et al. Screening for genes associated with cardiac fibrosis induced by aldosterone. Xi Bao Yu Fen Zi Mian Yi Xue Za Zhi Journal Of Cellular And Molecular Immuno 28(4):350-353 (2012) (English Abstract & Translation).
Chevillard et al. Two new polymorphisms in the human interferon gamma promoter. Eur J Immunogenetics 29:52-56 (2002).
Chiaretti et al.: Gene expression profile of adult T-cell acute lymphocytic leukemia identifies distinct subsets of patients with different responses to therapy and survival. Blood 103:2771-2778 (2004).
Cho et al.: Confirmation of a susceptibility locus for Crohn's disease on chromosome 16. Inflamm Bowel Dis. 3:186-190 (1997).
Cho et al.: Identification of novel susceptibility loci for inflammatory bowel disease on chromosome 1p, 3q and 4q: evidence for epistasis between 1p and IBD1. PNAS USA 95:7502-7507 (1998).
Cho, The Genetics and Immunopathogenesis of Inflammatory Bowel Disease, Nature Reviews, 2008, vol. 8, pp. 158-466.
Chu et al.: A genome-wide association study identifies two new risk loci for Graves' disease. Nature Genetics; 43/9:897-901 (2011).
Cippitelli et al. Retinoic acid-induced transcriptional modulation of the human interferongamma promoter. J Biol Chemistry 271:26783-26793 (1996).
Cippitelli et al.: Vitamin D3: a transcriptional modulator of the interferon-gamma gene. Eur J Immunol Abstract Only 28:3017-3030 (1998).
Clarke et al. An anti-TL1A antibody for the treatment of asthma and inflammatory bowel disease. MAbs 10(4):664-677 (2018).
Clunie et al.: Relevance of Thiopurine Methyltransferase Status in Rheumatology Patients Receiving Azathioprine, Rheumatology, 2004, vol. 41(1), pp. 13-18.
Cooper et al.: Systematic Assessment of Copy Number Variant Detection Via Genome-Wide SNP Genotyping, Nature Genetics, 2008, vol. 40, pp. 1199-1203.
Corominas et al.: Allelic Variants of the Thiopurine S-Methyltransferase Deficiency in Patients with Ulcerative Colitis and in Healthy Controls, 2000, vol. 95(9), pp. 2313-2317.
Costello et al.: Dissection of the inflammatory bowel disease transcriptome using genome wide cDNA microarrays. PloS Medicine 2:0771-0787 (2005).

(56) References Cited

OTHER PUBLICATIONS

Craik, Charles. Use of oligonucleotides for site-specific mutagenesis. BioTechniques 1985 :12-19, 1985.
Curran et al.: Genetic analysis of inflammatory bowel disease in a large European cohort supports linkage to chromosome 12 and 16. Gastroenterology 115:1066-1071 (1998).
Cushman et al.: Effects of estrogen and selective estrogen receptor modulators in hemostasis and inflammation: potential differences among drugs. Annals of New York Academy of Sciences Abstract Only 949:175-180 (2001).
Cushman et al.: Tamoxifen and cardiac risk factors in healthy women—suggestion of an anti-inflammatory effect, arteriosclerosis, thrombosis and vascular biology. Arterioscler Thromb Vasc Biol 21:251-266 (2001).
Cuzzocrea et al.: 17 beta-estradiol anti-inflammatory activity in Carrageenan-induced pleurisy. Endocrinology 141:1455-1463 (2000).
Dambacher et al.: Interleukin 31 mediates MAP kinase and STAT1/3 activation in intestinal epithelial cells and its expression is upregulated in inflammatory bowel disease. GUT. 56:1257-1265 (2007).
DbSNP Short Genetic Variations. Reference SNP(refSNP) Cluster Report: rs4855535. Printed Sep. 10, 2013, 5 pages. www.ncbi.nlm.nih.gov.
DbSNP Short Genetic Variations. Submitted SNP (ss) Details: ss566368983. NCBI. Uploaded Nov. 22, 2012. Retrieved Aug. 6, 2020. URL: https://www.ncbi.nlm.nih.gov/projects/SNP/snp_ss.cgi?subsnp_id=566368983.
Dbsnp, Short Genetic Variations, Submitted SNP(ss) Details: ss70756257,, Apr. 27, 2007, 1 page. https://www.ncbi.nlm.nih.gov.
De Domenico et al.: The Molecular Basis of Ferroportin Linked Hemochromatosis, Proc Natl Acad Sci USA, 2005, vol. 102(25), pp. 8955-8960.
Dermot et al.: Genetic epistasis of IL23/IL17 pathway genes in Crohn's disease. Inflamm Bowel Dis. 15(6):883-889 (2009).
Derrkx et al.: Tumor-necrosis-factor antibody treatment in Crohn's disease. The Lancet 342:173-174 (1993).
Desilva et al.: Pharmacogenetics of infliximab in Crohn's disease: the 5q31/IBD5 risk haplotype predict response. Gastroenterology 122:Abstract M1423 (2002).
Devlin et al.: NOD2 variants and antibody response to microbial antigens in Crohn's disease patients and their unaffected relatives. Gastroenterology 132:576-586 (2007).
Devlin et al.: NOD2 variants are significantly associated with sero-reactivity to microbial antigens in Crohn's disease. AGA Institute Digestive Disease Week, Abstract #442 Only (2006).
Devlin et al.: The p631 H variant of the TLR2 gene associated with sera-reactivity to microbial antigens in Jewish patients with Crohn's disease. Abstract Only (2007) Journal unknown.
Diamond et al.: Binding of the integrin Mac-1 (CD11 b/CD18) to the third immunoglobulin-like domain of ICAM01 (CD54) and its regulation by glycosylation. Cell 65:961-971 (1991).
Diamond et al.: ICAM-1 (CD54): A counter receptor for Mac-1 (CD11b/CD18). J Cell Biol. 111:3129-3139 (1990).
Diaz-Gallo et al. Differential association of two PTPN22 coding variants with Crohn's disease and ulcerative colitis. Inflammatory Bowel Diseases, vol. 17, No. 11, pp. 2287-2294, 2011.
Dib et al.: A comprehensive genetic map of the human based on 5,264 microsatellites. Nature 380:152-154 (1996).
Drach et al.: Interphase Fluorescence in Situ Hybridization Identifies Chromosomal Abnormalities in Plasma Cells from Patients with Monoclonal Gammopathy of Undetermined Significance, Blood, 1995, vol. 86, pp. 3915-3921.
Dubinsky et al.: CARD8: A novel association with childhood onset ulcerative colitis (UC). AGA Institute Abstract# T1983 p. A-587 (2006).
Dubinsky et al.: Familial expression of serological immune responses in pediatric IBD. J of Pediatric Gastroenterology and Nutrition Abstract #150 41:539 (2005).
Dubinsky et al.: IL-23 receptor (IL-23R) gene protects against pediatric Crohn's disease. Inflamm Bowel Disease 13:511-515 (2007).
Dubinsky et al.: Increased immune reactivity predicts aggressive complicating Crohn's disease in children. Abstract only (2007) Journal unknown.
Dubinsky et al.: Serum immune responses predict rapid disease progression among children with Crohn's disease: immune responses predict disease progression. Am J. Gastroenterology 101:360-367 (2006).
Dubinsky et al.: Synergism of NOD2 and ASCA (Anti-*Saccharomyces cerevisiae* Antibodies) Contributes to Disease Behavior in Pediatric Crohn's Disease (CD) Patients, Gastroenterology, 2003, vol. 124, pp. M1556.
Duerr et al.: A Genome-wide association study identifies IL23R as an inflammatory bowel disease gene. Science, 314:1461-1463, 2006.
Duerr et al.: Association between ulcerative colitis and a polymorphism in intron 2 of the interleukin-2 receptor antagonist gene. Gastroenterology Abstract Only 108:a812 (1995).
Duerr et al.: Homozygosity for an HLA class II group haplotype is associated with pANCA positive and familial ulcerative colitis. Abstract only Gastroenterology 108:a812 (1995).
Duerr et al.: Linkage and association between inflammatory bowel disease and a locus on chromosome 12. Am J Hum Genet 63:95-100 (1998).
Elgert, K., Immunology: Understanding the immune system. Wiley-Liss: New York, 1996, p. 323.
Email from James Jenkins referencing the "Amazon.com" website regarding exact publication date of "Immune Mechanism in Inflammatory Bowel Disease", edited by Richard S. Blumberg and Markus F. Neurath; Springer first edition. 2 Pages.
Erlandsson et al.: Effects of raloxifene, a selective estrogen receptor modulator on thymus T cell reactivity and inflammation in mice. Cellular Immunology 205:103-109 (2000).
Erlich et al.: Chapter 32: HLA DNA typing. PCR protocols. Edited by Innis et al. pp. 261-271 (1990).
Erpenbeck et al. Segmental allergen challenge in patients with atopic asthma leads to increased IL-9 expression in bronchoalveolar lavage fluid lymphocytes. J Allergy Clin Immunol 111(6):1319-1327, 2003.
Ewens et al.: The transmission/disequilibrium test: history, subdivision, and admixture. Am J Hum Genetics 57:455-464 (1995).
Fang et al.: Essential role of TNF receptor superfamily 25 (TNFRS25) in the development of allergic lung inflammation. J.Exp. Med., 205(5):1037-1048, 2008.
Fawcett et al.: Molecular cloning of ICAM-3, a third ligand for LFA-1, constitutively expressed on resting leukocytes. Nature 360:481-4. (1992).
Feder et al.: A novel MHC class 1-like gene is mutated in patients with hereditary heaemochromatosis. Nature Genetics 13:399-408 (1996).
Ferguson et al.: IL23R and IL12B SNPs and haplotypes strongly associate with Crohn's disease risk in a New Zealand population. Gastroenterology Research and Practice, 2010:12 pages, 2010.
Ferrante et al.: Predictors of early response to infliximab in patients with ulcerative colitis. Inflamm Bowel Disease 13:123-128 (2007).
Ferraris et al.: Analysis of CARD15 gene variants in Italian pediatric patients with inflammatory bowel disease. J of Pediatrics 147:272-273 (2005).
Fessler et al.: A genomic and proteomic analysis of activation of the human neutrophil by Lipopolysaccharide and its mediation by p38 mitogen-activated protein kinase. The Journal of Biological Chemistry, 277(35):31291-31302, 2002.
Fitzpatrick, LR, Novel Pharmacological Approaches for Inflammatory Bowel Disease: Targeting Key Intracellular Pathways and the IL-23/IL-17 Axis, International Journal of Inflammation, vol. 2012, pp. 1-8.
Fleshner et al.: Both preoperative pANCA and CBir1 flagellin expression in ulcerative colitis (UC) patients influence pouchitis development after illegal pouch-anal anastomosis (IPAA). Abstract only (2006) Journal unknown.
Flores et al. In vitro evaluation of the effects of candidate immunosuppressive drugs: flow cytometry and quantitative real-time PCR as two independent and correlated read-outs. Journal of Immunological Methods 289:123-135 (2004).

(56) References Cited

OTHER PUBLICATIONS

Forcione et al.: Anti-*Saccharomyces cerevisiae* antibody (ASCA) positivity is associated with increased risk for early surgery in Crohn's disease. GUT, 53:1117-1122, 2004.
Fox et al.: Estrogen regulates the IFN-gamma promoter. J Immunol 146:4362-4367 (1991).
Franke et al.: Genome-Wide Meta-Analysis Increases to 71 the Number of Confirmed Crohn's Disease Susceptibility Loci, Nature Genetics, 2010, vol. 42(12), pp. 1118-1125.
Fransen et al.: Inflammatory bowel disease: the genetic background and beyond. University of Groningen PhD Dissertation http://www.rug.nl/research/portal/files/12805965/Complete_dissertation.pdf (2014).
Fujikado et al.: Identification of arthritis related gene clusters by microarray analysis analysis of two independent mouse models for rheumatoid arthritis. Arthritis Research and Therapy 8:1-13 (2006).
Fujino et al.: Increased expression of interleukin 17 in inflammatory bowel disease gene. Gut 52:65-70 (2003).
Garcia-Bates et al.: GeneBank NM_001198.3, *Homo sapiens* PR Domain Containing 1, with ZNF Domain (PRDM1), Transcript Variant 1, mRNA, 2010 retrieved from: http://www.ncbi.nlm.nih.gov/nuccore/172072683? sat=13&satkey=10378402 on Jul. 7, 2011.
Garcia-Bates et al.: Peroxisome proliferator-activated receptor gamma ligands enhance human B cell antibody production and differentiation. J Immunology 183:6903-6912 (2009).
Gasche et al.: A simple classification of Crohn's disease: report of the working party for the world congresses of gastroenterology, Vienna. Inflammatory Bowel Disease 6:8-15 (2000).
GenBank Accession No. AF134726 (72 pgs.) (Mar. 27, 1999).
GenBank Accession No. AC007728 (31 pgs.) (Jun. 1, 2001).
GenBank Accession No. AF129756.1 (70 pgs.) (revised Nov. 12, 1999).
GenBank Accession No. AF385089 (3 pgs.) (Jul. 4, 2001).
GenBank Accession No. AF513860 (12 pgs.) Jul. 9, 2002).
GenBank Accession No. AX259776 (21 pgs.) (Oct. 26, 2001).
GenBank Accession No. NM022162 (5 pgs.) (Sep. 11, 2011).
GenBank Accession No. U89335 (25 pgs.) (Oct. 22, 1999).
GenBank Accession No. U89336 (27 pgs.) (Feb. 14, 1997).
GenBank AF252829.4 (49 pgs.) (Nov. 8, 2002).
Gene Card for IL12B(p40) (http://www.genecards.org/cgi-bin/carddisp.pl?gene=1L12B&keywords=i112b) accessed May 8, 2017.
Gene Card for IL17RD retrieved from: http://www.genecards.org/cgi-bin/carddisp.pl?gene=1L17RD&dearch=i117rd (Accessed May 2013).
GeneBank Accession No. AF450133 (10 pgs.) (Dec. 27, 2001).
GeneCard DR3 retrieved from: http://www.genecards.org/cgi-bin/carddisp.pl?gene=TNFRSF25&search=DR3 on Apr. 3, 2018; 16 pages.
GeneCard NOD2 gene (16 pgs) (Last update Jul. 2, 2009).
GeneCards, BRWD1 Gene-GeneCards | BRWD1 Protein | BRWD1 Antibody. Printed Sep. 10, 2013, 11 pages. www.genecards.org.
GeneCards for JAK2 retrieved from: http://www.genecards.org/cgi-bin/carddisp.pl?gene=JAK2search=jak2 on Oct. 25, 2019.
Gewirtz et al.: Dominant-negative TLR5 polymorphism reduces adaptive immune response to flagellin and negatively associates with Crohn's disease. Am J Physiol Gastrointest Liver Physiol. 290:G1157-G1163 (2006).
Ghosh et al.: Anti-TNF therapy in Crohn's disease Novartis Foundation Symposium 263:193-218 (2004).
Ghosh et al.: Natalizumab for active Crohn's disease. The New England Journal of Medicine, 348:24-32, 2003.
Giacomelli et al.: Combination therapy with cyclosporin and methotrexate in patients with early rheumatoid arthritis soon inhibits TNF production without decreasing TNF mRNA level: an in vivo and in vitro study. Clinical and Experimental Rheumatology 20:365-372 (2002).
Gianfrancesco et al.: Identification of a Novel Gene and a Common Variant Associated with Uric Acid Nephrolithiasis in a Sardinian Genetic Isolate, Am. J. Hum. Genet., 2003, vol. 72, pp. 1479-1491.

Gilmore et al.: Effect of estradiol on cytokine secretion by proteolipid protein-specific T cell clones isolated from multiple sclerosis patients and normal control subjects. Journal of Immunology. Abstract only.158:446-451 (1997).
Gonsky et al.: CD2 mediates activation of the IFN-gamma intronic STAT binding region in mucosal T cells. Eur J Immunol 33:1152-1162 (2003).
Gonsky et al.: Distinct Methylation of IFNG in the Gut, Journal of Interferon and Cytokine Research, 2009, vol. 29(7), pp. 407-414.
Gonsky et al.: Mucosa-specific targets for regulation of IFN-gamma expression: lamia propia cells use different cis-elements than peripheral blood T cells to regulate transactivation of IFN-gamma expression. J Immunol 164:1399-1407 2000.
Gout et al.: Death receptor-3, a new e-selectin counter-receptor that confers migration and survival advantages to colon carcinoma cells by triggering p38 and ERK MAPK activation. Cancer Research, 66(18):9117-9124, 2006.
Greenstein et al.: Perforating and non-perforating indications for repeated operation in Crohn's disease: evidence of two clinical forms. Gut 29:588-592 (1988).
Haertel et al.: Dose-dependent immunomodulatory effects of acetylsalicylic acid and indomethacin in human whole blood: potential role of cyclooxygenase-2 inhibition. Scandanavian Journal Immunology 60:412-420 (2004).
Hampe et al.: A genomewide analysis provides evidence for novel linkage in inflammatory bowel disease in a large European cohort. Am J Hum Genet 64:808-816 (1999).
Hampe et al.: A genome-wide association scan of nonsynonymous SNPs identifies a susceptibility variant for Crohn's disease in ATG16L1 Nature Genetics 39:207-211 (2007).
Hampe et al.: Association between insertion mutation in NOD2 gene and Crohn's disease in German and British populations. Lancet 357:1925-1928 (2001).
Hampe et al.: Association of NOD2 (CARD15) genotype with clinical course of Crohn's disease: a cohort study. Lancet 359:1661-1665 (2002).
Hanifi et al.: Genetic structure of IDDM1: two separate regions in the major histocompatibility complex contribute to susceptibility or protection. Diabetes A Journal of the American Diabetes Association 47:1-7 (1999).
Haritunians et al.: Genetic Predictors of Medically Refractory Ulcerative Colitis, Inflamm Bowel Dis., 2010, vol. 16 ;11), pp. 1830-1840.
Harnish et al. Beneficial effects of estrogen treatment in the HLA-B27 transgenic rat model of inflammatory bowel disease. Am J Physiol Gastrointest Liver Physiology 286:G118-124 (2004).
Hartel et al.: Delayed cytokine mRNA expression kinetics after T-lymphocyte costimulation: A quantitative measure of the efficacy of cyclosporin A-based immunosuppression. Clinical Chemistry 48:2225-2231 (2002).
Hazra et al.: Common variant of FUT2 are associated with plasma vitamin B12 levels. Nature Genetics 40:1160-1162 (2008).
Hegele, A., SNP Judgments and Freedom of Association, Arteriosclerosis, Thrombosis, and Vascular Biology, 2002, vol. 22, pp. 1058-1061.
Herbon et al. High-resolution SNP scan of chromosome 6p21 in pooled samples from patients with complex diseases. Genomics 81:510-518 (2003).
Heresbach et al.: NOD2/CARD15 gene polymorphisms in Crohn's disease: a genotype-phenotype analysis. Eur J Gastroenterology and Hepatology 16:55-62 (2004).
Hess et al.: The hydroxylamine of sulfamethoxazole synergizes with FK506 and cyclosporin A inhibiting T-cell proliferation. Journal of Pharmacology and Experimental Techniques. 281:540-548 (1996).
Heusch et al.: IL-9 exacerbates colitis induced by CD4+ CD45RBhigh T cells transfer, via directed activation of in vivo antigen-experienced T cells. Cytokine 56:PS1-056, p. 31 (2011).
Hirano et al.: Association Study of 71 European Crohn's Disease Susceptibility Loci in a Japanese Population, Inflammatory Bowel Diseases, 19(3):526-533, 2013.
Hirschhorn et al.: A comprehensive review of genetic association studies. Genetics in Medicine, 4(2):45-61, 2002.

(56) References Cited

OTHER PUBLICATIONS

Hlavaty et al.: Polymorphisms in apoptosis genes predict response to infliximab therapy in luminal and fistulizing Crohn's disease. Aliment Pharmacol Ther 22:613-626 2005.

Hodgson, John. Making monoclonals in microbes. Bio/Technology 9:421-425, 1991.

Hogg et al.: Adhesion molecules in cell interactions. Curr Opin Immunol. 5:383-390 (1993).

Hoh et al.: Trimming, Weighting and Grouping SNPs in Human Case-Control Association Studies, Genome Research, 2001, vol. 1, pp. 2115-2119.

Holliger et al.: Engineered antibody fragments and the rise of single domains. Nat. Biotechnol. 23(9):1126-36 (2005).

Honkanen et al.: Coxsackievirus up-regulates IL-17 immunity in human type 1 diabetes. Diabetologia, 54:Supp. 1, S1, Abstract S421, 2009.

Hornquist et al.: G(alpha) 1 2-Deficient Mice with Colitis Exhibit a Local Increase in Memory CD4+ T Cells and Promflammatmy TH1-Type Cytokines, J Immunol, 158:1068-1077, 1997.

Houdebine et al.: Production of Pharmaceutical Proteins from Transgenic Animals, J Biotech, 34 (1994): 269-287.

Hsu et al.: Attenuation of TH1 Response in Decoy Receptor 3 Transgenic Mice, J. Immunol, 175:5135-5145, 2005.

Hsu et al. The tale of TL1A in inflammation. Mucosal Immunol 4(4):368-370, 2011.

Hugot et al.: Association of Nod2 leucine-rich repeat variants with susceptibility to Crohn's disease. Nature 411:599-603 (2001).

Hugot et al.: Linkage analyses of chromosome 6 loci, including HLA, in familial C255 aggregations of Crohn's disease Get Aid. Am J Med Genet 52:207-213 (1994).

Hugot et al.: Mapping of a susceptibility locus for Crohn's disease on chromosome 16. Nature 379:821-823 (1996).

Hundorean et al.: Functional relevance of T helper 17 (Th17) cells and the IL-17 cytokine family in inflammatory bowel disease. Inflammatory Bowel Disease 18:180-186 (2012).

Huse et al. Generation of a large combinatorial library of the immunoglobulin repertoire in phage lambda. Science 246:1275-1281, 1989.

Huston et al. Protein engineering of antibody binding sites: Recovery of specific activity in an anti-digoxin single-chain Fv analogue produced in *Escherichia coli*. Proc. Natl. Acad. Sci. USA 85:5879-5883, 1988.

Ilumina Press Release dated Jan. 12, 2006, retrieved from: http://investor.illumina.com/phoenix.zhtml?=121278.

Inohara et al.: Human NOD1 confers responsiveness to bacterial lipopolysaccharides. J Biol Chem 276:2551-2554 (2001).

International Search Report for PCT/US2011/028694 dated Jul. 27, 2011.

Ioannidis et al.: Replication validity of genetic association studies Nature Genetics 29:306-309 (2001).

Ioannidis, J., Why Most Published Research Findings are False, PLoS Med, 2005, vol. 2(8):e124, pp. 0696-0701.

Ippoliti et al.: Combination of innate and adaptive immune alterations increased the likelihood of fibrostenosis in Crohn's disease. Inflamm Bowel Disease 16:1279-1285 (2010).

Ippoliti et al.: The relationship between abnormal innate and adaptive immune function and fibrostenosis in Crohn's disease patients. Abstract only. (2006) Journal unknown.

Iris et al.: Dense Alu clustering and a potential new member of the NFKB family within a 90 kilo base HLA Class III segment. Nature Genetics 3:137-145 (1993).

Israeli et al.: Anti-*Saccharomyces cerevisiaeand* Antineutrophil Cytoplasmic Antibodies as Predictors of Inflammatory Bowel Disease, Gut, 2005, vol. 54(9), pp. 1232-1236.

Jacob et al.: Definition of microsatellite size variants for Tnfa and Hsp70 in autoimmune and nonautoimmune mouse strains. Immunogenetics 36:182-188 (1992).

Jarjour et al.: The 8.5 kb Pstl allele of the stress protein gene Hsp70-2: An independent risk factor for systemic lupus erythematosus in African Americans. Hum Immunol 45:59-63 (1996).

Jikihara et al.: Interferon-y Inhibits the Synthesis and Release of Renin from Human Decidual Cells, Biology of Reproduction, 54:1311-1316, 1996.

Johnston et al. Present status and future prospects for HIV therapies. Science 260:1286-1293 (1993).

Jones et al. Replacing the complementarity-determining regions in a human antibody with those from a mouse. Nature 321:522-525, 1986.

Jongeneel et al.: Extensive genetic polymorphism in the human tumor necrosis factor region and relation to extended HLA haplotypes. PNAS USA 88:9717-9721 (1991).

Jostins et al.: Host-microbe interactions have shaped the genetic architecture of inflammatory bowel disease. Nature; 491/7422:119-124 (2012).

Juhasz et al.: Quantification of chemotherapeutic target gene mRNA expression in human breast cancer biopsies: comparison of real-time reverse transcription-PeR vs. relative quantification reverse transcription-PeR utilizing DNA sequence analysis of PCR product. Journal of Clinical Laboratory Analysis 17:184-194 (2003).

Jung et al.: Genotype/Phenotype analyses for 53 Crohn's disease associated genetic polymorphisms. PLOS/One, 7(12):e52223, 2012.

Juppner, H. Functional properties of the PTH/PTHrP receptor. Bone, 17(2):39S-42S, 1995.

Kakuta et al.: Su1746 Rare Variants of TNFSF15 Are Significantly Associated With Crohn's Disease in Non-Jewish Caucasian Independent of the Known Common Susceptibility SNPs, Gastroenterology, 144(5): S-466, 2013.

Karpuzoglu-Sahin et al.: Effects of long-term estrogen treatment on IFN-gamma, IL-2 and IL 4 gene expression and protein synthesis in spleen and thymus of normal C57BL/6 mice. Cytokine 14:208-217 (2001).

Karpuzoglu-Sahin et al.: Interferon-gamma levels are upregulated by 17-beta-estradiol and diethylstibestrol. J Reproductive Immunology 52:113-127 (2001).

Kasperkovitz et al.: Activation of the STAT1 Pathway in Rheumatoid Arthritis, Ann Rheum Dis, . 63:233-239, 2004.

Kasvosve et al.: Effect of Ferroportin Q248H Polymorphism on Iron Status in African Children, Am J Clin Nutr, 2005, vol. 82(5), pp. 1102-1106.

Kim et al. DQCAR113and DQCAR115 in combination with HLA-DRB1 alleles are significant markers of susceptibility to rheumatoid arthritis in the Korean population. Tissue Antigens 54:552-559 (1999).

Kim et al. Effects of IL-9 blockade on chronic airway inflammation of murine asthma models. Allergy: Eur J Allergy Clin Immunol Suppl 96(67):448, Nov. 2012.

Kim et al. Effects of interleukin-9 blockade on chronic airway inflammation in murine asthma models. Allergy Asthma Immunol Res 5(4):197-206, 2013.

Kirchhausen et al.: Location of the domains of ICAM-1 by immunolabeling and single-molecule electron microscopy. J. Leukocyte Biology 53:342-346 (1993).

Kita et al.: Sequence and expression of rat ICAM-1. Biochim Biophys Acta 1131:108-111 (1992).

Kite et al.: Use of in vivo-generated biofilms from hemodialysis catheters to test the efficacy of a novel antimicrobial catheter lock for biofilm eradication in vitro. J Clin Microbiol., 42.7 (2004): 3073-3076.

Klein et al.: Ex-vivo assessment of candidate anti-inflammatory agents in the treatment of Gram-negative sepsis. Immunology and Infectious Disease 4:33-35 (1994).

Kobayashi et al. Tryptophan H33 plays an important role in pyrimidine (6-4) pyrimidone photoproduct binding by a high-affinity antibody. Protein Eng. 12(10):879-884, 1999.

Koga et al.: Transanal Delivery of Angiotensin Converting Enzyme Inhibitor Prevents Colonic Fibrosis in a Mouse Colitis Model: Development of a Unique Mode of Treatment, Surgery, 144(2):259-268, 2008.

Kohler et al.: Derivation of specific antibody-producing tissue culture and tumor lines by cell fusion. Eur. J. Immunol. 6: 511-519 (1976).

(56) References Cited

OTHER PUBLICATIONS

Koutroubakis et al.: Tumor necrosis factor-alpha polymorphism in inflammatory bowel disease. Hellenic J of Gastroenterology 8:132-135 (1995).

Kugathansan et al.: L 1007FsinsC variant of CARD15/NOD2 is strongly associated with early onset and fibrostenosing behavior in pediatric Crohn's disease. Gasteroenterology 126(4 Supp 2):A68 524 (2004).

Kugathansan et al.: Loci on 20q13 and 21q22 are associated with pediatric onset inflammatory bowel disease. Nature Genetics 40:1211-1215 (2008).

Kutyavin, et al. 3'-Minor groove binder-DNA probes increase sequence specificity at PCR extension temperatures. Nucleic Acids Research, 28(2):655-661 (2000).

Kutyavin et al.: Oligonucleotides with conjugated dihyropyrroloindole tripeptides: base composition and backbone effects on hybridization. Nucleic Acid Res 25:3718-3723 (1997).

Lakatos et al.: NOD2/CARD15 mutations and genotype-phenotype correlations in patients with Crohn's disease. Hungarian multicenter study. Orvosi Hetilap 145:1403-1411 (2004).

Lal et al.: Antibiotic Therapy for Crohn's Disease: A Review, Canadian Journal of Gastroenterology, 2006, vol. 20(10), pp. 651-655.

Landegren et al. A Ligase-Mediated Gene Detection Technique. Science 241:1077-1080 (1988).

Lasky. Selectins: interpreters of cell-specific carbohydrate information during inflammation. Science 258:964-969 (1992).

Latham et al.: Estradiol treatment redirects the isotype of the autoantibody response and prevents the development of autoimmune arthritis. J of Immunol 171:5820-5827 (2003).

Laurence et al. Effect of tamoxifen on regulation of viral replication and human immunodeficiency virus (HIV) long terminal repeat-directed transcription in cells chronically infected with HIV-1. Blood 75:696-703 (1990).

Lawrance et al.: Ulcerative Colitis and Crohn's Disease: Distinctive Gene Expression Profiles and Novel Susceptibility Candidate Genes, Human Molecular Genetics, 10(5):pp. 445-456, 2001.

Lee et al.: Estrogen-mediated protection against HIV Tat protein-induced inflammatory pathways in human vascular endothelial cells. Cardiovascular Research 63:139-148 (2004).

Lemna et al.: Mutation analysis for heterozygote detection and the prenatal diagnosis of cystic fibrosis. N. Eng. J. Med. 322:291-296 (1990).

Leong et al.: NOD2/CARD15 gene polymorphisms and Crohn's disease in the Chinese population. Aliment Pharmacol Thera 17:1465-1470 (2003).

Leppkes et al.: RORγ-expressing Th17 cells induce murine chronic intestinal inflammation via redundant effects of IL-17A and IL-17F. Gastroenterology, 136:257-267, 2009.

Lesage et al.: CARD15/NOD2 mutational analysis and genotype-phenotype correlation in 612 patients with inflammatory bowel disease. Am J of Human Genetics 70:845-857 (2002).

Leung et al. Expression profiling identifies chemokine (C-C Motif) ligand 18 as an independent prognostic indicator of gastric cancer. Gastroenterology 127:457-469 (2004).

Levy-Coffman, Ellen, A Mosiac of People: The Jewish Story and a Reassessment of the DNA Evidence, Journal of Genetic Genealogy, 1:12-33, 2005.

Li et al.: Cloning, characterization and the complete 56.8-kilobase DNA sequence of the human NOTCH4 gene. Genomics 51:45-58 (1998).

Li et al.: New serological biomarkers of inflammatory bowel disease. World J of Gastroenterology14:5115-5124 (2008).

Li et al. TNFRSF1B Is Associated with ANCA in IBD. Inflammatory Bowel Diseases. 22(6):1346-1352 (2016).

Limbergen et al.: IL23R Arg381 Gin is associated with childhood onset inflammatory bowel disease in Scotland. Gut 56:1173-1174 (2007).

Lindner et al. Tamoxifen enhances interferon regulated gene expression in breast cancer cells. Molecular and Cellular Biochemistry 167:169-177 (1997).

Lipsky, P. Structure, function and regulation of molecules involved in leukocyte adhesion. New York: Springer-Verlag 1993 Book not included.

Liu et al.: Mucosal gene expression profiles following the colonization of immunocompetent defined-flora C3H mice with Helicobacter bilis: a prelude to typhlocolitis. Microbes and Infection 11:374-383 (2009).

Livak. Allelic discrimination using fluorogenic probes and the 5' nuclease assay. Genetic Analysis 14:143-149 (1999).

Lodes et al.: Bacterial flagellin is a dominant antigen in Crohn disease. Journal of Clinical Investigation 113:1296-1306 (2004).

Lorenz-Meyer. Inflammatory Bowel Disease Laboratory Diagnostics. (Reprints available from the City Hospital, Friedrichshafen, Federal Republic of Germany):3-29 (2008).

Louis et al. Association between polymorphism in IgG Fc receptor lila coding gene and biological response to infliximab in Crohn's disease. Aliment Pharmacol Ther 19:511-519 (2004).

Low et al.: High-Throughput Genomic Technology in Research and Clinical Management of Breast Cancer, Evolving Landscape of Genetic Epidemiological Studies, Breast Cancer Research, 8(3):209-214, 2006.

Lucentini, J. Gene association studies typically wrong. Scientist, 18(24):20, 2004.

MacDonald et al.: Tumor necrosis factor-alpha and interferon-gamma production measured at the single cell level in normal and inflamed human intestine Clin Exp Immunol 81:301-305 (1990).

Maggio-Price et al.: Helicobacter Infection is Required for Inflammation and Colon Cancer in Smad3-Deficient Mice, Cancer Research, 2006, vol. 66, pp. 828-838.

Maniatis, et al. Molecular Cloning. Cold Spring Harbor Laboratory, 1982.

Mansfield et al.: Novel genetic association between ulcerative colitis and the antiinflammatory cytokine interleukin-1 receptor antagonist. Gastroenterology 106:637-642 (1994).

Marrakchi et al.: Interleukin 10 promoter region polymorphisms in inflammatory bowel disease in Tunisian population. Inflamm. Res., 58:155-160, 2009.

Martin et al.: Recombination rates across the HLA complex: use of microsatellites as a rapid screen for recombinant chromosome. Human Molecular Genetics 4:423-428 (1995).

Martinez et al.: Regulation and Function of Proinflammatory TH17 Cells, Animals of the New York Academy of Sciences, 1143(1):188-211, 2008.

Martins et al.: Transcriptional repressor Blimp-1 regulates T cell homeostasis and function. Nature Immunology 7:457-265 (2006).

Mascheretti et al. Pharmacogenetic investigation of the TNF/TNF-receptor system in patients with Chronic active Crohn's disease treated with infliximib. The Pharmacogenomics Journal 2:127-136 (2002).

Matalka. The effect of estradiol but not progesterone on the production of cytokines in stimulated whole blood is concentration-dependent. Neuro Endocrinology Letters. Abstract only. 24:185-191 (2003).

Matejuk et al.: 17-beta-estradiol inhibits cytokine, chemokine and chemokine receptor mRNA expression in the central nervous system of female mice with experimental autoimmune encephalomyelitis. J of Neuroscience Research 65:529-542 (2001).

Matsunaga et al.: Application of differential display to identify genes for lung cancer detection in peripheral blood. Int J of Cancer 100:592-599 (2002).

McCall et al.: Constitutive expression of TNF-a and of an IL-8 gene is associated with genetic susceptibility to chronic granulomatous enterocolitis in inbred rats. AGA Abstracts page A740 (1993).

Mcever. leukocyte—endothelial cell interactions. Curr Opin Cell Bioi 4:840-849 (1992).

Mcgovern et al.: Genetic epistasis of IL23/IL 17 pathway genes in Crohn's disease. Inflamm Bowel Dis. 15:883-889 (2009).

Mcgovern et al.: Genetics of inflammatory bowel diseases. Gastroenterology 149(5):1163-1176 (2015).

(56) References Cited

OTHER PUBLICATIONS

Medrano et al. Role of TNFRSF1B polymorphisms in the response of Crohn's disease patients to infliximab. Human Immunology 75(1):71-75 (2014).
Mehmut et al.: Fas ligand and TNF-related apoptosis-inducing ligand induction on infiltrating lymphocytes in bladder carcinoma by Bacillus Calmette-Guerin treatment Urologica International 75:80-87 (2005).
Mei. Association between IL 17 A and Il 17RA genes and inflammatory bowel disease (IBD). Abstract only. (2007) Journal unknown.
Mei et al.: Familial expression of anti-*Escherichia coli* outer membrane porin C in relatives of patients with Crohn's disease. Gasteroenterology 130:1078-1085 (2006).
Melmed et al.: A prospective analysis of predictive factors for the diagnosis of Crohn's disease after Ileal pouch-anal anastomosis for ulcerative colitis. Abstract only. (2007) Journal Unknown.
Melmed et al.: Patients with inflammatory bowel disease are at risk for vaccine-preventable illness. Am J Gasteroenterol 101:1834-1840 (2006).
Mesange et al.: Ligands of the antiestrogen-binding site are able to inhibit virion production of human immunodeficiency virus 1-infected lymphocytes. Molecular Pharmacology 50:75-79 (1996) Abstract only.
Messer et al.: Polymorphic structure of the tumor necrosis factor (TNF) locus: an NcoI polymorphism in the first intron of TNF-8 gene correlates with a variant in amino acid position 26 and a reduced level of TNF-8 production. J Exp Med 173:209-219 (1991).
Meylan et al.: The TNF-family cytokine TL1A drives IL-13 dependent small intestinal inflammation. Muscosal Immunol., 4(2):172-185, 2011.
Michelsen et al.: IBD-Associated TL 1A Gene (TNFSF15) Haplotypes Determine Increased Expression of TL 1A Protein. PLoS One. 4:e4719 (2009).
Migone et al.: TL1A is a TNF-like Ligand for DR3 and TR6/DcR3 and Functions as a T cell Costimulator, Immunity, 16:479-492, 2002.
Milner et al. Polymorphic analysis of the three MHC-linked HSP70 genes. Immunogenetics 36:357-362 (1992).
Mingjia et al.: How oestrogen or progesterone might change a woman's susceptibility to HIV 1 infections. The Australian and New Zealand Journal of Obstetrics and Gynecology Abstract only. 42:472-475 (2002).
Misiewicz et al.: The estrogen antagonist tamoxifen inhibits carrageenan induced inflammation in Lewin female rats. Life Sciences 58:PL281-286 (1996).
Moghaddam et al.: Genetic structure of IDDM1: two separate regions in the major histocompatibility complex contribute to susceptibility or protection. Diabetes 47:263-269 (1998).
Morimoto et al. Single-step purification of F(ab')2 fragments of mouse monoclonal antibodies (immunoglobulins G1) by hydrophobic interaction high performance liquid chromatography using TSKgel Phenyl-5PW. J Biochem Biophys Methods 24:107-117 (1993).
Morinaga et al.: Database Uniprot (online), Mar. 8, 2011, Database Accession No. P02771.
Morinaga et al.: Primary structures of human a-fetoprotein and its mRNA. PNAS, 80:4604-4608, 1983.
Mow et al.: Association of antibody responses to microbial antigens and complications of small bowel Crohn's disease. Gastroenterology 126:414-424 (2004).
Mullins et al.: Perspective Series: Molecular Medicine in Genetically Engineered Animals, J Clin Invest, 97:1557-1560, 1996.
Mummidi et al.: Evolution of human and non-human primate CC chemokine receptor 5 gene and mRNA. Journal of Biological Chemistry, 275(5):18946-18961 (2000).
Mundwiler et al.: Inflammatory Bowel Disease Serologies in Ankylosing Spondylitis Patients: A Pilot Study, Arthritis Research and Therapy, 2009, vol. 11(6), pp. 2-8.
Murch et al.: Location of tumor necrosis factor alpha by immunochemistry in chronic inflammatory bowel disease. Gut 34:1705-1709 (1993).
Murillo et al.: CARD15 gene and the classification of Crohn's disease. Immunogenetics 54:59-61 (2002).
Murray et al.: GenBank Accession No. G08322 (Feb. 5, 1997).
Nadal et al.: Imbalance in the composition of the duodenal microbiota of children with coeliac disease. J Medical Microbiol. 56:1669-1674 (2007).
Nakamura et al.: In situ expression of the cell adhesion molecules in Inflammatory Bowel Disease; evidence of immunologic activation of vascular endothelial cells. Lab Investig 69(1):77-85 (1993).
Nakaya et al.: Estrogenic compounds suppressed interferon-gamma production in mouse splenocytes through direct cell-cell interaction. In Vitro Cell Dev Biol Anim 39:383-387 (2003).
Nalleweg et al.: Inflammatory bowel disease patients failing anti-TNF therapy show activation of the Th9/TH17 pathway. Gastroenterol 142(5)(Suppl1):S867-868; Abstract No. Tu1878 (2012).
Naundorf et at, IL-10 Interferes Directly with TCR-Induced IFN-[gamma] but not IL-17 Production in Memory T cells, European Journal of Immunology, 39(4):1066-1077, 2009.
Funke et al.: Functional characterisation of decoy receptor 3 in Crohn's disease; Gut 58(40):483-491 (2009).
Goswami et al.: A Brief History of IL-9; The Journal of Immunology; 186; 3283-3288 (2019).
Takedatsu et al.: TL1A (TNFSF15) Regulates the Development of Chronic Colitis By Modulating both T helper (TH) 1 and TH17 Activation; Gastroenterology; HHS Public Access; 135(2): 552-567 (2008).
NCBI Accession No. NM_001198.3 (5 pgs.) (Mar. 4, 2010).
NCBI Blast sequence search for SEQ ID No. 7; retrieved from: https://blast.ncbi.nlm.nih.gov/Blast.cgi on Sep. 12, 2018 (3 pgs.).
NCBI Gene Database, Gene ID: 133396, IL31RA interleukin 31 receptor A [*Homo sapiens* (human)}, [Retrieved online Aug. 31, 2018] Retrieved from https://www.ncbi.nlnnih.gov/gene/133396#gene-expression., Aug. 5, 2018 (16 pgs).
NCBI Gene Database, Gene ID: 3458, IFNG interferon gamma [*Homo sapiens* (human)}, [Retrieved online Aug. 31, 2018] Retrieved from <url :<a href="https://www.ncbi.nlnnih.gov/gene/3458#gene-expression>">https://www.ncbi.nlnnih.gov/gene/3458#gene-expression., Aug. 25, 2018 (16 pgs).</url :<a>.
NCBI Reference SNP Cluster Report ID rs2241880; Retrieved from: http://www.ncbi.nlm.nih.gov/projects/SNP/snp_ref. . 1gi?rs=2241880 on Sep. 23, 2016; 5 pages.
"NCBI Reference SNP Cluster Report ID rs2836878; Retrieve from: http://www.ncbi.nlm.nih.gov/projects/SNP/snp_ref. . 1gi?rs=2836878 on Sep. 23, 2016; 3 pages."
NCBI Reference SNP Cluster Report ID rs3764147; Retrieved from: http://www.ncbi.nlm.nih.gov/projects/SNP/snp_ref. . 1gi?rs=3764147 on Sep. 23, 2016; 4 pages.
NCBI Reference SNP Cluster Report ID rs762421; Retrieved from: http://www.ncbi.nlm.nih.gov/projects/SNP/snp_ref. . 1gi?rs=762421 on Sep. 23, 2016; 4 pages.
NCBI Reference SNP Cluster Report ID rs9271568; Retrieved from: http://www.ncbi.nlm.nih.gov/projects/SNP/snp_ref. . 1gi?rs=9271568 on Sep. 23, 2016; 3 pages.
NCBI SNP 10 rs12638201 (1 pg.) (Jan. 31, 2001).
NCBI SNP 10 rs2066844 (1 pg.) (created May 2, 1997).
NCBI SNP 10 rs2066845 (1 pg.) (created May 2, 1997).
NCBI SNP 10 rs2302600 (1 pg.) (Feb. 15, 1996).
NCBI SNP 10 rs746503 (1 pg.) (Dec. 7, 2000).
NCBI SNP 10 rs7613548 (1 pg.) (created Apr. 19, 2000).
NCBI SNP ID rs11209063.
NCBI SNP ID rs11209063, 2006, retrieved from: http://www.ncbi.nlm.nih.gov/projects/SNP/snp_ref.cgi?rs=11209063 (3 pgs.).
NCBI SNP ID rs12495640.
NCBI SNP ID rs12495640, 2006, retrieved from: http://www.ncbi.nlm.nih.gov/projects/SNP/snp_ref.cgi?rs=12495640 (3 pgs.).
NCBI SNP ID rs1495964, 2006, retrieved from: http://www.ncbi.nlm.nih.gov/projects/SNP/snp_ref.cgi?rs=1495964 (3 pgs.).
NCBI SNP ID rs1908632, 2006, retrieved from: http://www.ncbi.nlm.nih.gov/projects/SNP/snp_ref.cgi?rs=1908632 (3 pgs.).
NCBI SNP ID rs2066847 (1 pg.) (created May 2, 1997).
NCBI SNP ID rs6788981, 2006, retrieved from: http://www.ncbi.nlm.nih.gov/projects/SNP/snp_ref.cgi?rs-6788981 (3 pgs.).

(56) References Cited

OTHER PUBLICATIONS

NCBI SNP ID rs7374667, 2006, retrieved from: http://www.ncbi.nlm.nih.gov/projects/SNP/snp_ref.cgi?rs=7374667 (4 pgs).
NCBI SNP ID rs7374667 (2011).
Nedospasov et al.: DNA sequence polymorphism at the human tumor necrosis factor (TNF) locus. Numerous TNF/lymphotoxin alleles tagged by two closely linked microsatellitesin the upstream region of the lymphotoxin (TNF-beta) gene. J. Immunol. 147:1053-1059 (1991).
Nedospasov et al.: Genetic polymorphism of the human gene locus containing genes for tumor necrosis factors: ethnic differences in allele frequency distribution. Chemical Abstracts, 120(5):47183y (1994).
Nowak et al.: IL-9 as a mediator of Th17-driven inflammatory disease. Journal of Experimental Medicine 206(8):1653-1660 (2009).
Ogura et al.: A frameshift mutation in NOD2 associates with susceptibility to Crohn's disease. Nature 411:603-606 (2001).
Ogura et al.: NOD2, a Nod1/Apaf-1 family member that is restricted to monocytes and activates Nf-kb. J Biol Chem 276:4812-4818 (2001).
Oh et al.: A randomized, controlled trial to evaluate the effect of an anti-interleukin-9 monoclonal antibody in adults with uncontrolled asthma. Respiratory Research 14:93 (2013).
Ohmen et al.: Susceptibility locus for inflammatory bowel disease on chromosome 16 has a role in Crohn's disease, but not in ulcerative colitis. Hum Mol Genet 5:1679-1683 (1996).
Okazaki et al.: Contributions of the IBD5, IL23R, ATG16L 1, and NOD2 to Crohn's disease risk in a population-based case-controlled study: evidence of gene-gene interaction. Inflamm Bowel Disease 14:1528-1541 (2008).
Orholm et al.: Familial occurrence of inflammatory bowel disease. New England Journal of Medicine 324:84-88 (1991).
Over et al.: Thromphilia and inflammatory bowel disease: does factor V mutation have a role? European Journal of Gastroenterology and Hepatology 10:827-829 (1998).
Owerbach et al. The HOXD8 locus (2q31) is linked to type I diabetes—interaction with chromosome 6 and 11 disease susceptibility genes. Diabetes 44:132-136 (1995).
Pallone et al.: Genetic and Pathogenetic Insights into Inflammatory Bowel Disease, Current Gastroenterology Reports, 2003, vol. 5, pp. 487-492.
Papadakis et al.: An interaction between IL-23R and IL-17A and between IL-23R and IL 17RA haplotypes is necessary for susceptibility to Crohn's disease. Abstract only. (2007) Journal unknown.
Papadakis et al.: Anti-Flagellin (Cbir1) phenotypic and genetic Crohn's Disease associations. Inflamm Bowel Dis 13(5):524-530 (2007).
Papadakis et al.: Dominant Role for TL1A/DR3 Pathway in IL-12 plus IL-18-Induced IFN-γ Production by Peripheral Blood and Mucosal CCR9+ T Lymphocytes. the Journal of Immunology. 174:4985-4900 (2005).
Papadakis et al.: IL1A synergizes with IL-12 and IL-18 to enhance IFN-y production in human T cells and NK cells, The Journal of Immunology, 172:7002-7007, 2004.
Papadakis et al.: Phenotypic and functional characterization of CCR9+ T lymphocytes in small intestinal Crohn's disease. Abstract only. (2006). Journal unknown.
Papp et al.: Seroreactivity to microbial components in Crohn's disease is associated with Ileal involvement, noninflammatory disease behavior and NOD2/CARD15 genotype but not with risk for surgery in a Hungarian cohort of IBO patients. Inflamm Bowel Disease 13:984-992 (2007).
Pappu et al.: TL1A-DR3 interaction regulates Th17 cell function and Th17-Mediated autoimmune disease. Journal of Experimental Medicine, 205(5):1049-1062, 2008.
Parente et al.: Bowel Ultrasound in Assessment of Crohn's Disease and Detection of Related Small Bowel Strictures: A Prospective Comparative Study Versus X Ray and Intraoperative Findings, Gut, 50: 490-495, 2002.
Parkes et al.: Susceptibility loci in inflammatory bowel disease. Lancet 348:1588 (1996).
Parrello et al.: Upregulation of the IL-12 receptor beta 2 chain in Crohn's disease. J Immunol 165:7234-7239 (2000).
Partanen et al.: Low degree of DNA polymorphism in the HLA-linked lymphotoxin (tumor necrosis factor-B) gene. Scand J. Immunol. 28:313-316 (1988).
Paul. Chapter 19. Fundamental Immunology 4th edition pp. 663-665 (1998).
PCT/2011/028694 International Preliminary Report on Patentability dated Sep. 18, 2012.
PCT/2011/028694 International Search Report and Written Opinion dated Jul. 27, 2011.
PCT/2012/030614 International Search Report and Written Opinion dated Sep. 28, 2012.
PCT/US1995/001434 International Preliminary Examination Report dated May 22, 1996.
PCT/US1995/001434 International Search Report dated Jul. 21, 1995.
PCT/US1995/001434 Written Opinion dated Nov. 17, 1995.
PCT/US1995/006107 International Preliminary Examination Report dated Jun. 5, 1996.
PCT/US1995/006107 International Search Report dated Oct. 6, 1995.
PCT/US1995/006107 Written Opinion dated Feb. 12, 1996.
PCT/US1997/000042 International Preliminary Examination Report dated Apr. 1, 1998.
PCT/US1997/000042 International Search Report dated Apr. 21, 1997, mailed May 14, 1997.
PCT/US1997/000042 Written Opinion dated Oct. 29, 1997.
PCT/US2000/025112 International Preliminary Examination Report dated Dec. 20, 2001.
PCT/US2000/025112 International Search Report dated Aug. 6, 2001.
PCT/US2003/023926 International Preliminary Examination Report dated Aug. 19, 2004.
PCT/US2003/023926 International Search Report dated Jun. 23, 2004.
PCT/US2005/018161 International Preliminary Report on Patentability dated Apr. 15, 2009.
PCT/US2005/018161 International Search Report dated Jun. 4, 2008.
PCT/US2005/018161 Written Opinion dated Jun. 4, 2008.
PCT/US2005/044335 International Preliminary Examination Report dated Jun. 13, 2007.
PCT/US2005/044335 International Search Report dated Sep. 22, 2006.
PCT/US2005/044335 Written Opinion mailed Sep. 22, 2006; dated Aug. 26, 2006.
PCT/US2006/22427 International Search Report Dated Sep. 5, 2006 EP Application 2006772657.
PCT/US2007/008597 International Preliminary Examination Report dated Oct. 8, 2008.
PCT/US2007/008597 International Search Report dated Jun. 4, 2008.
PCT/US2007/008597 Written Opinion dated Jun. 4, 2008.
PCT/US2008/054033 International Preliminary Examination Report dated Aug. 19, 2009.
PCT/US2008/054033 International Search Report dated Aug. 21, 2008.
PCT/US2008/054033 Written Opinion Aug. 21, 2008.
PCT/US2008/055020 International Preliminary Report on Patentability dated Aug. 26, 2009.
PCT/US2008/055020 International Search Report and Written Opinion dated Aug. 14, 2008, 8 pages.
PCT/US2008/055236 International Preliminary Examination Report dated Sep. 1, 2009.
PCT/US2008/055236 International Search Report and Written Opinion dated Nov. 14, 2008.
PCT/US2008/056103 International Preliminary Report on Patentability dated Nov. 24, 2009.
PCT/US2008/056103 International Search Report dated Sep. 3, 2008.

(56) References Cited

OTHER PUBLICATIONS

PCT/US2008/056103 Written Opinion dated Sep. 3, 2008.
PCT/US2008/057028 International Preliminary Report on Patentability dated Sep. 15, 2009.
PCT/US2008/057028 International Search Report dated Oct. 10, 2008.
PCT/US2008/057028 Written Opinion dated Oct. 10, 2008.
PCT/US2008/057820 International Preliminary Report on Patentability dated Sep. 22, 2009.
PCT/US2008/057820 International Search Report dated Sep. 11, 2008.
PCT/US2008/057820 Written Opinion dated Sep. 11, 2008.
PCT/US2008/061652 International Preliminary Report on Patentability dated Oct. 27, 2009.
PCT/US2008/061652 International Search Report dated Dec. 1, 2008.
PCT/US2008/061652 Written Opinion dated Dec. 1, 2008.
PCT/US2008/062531 International Preliminary Report on Patentability dated Nov. 10, 2009.
PCT/US2008/062531 International Search Report and Written Opinion dated Nov. 18, 2008.
PCT/US2008/063202 International Preliminary Examination Report dated Nov. 10, 2009.
PCT/US2008/063202 International Search Report dated Nov. 18, 2008.
PCT/US2008/063202 Written Opinion dated Nov. 18, 2008.
PCT/US2008/080526 International Preliminary Report on Patentability dated Apr. 20, 2010.
PCT/US2008/080526 International Search Report and Written Opinion dated Mar. 25, 2009, 11 pages.
PCT/US2009/044720 International Preliminary Report on Patentability dated Nov. 23, 2010.
PCT/US2009/044720 International Search Report dated Nov. 5, 2009.
PCT/US2009/044720 Written Opinion dated Nov. 5, 2009.
PCT/US2009/048319 International Preliminary Report on Patentability dated Jan. 5, 2011.
PCT/US2009/048319 International Search Report and Written Opinion dated Nov. 6, 2009.
PCT/US2009/059190 International Preliminary Report on Patentability dated Apr. 5, 2011.
PCT/US2009/059190 International Search Report and Written Opinion dated Mar. 16, 2010.
PCT/US2009/061698 International Preliminary Report on Patentability dated Apr. 26, 2011.
PCT/US2009/061698 International Search Report dated Mar. 16, 2010.
PCT/US2009/061698 Written Opinion dated Mar. 16, 2010.
PCT/US2009/065928 International Preliminary Report on Patentability dated May 31, 2011.
"PCT/US2009/065928 International Search Report dated Aug. 3, 2010".
PCT/US2009/065928 Written Opinion dated Aug. 3, 2010.
PCT/US2009/069531 International Preliminary Report on Patentability dated Jun. 29, 2011.
PCT/US2009/069531 International Search Report and Written Opinion dated Aug. 4, 2010, 11 pages.
PCT/US2009/069534 International Search Report dated Mar. 1, 2010.
PCT/US2009/069541 International Preliminary Report on Patentability dated Jun. 29, 2011.
PCT/US2009/069541 International Search Report dated Mar. 4, 2010.
PCT/US2009/069541 Written Opinion dated Mar. 4, 2010.
PCT/US2010/020921 International Report on Patentability dated Jul. 19, 2011.
PCT/US2010/020921 International Search Report and Written Opinion dated May 5, 2010.
PCT/US2010/030359 International Preliminary Report on Patentability Oct. 11, 2011.
PCT/US2010/030359 International Search report and Written Opinion dated Aug. 11, 2010.
PCT/US2010/043427 International Search Report dated Dec. 3, 2010.
PCT/US2011/021180 International Preliminary Report on Patentability dated Jun. 15, 2011.
PCT/US2011/021180 International Search Report and Written Opinion dated Jun. 15, 2011.
PCT/US2011/021382 International Preliminary Report on Patentability dated Jul. 17, 2012.
PCT/US2011/021382 International Search Report and Written Opinion dated Mar. 15, 2011.
PCT/US2012/030611 International Preliminary Report on Patentability dated Oct. 1, 2013.
PCT/US2012/030611 International Search Report and Written Opinion dated Sep. 7, 2012.
PCT/US2012/030616 International Preliminary Report on Patentability dated Nov. 19, 2013.
PCT/US2012/030616 International Search Report and Written Opinion dated Sep. 17, 2012.
PCT/US2014/032054 International Preliminary Report on Patentability Sep. 29, 2015, 12 pages.
PCT/US2014/032054 International Search Report and Written Opinion dated Aug. 5, 2014, 14 pages.
PCT/US2014/038333 International Preliminary Report on Patentability dated Nov. 17, 2015.
PCT/US2014/038333 International Search Report and Written Opinion dated Nov. 20, 2014.
PCT/US2014/038468 International Preliminary Report on Patentability Nov. 17, 2015, 7 pages.
PCT/US2014/038468 International Search Report and Written Opinion dated Nov. 18, 2014, 11 pages.
PCT/US2014/047326 International Preliminary Report on Patentability dated Jan. 19, 2016, 7 pages.
PCT/US2014/047326 International Search Report and Written Opinion dated Dec. 22, 2014, 9 pages.
PCT/US2014/054425 International Preliminary Report on Patentability dated Mar. 8, 2016.
PCT/US2014/054425 International Search Report and Written Opinion dated Dec. 31, 2014, 12 pages.
PCT/US2016/022494 International Search Report and Written Opinion dated Jun. 3, 2016.
PCT/US2016/032180 International Preliminary Report on Patentability dated Nov. 30, 2017.
PCT/US2016/032180 International Search Report and Written Opinion dated Aug. 19, 2016, 8 pages.
PCT/US2017/023082 International Search Report and Written Opinion dated Aug. 15, 2017.
PCT/US2017/058019 International Search Report and Written Opinion dated Feb. 15, 2018.
PCT/US2018/028397 International Search Report and Written Opinion dated Jul. 9, 2018.
Peltekova et al.: Functional variants of OCTN cation transporter genes are associated with Crohn disease. Nature Genetics, 16(5):471-475, 2004.
Pennisi, E. A Closer look at SNPs suggests difficulties. Science, 281(5384):1787-1789, 1998.
Pericak-Vance et al.: Approaches to gene mapping in complex human diseases. Wiley-Liss New York 1998.
Perkin Elmer Catalog 1992, p. 12.
Picornell et al.: TNFSF15 is an ethnic specific IBD gene. Inflamm. Bowel Disease, 13(11):1333-1338, 2007.
Pierik et al. Tumour Necrosis Factor-a Receptor 1 and 2 Polymorphisms in Inflammatory Bowel Disease and their Association with Response to Infliximab. Alimentary Pharmacology & Therapeutics 20(3):303-310 (2004).
Pinchuk et al.: Human Colonic Myofibroblast Promote Expansion of CD4+ CD25high Foxp3+ Regulatory T Cells, Gastroenterology, 140(7):2019-2030, pp. 1-19, and p. 8, 2011.
Plevy et al.: A role of TNF-alpha and mucosal T-helper-1 cytokines in the pathogenesis of Crohn's disease. The Journal of Immunology 84:1397-1398 (2004).

(56) References Cited

OTHER PUBLICATIONS

Plevy et al.: Increased mucosal tnf-alpha mrna levels and numbers of tnf-alpha producing cells are unique to mucosal inflammation in crohn's disease, Faseb Journal, Abstract 5849 8:A1010 (Apr. 1994).
Plevy et al.: The tumor necrosis factor (TNF) microsatellite haplotype A2B1C204E1 correlates with increased TNF production in Crohn's disease. Abstract only AASLD at Digestive disease week (1995).
Plevy et al. TNF-alpha MRNA levels differentiated mucosal inflammation in crohn's disease from ulcerative colitis. J. Immunology 150:10a (1993).
Plevy et al.: Tumor necrosis factor microsatellites define Crohn's disease—associated haplotype on chromosome 6. Gasteroenterology 110:1053-1060 (1996).
Plevy et al., Tumor necrosis factor (TFN) microsatellite associations with HLA-DR2+ patients define Crohn's disease (cd) and ulcerative colitis (uc)-specific genotypes. Gastroenterology 106:A754 (1994).
PLINK user guide—Chapter 11. Association. 21 pages printed from https://zzz.bwh.harvard.edu/plink/anal.shtml on Dec. 15, 2020, document last modified Wednesday Jan. 25, 2017.
Pociot et al.: A tumor necrosis factor beta gene polymorphism in relation to monokine secretion and insulin dependent diabetes mellitus. Scand J. Immunol., 33:37-49 (1991).
Pociot et al.: Association of tumor necrosis factor and class II major histocompatibility complex alles with secretion of tnf alfa and tnf beta by human mononuclear cells: a possible link to insulin-dependent diabetes mellitus. Abstract only. Eur. J. Immunology 23:224-231 (1993).
Poicot et al.: Polymorphic analysis of the human MHC-linked heat shock protein 70 (HSP70- and HSP70-Hom genes in insulin-dependent diabetes mellitus (IOOM). Scand J Immunol 38:491-495 (1993).
Polanczyk et al.: The protective effect of 17beta-estradiol on experimental autoimmune encephalomyelitis is mediated through estrogen receptor-a. American J of Pathology 163:1599-1605 (2003).
Potts et al.: Using microbicides to fight the spread of HIV. Science 300:431 (2003).
Prehn et al.: The T Cell Costimulator TL 1A Is Induced by Fe R Signaling in Human Monocytes and Dendritic Cells. J Immunol 178:4033-4038 (2007).
Prideaux et al.: Inflammatory Bowel Disease in Asia: A Systematic Review, Journal of Gastroenterology and Hepatology, 27(8):1266-1280, 2012.
Prometheus Biosciences, Inc. Form S-1 Registration Statement as filed with the Securities and Exchange Commission on Feb. 19, 2021 (246 pages).
Queen et al. A humanized antibody that binds to the interleukin 2 receptor. PNAS USA 86:10029-10032 (1989).
Radlmayr et al.: The c-insertion mutation of the NOD2 gene is associated with fistulizing and fibrostenotic phenotypes in Crohn's diseases. Gasterenterology 122:2091-2095 (2002).
Raychaudhuri et al.: Genetic Variants at CD28, PRDM1 and CD2/CD58 are Associated with Rheumatoid Arthritis Risk, Nature Genetics, 2009, vol. 41(12), pp. 1313-1318, and online methods.
R&D datasheet for human/mouse TL1A/TNFSF15 antibody, catalog No. MAB7441; clone #293327 (Feb. 7, 2018).
Rector et al.: Mannan-binding lectin (MBL) gene polymorphisms in ulcerative colitis and Crohn's disease. Genes and Immunity 2:323-328 (2001).
Redon et al. Global variation in copy number in the human genome. Nature. 444(7118): 444-54 (2006).
Reference SNP Cluster report for rs2986754 retrieved from: http://www.ncbi.nlm.nih.gov/projects/SNP/snp_ref.cgi?rs=2986754 on Sep. 13, 2016; 3 pages.
Reference SNP Cluster report for rs746503 retrieved from: http://www.ncbi.nlm.nih.gov/projects/SNP/snp_ref.cgi?rs+746503 on Sep. 15, 2016; 4 pages.
Reference SNP (refSNP) Cluster Report: rs598672, pp. 1-4 printed from www.ncbi.nlm.nih.gov (2020).
Reference SNP (refSNP) Cluster Report: rs666595, pp. 1-4 printed from www.ncbi.nlm.nih.gov (2020).
Reichwald et al. TL1A induces TCR independent IL-6 and TNF-alpha production and growth of PLZF leukocytes. PLOS ONE 9(1): e85793, 2013.
Reinecker et al.: Enhanced secretion of tumor necrosis factor-alpha, IL-6 and IL-1 beta by isolated lamina propia mononuclear cells from patients with ulcerative colitis and Crohn's disease Clin Exp Immunol 94:174-181 (1993).
Richard et al. The TNF-family cytokine TL1A: from lymphocyte costimulator to disease co-conspirator. J Leukocyte Biol 98:333-345 2015.
Riechmann et al. Reshaping human antibodies for therapy. Nature, 332.6162:323-7 (1988).
Rieder et al.: Intestinal Fibrosis in Inflammatory Bowel Disease-Current Knowledge and Future Perspectives, J.Crohns Colitis, 2:279-290, 2008.
Rioux et al.: Genetic Variation in the 5q31 Cytokine Gene Cluster Confers Susceptibility to Crohn Disease, Nature Genetics, 2001, vol. 29(2), pp. 223-228.
Rioux et al.: Genome-wide association study identifies new susceptibility loci for Crohn disease and implicates autophagy in disease pathogenesis. Nature Genetics 39(5):596-604 (2007).
Rodriguez-Caballero et al.: A new simple whole blood flow cytometry-based method for simultaneous identification of activated cells and quantitative evaluation of cytokines released during activation Laboratory Investigation 84:1387-1398 (2004).
Roth et al.: Familial empiric risk estimates of inflammatory bowel disease in Ashkenazi Jews. Gastroenterology 96:1016-1020 (1989).
Roth et al.: Geographic origins of Jewish patients with inflammatory bowel disease. Gastroenterology 97:900-904 (1989).
Rothe et al.: The human combinatorial antibody library HuCAL GOLD combines diversification of all six CDRs according to the natural immune system with a novel display method for efficient selection of high-affinity antibodies. J. Mol. Bio. 376:1182-1200, 2008.
Rotter et al.: TLR5 polymorphisms are associated with OmpC and CBir1 expression and with severity of Crohn's disease in Ashkenazi Jews. Abstract only (2004). Journal unknown.
Roussomoustakaki et al.: Genetic markers may predict disease behavior in patients with ulcerative colitis. Gastroenterology, 112:1845-1853, 1997.
Rozen et al.: Crohn's disease in the Jewish population of Tei-Aviv-Yafo: epidemiologic and clinical aspects. Gastroenterology 76:25-30 (1979).
Salem. Estrogen, a double-edged sword: modulation of TH1- and THw- medicated inflammations by differential regulation of T J1/TH2 cytokine production. Inflammation and Allergy 3:97-104 (2004).
Salem et al.: Mediation of the immunomodulatory effect of beta-estradiol on inflammatory response by inhibition of recruitment and activation of inflammatory cells and their gene expression of TNF-alpha and IFN-gamma. Inti Archives of Allergy and Immunology Abstract Only. 121:235-245 (2000).
Saruta et al.: High frequency haplotypes in the X-chromosome locus TLR8 are associated with both CD and UC in females. Inflammatory Bowel Disease. 15(3):321-327 (2009).
Saruta et al.: TLR8-mediated activation of human monocytes inhibits TL 1A expression. Eur J Immunol 39:2195-2202 (2009).
Sategna-Guidetti et al.: Tumor necrosis factor cachectin in Crohn's disease—relation of C385 serum concentration to disease activity. Recenti Progressi 84:93-99 (1993).
Satsangi et al.: Contribution of Genes of the Major Histocompatibility Complex to Susceptibility and Disease Phenotype in Inflammatory Bowel Disease, The Lancet, 347:1212-1217, 1996.
Satsangi et al.: The genetics of inflammatory bowel disease. Gut 40:572-574 (1997).
Saxon et al.: A distinct subset of antineutrophil cytoplasmic antibodies is associated with inflammatory bowel disease. J Allergy Clin. Immunol. 86:202-210 (1990).
Schimanski et al.: Effect of chemokine receptors CXCR4 and CCR7 on the metastatic behavior of human colorectal cancer Clinical Cancer Research 11:1743-1750 (2005).

(56) References Cited

OTHER PUBLICATIONS

Schluender et al.: Does infliximab influence surgical morbidity or long-term outcome of Ileal pouch-anal anastomosis in patients with ulcerative colitis. Abstract only. (2006). Journal Unknown.
Schluender et al.: Does preoperative wireless endoscopic capsule predict long-term outcome after Ileal pouch-anal anastomosis (IPAA)? Abstract only. (2006). Journal unknown.
Schoelmerich. Inflammatory Bowel Diseases: early symptoms and differential (Reprints available from University of Freiburg, Department of Internal Medicine, Hugstetter Strasse 55, 0-7800 Freiburg, W. Germany pp. 2-20 (2017).
Scientists Discover New Gene Associated with Crohn's Disease. BusinessWire https://www.businesswire.com/news/home/20070124005277/en/Scientists-Discover-New-Gene-Crohns-Disease (Jan. 24, 2017).
See et al.: Increased tumor necrosis factor alpha (TNF-alpha) and natural killer cell (NK) function using an integrative approach in late stage cancers. Immunological Investigations 31:137-153 (2002).
Seidelin et al.: Upregulation of cIAP2 in Regenerating Coloncytes in Ulcerative Colitis, Virchows Arch, 451:1031-1038, 2007.
Shanahan et al.: Inflammatory Bowel Disease. Textbook of Internal Medicine. W.N. Kelle et al. (editor) 2nd edition J. B. Lippincott Company, Philadelphia 81:489-502 (1992).
Shetty et al.: Pharmacogenomics of response to anti-tumor necrosis factor therapy in patients with Crohn's disease. American Journal of Pharmacogenomics 2:215-221 (2002).
Shih et al.: Constitutive TL1A (TNFSF15) Expression on Lymphoid or Myeloid Cells Leads to Mild Intestinal Inflammation and Fibrosis, PLOS One, 6(1), pp. 1-16, 2011.
Shih et al.: Inhibition of a novel fibrogenic factor Tl 1a reverses established colonic fibrosis. Mucosal Immunol., 7(6): 1492-1503, 2014.
Shih et al. Reversal of murine colitis and fibrosis by neutralizing TL1A antibody: potential novel therapy to alter natural history of Crohn's disease. Gastroenterol 142(5):S84, Abstract #357, 2012.
Shih et at, Microbial Induction of Inflammatory Bowel Disease Associated Gene TL1A (TNFSF15) in Antigen Presenting Cells, Eur. J. Immunol., 39:3239-3250, 2009.
Shovam et al.: Evaluation of the BioPiex 2200 ANA screen: Analysis of 510 healthy subjects: incidence of natural/predictive autoantibodies. Annals of the New York Academy of Science, 1050:380-388 (2005).
Silman et al.: Epidemiology and genetics of rheumatoid arthritis. Arthritis Research 4 Supp 3:S265-S272 (2002).
Silverberg et al.: Evidence for linkage between Crohn's disease (CD) and a locus near the major histocompatibility complex (MHC) on chromosome 6 in a Canadian inflammatory bowel disease (IBO) population. Gastroenterology 116:G3560 AGA Abstracts (1999).
Silverberg et al.: The HLA DRBL 0103 allele is associated with Crohn's disease (CD) in a Toronto inflammatory bowel disease (IBO) population. Gastroenterology 116:G3559 AGA Abstracts (1999).
Singal et al.: D6S273 microsatellite polymorphism and susceptibility to Rhematoid Arthritis. Tissue Antigens 52:353-358 (1998).
Singal et al.: Genetics of rheumatoid arthritis (RA): two separate regions in the major histocompatibility complex contribute to susceptibility to RA. Immunol Lett 69:301-306, (1999).
Sitaraman et al.: Elevated flagellin-specific immunoglobulins in Crohn's disease. Am J Physiol Gastrointest Liver Physiol 288:G403-G406 (2005).
Smith. Adherence of neutrophils to canine cardiac myocyyes in vitro is dependent on intercellular adhesion molecule-1. J Clin Invest 88:1216-1223 (1991).
Smith et al.: Cooperative interactions of LFA-1 and Mac-1 with intercellular adhesion molecule-1 in facilitating adherence and transendothelial migration of human neurophils in vitro. J Clin Invest 83:2008-2017 (1989).
Smith et al.: Estrogen protects against vaginal transmission of simian immunodeficiency virus. J Infectious Diseases 182:708-715 (2000).
Smith et al.: Recognition of an endothelial determinant for CD18-dependent human neutrophil adherence and transendothelial migration. J Clin Invest 82:1746-1756 (1988).
Smith et al. Topical estrogen protects against SIV vaginal transmission without evidence of systemic effect. AIDS 18:1637-1643 (2004).
Smith. Transendothelial Migration, in Breakthroughs in Molecular Biology, vol. 4: Adhesion: Its Role in Inflammatory Disease. Harlan, J. and Liu D., eds., W. H. Freeman & Co. New York. pp. 83-115 (1992).
Sobrino et al.: SNP's in Forensic Genetics: A Review on SNP Typing Methodologies, Forensic Science International, 154:181-194, 2005.
Spinelli et al.: Intestinal Fibrosis in Crohn's Disease: Medical Treatment or Surgery?, Current Drug Targets, 11(2):242-248, 2010.
Springer et al.: Adhesion receptors of the immune system. Nature 346:425-433 (1990).
Staunton et al.: Primary Structure of ICAM-1 demonstrates interaction between member of the immunoglobulin and integrin supergene families. Cell 52:925-933 (1988).
Staunton et al. The arrangement of the immunoglobulin-like domains of ICAM-1and binding sites for LFA-1 and rhinovirus. Cell 61:243-254 (1990).
Steer et al.: Development of rheumatoid arthritis is not associated with two polymorphisms in the Crohn's disease gene CARD15 Rheumatology 42:304-307 (2003).
Stites et al.: Chapter 22 of the 4th edition of Basic and Clinical Immunology, Lange Medical Publications, Los Altos, California, p. 325-365 (1982).
Stratagene Catalog. 1988; p39. Gene Characterization Kits. Table of Contents.
Strater et al.: Expression of TRAIL and TRAIL receptors in colon carcinoma: TRAIL-R1 is an independent prognostic parameter. Clinical Cancer Research 8:3734-3740 (2002).
Strober et at, Proinflammatoly Cytokines in Pathogenesis of Inflammatory Bowel Diseases, Gastroenterology, 140(6):1756-1767, 2011.
Strong, S. Surgical management of Crohn's disease. in: Surgical Treatment: Evidence Based and Problem Oriented. Holzheimer and Mannick, editors. Munich: Zuckschwerdt, 7 pages, 2001.
Stulik et al.: The different expression of proteins recognized by monoclonal anti-heat shock protein 70 (hsp70) antibody in human colonic diseases. Electrophoresis 18:625-628 (1997).
Su. Different haplotypes of IL 12B (p40) genes are associated with clinical Crohn's disease (CD) and with CD patients expressing Cbir1 antibodies, respectively. Abstract only (2007). Journal unknown.
Sugaya et al.: Gene organization of human NOTCH4 and (CTG)n polymorphism in this human counterpart gene of mouse proto-oncogene Int3. Gene 189:235-244 (1997).
Sugaya et al.: Three genes in the human MHC class III region near the junction with the class II: gene for receptor of advanced glycosylation end products, PBX2 homeobox gene and a notch homolog, human counterpart of mouse mammary tumor gene int-3. Genomics 23:408-419 (1994).
Sullivan et al.: Prevalence of a mutation causing C2 deficiency in systemic lupus erythematosus. J of Rheumatology 21:1128-1133 (1994).
Syvanen, Ann-Christine, Accessing Genetic Variation: Genotyping Single Nucleotide Polymorphisms, Nature Reviews, 2: 930, 2001.
Takedatsu et al.: Linkage of CD-related serological phenotypes: NFKB1 haplotypes are associated with anti-CBir1 & ASCA, and show reduced NF-KB activation. Gut. 58:60-67 (2009).
Takedatsu. Reduced nuclear factor (NF)-kB expression in cell lines from anti-CBir1-associated NFKB1 haplotypes. Abstract only. (2007). Journal unknown.
Targan et al.: Antibodies to a novel flagellin (CBir1) define a unique serologic response in Crohn's disease (CD). Gastroenterology Abstract only 126(4), Suppl 2:A113 (2004).
Targan et al.: Antibodies to CBir1 flagellin define a unique response that is associated independently with complicated Crohn's disease. Gastroenterology 128:2020-2028 (2005).
Targan et al.: Definition of a lamina propia T cells responsive state enhanced cytokine responsiveness of T cells stimulated through the CD2 pathway. J Immunol 154:664-675 (1995).

(56) References Cited

OTHER PUBLICATIONS

Targan et al.: TL1A (TNFSF15): A Master Regulator of Mucosal Inflammation, Advances in Experimental Medicine and Biology, 691: 681-683 , 2011.
Tarlow et al.: Polymorphism in human IL-1 receptor antagonist gene intron 2 is caused by variable numbers of an 86-bp tandem repeat. Hum Genet 91:403-404 (1993).
Taylor et al.: Analysis of IBD5-related polymorphisms: IRF1 but not SLC22A4 or SLC22A5 is associated with 18D in Puerto Rican populations. Digestive Disease Week Abstract only (2006). Journal unknown.
Taylor et al.: ANCA pattern and LTA haplotype relationship to clinical responses to anti-TNF antibody treatment in Crohn's disease. Gastroenterology, 120:1347-1355, 2001.
Taylor et al.: Genes regulating the expression of antibody to C8irl flagellin in humans are located within a syntenic region to the major mouse colitogenic locus Cdcs1. AGA Institute Abstract #444 p. A-64 (2006).
Taylor et al.: IL23R haplotypes provide a large population attributable risk for Crohn's disease. Inflammatory Bowel 14:1185-1191 (2008).
Taylor et al.: Linkage disequilibrium mapping identifies a Class III major histocompatibility complex (MHC) susceptibility haplotypes to Crohn's disease in Ashkenazi Jews. American Journal of Human Genetics. 65(4): A102, abstract 534 (1999).
Taylor et al.: Specific clinical and immunological features in Crohn's disease patients are associated with the MHC class III marker Notch4. Gastroenterology. 118(Supp 2):A869, Abstract 4830 (2000).
The Wellcome Trust Case Control Consortium, Genome-Wide Association Study of 14,000 Cases of Seven Common Diseases and 3,000 Shared Controls, Nature, 2007, vol. 447, pp. 661-678.
Thisteda. What is a P-value. Departments of Statistics and Health Studies. The University of Chicago. (May 25, 1988).
Thomas et al.: Estrogen and raloxifen activities on amyloid-beta-induced inflammatory reaction. Microvascular Research 61:28-39 (2001).
Thomas et al.: The TNF Family Member TL1A induces IL-22 Secretion in Committed Human TH17 Cells Via IL-9 Induction, Journal of Leukocyte Biology, 101:1-20, 2016.
Tomassini et al.: cDNA cloning reveals that the major group rhinovirus receptor on Hela cells in intercellular adhesion molecule-1. PNAS USA 86:4907-4911 (1989).
Tomlinson et al.: Methods for generating multivalent and bispecific antibody fragments. Methods Enzymol 326:461-479 (2000).
Tong Ren Tang Health Center Editorial Board: Fruity Health Care Dictionary p. 153 (Jan. 31, 2013).
Torok et al.: Crohn's disease is associated with a Toll-like receptor-9 polymorphism. Gastroenterology 127:365-368 (2004).
Torres et al.: Newborn screening for Hermansky-pudlak syndrome Type 3 in Puerto Rico. Blood 108:3290 (2006).
Torres et al.: The Hermansky-pudlak 1 (HPS1) gene is associated with IBD in Puerto Rico independent of the known HPS1 insertion mutation. Abstract only, 2006 Journal unknown, 1 page.
Tountas et al.: Genetic association between allele 2 of IL-1 receptor antagonist (IL-1 ra) and ulcerative colitis in Los Angeles based hispanic population. Abstract XP000673112 only. Gastroenterology 108:806-813 (1995).
Tountas et al. Heterogenous association between allele 2 of IL-2 receptor antagonist (ILC4371 RA) and ulcerative colitis in Jewish and non-Jewish populations. Abstract XP000673114 only. J. Investigative Medicine 44(1) (1996).
Tountas et al.: Increased carriage of allele 2 of IL-1 receptor antagonist (IL-1ra) in Jewish population: the strongest known genetic association in ulcerative colitis. American Gastroenterology Association Abstract Only (1996).
Trachtenberg et al.: Rare HLA DR-DQ haplotypes associated with inflammatory bowel disease. Human Immunol 55 (supp. 1):59 Abstract #42 (1997).
Tremelling et al.: Contribution of TNFSF15 Gene Variants to Crohn's Disease Susceptibility Confirmed in UK Population, Inflammatory Bowel Diseases, 14(6):733-737, 2008.
Tromm et al.: Inflammatory Bowel Disease: endoscopic diagnostics. (Reprints available at the Department of Gastroenterology and Hepatology "Bergmannshell" Hospital) 19th El., Falk Foundation, University of Bochum, Federal Republic of Germany pp. 3-38 (2009).
Trowsdale et al.: Map of the human MHC. Immunol. Today 12:443-446 (1991).
Turchan et al.: Estrogen protects against the synergistic toxicity by HIV proteins, methamphetamine and cocaine. BMC Neuroscience 2:3 (2001).
Udalova et al.: Highly informative typing of the human TNF locus using six adjacent polymorphic markers Genomics 16:180-186 (1993).
UniprotKB Database, Q8NI17 (IL31R_Human), Retrieved online Sep. 5, 2019. Retrieved from <url <a= href=>https://www.uniprot.org/uniprot/Q8NI17. Jul. 31, 2019 .</url>.
U.S. Appl. No. 08/196,003 Office Action dated Dec. 12, 1995.
U.S. Appl. No. 08/196,003 Office Action dated Oct. 2, 1996.
U.S. Appl. No. 08/245,297 Office Action dated Dec. 9, 1996.
U.S. Appl. No. 08/245,297 Office Action dated Jan. 22, 1996.
U.S. Appl. No. 08/245,297 Office Action dated Jul. 11, 1996.
U.S. Appl. No. 08/245,297 Office Action dated Mar. 15, 1995.
U.S. Appl. No. 08/587,911 Office Action dated Apr. 15, 1997.
U.S. Appl. No. 08/587,911 Office Action dated Jan. 5, 1998.
U.S. Appl. No. 08/587,911 Office Action dated Jul. 6, 1998.
U.S. Appl. No. 08/798,668 Notice of Allowance dated Apr. 29, 1999.
U.S. Appl. No. 08/798,668 Office Action dated Aug. 10, 1997.
U.S. Appl. No. 08/798,668 Office Action dated Jan. 29, 1998.
U.S. Appl. No. 08/798,668 Office Action dated Jun. 6, 1997.
U.S. Appl. No. 08/933,824 Office Action dated Apr. 14, 1998.
U.S. Appl. No. 08/933,824 Office Action dated Jan. 5, 1999.
U.S. Appl. No. 09/395,345 Office Action dated May 3, 2000.
U.S. Appl. No. 09/395,345 Office Action dated May 9, 2001.
U.S. Appl. No. 09/395,345 Office Action dated Nov. 21, 2000.
U.S. Appl. No. 09/419,406 Notice of Allowance dated Mar. 19, 2002.
U.S. Appl. No. 09/419,406 Office Action dated Apr. 24, 2000.
U.S. Appl. No. 09/419,406 Office Action dated Dec. 28, 2000.
U.S. Appl. No. 09/419,406 Office Action dated Jul. 17, 2001.
U.S. Appl. No. 09/419,408 Office Action dated May 30, 2002.
U.S. Appl. No. 09/419,408 Office Action dated Nov. 14, 2002.
U.S. Appl. No. 09/419,408 Office Action dated Feb. 1, 2000.
U.S. Appl. No. 10/075,425 Office Action dated Jun. 17, 2005.
U.S. Appl. No. 10/075,425 Office Action dated Oct. 1, 2004.
U.S. Appl. No. 10/356,736 Office Action dated Apr. 10, 2006.
U.S. Appl. No. 10/356,736 Office Action dated Apr. 26, 2007.
U.S. Appl. No. 10/356,736 Office Action dated Aug. 14, 2008.
U.S. Appl. No. 10/356,736 Office Action dated Jul. 7, 2005.
U.S. Appl. No. 10/356,736 Office Action dated Nov. 30, 2007.
U.S. Appl. No. 10/526,256 Office Action dated Aug. 25, 2009.
U.S. Appl. No. 10/526,256 Office Action dated Dec. 29, 2008.
U.S. Appl. No. 10/526,256 Office Action dated May 9, 2008.
U.S. Appl. No. 11/720,785 Office Action dated Dec. 23, 2010.
U.S. Appl. No. 11/720,785 Office Action dated Jul. 19, 2010.
U.S. Appl. No. 12/032,442 Restriction Requirement dated May 11, 2010.
U.S. Appl. No. 12/196,505 Final Office Action dated Dec. 7, 2012.
U.S. Appl. No. 12/196,505 Final Office Action dated Nov. 4, 2011.
U.S. Appl. No. 12/196,505 Final Office Action dated Nov. 9, 2010.
U.S. Appl. No. 12/196,505 Non-Final Office Action dated Apr. 12, 2010.
U.S. Appl. No. 12/196,505 Non-Final Office Action dated Jun. 14, 2013.
U.S. Appl. No. 12/196,505 Non-Final Office Action dated Mar. 25, 2011.
U.S. Appl. No. 12/196,505 Non-Final Office Action dated May 15, 2012.
U.S. Appl. No. 12/196,505 Restriction Requirement dated Apr. 23, 2009.

(56) References Cited

OTHER PUBLICATIONS

U.S. Appl. No. 12/527,376 Final Office Action dated May 25, 2012.
U.S. Appl. No. 12/527,376 Office Action dated Oct. 19, 2011.
U.S. Appl. No. 12/527,376 Restriction Requirement dated Sep. 1, 2011.
U.S. Appl. No. 12/528,055 Office Action dated Jul. 21, 2014.
U.S. Appl. No. 12/528,055 Office Action dated Apr. 30, 2015.
U.S. Appl. No. 12/528,055 Office Action dated Jun. 27, 2011.
U.S. Appl. No. 12/528,055 Office Action dated Mar. 1, 2016.
U.S. Appl. No. 12/528,055 Office Action dated Mar. 27, 2012.
U.S. Appl. No. 12/528,055 Restriction Requirement dated Apr. 6, 2011.
U.S. Appl. No. 12/528,668 Final Office Action dated Mar. 21, 2012.
U.S. Appl. No. 12/528,668 Non-Final Office Action dated Sep. 25, 2013.
U.S. Appl. No. 12/528,668 Office Action dated Sep. 2, 2011.
U.S. Appl. No. 12/528,668 Restriction Requirement dated May 18, 2011.
U.S. Appl. No. 12/529,106 Office Action dated Oct. 14, 2011.
U.S. Appl. No. 12/530,390 Office Action dated Mar. 25, 2011.
U.S. Appl. No. 12/599,549 Office Action dated Apr. 26, 2011.
U.S. Appl. No. 12/675,718 Office Action dated Feb. 6, 2013.
U.S. Appl. No. 12/675,718 Restriction Requirement dated Aug. 7, 2012.
U.S. Appl. No. 13/130,998 Office Action dated Apr. 2, 2018.
U.S. Appl. No. 13/130,998 Office Action dated Apr. 29, 2015.
U.S. Appl. No. 13/130,998 Office Action dated Aug. 14, 2015.
U.S. Appl. No. 13/130,998 Office Action dated Feb. 21, 2017.
U.S. Appl. No. 13/130,998 Office Action dated Feb. 4, 2014.
U.S. Appl. No. 13/130,998 Office Action dated Jun. 13, 2016.
U.S. Appl. No. 13/130,998 Office Action dated Oct. 4, 2017.
U.S. Appl. No. 13/130,998 Office Action dated Sep. 16, 2013.
U.S. Appl. No. 13/140,874 Restriction Requirement dated Feb. 22, 2013.
U.S. Appl. No. 13/263,707 Office Action dated Apr. 6, 2015.
U.S. Appl. No. 13/263,707 Office Action dated Aug. 1, 2014.
U.S. Appl. No. 13/263,707 Office Action dated Dec. 22, 2015.
U.S. Appl. No. 13/263,707 Office Action dated Feb. 26, 2014.
U.S. Appl. No. 13/263,707 Office Action dated Jul. 6, 2017.
U.S. Appl. No. 13/263,707 Office Action dated Jun. 19, 2013.
U.S. Appl. No. 13/263,707 Office Action dated Jun. 27, 2016.
U.S. Appl. No. 13/263,707 Office Action dated Nov. 28, 2016.
U.S. Appl. No. 13/263,707 Office Action dated Sep. 17, 2018.
U.S. Appl. No. 13/372,359 Office Action dated Jan. 12, 2016.
U.S. Appl. No. 13/372,359 Office Action dated Jan. 23, 2015.
U.S. Appl. No. 13/372,359 Office Action dated Jul. 21, 2016.
U.S. Appl. No. 13/372,359 Office Action dated Jul. 27, 2015.
U.S. Appl. No. 13/372,359 Office Action dated Jun. 23, 2014.
U.S. Appl. No. 13/372,359 Office Action dated Jun. 8, 2017.
U.S. Appl. No. 13/372,359 Office Action dated Nov. 17, 2016.
U.S. Appl. No. 14/722,018 Office Action dated May 12, 2017.
U.S. Appl. No. 14/722,018 Office Action dated Nov. 14, 2017.
U.S. Appl. No. 14/779,893 Final Office Action dated Apr. 26, 2019.
U.S. Appl. No. 14/779,893 Office Action dated Jul. 5, 2017.
U.S. Appl. No. 14/779,893 Office Action dated Mar. 21, 2018.
U.S. Appl. No. 14/779,893 Office Action dated Sep. 12, 2019.
U.S. Appl. No. 14/779,893 Office Action dated Sep. 7, 2018.
U.S. Appl. No. 14/847,705 Office Action dated Sep. 8, 2017.
U.S. Appl. No. 14/890,699 Office Action dated Mar. 7, 2018.
U.S. Appl. No. 14/890,699 Office Action dated May 19, 2017.
U.S. Appl. No. 14/890,712 Office Action dated Dec. 6, 2017.
U.S. Appl. No. 14/900,024 Office Action dated Apr. 16, 2018.
U.S. Appl. No. 14/915,544 Office Action dated Mar. 22, 2018.
U.S. Appl. No. 15/245,875 Office Action dated Jan. 18, 2018.
U.S. Appl. No. 15/245,875 Office Action dated Jun. 12, 2018.
U.S. Appl. No. 15/557,213 Restriction Requirement dated May 21, 2019.
U.S. Appl. No. 15/792,266 Office Action dated Aug. 6, 2018.
U.S. Appl. No. 15/868,763 Final Office Action dated Oct. 1, 2019.
U.S. Appl. No. 15/868,763 Office Action dated Feb. 21, 2019.
U.S. Appl. No. 15/868,763 Restriction Requirement dated Dec. 6, 2018.
U.S. Appl. No. 15/921,160 Office Action dated Feb. 27, 2020.
U.S. Appl. No. 15/946,632 Office Action dated May 1, 2020.
U.S. Appl. No. 15/946,632 Restriction Requirement dated Nov. 22, 2019.
U.S. Appl. No. 16/025,769 Final Office Action dated Dec. 18, 2020.
U.S. Appl. No. 16/025,769 Office Action dated Jul. 6, 2020.
U.S. Appl. No. 16/025,769 Restriction Requirement dated Feb. 11, 2020.
U.S. Appl. No. 16/355,376 Restriction Requirement dated Jun. 5, 2020.
U.S. Appl. No. 16/388,101 Restriction Requirement dated Jul. 10, 2020.
U.S. Appl. No. 13/130,998_52388-707-831_Notice of Abandonment_Dec. 17, 2018.
Vaidya et al.: The cytotoxic T lymphocyte antigen-4 is a major Graves' disease locus. Human Molecular Genetics 8:1195-1199 (1999).
Vasiliauskas et al.: Marker antibody expression stratifies Crohn's disease into immunologically homogeneous subgroups with distinct clinical characteristics. Gut 47:487-496 (2000).
Vasiliauskas et al.: Perinuclear antineutrophil cytoplasmic antibodies in patients with Crohn's disease define a clinical subgroups. Gastroenterology 110:1810-1819 (1996).
Vavassori et al.: CARD15 mutation analysis in an Italian population: Leu1007fsinsC but neither Arg702Trp nor Gly908Arg mutations are associated with Crohn's disease. Inflamm Bowel Dis 10:116-121 (2004).
Verdu et al.: Modulatory effects of estrogen in two murine models of experimental colitis. American J Physiology 283:G27-G36 (2002).
Verhoeyen et al. Reshaping human antibodies: Grafting an antilysozyme activity. Science 239:1534-1536 (1988).
Vermeire et al.: Current Status of Genetics Research in Inflammatory Bowel Disease, Genes and Immunity, 2005, vol. 6, pp. 637-645.
Vermiere et al.: CARD15 genetic variation in a Quebec population: prevalence, genotype-phenotype relationship and haplotype structure. Am J Hum Genet 71:74-83 (2002).
Verthelyi et al. Sex hormone levels correlate with the activity of cytokine-secreting cells in vivo. Immunology 100:384-390 (2000).
Voraberger et al.: Cloning on the human gene for intercellular adhesion molecule-1 and analysis of its 5'regulatory region. J Immunol 147:2777-2786 (1991).
Walder et al. Oligodeoxynucleotide-directed mutagenesis using the yeast transformation system. Gene 42:133-139, 1986.
Wall et al.: Transgenic Dairy Cattle: Genetic Engineering on a Large Scale, J. Dairy Sci, 80: 2213-2224, 1997.
Wang et al.: Diverse Genome-Wide Association Studies Associate the IL12/IL23 pathway with Crohn Disease, Am J. Hum. Genet., 2009, vol. 84(3), pp. 399-405.
Ward et al. Binding activities of a repertoire of single immunoglobulin variable domains secreted from *Escherichia coli*. Nature 334:544-54, 1989.
Warzocha et al.: Tumor necrosis factor ligand receptor system can predict treatment outcome of lymphoma patients. Journal of Clinical Oncology 15:499-508 (1997).
Webb et al.: Genetic variability at the human tumor necrosis factor loci. J. Immunol 145:1278-1285 (1993).
Weber et al. Abundant class of human DNA polymorphisms which can be typed using the polymerase chain reaction. Am J Hum Genet 44:388-396 (1989).
Wen et al.: TL1A-induced NF-kB activation and c-IAP2 production prevent DR3-mediated C456 apoptosis in TF-1 cells. J Biol Chem 278:39251-39258 (2003).
Whisnant et al.: Rheumatoid Arthritis: Treatment with Azathioprine (Imuran (R)), Clinical Side-Effects and Laboratory Abnormalities, Ann Rheum Dis., 1982, vol. 41, pp. 44-47.
Williams et al.: Optimization strategies for the polymerase chain reaction. Biotechniques 7:762-768 (1989).
Wouters et al.: Inter- and intra-individual variation of endotoxin- and beta (1-3)-glucan-induced cytokine responses in a whole blood assay. Toxicology and Industrial Health 18:15-27 (2002).

(56) References Cited

OTHER PUBLICATIONS

Written Opinion for PCT/US2011/028694 dated Jul. 27, 2011.
Wu et al.: Genome-wide gene expression differences in Crohn's disease and ulcerative colitis from endoscopic pinch biopsies: Insights into distinctive pathogenesis. Inflammatory Bowel Disease, 13:807-821, 2007.
Wu et al. Tamoxifen alleviates disease severity and decreases double negative T cells in autoimmune MRL-lpr/lpr mice. Immunology 100:110-118 (2000).
Wu et al.: Tamoxifen decreases renal inflammation and alleviates disease severity in autoimmune NZBIW F1 mice. Scandinavian Journal of Immunology 52:393-400 (2000).
Xiao et al.: Interaction of Cocksackievirus A21 with its cellular receptor ICAM-1. J Viral 75:2444-2451 (2001).
Yagi et al.: Interleukin-31 stimulates production of inflammatory mediators from human colonic subepithelial myofibroblasts. International Journal of Molecular Medicine, 19:941-946, 2007.
Yamamoto-Furusho et al.: Complotype SC30 is associated with susceptibility to develop severe C462 ulcerative colitis in Mexicans. J Clin Gasterol 27:178-180 (1998).
Yamazaki et al.: Absence of mutation in the NOD2/CARD15 gene among 483 Japanese patients with Crohn's disease. Hum Mol Genet 47:469-472 (2002).
Yamazaki et al.: Association analysis of genetic variants in IL23R, ATG16L 1 and 5p13.1 loci with Crohn's disease in Japanese patients. J Hum Genet 52:575-582 (2007).
Yamazaki et al.: Single nucleotide polymorphisms in TNFSF15 confers susceptibility to Crohn's disease. Hum Mol Genet 14:3499-3506 (2005).
Yang et al.: Association of intercellular adhesion molecule-1 (ICAM-1) gene with subsets of Inflammatory Bowel Disease (IBO) stratified by anti-neutrophil cytoplasmic antibodies I (AN CAs). Clinical Research Abstract only 42(1):76A (1994).
Yang et al.: Familial empirical risks for inflammatory bowel disease: differences between Jews and non-Jews. Gut 34:517-524 (1993).
Yang et al. Genetic aspects of idiopathic inflammatory bowel disease. Kirschner and Shorter (Eds.), Inflammatory Bowel Disease Baltimore: Williams and Wilkins pp. 301-331 (1995).
Yang et al.: Genetic Heterogeneity within UC and Crohn's defined by anti-neutrophil cytoplasmic antibodies (AN CAs) and intercellular adhesion molecule-1 (ICAM-1) polymorph isms. Gastroenterology 106(4):A794 AGA Abstract (1994).
Yang et al.: Intercellular adhesion molecule 1 gene association with immunologic subsets of inflammatory bowel disease. Gastroenterology 109:440-448 (1995).
Yang et al.: Linkage of Crohn's disease to the major histocompatibility complex region is detected by multiple non-parametric analyses. Gut. 44 pp. 519-526 (1999).
Yang et al. The R241 allele of ICAM-1 is associated with a distinct clinical subgroup of Crohn's disease (CD) characterized by perinuclear ANCA (pANCA) production. Abstract only. American Gastroenterological Association and American Association for the study of Liver disease. May 19-22, 1996.
Yang et al.: Ulcerative colitis: a genetically heterogenous disorder defined by genetic (HLA class II) and subclinical (antineutrophil cytoplasmic antibodies) markers J. Clin. Invest., 92:1080-1084 (1993).
Yang, Suk-Kyun et al.: Association of TNFSF15 with Crohn's Disease in Koreans, American Journal of Gastroenterology 2008;103:1437-1442.
Yeager et al.: Genome-wide association study of prostate cancer identifies a second risk locus at 8q24. Nature Genetics, 39(5):645-649, 2007.
Yoon et al. Colonic Phenotypes Are Associated with Poorer Response to Anti-TNF Therapies in Patients with IBD. Inflammatory Bowel Diseases. 23(8):1382-1393 (2017).
Yoon et al.: Decreased potency of the Vibrio cholerae sheathed flagellum to trigger host innate immunity. Infection and Immunity 76:1282-1288 (2008).
Younes et al.: Clinical implication of the tumor necrosis factor family in benign and malignant hematologic disorders. Cancer 98:458-467 (2003).
Younes et al.: Emerging applications of the tumor necrosis factor family if ligands and receptors in cancer therapy. J Clin Oncol 21:3526-3534, (2003).
Zaahl et al.: Analysis of the three common mutations in the CARD15 gene (R702W, G908R and 1007fs) in South African colored patients with inflammatory bowel disease. Molecular and Cellular Probes 19:278-281 (2005).
Zhang et al.: Critical role of IL-17 receptor signaling in acute TNBS-induced colitis. Inflamm Bowel Dis 12:382-388 (2006).
Zhang et al. Estrogen affects the differentiation and function of splenic monocyte-derived dendritic cells from normal rats. Abstract Only. 20:129-134 (2004).
Zhang et al.: Structures and biological functions of IL-31 and IL-31 receptors. Cytokine Growth Factor. 19(5-6):347-356 (2008).
Zheng et al.: 2013 AGA Abstracts 2013 144 5 Supplement 1: p. S-132; Abstract 735 (2013).
Zheng et al.: Dynamic expression and significance of IL-31 in the process of pulmonary fibrosis in experimental mice. Shadong Medical Journal. 49(13):26-27 (2009).
Zheng et al.: Sustained TL1A (TNFSF15) Expression on both Lymphoid and Myeloid Cells Leads to Mild Spontaneous Intestinal Inflammation and Fibrosis. European Journal of Microbiology and Immunology 3(1):11-20 (2013).
Ziegler et al.: Detectable serum flagellin and liposaccharide and upregulated anti-flagellin and liposaccharide immunoglobulins in human short bowel syndrome. Am J Physiol Regul IntegrComp Physiol. 294:R402-R410 (2008).
Zill et al.: SNP and Haplotype Analysis of a Novel Tryptophan Hydroxylase Isoform (TPH2) Gene Provide Evidence for Association with Major Depression, Molecular Psychiatry, 2004, vol. 9, pp. 1030-1036.

* cited by examiner

| snp | CHR | BP | A1 | F_A | F_U | A2 | fisher_p | OR | l_p | loci |
|---|---|---|---|---|---|---|---|---|---|---|
| rs4855535 | 3 | 69017124 | G | 0.5714 | 0.05556 | T | 6.987E-06 | 22.67 | 5.1557093 | FAM19A4 |
| rs17048128 | 3 | 69028502 | A | 0.5714 | 0.05556 | G | 6.987E-06 | 22.67 | 5.1557093 | FAM19A4 |
| rs17048129 | 3 | 69031452 | A | 0.5714 | 0.05556 | G | 6.987E-06 | 22.67 | 5.1557093 | FAM19A4 |
| rs17039556 | 4 | 161545059 | A | 0.7143 | 0.1296 | G | 8.744E-06 | 16.79 | 5.0582899 | |
| rs2983478 | 14 | 94433843 | C | 1 | 0.4167 | T | 1.555E-05 | | 4.8082696 | |
| rs12640159 | 4 | 161586073 | A | 0.7857 | 0.1944 | G | 1.882E-05 | 15.19 | 4.7253804 | |
| rs13079040 | 3 | 68988334 | C | 0.7143 | 0.1574 | T | 3.361E-05 | 13.38 | 4.4735315 | FAM19A4 |
| rs880330 | 7 | 67842575 | T | 0.7857 | 0.213 | C | 3.927E-05 | 13.55 | 4.4059391 | |
| rs4776127 | 15 | 51373815 | G | 0.7857 | 0.213 | A | 3.927E-05 | 13.55 | 4.4059391 | |
| rs2057917 | 7 | 67867804 | C | 0.8571 | 0.2778 | T | 4.331E-05 | 15.6 | 4.3634118 | |
| rs4936810 | 11 | 122843102 | G | 0.8571 | 0.2778 | T | 4.331E-05 | 15.6 | 4.3634118 | |
| rs13077937 | 3 | 88620181 | G | 0.6429 | 0.1204 | A | 0.0000469 | 13.15 | 4.3288272 | |
| rs4960945 | 8 | 88868301 | G | 0.6429 | 0.1204 | T | 0.0000469 | 13.15 | 4.3288272 | |
| rs4859033 | 3 | 88601013 | G | 0.7143 | 0.1667 | A | 5.032E-05 | 12.5 | 4.2982594 | |
| rs969774 | 14 | 19631920 | T | 0.7143 | 0.1667 | C | 5.032E-05 | 12.5 | 4.2982594 | |
| rs11071331 | 15 | 55621184 | T | 0.7143 | 0.1667 | C | 5.032E-05 | 12.5 | 4.2982594 | CGNL1 |
| rs3764584 | 19 | 2471716 | T | 0 | 0.5648 | C | 5.265E-05 | 0 | 4.2786016 | GNG7 |
| rs13103431 | 4 | 161589079 | T | 0.7857 | 0.2222 | G | 5.552E-05 | 12.83 | 4.2555505 | |
| rs919329 | 5 | 28009510 | G | 0.5 | 0.05556 | T | 6.294E-05 | 17 | 4.2010733 | |
| rs12856567 | 23 | 39572159 | G | 0.6667 | 0.1098 | A | 7.274E-05 | 16.22 | 4.1382267 | |
| rs11768422 | 7 | 67807659 | T | 0.7857 | 0.2315 | C | 7.749E-05 | 12.17 | 4.1107543 | |
| rs2723829 | 12 | 11819364 | A | 0.8571 | 0.2963 | G | 7.893E-05 | 14.25 | 4.1027579 | ETV6 |
| rs10785007 | 12 | 71799725 | C | 0 | 0.5192 | T | 9.794E-05 | 0 | 4.0090399 | |
| rs10107666 | 8 | 14741501 | T | 0.8571 | 0.3056 | C | 0.0001052 | 13.64 | 3.9779843 | SGCZ |
| rs10104703 | 8 | 14741552 | A | 0.8571 | 0.3056 | C | 0.0001052 | 13.64 | 3.9779843 | SGCZ |
| rs13092167 | 3 | 59747382 | G | 0.7857 | 0.2407 | A | 0.0001068 | 11.56 | 3.9714287 | FHIT |
| rs11700340 | 20 | 59707924 | C | 0.7857 | 0.2407 | A | 0.0001068 | 11.56 | 3.9714287 | CDH4 |
| rs464557 | 16 | 82385954 | G | 0.6429 | 0.1389 | A | 0.0001126 | 11.16 | 3.9484616 | CDH13 |
| rs254343 | 16 | 82393257 | C | 0.6429 | 0.1389 | T | 0.0001126 | 11.16 | 3.9484616 | |
| rs7960773 | 12 | 125627131 | G | 0.2857 | 0 | T | 0.000114 | | 3.9430951 | |
| rs11058720 | 12 | 125629813 | A | 0.2857 | 0 | G | 0.000114 | | 3.9430951 | |
| rs17699529 | 8 | 94345308 | C | 0.5 | 0.06481 | T | 0.0001189 | 14.43 | 3.9248181 | |
| rs5752585 | 22 | 26266871 | A | 0.5 | 0.06481 | C | 0.0001189 | 14.43 | 3.9248181 | |
| rs9866579 | 3 | 118096151 | A | 0.4286 | 0.03704 | G | 0.000122 | 19.5 | 3.9136402 | |
| rs6777752 | 3 | 118106511 | G | 0.4286 | 0.03704 | A | 0.000122 | 19.5 | 3.9136402 | |
| rs11061121 | 12 | 129791564 | T | 0.4286 | 0.03704 | C | 0.000122 | 19.5 | 3.9136402 | LOC729014 |
| rs2318480 | 14 | 19661054 | A | 0.4286 | 0.03704 | G | 0.000122 | 19.5 | 3.9136402 | |
| rs12635949 | 3 | 69029799 | C | 0.5714 | 0.1019 | T | 0.0001363 | 11.76 | 3.8655041 | FAM19A4 |
| rs4557199 | 3 | 77151956 | C | 0.5714 | 0.1019 | T | 0.0001363 | 11.76 | 3.8655041 | |
| rs4947404 | 7 | 52263829 | A | 0.5714 | 0.1019 | G | 0.0001363 | 11.76 | 3.8655041 | |
| rs6466213 | 7 | 77892967 | A | 0.5714 | 0.1019 | C | 0.0001363 | 11.76 | 3.8655041 | MAGI2 |
| rs984071 | 9 | 112178851 | T | 0.8571 | 0.3148 | C | 0.000139 | 13.06 | 3.8569852 | SVEP1 |
| rs6425838 | 1 | 34027003 | T | 0.7857 | 0.25 | C | 0.0001457 | 11 | 3.8365404 | CSMD2 |
| rs603688 | 8 | 2872872 | T | 0.7143 | 0.1944 | C | 0.0001513 | 10.36 | 3.8201611 | CSMD1 |
| rs10014285 | 4 | 161527422 | A | 0.6429 | 0.1481 | G | 0.000168 | 10.35 | 3.7746907 | |
| rs12896479 | 14 | 75768562 | T | 0.6429 | 0.1481 | G | 0.000168 | 10.35 | 3.7746907 | |
| rs11734574 | 4 | 131343294 | C | 0.8571 | 0.3208 | T | 0.0001686 | 12.71 | 3.7731424 | |
| rs12407980 | 1 | 48993224 | G | 0.8571 | 0.3241 | A | 0.0001823 | 12.51 | 3.7392133 | AGBL4, C1orf165 |

FIG. 1A

| | | | | | | | | | |
|---|---|---|---|---|---|---|---|---|---|
| rs1323690 | 11 | 34457263 | T | 0.8571 | 0.3241 | C | 0.0001823 | 12.51 | 3.7392133 | ELF5 |
| rs10144441 | 14 | 58388714 | G | 0.8571 | 0.3241 | A | 0.0001823 | 12.51 | 3.7392133 | |
| rs13168690 | 5 | 7202777 | T | 0.6429 | 0.1509 | C | 0.0001933 | 10.13 | 3.7137681 | |
| rs2200520 | 15 | 51372185 | T | 0.7857 | 0.2593 | C | 0.0001965 | 10.48 | 3.7066374 | |
| rs12439607 | 15 | 51381505 | G | 0.7857 | 0.2593 | T | 0.0001965 | 10.48 | 3.7066374 | |
| rs681478 | 22 | 24226979 | T | 0.8333 | 0.2685 | C | 0.0002086 | 13.62 | 3.6806857 | |
| rs7003556 | 8 | 5213929 | T | 0.5 | 0.07407 | C | 0.0002105 | 12.5 | 3.6767479 | |
| rs4974227 | 3 | 60723766 | G | 0.7143 | 0.2037 | A | 0.0002116 | 9.773 | 3.6744843 | FHIT |
| rs1023793 | 3 | 59302501 | G | 0.5714 | 0.1111 | A | 0.0002157 | 10.67 | 3.6661499 | |
| rs820082 | 6 | 35139419 | A | 0.5714 | 0.1111 | G | 0.0002157 | 10.67 | 3.6661499 | ANKS1A |
| rs1917716 | 7 | 45430747 | A | 0.5714 | 0.1111 | C | 0.0002157 | 10.67 | 3.6661499 | |
| rs704014 | 10 | 80502780 | A | 0.5714 | 0.1111 | G | 0.0002157 | 10.67 | 3.6661499 | |
| rs3758947 | 11 | 17457786 | T | 0.5714 | 0.1111 | C | 0.0002157 | 10.67 | 3.6661499 | |
| rs12797160 | 11 | 134108466 | A | 0.3571 | 0.01961 | G | 0.0002278 | 27.78 | 3.6424463 | LOC729893 |
| rs10159239 | 1 | 245673675 | A | 1 | 0.4907 | G | 0.0002332 | | 3.6322715 | NLRP3 |
| rs10152918 | 15 | 88152578 | A | 0 | 0.5 | G | 0.000236 | 0 | 3.627088 | |
| rs7559777 | 2 | 121312086 | T | 0.8571 | 0.3333 | G | 0.0002373 | 12 | 3.6247023 | GLI2 |
| rs1489636 | 2 | 163734443 | C | 0.9286 | 0.3981 | T | 0.0002432 | 19.65 | 3.6140364 | |
| rs1821942 | 3 | 61091049 | G | 0.6429 | 0.1574 | A | 0.0002453 | 9.635 | 3.6103025 | FHIT |
| rs1194707 | 10 | 53870134 | A | 0.6429 | 0.1574 | G | 0.0002453 | 9.635 | 3.6103025 | |
| rs1561662 | 10 | 53910718 | A | 0.6429 | 0.1574 | G | 0.0002453 | 9.635 | 3.6103025 | |
| rs11677188 | 2 | 98112642 | T | 0 | 0.4907 | C | 0.0002515 | 0 | 3.599462 | VWA3B |
| rs13396689 | 2 | 98125279 | G | 0 | 0.4907 | A | 0.0002515 | 0 | 3.599462 | VWA3B |
| rs17819978 | 18 | 70569789 | C | 0.4286 | 0.0463 | T | 0.0002521 | 15.45 | 3.5984272 | ZNF407 |
| rs4408289 | 11 | 6667523 | A | 0.7857 | 0.2685 | G | 0.0002623 | 9.989 | 3.5812017 | |
| rs1207592 | 22 | 24227330 | A | 0.7857 | 0.2685 | C | 0.0002623 | 9.989 | 3.5812017 | |
| rs1387588 | 2 | 163723934 | C | 0.07143 | 0.5926 | T | 0.0002664 | 0.05288 | 3.5744658 | |
| rs1979771 | 18 | 14557390 | G | 0.07143 | 0.5926 | T | 0.0002664 | 0.05288 | 3.5744658 | |
| rs11100264 | 4 | 140902337 | C | 0 | 0.4815 | T | 0.00028 | 0 | 3.552842 | MAML3 |
| rs1586030 | 8 | 3496385 | C | 0 | 0.4815 | T | 0.00028 | 0 | 3.552842 | CSMD1 |
| rs3745101 | 19 | 57777625 | C | 0 | 0.4815 | T | 0.00028 | 0 | 3.552842 | ZNF701 |
| rs17507263 | 20 | 9933041 | G | 0 | 0.4815 | A | 0.00028 | 0 | 3.552842 | |
| rs1340704 | 13 | 75404658 | G | 0.07143 | 0.5849 | A | 0.0002978 | 0.05459 | 3.5260753 | |
| rs2189439 | 7 | 29413667 | A | 0.9286 | 0.4167 | G | 0.000304 | 18.2 | 3.5171264 | CHN2 |
| rs2189440 | 7 | 29413794 | T | 0.9286 | 0.4167 | C | 0.000304 | 18.2 | 3.5171264 | CHN2 |
| rs4287512 | 15 | 62997194 | T | 0.07143 | 0.5833 | C | 0.000304 | 0.05495 | 3.5171264 | |
| rs6756742 | 2 | 98066320 | T | 0.8571 | 0.3426 | C | 0.0003068 | 11.51 | 3.5131446 | |
| rs6543280 | 2 | 98067475 | C | 0.8571 | 0.3426 | T | 0.0003068 | 11.51 | 3.5131446 | |
| rs2062365 | 2 | 151544236 | T | 0.8571 | 0.3426 | C | 0.0003068 | 11.51 | 3.5131446 | |
| rs1905744 | 2 | 151544451 | T | 0.8571 | 0.3426 | G | 0.0003068 | 11.51 | 3.5131446 | |
| rs6100556 | 20 | 57701043 | T | 0.8571 | 0.3426 | G | 0.0003068 | 11.51 | 3.5131446 | PHACTR3 |
| rs272456 | 5 | 6537012 | A | 0 | 0.4722 | G | 0.0003226 | 0 | 3.4913356 | FLJ25076 |
| rs6868112 | 5 | 40851764 | C | 0 | 0.4722 | A | 0.0003226 | 0 | 3.4913356 | |
| rs7725810 | 5 | 40863064 | C | 0 | 0.4722 | T | 0.0003226 | 0 | 3.4913356 | |
| rs2349682 | 2 | 5405625 | C | 0.5714 | 0.1204 | T | 0.0003306 | 9.744 | 3.4806972 | |
| rs4974241 | 3 | 60750500 | T | 0.5714 | 0.1204 | C | 0.0003306 | 9.744 | 3.4806972 | FHIT |
| rs923512 | 3 | 68995221 | G | 0.5714 | 0.1204 | A | 0.0003306 | 9.744 | 3.4806972 | FAM19A4 |
| rs1761628 | 6 | 118781084 | T | 0.5714 | 0.1204 | G | 0.0003306 | 9.744 | 3.4806972 | |
| rs1761630 | 6 | 118782630 | C | 0.5714 | 0.1204 | T | 0.0003306 | 9.744 | 3.4806972 | |

FIG. 1B

| | | | | | | | | | |
|---|---|---|---|---|---|---|---|---|---|
| rs12910328 | 15 | 29159268 | T | 0.5714 | 0.1204 | C | 0.0003306 | 9.744 | 3.4806972 | TRPM1 |
| rs1898618 | 4 | 118199183 | C | 0 | 0.4706 | T | 0.000338 | 0 | 3.4710833 | |
| rs1811264 | 12 | 97027466 | C | 0.7857 | 0.2778 | T | 0.0003469 | 9.533 | 3.4597957 | |
| rs2200522 | 15 | 51362944 | C | 0.7857 | 0.2778 | A | 0.0003469 | 9.533 | 3.4597957 | |
| rs7214248 | 17 | 25598303 | A | 0.7857 | 0.2778 | G | 0.0003469 | 9.533 | 3.4597957 | BLMH |
| rs1050565 | 17 | 25600202 | G | 0.7857 | 0.2778 | A | 0.0003469 | 9.533 | 3.4597957 | BLMH |
| rs9811499 | 3 | 59300424 | T | 0.6429 | 0.1667 | C | 0.0003512 | 9 | 3.4544455 | |
| rs11782013 | 8 | 88720153 | G | 0.6429 | 0.1667 | A | 0.0003512 | 9 | 3.4544455 | |
| rs6993181 | 8 | 88755036 | G | 0.6429 | 0.1667 | A | 0.0003512 | 9 | 3.4544455 | |
| rs7828921 | 8 | 88816298 | G | 0.6429 | 0.1667 | A | 0.0003512 | 9 | 3.4544455 | |
| rs1194649 | 10 | 53839390 | T | 0.6429 | 0.1667 | C | 0.0003512 | 9 | 3.4544455 | |
| rs1045653 | 2 | 225338679 | A | 0.5 | 0.08333 | G | 0.0003531 | 11 | 3.4521023 | DOCK10 |
| rs11712727 | 3 | 64685061 | A | 0.5 | 0.08333 | C | 0.0003531 | 11 | 3.4521023 | LOC730057 |
| rs10504973 | 8 | 98481327 | A | 0.5 | 0.08333 | G | 0.0003531 | 11 | 3.4521023 | |
| rs13129968 | 4 | 186742187 | A | 0.07143 | 0.5741 | G | 0.0003575 | 0.05707 | 3.446724 | SORBS2 |
| rs1157669 | 11 | 34374446 | A | 0.9286 | 0.4259 | G | 0.0003575 | 17.52 | 3.446724 | |
| rs2191351 | 17 | 25783161 | T | 0.9286 | 0.4259 | C | 0.0003575 | 17.52 | 3.446724 | CPD |
| rs1720545 | 3 | 64927793 | G | 0 | 0.463 | T | 0.0003804 | 0 | 3.4197595 | |
| rs10496839 | 2 | 140766339 | T | 0.5 | 0.08491 | C | 0.0003938 | 10.78 | 3.4047243 | LRP1B |
| rs2369476 | 1 | 158388112 | A | 0.7143 | 0.2222 | C | 0.0003968 | 8.75 | 3.4014283 | ATP1A4 |
| rs12649063 | 4 | 186707415 | T | 0.07143 | 0.5648 | C | 0.0004289 | 0.05927 | 3.367644 | |
| rs216476 | 17 | 25890772 | T | 0.9286 | 0.4352 | C | 0.0004289 | 16.87 | 3.367644 | |
| rs216484 | 17 | 25895301 | A | 0.9286 | 0.4352 | G | 0.0004289 | 16.87 | 3.367644 | |
| rs17667217 | 14 | 81894043 | A | 0.3571 | 0.02778 | G | 0.0004429 | 19.44 | 3.3536943 | |
| rs10520094 | 15 | 36690462 | A | 0.3571 | 0.02778 | G | 0.0004429 | 19.44 | 3.3536943 | |
| rs7272567 | 20 | 40219855 | T | 0.3571 | 0.02778 | C | 0.0004429 | 19.44 | 3.3536943 | PTPRT |
| rs2631731 | 4 | 8480717 | T | 0.7857 | 0.287 | C | 0.0004546 | 9.108 | 3.3423706 | ACOX3 |
| rs1949733 | 4 | 8554259 | A | 0.7857 | 0.287 | G | 0.0004546 | 9.108 | 3.3423706 | |
| rs4361657 | 7 | 67822769 | T | 0.7857 | 0.287 | C | 0.0004546 | 9.108 | 3.3423706 | |
| rs755804 | 19 | 60941257 | T | 0.7857 | 0.287 | C | 0.0004546 | 9.108 | 3.3423706 | NLRP9 |
| rs6027558 | 20 | 58381559 | A | 0.7857 | 0.287 | G | 0.0004546 | 9.108 | 3.3423706 | |
| rs6427504 | 1 | 158391499 | G | 0.7143 | 0.2264 | A | 0.0004628 | 8.542 | 3.3346066 | ATP1A4 |
| rs17079099 | 8 | 2866477 | T | 0.6429 | 0.1731 | C | 0.0004641 | 8.6 | 3.3333884 | CSMD1 |
| rs7616813 | 3 | 118140859 | T | 0.4286 | 0.05556 | C | 0.0004734 | 12.75 | 3.3247717 | |
| rs10519702 | 5 | 121866811 | G | 0.4286 | 0.05556 | A | 0.0004734 | 12.75 | 3.3247717 | |
| rs11067974 | 12 | 115218570 | C | 0.4286 | 0.05556 | T | 0.0004734 | 12.75 | 3.3247717 | |
| rs7623995 | 3 | 68905991 | G | 0.5714 | 0.1296 | A | 0.0004927 | 8.952 | 3.3074174 | FAM19A4 |
| rs9388278 | 6 | 124026860 | A | 0.5714 | 0.1296 | G | 0.0004927 | 8.952 | 3.3074174 | |
| rs13090878 | 3 | 59294515 | C | 0.6429 | 0.1759 | T | 0.0004937 | 8.432 | 3.3065369 | |
| rs9871910 | 3 | 69054550 | G | 0.6429 | 0.1759 | A | 0.0004937 | 8.432 | 3.3065369 | FAM19A4 |
| rs9814149 | 3 | 88621706 | T | 0.6429 | 0.1759 | G | 0.0004937 | 8.432 | 3.3065369 | |
| rs1336974 | 6 | 117179344 | A | 0.6429 | 0.1759 | C | 0.0004937 | 8.432 | 3.3065369 | C6orf189 |
| rs4762485 | 12 | 97302491 | T | 0.6429 | 0.1759 | C | 0.0004937 | 8.432 | 3.3065369 | |
| rs10131515 | 14 | 58384905 | C | 0.6429 | 0.1759 | A | 0.0004937 | 8.432 | 3.3065369 | |
| rs719988 | 23 | 85035022 | T | 0.75 | 0.2195 | C | 0.0005111 | 10.67 | 3.2914941 | CHM |
| rs869896 | 1 | 44220697 | T | 0.2857 | 0.009259 | C | 0.0005312 | 42.8 | 3.2747419 | B4GALT2 |
| rs9360459 | 6 | 72309728 | T | 0.2857 | 0.009259 | C | 0.0005312 | 42.8 | 3.2747419 | |
| rs6927647 | 6 | 72346372 | G | 0.2857 | 0.009259 | A | 0.0005312 | 42.8 | 3.2747419 | |
| rs4416886 | 9 | 73923515 | T | 0.2857 | 0.009259 | C | 0.0005312 | 42.8 | 3.2747419 | |

FIG. 1C

| SNP | Chr | Position | Allele1 | Freq1 | Freq2 | Allele2 | P-value | OR | Score | Gene |
|---|---|---|---|---|---|---|---|---|---|---|
| rs6040544 | 20 | 11261614 | G | 0.2857 | 0.009259 | A | 0.0005312 | 42.8 | 3.2747419 | |
| rs575633 | 1 | 84237624 | A | 0.7143 | 0.2315 | C | 0.0005334 | 8.3 | 3.272947 | TTLL7 |
| rs1693232 | 1 | 231802517 | A | 0.7143 | 0.2315 | G | 0.0005334 | 8.3 | 3.272947 | |
| rs7634255 | 3 | 161843390 | T | 0.7143 | 0.2315 | C | 0.0005334 | 8.3 | 3.272947 | |
| rs6766478 | 3 | 192769221 | A | 0.7143 | 0.2315 | G | 0.0005334 | 8.3 | 3.272947 | |
| rs11134466 | 5 | 166972188 | T | 0.7143 | 0.2315 | C | 0.0005334 | 8.3 | 3.272947 | ODZ2 |
| rs10485886 | 7 | 77895776 | T | 0.7143 | 0.2315 | C | 0.0005334 | 8.3 | 3.272947 | MAGI2 |
| rs2399685 | 11 | 92934982 | C | 0.7143 | 0.2315 | T | 0.0005334 | 8.3 | 3.272947 | |
| rs35693 | 12 | 99503643 | T | 0.7143 | 0.2315 | C | 0.0005334 | 8.3 | 3.272947 | GAS2L3 |
| rs405478 | 16 | 82389805 | A | 0.7143 | 0.2315 | C | 0.0005334 | 8.3 | 3.272947 | |
| rs6730278 | 2 | 44290721 | A | 0.5 | 0.09259 | G | 0.0005662 | 9.8 | 3.2470301 | PPM1B |
| rs933984 | 2 | 204707718 | T | 0.5 | 0.09259 | G | 0.0005662 | 9.8 | 3.2470301 | |
| rs9805984 | 14 | 51201493 | T | 0.5 | 0.09259 | G | 0.0005662 | 9.8 | 3.2470301 | FRMD6 |
| rs10141001 | 14 | 51201951 | A | 0.5 | 0.09259 | G | 0.0005662 | 9.8 | 3.2470301 | FRMD6 |
| rs682133 | 8 | 2871989 | T | 0.6429 | 0.1792 | C | 0.0005664 | 8.242 | 3.2468768 | CSMD1 |
| rs4851462 | 2 | 97723595 | C | 0.7857 | 0.2963 | T | 0.0005907 | 8.708 | 3.228633 | |
| rs940136 | 4 | 8499892 | G | 0.7857 | 0.2963 | A | 0.0005907 | 8.708 | 3.228633 | |
| rs10942722 | 5 | 74219900 | G | 0.7857 | 0.2963 | T | 0.0005907 | 8.708 | 3.228633 | |
| rs10788478 | 10 | 87797370 | A | 0.7857 | 0.2963 | G | 0.0005907 | 8.708 | 3.228633 | GRID1 |
| rs1006920 | 17 | 52604886 | A | 0.7857 | 0.2963 | G | 0.0005907 | 8.708 | 3.228633 | |
| rs11672145 | 19 | 12361149 | G | 0.7857 | 0.2963 | T | 0.0005907 | 8.708 | 3.228633 | ZNF799 |
| rs967023 | 8 | 88721133 | A | 0.6667 | 0.1731 | G | 0.0006369 | 9.556 | 3.1959288 | |
| rs323928 | 7 | 34700776 | T | 0 | 0.4565 | C | 0.0006795 | 0 | 3.1678105 | AAA1, NPSR1 |
| rs1898866 | 4 | 161529827 | C | 0.6429 | 0.1852 | T | 0.0006826 | 7.92 | 3.1658337 | |
| rs7677076 | 4 | 161530598 | A | 0.6429 | 0.1852 | G | 0.0006826 | 7.92 | 3.1658337 | |
| rs12526079 | 6 | 99671936 | A | 0.6429 | 0.1852 | G | 0.0006826 | 7.92 | 3.1658337 | |
| rs11261084 | 1 | 19032244 | A | 0.7143 | 0.2407 | G | 0.0007087 | 7.885 | 3.1495376 | |
| rs11265329 | 1 | 158362070 | T | 0.7143 | 0.2407 | C | 0.0007087 | 7.885 | 3.1495376 | ATP1A2 |
| rs6744417 | 2 | 98131355 | C | 0.7143 | 0.2407 | T | 0.0007087 | 7.885 | 3.1495376 | VWA3B |
| rs7603077 | 2 | 151593802 | G | 0.7143 | 0.2407 | A | 0.0007087 | 7.885 | 3.1495376 | |
| rs11204005 | 8 | 12895576 | G | 0.7143 | 0.2407 | A | 0.0007087 | 7.885 | 3.1495376 | |
| rs10888160 | 8 | 12896188 | T | 0.7143 | 0.2407 | C | 0.0007087 | 7.885 | 3.1495376 | |
| rs3098360 | 10 | 58495356 | C | 0.7143 | 0.2407 | T | 0.0007087 | 7.885 | 3.1495376 | |
| rs1504568 | 12 | 97017215 | A | 0.7143 | 0.2407 | C | 0.0007087 | 7.885 | 3.1495376 | |
| rs3751335 | 13 | 28753822 | T | 0.7143 | 0.2407 | C | 0.0007087 | 7.885 | 3.1495376 | KIAA0774 |
| rs2069334 | 14 | 58368941 | A | 0.7143 | 0.2407 | G | 0.0007087 | 7.885 | 3.1495376 | |
| rs10130841 | 14 | 58390147 | G | 0.7143 | 0.2407 | A | 0.0007087 | 7.885 | 3.1495376 | |
| rs4668565 | 2 | 5404548 | C | 0.5714 | 0.1389 | T | 0.0007161 | 8.267 | 3.1450263 | |
| rs4735211 | 8 | 94367360 | T | 0.5714 | 0.1389 | C | 0.0007161 | 8.267 | 3.1450263 | |
| rs3758280 | 9 | 33439952 | T | 0.5714 | 0.1389 | C | 0.0007161 | 8.267 | 3.1450263 | |
| rs11217593 | 11 | 119327504 | A | 0.5714 | 0.1389 | G | 0.0007161 | 8.267 | 3.1450263 | |
| rs6630695 | 23 | 14539311 | G | 0.75 | 0.2317 | A | 0.0007238 | 9.947 | 3.1403814 | GLRA2 |
| rs12130711 | 1 | 245674265 | T | 0 | 0.4537 | C | 0.0007391 | 0 | 3.1312968 | NLRP3 |
| rs11191839 | 10 | 105624885 | A | 0 | 0.4537 | G | 0.0007391 | 0 | 3.1312968 | |
| rs12889741 | 14 | 69955785 | A | 0 | 0.4537 | C | 0.0007391 | 0 | 3.1312968 | |
| rs8088963 | 18 | 57198294 | G | 0 | 0.4537 | A | 0.0007391 | 0 | 3.1312968 | |
| rs7005262 | 8 | 14903851 | A | 0.8571 | 0.3519 | G | 0.0007433 | 11.05 | 3.1288359 | SGCZ |
| rs13251017 | 8 | 14912887 | AC | 0.8571 | 0.3519 | T | 0.0007433 | 11.05 | 3.1288359 | SGCZ |

FIG. 1D

| | | | | | | | | | |
|---|---|---|---|---|---|---|---|---|---|
| rs13251961 | 8 | 14913179 | C | 0.8571 | 0.3519 | T | 0.0007433 | 11.05 | 3.1288359 | SGCZ |
| rs12550462 | 8 | 14913506 | C | 0.8571 | 0.3519 | T | 0.0007433 | 11.05 | 3.1288359 | SGCZ |
| rs2840649 | 23 | 121345910 | G | 0.3333 | 0.0122 | A | 0.0007539 | 40.5 | 3.1226863 | |
| rs7053253 | 23 | 39774364 | T | 0.6667 | 0.1707 | C | 0.0007546 | 9.714 | 3.1222832 | |
| rs6549392 | 3 | 71621386 | T | 0.7857 | 0.3056 | G | 0.0007612 | 8.333 | 3.1185012 | FOXP1 |
| rs4696828 | 4 | 8506504 | A | 0.7857 | 0.3056 | G | 0.0007612 | 8.333 | 3.1185012 | C4orf23 |
| rs4762486 | 12 | 97302567 | T | 0.7857 | 0.3056 | C | 0.0007612 | 8.333 | 3.1185012 | |
| rs6761283 | 2 | 209990576 | C | 0.8571 | 0.3585 | T | 0.0007652 | 10.74 | 3.116225 | |
| rs2469389 | 8 | 3500873 | T | 0 | 0.4444 | C | 0.0007706 | 0 | 3.113171 | CSMD1 |
| rs1683163 | 12 | 25124885 | C | 0 | 0.4444 | T | 0.0007706 | 0 | 3.113171 | LRMP |
| rs3859301 | 18 | 13440234 | C | 0 | 0.4444 | T | 0.0007706 | 0 | 3.113171 | C18orf1 |
| rs1965402 | 1 | 15190986 | G | 0.8571 | 0.3611 | A | 0.0007839 | 10.62 | 3.1057393 | KIAA1026 |
| rs1446596 | 2 | 209993773 | G | 0.8571 | 0.3611 | A | 0.0007839 | 10.62 | 3.1057393 | |
| rs10005281 | 4 | 161583013 | A | 0.8571 | 0.3611 | G | 0.0007839 | 10.62 | 3.1057393 | |
| rs10794008 | 10 | 127227908 | G | 0.8571 | 0.3611 | A | 0.0007839 | 10.62 | 3.1057393 | |
| rs2311789 | 23 | 115546167 | G | 0.3333 | 0.0125 | A | 0.0008214 | 39.5 | 3.0854453 | |
| rs12677379 | 8 | 12894120 | G | 0.7143 | 0.2453 | A | 0.000825 | 7.692 | 3.0835461 | |
| rs16866089 | 2 | 225213336 | C | 0.4286 | 0.06481 | T | 0.0008253 | 10.82 | 3.0833882 | |
| rs7710100 | 5 | 134796228 | G | 0.4286 | 0.06481 | A | 0.0008253 | 10.82 | 3.0833882 | |
| rs17078724 | 13 | 22894197 | C | 0.4286 | 0.06481 | A | 0.0008253 | 10.82 | 3.0833882 | |
| rs279955 | 8 | 94092322 | A | 0.7857 | 0.3077 | G | 0.0008314 | 8.25 | 3.08019 | |
| rs1584783 | 4 | 140879842 | T | 0 | 0.4352 | C | 0.0008379 | 0 | 3.0768078 | MAML3 |
| rs7678266 | 4 | 140887824 | T | 0 | 0.4352 | C | 0.0008379 | 0 | 3.0768078 | MAML3 |
| rs4242300 | 6 | 156658003 | C | 0 | 0.4352 | T | 0.0008379 | 0 | 3.0768078 | |
| rs1034716 | 7 | 29400969 | G | 0 | 0.4352 | A | 0.0008379 | 0 | 3.0768078 | CHN2 |
| rs10846765 | 12 | 123940680 | A | 0 | 0.4352 | G | 0.0008379 | 0 | 3.0768078 | |
| rs8022575 | 14 | 34217176 | A | 0 | 0.4352 | C | 0.0008379 | 0 | 3.0768078 | |
| rs2725627 | 15 | 51979784 | A | 0 | 0.4352 | G | 0.0008379 | 0 | 3.0768078 | |
| rs1862892 | 2 | 45385870 | T | 0.8571 | 0.3704 | C | 0.0008629 | 10.2 | 3.0640395 | LOC730059 |
| rs7042161 | 9 | 112237084 | T | 0.8571 | 0.3704 | C | 0.0008629 | 10.2 | 3.0640395 | SVEP1 |
| rs7043404 | 9 | 112241097 | G | 0.8571 | 0.3704 | T | 0.0008629 | 10.2 | 3.0640395 | SVEP1 |
| rs7314409 | 12 | 31803830 | G | 0.8571 | 0.3704 | A | 0.0008629 | 10.2 | 3.0640395 | |
| rs11146953 | 12 | 131665980 | T | 0.8571 | 0.3704 | C | 0.0008629 | 10.2 | 3.0640395 | KIAA1545 |
| rs994859 | 3 | 63155203 | T | 0.5 | 0.1019 | C | 0.0008737 | 8.818 | 3.0586377 | |
| rs6770731 | 3 | 63156168 | T | 0.5 | 0.1019 | C | 0.0008737 | 8.818 | 3.0586377 | |
| rs2367763 | 3 | 63188675 | A | 0.5 | 0.1019 | G | 0.0008737 | 8.818 | 3.0586377 | |
| rs3733665 | 5 | 149213748 | G | 0.5 | 0.1019 | A | 0.0008737 | 8.818 | 3.0586377 | |
| rs1743242 | 6 | 118771801 | A | 0.5 | 0.1019 | C | 0.0008737 | 8.818 | 3.0586377 | |
| rs6942609 | 7 | 100682200 | A | 0.5 | 0.1019 | G | 0.0008737 | 8.818 | 3.0586377 | |
| rs16910063 | 10 | 58474305 | A | 0.5 | 0.1019 | G | 0.0008737 | 8.818 | 3.0586377 | |
| rs10998921 | 10 | 71125879 | C | 0.5 | 0.1019 | T | 0.0008737 | 8.818 | 3.0586377 | |
| rs12430711 | 13 | 42324586 | G | 0.5 | 0.1019 | A | 0.0008737 | 8.818 | 3.0586377 | |
| rs12902840 | 15 | 29140275 | T | 0.5 | 0.1019 | C | 0.0008737 | 8.818 | 3.0586377 | TRPM1 |
| rs8039189 | 15 | 29146495 | T | 0.5 | 0.1019 | G | 0.0008737 | 8.818 | 3.0586377 | TRPM1 |
| rs2820229 | 6 | 35184054 | G | 0.7143 | 0.2449 | A | 0.0008763 | 7.708 | 3.0573472 | |
| rs5935714 | 23 | 14073189 | G | 0.5833 | 0.122 | A | 0.0008774 | 10.08 | 3.0568024 | |
| rs7060021 | 23 | 14077199 | A | 0.5833 | 0.122 | C | 0.0008774 | 10.08 | 3.0568024 | |
| rs6690040 | 1 | 90833710 | G | 0.5714 | 0.1442 | A | 0.0009148 | 7.911 | 3.0386738 | |
| rs5988206 | 23 | 113541942 | C | 0 | 0.5 | T | 0.0009259 | 0 | 3.0334359 | |

FIG. 1E

| snp | CHR | BP | A1 | F_A | F_U | A2 | fisher_p | OR | l_p | loci |
|---|---|---|---|---|---|---|---|---|---|---|
| rs17421247 | 1 | 4624817 | T | 0.6429 | 0.1944 | C | 0.0009294 | 7.457 | 3.0317973 | AJAP1 |
| rs1507894 | 8 | 88855893 | G | 0.6429 | 0.1944 | T | 0.0009294 | 7.457 | 3.0317973 | |
| rs835808 | 11 | 44831214 | A | 0.6429 | 0.1944 | G | 0.0009294 | 7.457 | 3.0317973 | |
| rs588030 | 19 | 7788551 | G | 0.6429 | 0.1944 | A | 0.0009294 | 7.457 | 3.0317973 | |
| rs780242 | 1 | 231752014 | A | 0.7143 | 0.25 | G | 0.0009316 | 7.5 | 3.0307705 | |
| rs317588 | 3 | 4021691 | A | 0.7143 | 0.25 | G | 0.0009316 | 7.5 | 3.0307705 | |
| rs2367209 | 3 | 161881579 | A | 0.7143 | 0.25 | C | 0.0009316 | 7.5 | 3.0307705 | |
| rs6810359 | 3 | 189992908 | T | 0.3571 | 0.03704 | G | 0.0009316 | 14.44 | 3.0307705 | LPP |
| rs11984112 | 7 | 137469409 | C | 0.3571 | 0.03704 | T | 0.0009316 | 14.44 | 3.0307705 | |
| rs1317274 | 13 | 94372419 | C | 0.3571 | 0.03704 | T | 0.0009316 | 14.44 | 3.0307705 | |
| rs10405167 | 19 | 6218757 | G | 0.7143 | 0.25 | A | 0.0009316 | 7.5 | 3.0307705 | MLLT1 |
| rs576895 | 22 | 24261580 | C | 0.7143 | 0.25 | T | 0.0009316 | 7.5 | 3.0307705 | |
| rs984070 | 9 | 112178391 | T | 0.75 | 0.25 | C | 0.0009398 | 9 | 3.0269646 | SVEP1 |
| rs7791836 | 7 | 87899093 | G | 0 | 0.4259 | A | 0.0009427 | 0 | 3.0256265 | |
| rs2469407 | 8 | 3493770 | G | 0 | 0.4259 | A | 0.0009427 | 0 | 3.0256265 | CSMD1 |
| rs6468833 | 8 | 103593637 | G | 0 | 0.4259 | A | 0.0009427 | 0 | 3.0256265 | |
| rs10842458 | 12 | 25118569 | C | 0 | 0.4259 | T | 0.0009427 | 0 | 3.0256265 | LRMP |
| rs6431936 | 2 | 8424878 | A | 0 | 0.4245 | G | 0.0009652 | 0 | 3.0153827 | |
| rs2278700 | 2 | 97793814 | C | 0.7857 | 0.3148 | T | 0.0009735 | 7.98 | 3.011664 | TMEM131 |
| rs16863792 | 2 | 176990201 | A | 0.7857 | 0.3148 | G | 0.0009735 | 7.98 | 3.011664 | |
| rs1525922 | 3 | 192745333 | C | 0.7857 | 0.3148 | T | 0.0009735 | 7.98 | 3.011664 | |
| rs1583732 | 4 | 161539927 | A | 0.7857 | 0.3148 | C | 0.0009735 | 7.98 | 3.011664 | |
| rs6453083 | 5 | 74111114 | A | 0.7857 | 0.3148 | G | 0.0009735 | 7.98 | 3.011664 | |
| rs2515032 | 8 | 119563481 | C | 0.7857 | 0.3148 | T | 0.0009735 | 7.98 | 3.011664 | SAMD12 |
| rs1487971 | 17 | 25596879 | A | 0.7857 | 0.3148 | G | 0.0009735 | 7.98 | 3.011664 | |
| rs11034493 | 11 | 4861778 | G | 0.8571 | 0.3796 | A | 0.0009834 | 9.805 | 3.0072698 | |
| rs1945443 | 11 | 21365895 | G | 0.8571 | 0.3796 | A | 0.0009834 | 9.805 | 3.0072698 | NELL1 |
| rs747250 | 11 | 129776888 | G | 0.8571 | 0.3796 | T | 0.0009834 | 9.805 | 3.0072698 | FLJ34521 |
| rs10879571 | 12 | 71837819 | A | 0.8571 | 0.3796 | G | 0.0009834 | 9.805 | 3.0072698 | |
| rs5001655 | 13 | 96394772 | A | 0.8571 | 0.3796 | G | 0.0009834 | 9.805 | 3.0072698 | |
| rs11867581 | 17 | 25646354 | G | 0.8571 | 0.3796 | A | 0.0009834 | 9.805 | 3.0072698 | |
| rs8073378 | 17 | 25653889 | A | 0.8571 | 0.3796 | G | 0.0009834 | 9.805 | 3.0072698 | |
| rs9959914 | 18 | 48946456 | G | 0.8571 | 0.3796 | A | 0.0009834 | 9.805 | 3.0072698 | DCC |
| rs2163854 | 19 | 61444704 | G | 0.8571 | 0.3796 | A | 0.0009834 | 9.805 | 3.0072698 | |
| rs2032327 | 21 | 44441756 | G | 0.8571 | 0.3796 | A | 0.0009834 | 9.805 | 3.0072698 | |
| rs33998 | 5 | 141949111 | T | 0.07143 | 0.5556 | C | 0.0009894 | 0.06154 | 3.0046281 | |
| rs2531841 | 7 | 34686074 | C | 0.07143 | 0.5556 | T | 0.0009894 | 0.06154 | 3.0046281 | AAA1, NPSR1 |
| rs11179559 | 12 | 71811892 | A | 0.07143 | 0.5556 | C | 0.0009894 | 0.06154 | 3.0046281 | |
| rs1982607 | 13 | 75440483 | T | 0.07143 | 0.5556 | C | 0.0009894 | 0.06154 | 3.0046281 | |
| rs7338771 | 13 | 75444822 | T | 0.07143 | 0.5556 | C | 0.0009894 | 0.06154 | 3.0046281 | |
| rs509497 | 18 | 6947193 | C | 0.9286 | 0.4519 | T | 0.0009899 | 15.77 | 3.0044087 | LAMA1 |

| snp | CHR | BP | A1 | F_A | F_U | A2 | fisher_p | OR | l_p | loci |
|---|---|---|---|---|---|---|---|---|---|---|
| rs6928719 | 6 | 166117879 | C | 0.1875 | 0.6711 | A | 5.292E-06 | 0.1131 | 5.2763802 | |
| rs6928737 | 6 | 166118611 | G | 0.1875 | 0.6579 | A | 7.617E-06 | 0.12 | 5.118216 | |
| rs12857230 | 13 | 42654650 | G | 0.7188 | 0.25 | T | 8.917E-06 | 7.667 | 5.0497812 | |
| rs11713998 | 3 | 168613099 | T | 0.4375 | 0.06579 | C | 1.437E-05 | 11.04 | 4.8425432 | |
| rs4762507 | 12 | 97659769 | T | 0 | 0.3553 | C | 0.0000171 | 0 | 4.7670039 | ANKS1B |

FIG. 1F

| | | | | | | | | | |
|---|---|---|---|---|---|---|---|---|---|
| rs1838990 | 3 | 63142891 | C | 0.09375 | 0.5132 | T | 2.815E-05 | 0.09814 | 4.5505216 | |
| rs13144587 | 4 | 67295867 | C | 0.4375 | 0.07895 | A | 3.895E-05 | 9.074 | 4.4094925 | |
| rs12918939 | 16 | 64698060 | G | 0.4375 | 0.07895 | A | 3.895E-05 | 9.074 | 4.4094925 | |
| rs6904237 | 6 | 166121014 | C | 0.1875 | 0.6316 | T | 4.141E-05 | 0.1346 | 4.3828948 | |
| rs5999636 | 22 | 33661041 | T | 0 | 0.3289 | C | 4.165E-05 | 0 | 4.380385 | |
| rs7288089 | 22 | 33671316 | T | 0 | 0.3289 | C | 4.165E-05 | 0 | 4.380385 | |
| rs10953428 | 7 | 103814099 | T | 0.0625 | 0.4474 | C | 4.902E-05 | 0.08235 | 4.3096267 | LHFPL3 |
| rs1989823 | 7 | 103823052 | C | 0.0625 | 0.4474 | T | 4.902E-05 | 0.08235 | 4.3096267 | LHFPL3 |
| rs7335910 | 13 | 24220725 | G | 0.0625 | 0.4474 | A | 4.902E-05 | 0.08235 | 4.3096267 | |
| rs4831616 | 8 | 14511299 | T | 0.4375 | 0.08108 | C | 4.997E-05 | 8.815 | 4.3012907 | SGCZ |
| rs33053 | 3 | 161084457 | T | 0.03125 | 0.3947 | C | 4.998E-05 | 0.04946 | 4.3012037 | SCHIP1 |
| rs1439123 | 12 | 97600447 | C | 0.03125 | 0.3947 | T | 4.998E-05 | 0.04946 | 4.3012037 | APAF1 |
| rs11598274 | 10 | 130794532 | T | 0.4063 | 0.06579 | G | 5.073E-05 | 9.716 | 4.2947351 | |
| rs11111712 | 12 | 102605853 | T | 0.4063 | 0.06579 | C | 5.073E-05 | 9.716 | 4.2947351 | STAB2 |
| rs9924119 | 16 | 69900898 | C | 0.4063 | 0.06579 | T | 5.073E-05 | 9.716 | 4.2947351 | |
| rs4346287 | 18 | 60381151 | A | 0.4063 | 0.06579 | G | 5.073E-05 | 9.716 | 4.2947351 | |
| rs11671104 | 19 | 22586526 | C | 0.2813 | 0.01316 | A | 5.672E-05 | 29.35 | 4.2462638 | |
| rs12186252 | 4 | 6166295 | T | 0.5938 | 0.1842 | C | 5.976E-05 | 6.473 | 4.2235894 | JAKMIP1 |
| rs11695174 | 2 | 9705766 | T | 0.3125 | 0.02632 | C | 6.953E-05 | 16.82 | 4.1578278 | |
| rs299728 | 18 | 44424510 | T | 0 | 0.3158 | C | 7.817E-05 | 0 | 4.1069599 | KIAA0427 |
| rs6791663 | 3 | 183452046 | A | 0.4375 | 0.09211 | G | 9.481E-05 | 7.667 | 4.0231459 | |
| rs7779755 | 7 | 26538363 | A | 0.75 | 0.3289 | G | 0.000101 | 6.12 | 3.9956786 | |
| rs740182 | 7 | 26543060 | A | 0.75 | 0.3289 | G | 0.000101 | 6.12 | 3.9956786 | |
| rs1596860 | 13 | 24293067 | G | 0.03125 | 0.3816 | A | 0.000101 | 0.05228 | 3.9956786 | RNF17 |
| rs9507425 | 13 | 24338318 | A | 0.03125 | 0.3816 | G | 0.000101 | 0.05228 | 3.9956786 | RNF17 |
| rs2356417 | 16 | 69913636 | C | 0.4 | 0.06757 | T | 0.0001122 | 9.2 | 3.9500071 | |
| rs2288726 | 12 | 97608518 | T | 0.03125 | 0.3684 | G | 0.0001184 | 0.0553 | 3.9266483 | APAF1 |
| rs6758414 | 2 | 121012955 | A | 0.2188 | 0 | G | 0.0001207 | | 3.9182927 | |
| rs9520550 | 13 | 107135055 | A | 0.2188 | 0 | G | 0.0001207 | | 3.9182927 | LOC728215 |
| rs7320808 | 13 | 107138864 | T | 0.2188 | 0 | C | 0.0001207 | | 3.9182927 | LOC728215 |
| rs4113420 | 13 | 107154330 | T | 0.2188 | 0 | C | 0.0001207 | | 3.9182927 | LOC728215 |
| rs2117193 | 9 | 18751368 | C | 0.1875 | 0.5921 | T | 0.0001246 | 0.159 | 3.904482 | |
| rs4690523 | 4 | 178598156 | C | 0.1563 | 0.5526 | T | 0.0001254 | 0.1499 | 3.9017025 | AGA |
| rs995992 | 7 | 26543445 | C | 0.75 | 0.3421 | T | 0.0001271 | 5.769 | 3.8958544 | |
| rs7901425 | 10 | 130778057 | C | 0.4063 | 0.07895 | T | 0.0001295 | 7.982 | 3.8877302 | |
| rs9814318 | 3 | 63136521 | T | 0.09375 | 0.473 | C | 0.0001373 | 0.1153 | 3.8623295 | |
| rs4688381 | 3 | 63202226 | A | 0.09375 | 0.4737 | G | 0.0001406 | 0.1149 | 3.8520147 | |
| rs12193060 | 6 | 99797170 | G | 0 | 0.3026 | A | 0.0001604 | 0 | 3.7947956 | |
| rs2767001 | 9 | 112623833 | A | 0.5625 | 0.1842 | G | 0.0001681 | 5.694 | 3.7744323 | |
| rs1424140 | 16 | 69932963 | T | 0.5625 | 0.1842 | C | 0.0001681 | 5.694 | 3.7744323 | |
| rs3802431 | 9 | 110932446 | G | 0.375 | 0.06579 | A | 0.0001689 | 8.52 | 3.7723704 | |
| rs12774599 | 10 | 130795782 | T | 0.375 | 0.06579 | G | 0.0001689 | 8.52 | 3.7723704 | |
| rs642407 | 5 | 32542605 | A | 0.09375 | 0.4605 | G | 0.0001706 | 0.1212 | 3.768021 | |
| rs3748088 | 7 | 139864139 | T | 0.09375 | 0.4605 | C | 0.0001706 | 0.1212 | 3.768021 | DENND2A |
| rs10078211 | 5 | 57999775 | T | 0 | 0.2895 | C | 0.0001777 | 0 | 3.7503126 | RAB3C |
| rs6568842 | 6 | 114907070 | A | 0 | 0.2895 | G | 0.0001777 | 0 | 3.7503126 | |
| rs9298648 | 8 | 38918214 | A | 0.0625 | 0.4189 | G | 0.0001846 | 0.09247 | 3.7337683 | PLEKHA2 |

FIG. 2A

| | | | | | | | | | |
|---|---|---|---|---|---|---|---|---|---|
| rs1549599 | 3 | 37506369 | G | 0.6563 | 0.2632 | A | 0.0001906 | 5.345 | 3.7198771 | ITGA9 |
| rs4854942 | 3 | 180871100 | C | 0.0625 | 0.4211 | T | 0.0001932 | 0.09167 | 3.7139929 | USP13 |
| rs586125 | 18 | 40693077 | C | 0.4688 | 0.1184 | T | 0.0002033 | 6.569 | 3.6918626 | SETBP1 |
| rs1554937 | 21 | 40500245 | C | 0.6875 | 0.2895 | T | 0.0002078 | 5.4 | 3.6823545 | DSCAM |
| rs10275945 | 7 | 9323375 | A | 0.3438 | 0.05263 | C | 0.0002083 | 9.429 | 3.6813107 | |
| rs9915945 | 17 | 6089542 | A | 0.3438 | 0.05263 | G | 0.0002083 | 9.429 | 3.6813107 | |
| rs17020744 | 2 | 81845572 | A | 0.25 | 0.01316 | G | 0.0002115 | 25 | 3.6746896 | |
| rs7326004 | 13 | 107155619 | T | 0.25 | 0.01316 | C | 0.0002115 | 25 | 3.6746896 | LOC728215 |
| rs4326996 | 15 | 61567335 | G | 0.25 | 0.01316 | T | 0.0002115 | 25 | 3.6746896 | |
| rs2162296 | 19 | 41792090 | T | 0.25 | 0.01316 | C | 0.0002115 | 25 | 3.6746896 | ZNF382 |
| rs1673082 | 19 | 41932981 | A | 0.25 | 0.01316 | G | 0.0002115 | 25 | 3.6746896 | |
| rs2945861 | 8 | 8321077 | T | 0.0625 | 0.4079 | C | 0.0002144 | 0.09677 | 3.6687752 | |
| rs680951 | 10 | 6267388 | C | 0.03125 | 0.3553 | T | 0.0002199 | 0.05854 | 3.6577748 | |
| rs6864728 | 5 | 2680030 | G | 0.5313 | 0.1579 | A | 0.0002232 | 6.044 | 3.6513058 | |
| rs7122962 | 11 | 123818932 | A | 0.5313 | 0.1579 | G | 0.0002232 | 6.044 | 3.6513058 | |
| rs2938033 | 18 | 43510320 | G | 0.5313 | 0.1579 | A | 0.0002232 | 6.044 | 3.6513058 | |
| rs6532729 | 4 | 99365459 | C | 0.5938 | 0.2105 | T | 0.0002244 | 5.481 | 3.6489771 | |
| rs10416755 | 19 | 39975287 | A | 0.3125 | 0.03947 | G | 0.0002389 | 11.06 | 3.6217839 | |
| rs2834772 | 21 | 35405029 | T | 0.3125 | 0.03947 | C | 0.0002389 | 11.06 | 3.6217839 | |
| rs4659630 | 1 | 234359973 | C | 0.1875 | 0.5789 | T | 0.0002589 | 0.1678 | 3.5868679 | |
| rs585224 | 12 | 51209139 | A | 0.5938 | 0.2162 | G | 0.0002626 | 5.298 | 3.5807053 | |
| rs12696221 | 3 | 166354274 | G | 0.75 | 0.3553 | A | 0.0002667 | 5.444 | 3.573977 | |
| rs721250 | 2 | 59630520 | G | 0.7188 | 0.3289 | A | 0.0002721 | 5.213 | 3.5652715 | |
| rs6853651 | 4 | 157343816 | A | 0.7188 | 0.3289 | C | 0.0002721 | 5.213 | 3.5652715 | |
| rs2340252 | 4 | 157348668 | A | 0.7188 | 0.3289 | C | 0.0002721 | 5.213 | 3.5652715 | |
| rs7157453 | 14 | 54228954 | C | 0.7188 | 0.3289 | T | 0.0002721 | 5.213 | 3.5652715 | SAMD4A |
| rs13382133 | 19 | 17719936 | C | 0.7188 | 0.3289 | T | 0.0002721 | 5.213 | 3.5652715 | |
| rs9884594 | 4 | 99578341 | A | 0.6875 | 0.3026 | G | 0.0002792 | 5.07 | 3.5540846 | RAP1GDS1 |
| rs694126 | 5 | 32551319 | C | 0.6875 | 0.3026 | T | 0.0002792 | 5.07 | 3.5540846 | |
| rs7776 | 9 | 110822352 | C | 0.5313 | 0.1711 | A | 0.0002969 | 5.492 | 3.5273898 | C9orf5 |
| rs2141599 | 3 | 178325169 | T | 0.625 | 0.2368 | C | 0.0003044 | 5.37 | 3.5165554 | TBL1XR1 |
| rs277973 | 5 | 70995578 | T | 0.625 | 0.2368 | G | 0.0003044 | 5.37 | 3.5165554 | |
| rs12933802 | 16 | 87649419 | A | 0.3667 | 0.06579 | G | 0.0003062 | 8.221 | 3.5139948 | |
| rs6933285 | 6 | 120383898 | T | 0.1875 | 0.5658 | C | 0.0003085 | 0.1771 | 3.5107448 | |
| rs1569757 | 6 | 120389030 | G | 0.1875 | 0.5658 | A | 0.0003085 | 0.1771 | 3.5107448 | |
| rs2110871 | 7 | 77918484 | A | 0.5938 | 0.2237 | G | 0.0003194 | 5.072 | 3.4956651 | MAGI2 |
| rs1274399 | 10 | 92347510 | T | 0.5938 | 0.2237 | C | 0.0003194 | 5.072 | 3.4956651 | |
| rs669379 | 12 | 51213665 | G | 0.5938 | 0.2237 | A | 0.0003194 | 5.072 | 3.4956651 | |
| rs12709230 | 16 | 8449241 | C | 0.5938 | 0.2237 | T | 0.0003194 | 5.072 | 3.4956651 | |
| rs7755154 | 6 | 2558943 | T | 0.4688 | 0.1316 | C | 0.0003307 | 5.824 | 3.4805658 | |
| rs4772778 | 13 | 105835851 | A | 0.4688 | 0.1316 | G | 0.0003307 | 5.824 | 3.4805658 | |
| rs10077599 | 5 | 58022400 | A | 0 | 0.2763 | G | 0.0003311 | 0 | 3.4800408 | RAB3C |
| rs10472069 | 5 | 58041554 | C | 0 | 0.2763 | T | 0.0003311 | 0 | 3.4800408 | RAB3C |
| rs7350156 | 9 | 133715383 | G | 0.25 | 0.6316 | A | 0.0003338 | 0.1944 | 3.4765137 | |
| rs6504487 | 17 | 62553814 | A | 0.75 | 0.3684 | C | 0.0003338 | 5.143 | 3.4765137 | HELZ |
| rs7211695 | 17 | 62666433 | G | 0.75 | 0.3684 | A | 0.0003338 | 5.143 | 3.4765137 | HELZ |
| rs6481260 | 10 | 58633464 | C | 0.6 | 0.2083 | T | 0.0003468 | 5.7 | 3.4599209 | |
| rs5970533 | 23 | 150005809 | T | 0.08 | 0.4912 | C | 0.0003566 | 0.09006 | 3.4478187 | |

FIG. 2B

| | | | | | | | | | |
|---|---|---|---|---|---|---|---|---|---|
| rs7837164 | 8 | 14510052 | C | 0.4375 | 0.1053 | T | 0.0003605 | 6.611 | 3.4430947 | SGCZ |
| rs589623 | 11 | 102587800 | C | 0.4375 | 0.1053 | T | 0.0003605 | 6.611 | 3.4430947 | DYNC2H1 |
| rs660994 | 11 | 102616867 | G | 0.4375 | 0.1053 | T | 0.0003605 | 6.611 | 3.4430947 | DYNC2H1 |
| rs1891020 | 1 | 159961078 | A | 0.625 | 0.25 | G | 0.0003681 | 5 | 3.4340342 | FCRLB |
| rs1417582 | 1 | 159962712 | T | 0.625 | 0.25 | C | 0.0003681 | 5 | 3.4340342 | FCRLB |
| rs1572705 | 1 | 236374168 | A | 0.625 | 0.25 | G | 0.0003681 | 5 | 3.4340342 | |
| rs11246756 | 12 | 130743401 | G | 0.625 | 0.25 | T | 0.0003681 | 5 | 3.4340342 | |
| rs7771891 | 6 | 2570303 | G | 0.375 | 0.07895 | A | 0.0004052 | 7 | 3.3923306 | C6orf195 |
| rs7759042 | 6 | 2574150 | C | 0.375 | 0.07895 | T | 0.0004052 | 7 | 3.3923306 | C6orf195 |
| rs7715908 | 5 | 172176301 | G | 0.4688 | 0.1351 | A | 0.0004058 | 5.647 | 3.391688 | |
| rs12489904 | 3 | 20359631 | G | 0.125 | 0.4868 | A | 0.0004131 | 0.1506 | 3.3839448 | |
| rs11719694 | 3 | 20363109 | T | 0.125 | 0.4868 | C | 0.0004131 | 0.1506 | 3.3839448 | |
| rs326832 | 20 | 55952451 | A | 0.125 | 0.4868 | G | 0.0004131 | 0.1506 | 3.3839448 | |
| rs2028211 | 2 | 127618127 | C | 0.6563 | 0.2763 | A | 0.0004284 | 5 | 3.3681505 | |
| rs7611110 | 3 | 183421131 | C | 0.6563 | 0.2763 | A | 0.0004284 | 5 | 3.3681505 | |
| rs4444698 | 3 | 183422848 | C | 0.6563 | 0.2763 | T | 0.0004284 | 5 | 3.3681505 | |
| rs320719 | 7 | 136674049 | A | 0.6563 | 0.2763 | G | 0.0004284 | 5 | 3.3681505 | PTN |
| rs320682 | 7 | 136688632 | C | 0.6563 | 0.2763 | T | 0.0004284 | 5 | 3.3681505 | |
| rs6092527 | 20 | 55746462 | A | 0.6563 | 0.2763 | G | 0.0004284 | 5 | 3.3681505 | |
| rs2808067 | 10 | 32085938 | A | 0.5625 | 0.1974 | G | 0.0004322 | 5.229 | 3.3643152 | |
| rs7073183 | 10 | 58640012 | C | 0.5625 | 0.1974 | T | 0.0004322 | 5.229 | 3.3643152 | |
| rs4794558 | 17 | 50702952 | A | 0.5625 | 0.1974 | G | 0.0004322 | 5.229 | 3.3643152 | HLF |
| rs6627850 | 23 | 150008593 | C | 0.08 | 0.4737 | T | 0.0004343 | 0.09662 | 3.3622102 | |
| rs666595 | 10 | 6268232 | T | 0.03125 | 0.3421 | C | 0.0004413 | 0.06203 | 3.3552661 | |
| rs1048878 | 20 | 49646660 | C | 0.03125 | 0.3421 | T | 0.0004413 | 0.06203 | 3.3552661 | ATP9A |
| rs10910365 | 1 | 232346267 | A | 0.5313 | 0.1842 | G | 0.0004653 | 5.019 | 3.3322669 | SLC35F3 |
| rs2373001 | 2 | 37451925 | C | 0.1875 | 0 | T | 0.0004736 | | 3.3245883 | QPCT |
| rs9553435 | 13 | 24235300 | A | 0.03125 | 0.3289 | C | 0.0004813 | 0.06581 | 3.3175841 | RNF17 |
| rs4883688 | 13 | 62434248 | C | 0.03125 | 0.3289 | T | 0.0004813 | 0.06581 | 3.3175841 | |
| rs1878059 | 18 | 42488544 | A | 0.03125 | 0.3289 | G | 0.0004813 | 0.06581 | 3.3175841 | LOC647011 |
| rs2423222 | 20 | 7297731 | T | 0.03125 | 0.3289 | C | 0.0004813 | 0.06581 | 3.3175841 | |
| rs2315656 | 20 | 61888781 | G | 0.125 | 0.4737 | A | 0.0004872 | 0.1587 | 3.3122927 | ZBTB46 |
| rs12591365 | 15 | 23611690 | G | 0.1563 | 0.5263 | A | 0.0005032 | 0.1667 | 3.2982594 | |
| rs8032023 | 15 | 59199434 | C | 0.1563 | 0.5263 | T | 0.0005032 | 0.1667 | 3.2982594 | RORA |
| rs2680700 | 17 | 53795541 | A | 0.6563 | 0.2857 | C | 0.0005263 | 4.773 | 3.2787666 | RNF43 |
| rs6963754 | 7 | 9292495 | C | 0.5 | 0.1579 | T | 0.0005271 | 5.333 | 3.278107 | |
| rs1322473 | 9 | 7969832 | T | 0.5 | 0.1579 | C | 0.0005271 | 5.333 | 3.278107 | |
| rs2439422 | 15 | 64764858 | G | 0.5 | 0.1579 | A | 0.0005271 | 5.333 | 3.278107 | |
| rs12957369 | 18 | 22190589 | A | 0.5 | 0.1579 | G | 0.0005271 | 5.333 | 3.278107 | TAF4B |
| rs12962768 | 18 | 22220594 | C | 0.5 | 0.1579 | T | 0.0005271 | 5.333 | 3.278107 | TAF4B |
| rs1028005 | 4 | 46635775 | C | 0.4375 | 0.1184 | T | 0.0005297 | 5.79 | 3.27597 | GABRA4 |
| rs323391 | 17 | 69199193 | A | 0.4375 | 0.1184 | C | 0.0005297 | 5.79 | 3.27597 | |
| rs3935319 | 7 | 9334882 | T | 0.3438 | 0.06579 | C | 0.0005303 | 7.438 | 3.2754784 | |
| rs10099199 | 8 | 18422501 | C | 0.3438 | 0.06579 | T | 0.0005303 | 7.438 | 3.2754784 | |
| rs7581 | 9 | 110819068 | G | 0.3438 | 0.06579 | A | 0.0005303 | 7.438 | 3.2754784 | C9orf5 |
| rs7200766 | 16 | 87658525 | T | 0.3438 | 0.06579 | C | 0.0005303 | 7.438 | 3.2754784 | |
| rs4574540 | 5 | 124095527 | G | 0.6563 | 0.2895 | A | 0.0005399 | 4.686 | 3.2676867 | ZNF608 |

FIG. 2C

| | | | | | | | | | |
|---|---|---|---|---|---|---|---|---|---|
| rs7741833 | 6 | 121042746 | A | 0.6563 | 0.2895 | G | 0.0005399 | 4.686 | 3.2676867 | |
| rs1431093 | 7 | 136666837 | T | 0.6563 | 0.2895 | G | 0.0005399 | 4.686 | 3.2676867 | PTN |
| rs1536833 | 10 | 30739271 | A | 0.6563 | 0.2895 | G | 0.0005399 | 4.686 | 3.2676867 | |
| rs303436 | 10 | 30771899 | C | 0.6563 | 0.2895 | A | 0.0005399 | 4.686 | 3.2676867 | MAP3K8 |
| rs12283389 | 11 | 86248925 | T | 0.6563 | 0.2895 | C | 0.0005399 | 4.686 | 3.2676867 | |
| rs1548518 | 12 | 46439262 | T | 0.6563 | 0.2895 | C | 0.0005399 | 4.686 | 3.2676867 | RAPGEF3 |
| rs12904249 | 15 | 23622445 | A | 0.6563 | 0.2895 | G | 0.0005399 | 4.686 | 3.2676867 | ATP10A |
| rs17777549 | 3 | 78417789 | C | 0 | 0.3182 | T | 0.0005487 | 0 | 3.260665 | |
| rs2795492 | 9 | 99953197 | A | 0.1563 | 0.5132 | G | 0.0005522 | 0.1757 | 3.2579036 | CORO2A |
| rs7115014 | 11 | 102310143 | A | 0.1563 | 0.5132 | G | 0.0005522 | 0.1757 | 3.2579036 | |
| rs9867568 | 3 | 23741555 | C | 0.6875 | 0.3158 | T | 0.0005592 | 4.767 | 3.2524328 | |
| rs598672 | 10 | 30782394 | C | 0.6875 | 0.3158 | T | 0.0005592 | 4.767 | 3.2524328 | MAP3K8 |
| rs12336075 | 9 | 110422596 | G | 0.5625 | 0.2105 | A | 0.0005696 | 4.821 | 3.24443 | |
| rs1275273 | 10 | 58676561 | A | 0.5625 | 0.2105 | G | 0.0005696 | 4.821 | 3.24443 | |
| rs236736 | 23 | 150022841 | T | 0.6 | 0.193 | C | 0.0005805 | 6.273 | 3.2361978 | |
| rs6550478 | 3 | 37501017 | A | 0.2813 | 0.6579 | G | 0.000583 | 0.2035 | 3.2343314 | ITGA9 |
| rs1607077 | 4 | 92648984 | G | 0.1875 | 0.5526 | A | 0.0005934 | 0.1868 | 3.2266525 | |
| rs7677659 | 4 | 92650752 | C | 0.1875 | 0.5526 | T | 0.0005934 | 0.1868 | 3.2266525 | |
| rs12705208 | 7 | 103808264 | G | 0.1875 | 0.5526 | A | 0.0005934 | 0.1868 | 3.2266525 | LHFPL3 |
| rs4766100 | 12 | 3305142 | G | 0.1875 | 0.5526 | A | 0.0005934 | 0.1868 | 3.2266525 | |
| rs11795873 | 23 | 19588579 | G | 0.84 | 0.4211 | A | 0.0005945 | 7.219 | 3.2258481 | SH3KBP1 |
| rs1934908 | 1 | 159947492 | T | 0.7813 | 0.4079 | C | 0.0006131 | 5.184 | 3.2124687 | FCRLA |
| rs10215963 | 7 | 26550306 | A | 0.7813 | 0.4079 | C | 0.0006131 | 5.184 | 3.2124687 | |
| rs10753789 | 1 | 160572831 | G | 0.09375 | 0.4342 | A | 0.000626 | 0.1348 | 3.2034257 | NOS1AP |
| rs7899958 | 10 | 131493116 | G | 0.09375 | 0.4342 | A | 0.000626 | 0.1348 | 3.2034257 | |
| rs1860394 | 12 | 3309312 | A | 0.09375 | 0.4342 | C | 0.000626 | 0.1348 | 3.2034257 | |
| rs6550169 | 3 | 32888097 | T | 0.25 | 0.6184 | C | 0.0006494 | 0.2057 | 3.1874877 | TRIM71 |
| rs1173179 | 5 | 4856549 | T | 0.25 | 0.6184 | G | 0.0006494 | 0.2057 | 3.1874877 | |
| rs7520519 | 1 | 159962263 | G | 0.3125 | 0.05263 | T | 0.000662 | 8.182 | 3.179142 | FCRLB |
| rs17013522 | 4 | 129794377 | C | 0.3125 | 0.05263 | T | 0.000662 | 8.182 | 3.179142 | |
| rs2433101 | 8 | 25605445 | C | 0.3125 | 0.05263 | T | 0.000662 | 8.182 | 3.179142 | |
| rs2433105 | 8 | 25605996 | G | 0.3125 | 0.05263 | T | 0.000662 | 8.182 | 3.179142 | |
| rs6755276 | 2 | 33795430 | C | 0 | 0.2632 | T | 0.000669 | 0 | 3.1745739 | |
| rs11073678 | 15 | 85206147 | A | 0 | 0.2632 | G | 0.000669 | 0 | 3.1745739 | |
| rs8036797 | 15 | 85236643 | T | 0 | 0.2632 | G | 0.000669 | 0 | 3.1745739 | |
| rs1323723 | 1 | 110615530 | T | 0.2813 | 0.6447 | C | 0.0006899 | 0.2156 | 3.1612139 | |
| rs12622579 | 2 | 41352004 | C | 0.7188 | 0.3553 | T | 0.0006899 | 4.638 | 3.1612139 | |
| rs809845 | 13 | 49622056 | T | 0.2813 | 0.6447 | C | 0.0006899 | 0.2156 | 3.1612139 | |
| rs10863402 | 1 | 216807938 | G | 0.09375 | 0.4211 | A | 0.0006907 | 0.1422 | 3.1607105 | |
| rs10929527 | 2 | 8526851 | C | 0.09375 | 0.4211 | T | 0.0006907 | 0.1422 | 3.1607105 | |
| rs236855 | 6 | 79398610 | G | 0.09375 | 0.4211 | A | 0.0006907 | 0.1422 | 3.1607105 | |
| rs625061 | 11 | 102537638 | G | 0.09375 | 0.4211 | T | 0.0006907 | 0.1422 | 3.1607105 | DYNC2H1 |
| rs876026 | 12 | 75190027 | T | 0.09375 | 0.4211 | C | 0.0006907 | 0.1422 | 3.1607105 | |
| rs2680698 | 17 | 53800383 | C | 0.09375 | 0.4211 | T | 0.0006907 | 0.1422 | 3.1607105 | RNF43 |
| rs4811738 | 20 | 54698950 | C | 0.09375 | 0.4211 | T | 0.0006907 | 0.1422 | 3.1607105 | |
| rs2300769 | 3 | 180903360 | A | 0.7813 | 0.4211 | C | 0.0006973 | 4.911 | 3.1565803 | USP13 |
| rs197419 | 1 | 112116973 | C | 0.5938 | 0.2368 | A | 0.0007 | 4.709 | 3.154902 | |
| rs1500422 | 3 | 20695142 | T | 0.5938 | 0.2368 | C | 0.0007 | 4.709 | 3.154902 | |

FIG. 2D

| | | | | | | | | | |
|---|---|---|---|---|---|---|---|---|---|
| rs11953826 | 5 | 174410242 | C | 0.5938 | 0.2368 | A | 0.0007 | 4.709 | 3.154902 | |
| rs1569091 | 7 | 94356064 | A | 0.5938 | 0.2368 | G | 0.0007 | 4.709 | 3.154902 | |
| rs2035590 | 12 | 114510223 | T | 0.5938 | 0.2368 | C | 0.0007 | 4.709 | 3.154902 | |
| rs9569891 | 13 | 58048371 | T | 0.5938 | 0.2368 | C | 0.0007 | 4.709 | 3.154902 | |
| rs822711 | 3 | 166486499 | C | 0 | 0.25 | T | 0.0007093 | 0 | 3.14917 | |
| rs13281010 | 8 | 17441995 | C | 0 | 0.25 | T | 0.0007093 | 0 | 3.14917 | SLC7A2 |
| rs11003258 | 10 | 54352401 | T | 0 | 0.25 | C | 0.0007093 | 0 | 3.14917 | |
| rs1073051 | 20 | 17793755 | A | 0 | 0.25 | G | 0.0007093 | 0 | 3.14917 | |
| rs1105355 | 16 | 82633064 | C | 0.1875 | 0.5395 | A | 0.00072 | 0.197 | 3.1426675 | LOC146167 |
| rs16953945 | 17 | 4319847 | A | 0.1875 | 0.5395 | G | 0.00072 | 0.197 | 3.1426675 | SPNS3 |
| rs2362255 | 1 | 244130482 | C | 0.2188 | 0.01316 | T | 0.0007565 | 21 | 3.1211911 | SMYD3 |
| rs12996382 | 2 | 166768141 | C | 0.2188 | 0.01316 | T | 0.0007565 | 21 | 3.1211911 | SCN9A |
| rs13090386 | 3 | 103158639 | A | 0.2188 | 0.01316 | C | 0.0007565 | 21 | 3.1211911 | |
| rs10517174 | 4 | 46677583 | A | 0.2188 | 0.01316 | G | 0.0007565 | 21 | 3.1211911 | GABRA4 |
| rs17030758 | 4 | 102245160 | G | 0.2188 | 0.01316 | A | 0.0007565 | 21 | 3.1211911 | PPP3CA |
| rs6862847 | 5 | 108735450 | G | 0.2188 | 0.01316 | A | 0.0007565 | 21 | 3.1211911 | PJA2 |
| rs12654614 | 5 | 162918233 | G | 0.2188 | 0.01316 | A | 0.0007565 | 21 | 3.1211911 | |
| rs1484248 | 10 | 106984746 | G | 0.2188 | 0.01316 | A | 0.0007565 | 21 | 3.1211911 | SORCS3 |
| rs10884125 | 10 | 107010780 | G | 0.2188 | 0.01316 | A | 0.0007565 | 21 | 3.1211911 | SORCS3 |
| rs4606589 | 13 | 62363177 | C | 0.2188 | 0.01316 | A | 0.0007565 | 21 | 3.1211911 | |
| rs7493402 | 14 | 100882328 | G | 0.2188 | 0.01316 | A | 0.0007565 | 21 | 3.1211911 | |
| rs12462101 | 19 | 51426846 | C | 0.2188 | 0.01316 | T | 0.0007565 | 21 | 3.1211911 | |
| rs7556371 | 1 | 202723959 | G | 0.5 | 0.1711 | A | 0.0007714 | 4.846 | 3.1127204 | PIK3C2B |
| rs449095 | 4 | 103332760 | A | 0.5 | 0.1711 | G | 0.0007714 | 4.846 | 3.1127204 | |
| rs6875512 | 5 | 31367532 | C | 0.5 | 0.1711 | A | 0.0007714 | 4.846 | 3.1127204 | |
| rs10816772 | 9 | 110925690 | C | 0.5 | 0.1711 | T | 0.0007714 | 4.846 | 3.1127204 | |
| rs2417976 | 9 | 110930170 | A | 0.5 | 0.1711 | C | 0.0007714 | 4.846 | 3.1127204 | |
| rs11641362 | 16 | 83893452 | T | 0.5 | 0.1711 | G | 0.0007714 | 4.846 | 3.1127204 | |
| rs37389 | 5 | 35120937 | T | 0.2813 | 0.03947 | C | 0.0007766 | 9.522 | 3.1098026 | PRLR |
| rs6887887 | 5 | 142516106 | A | 0.2813 | 0.03947 | G | 0.0007766 | 9.522 | 3.1098026 | ARHGAP26 |
| rs17120994 | 8 | 15035830 | C | 0.2813 | 0.03947 | T | 0.0007766 | 9.522 | 3.1098026 | SGCZ |
| rs502357 | 11 | 91953156 | T | 0.2813 | 0.03947 | C | 0.0007766 | 9.522 | 3.1098026 | FAT3 |
| rs2075379 | 12 | 29707647 | G | 0.2813 | 0.03947 | A | 0.0007766 | 9.522 | 3.1098026 | TMTC1 |
| rs12585317 | 13 | 56458934 | T | 0.2813 | 0.03947 | C | 0.0007766 | 9.522 | 3.1098026 | |
| rs9569579 | 13 | 56486602 | A | 0.2813 | 0.03947 | G | 0.0007766 | 9.522 | 3.1098026 | |
| rs9563481 | 13 | 56690719 | A | 0.2813 | 0.03947 | C | 0.0007766 | 9.522 | 3.1098026 | |
| rs9563483 | 13 | 56716744 | C | 0.2813 | 0.03947 | T | 0.0007766 | 9.522 | 3.1098026 | |
| rs6076519 | 20 | 3379140 | G | 0.2813 | 0.03947 | A | 0.0007766 | 9.522 | 3.1098026 | |
| rs4143737 | 9 | 72679274 | T | 0.0625 | 0.3784 | C | 0.000783 | 0.1095 | 3.1062382 | TRPM3 |
| rs533202 | 2 | 166691427 | A | 0.25 | 0.02632 | C | 0.0008309 | 12.33 | 3.0804512 | |
| rs479250 | 2 | 166691902 | G | 0.25 | 0.02632 | A | 0.0008309 | 12.33 | 3.0804512 | |
| rs10486067 | 7 | 13890487 | G | 0.25 | 0.02632 | A | 0.0008309 | 12.33 | 3.0804512 | |
| rs3801091 | 7 | 13921849 | T | 0.25 | 0.02632 | C | 0.0008309 | 12.33 | 3.0804512 | ETV1 |
| rs7185008 | 16 | 78501239 | A | 0.25 | 0.02632 | G | 0.0008309 | 12.33 | 3.0804512 | |
| rs17742683 | 17 | 39234600 | C | 0.25 | 0.02632 | T | 0.0008309 | 12.33 | 3.0804512 | MPP3 |
| rs17093560 | 20 | 29789374 | A | 0.25 | 0.02632 | G | 0.0008309 | 12.33 | 3.0804512 | TPX2 |
| rs285684 | 19 | 38963499 | T | 0.03125 | 0.3243 | C | 0.0008459 | 0.0672 | 3.072681 | |

FIG. 2E

| | | | | | | | | | |
|---|---|---|---|---|---|---|---|---|---|
| rs10204812 | 2 | 236075518 | A | 0.0625 | 0.3684 | G | 0.0008572 | 0.1143 | 3.0669178 | CENTG2 |
| rs35684 | 3 | 10301686 | G | 0.0625 | 0.3684 | A | 0.0008572 | 0.1143 | 3.0669178 | C3orf42, GHRL |
| rs1453546 | 11 | 58979902 | G | 0.0625 | 0.3684 | A | 0.0008572 | 0.1143 | 3.0669178 | OR4D6 |
| rs4704050 | 5 | 70829327 | G | 0.625 | 0.2632 | A | 0.0008632 | 4.667 | 3.0638886 | BDP1 |
| rs1886714 | 16 | 19970009 | C | 0.625 | 0.2632 | T | 0.0008632 | 4.667 | 3.0638886 | GPR139 |
| rs4813023 | 20 | 10142246 | T | 0.625 | 0.2632 | C | 0.0008632 | 4.667 | 3.0638886 | |
| rs2071931 | 1 | 9251876 | A | 0.4063 | 0.1053 | G | 0.0008636 | 5.816 | 3.0636874 | H6PD |
| rs7523762 | 1 | 159946268 | T | 0.4063 | 0.1053 | C | 0.0008636 | 5.816 | 3.0636874 | FCRLA |
| rs1891019 | 1 | 159958057 | C | 0.4063 | 0.1053 | T | 0.0008636 | 5.816 | 3.0636874 | FCRLB |
| rs2099380 | 1 | 224720875 | T | 0.4063 | 0.1053 | C | 0.0008636 | 5.816 | 3.0636874 | |
| rs17066769 | 8 | 3494133 | G | 0.4063 | 0.1053 | A | 0.0008636 | 5.816 | 3.0636874 | CSMD1 |
| rs1002665 | 9 | 103669957 | A | 0.4063 | 0.1053 | G | 0.0008636 | 5.816 | 3.0636874 | |
| rs10764855 | 10 | 130809932 | A | 0.4063 | 0.1053 | G | 0.0008636 | 5.816 | 3.0636874 | |
| rs188916 | 4 | 188023310 | C | 0.125 | 0.4605 | T | 0.000885 | 0.1673 | 3.0530567 | |
| rs4409101 | 5 | 42891883 | G | 0.125 | 0.4605 | A | 0.000885 | 0.1673 | 3.0530567 | |
| rs7460819 | 8 | 136804688 | C | 0.125 | 0.4605 | T | 0.000885 | 0.1673 | 3.0530567 | |
| rs12964446 | 18 | 73061991 | C | 0.125 | 0.4605 | A | 0.000885 | 0.1673 | 3.0530567 | |
| rs1405373 | 2 | 52577564 | C | 0.03125 | 0.3158 | T | 0.0008877 | 0.06989 | 3.0517338 | |
| rs10519265 | 15 | 77715278 | A | 0.03125 | 0.3158 | G | 0.0008877 | 0.06989 | 3.0517338 | |
| rs9823776 | 3 | 63414374 | A | 0.4375 | 0.1316 | G | 0.0009018 | 5.133 | 3.0448898 | SYNPR |
| rs1009848 | 7 | 142265373 | C | 0.4375 | 0.1316 | T | 0.0009018 | 5.133 | 3.0448898 | EPHB6 |
| rs1530599 | 18 | 22085647 | G | 0.4375 | 0.1316 | A | 0.0009018 | 5.133 | 3.0448898 | TAF4B |
| rs2893630 | 1 | 236480543 | A | 0.5938 | 0.25 | C | 0.0009328 | 4.385 | 3.0302115 | |
| rs1492523 | 4 | 167571796 | T | 0.5938 | 0.25 | C | 0.0009328 | 4.385 | 3.0302115 | |
| rs10857379 | 4 | 167619466 | G | 0.5938 | 0.25 | A | 0.0009328 | 4.385 | 3.0302115 | |
| rs277921 | 5 | 71000819 | G | 0.5938 | 0.25 | A | 0.0009328 | 4.385 | 3.0302115 | |
| rs10516126 | 5 | 174414039 | G | 0.5938 | 0.25 | A | 0.0009328 | 4.385 | 3.0302115 | |
| rs1025547 | 9 | 8654838 | G | 0.5938 | 0.25 | T | 0.0009328 | 4.385 | 3.0302115 | PTPRD |
| rs1649053 | 10 | 59991493 | G | 0.5938 | 0.25 | A | 0.0009328 | 4.385 | 3.0302115 | BICC1 |
| rs8073498 | 17 | 7510423 | C | 0.5938 | 0.25 | A | 0.0009328 | 4.385 | 3.0302115 | |
| rs1979285 | 5 | 172176908 | C | 0.4688 | 0.1447 | T | 0.0009502 | 5.214 | 3.022185 | |
| rs4946815 | 6 | 107567039 | A | 0.4688 | 0.1447 | C | 0.0009502 | 5.214 | 3.022185 | |
| rs1416326 | 9 | 102608530 | G | 0.4688 | 0.1447 | T | 0.0009502 | 5.214 | 3.022185 | |
| rs4551896 | 13 | 109880158 | C | 0.4688 | 0.1447 | A | 0.0009502 | 5.214 | 3.022185 | |
| rs2051742 | 16 | 27881919 | T | 0.4688 | 0.1447 | C | 0.0009502 | 5.214 | 3.022185 | |

FIG. 2F

| snp | CHR | BP | A1 | F_A | F_U | A2 | fisher_p | OR | l_p | loci |
|---|---|---|---|---|---|---|---|---|---|---|
| rs9915945 | 17 | 6089542 | A | 0.3636 | 0.05128 | G | 1.539E-05 | 10.57 | 4.8127614 | |
| rs323391 | 17 | 69199193 | A | 0.4773 | 0.1154 | C | 1.732E-05 | 7 | 4.7614521 | |
| rs7335910 | 13 | 24220725 | G | 0.09091 | 0.4615 | A | 1.775E-05 | 0.1167 | 4.7508016 | |
| rs1549599 | 3 | 37506369 | G | 0.6818 | 0.2692 | A | 1.852E-05 | 5.816 | 4.732359 | ITGA9 |
| rs1554983 | 16 | 77425340 | A | 0.3182 | 0.7179 | G | 2.387E-05 | 0.1833 | 4.6221476 | |
| rs11695174 | 2 | 9705766 | T | 0.2955 | 0.02564 | C | 2.682E-05 | 15.94 | 4.5715412 | |
| rs1569091 | 7 | 94356064 | A | 0.6136 | 0.2308 | G | 3.676E-05 | 5.294 | 4.4346245 | |
| rs4794558 | 17 | 50702952 | A | 0.5682 | 0.1923 | G | 4.192E-05 | 5.526 | 4.3775787 | HLF |
| rs17020744 | 2 | 81845572 | A | 0.25 | 0.01282 | G | 4.771E-05 | 25.67 | 4.3213906 | |
| rs4326996 | 15 | 61567335 | G | 0.25 | 0.01282 | T | 4.771E-05 | 25.67 | 4.3213906 | |
| rs1439123 | 12 | 97600447 | C | 0.06818 | 0.3974 | T | 5.355E-05 | 0.1109 | 4.2712405 | APAF1 |
| rs4762507 | 12 | 97659769 | T | 0.04545 | 0.359 | C | 5.591E-05 | 0.08503 | 4.2525105 | ANKS1B |
| rs17066769 | 8 | 3494133 | G | 0.4318 | 0.1026 | A | 6.178E-05 | 6.65 | 4.2091521 | CSMD1 |
| rs1002665 | 9 | 103669957 | A | 0.4318 | 0.1026 | G | 6.178E-05 | 6.65 | 4.2091521 | |
| rs6719949 | 2 | 220404542 | C | 0.1364 | 0.5 | T | 7.055E-05 | 0.1579 | 4.151503 | |
| rs1838990 | 3 | 63142891 | C | 0.1364 | 0.5 | T | 7.055E-05 | 0.1579 | 4.151503 | |
| rs6481260 | 10 | 58633464 | C | 0.6 | 0.2162 | T | 7.238E-05 | 5.438 | 4.1403814 | |
| rs11713998 | 3 | 168613099 | T | 0.3636 | 0.0641 | C | 7.475E-05 | 8.343 | 4.1263888 | |
| rs3802431 | 9 | 110932446 | G | 0.3636 | 0.0641 | A | 7.475E-05 | 8.343 | 4.1263888 | |
| rs11598274 | 10 | 130794532 | T | 0.3636 | 0.0641 | G | 7.475E-05 | 8.343 | 4.1263888 | |
| rs4346287 | 18 | 60381151 | A | 0.3636 | 0.0641 | G | 7.475E-05 | 8.343 | 4.1263888 | |
| rs10814297 | 9 | 35900945 | A | 0.09091 | 0.4231 | G | 8.433E-05 | 0.1364 | 4.0740179 | LOC158376 |
| rs7689639 | 4 | 25184635 | A | 0.02273 | 0.3026 | G | 9.583E-05 | 0.05359 | 4.0184985 | |
| rs2017041 | 22 | 33670103 | C | 0.1591 | 0.5128 | A | 0.0001009 | 0.1797 | 3.9961088 | |
| rs10490046 | 2 | 40484182 | G | 0.06818 | 0.3846 | T | 0.0001019 | 0.1171 | 3.9918258 | SLC8A1 |
| rs12857230 | 13 | 42654650 | G | 0.6364 | 0.2692 | T | 0.0001046 | 4.75 | 3.9804683 | |
| rs7073183 | 10 | 58640012 | C | 0.5682 | 0.2051 | T | 0.0001115 | 5.099 | 3.9527251 | |
| rs4075196 | 1 | 225608852 | A | 0.1818 | 0.5385 | G | 0.0001165 | 0.1905 | 3.9336741 | |
| rs1522858 | 2 | 79151979 | A | 0.6818 | 0.3077 | G | 0.0001193 | 4.821 | 3.9233596 | |
| rs9884594 | 4 | 99578341 | A | 0.6818 | 0.3077 | G | 0.0001193 | 4.821 | 3.9233596 | RAP1GDS1 |
| rs10497714 | 2 | 191875525 | G | 0 | 0.2436 | A | 0.000126 | 0 | 3.8996295 | MYO1B |
| rs694126 | 5 | 32551319 | C | 0.6591 | 0.2949 | T | 0.0001265 | 4.623 | 3.8979095 | |
| rs1548518 | 12 | 46439262 | T | 0.6591 | 0.2949 | C | 0.0001265 | 4.623 | 3.8979095 | RAPGEF3 |
| rs171406 | 3 | 10358517 | G | 0.25 | 0.6154 | A | 0.0001389 | 0.2083 | 3.8572978 | ATP2B2 |
| rs1275273 | 10 | 58676561 | A | 0.5682 | 0.2179 | G | 0.0001428 | 4.721 | 3.8452718 | |
| rs11671104 | 19 | 22586526 | C | 0.2273 | 0.01282 | A | 0.0001434 | 22.65 | 3.8434508 | |
| rs7813880 | 8 | 3499100 | T | 0.3636 | 0.07692 | G | 0.0001458 | 6.857 | 3.8362425 | CSMD1 |
| rs7901425 | 10 | 130778057 | C | 0.3636 | 0.07692 | T | 0.0001458 | 6.857 | 3.8362425 | |
| rs1023825 | 2 | 79099616 | T | 0.5909 | 0.2308 | G | 0.0001497 | 4.815 | 3.8247782 | |
| rs6532729 | 4 | 99365459 | C | 0.5909 | 0.2308 | T | 0.0001497 | 4.815 | 3.8247782 | |
| rs277973 | 5 | 70995578 | T | 0.5909 | 0.2308 | G | 0.0001497 | 4.815 | 3.8247782 | |
| rs9569891 | 13 | 58048371 | T | 0.5909 | 0.2308 | C | 0.0001497 | 4.815 | 3.8247782 | |
| rs6550478 | 3 | 37501017 | A | 0.2955 | 0.6538 | G | 0.000163 | 0.222 | 3.7878124 | ITGA9 |
| rs7081958 | 10 | 58606559 | A | 0.5227 | 0.1795 | G | 0.0001652 | 5.007 | 3.78199 | |
| rs12242643 | 10 | 58615726 | C | 0.5227 | 0.1795 | T | 0.0001652 | 5.007 | 3.78199 | |
| rs3213858 | 5 | 146760179 | T | 0.3409 | 0.0641 | C | 0.0001773 | 7.552 | 3.7512913 | DPYSL3 |
| rs820082 | 6 | 35139419 | A | 0.3409 | 0.0641 | G | 0.0001773 | 7.552 | 3.7512913 | ANKS1A |
| rs12774599 | 10 | 130795782 | T | 0.3409 | 0.0641 | G | 0.0001773 | 7.552 | 3.7512913 | |
| rs2288726 | 12 | 97608518 | T | 0.06818 | 0.3718 | G | 0.0001983 | 0.1236 | 3.7026773 | APAF1 |

FIG. 3A

| | | | | | | | | | |
|---|---|---|---|---|---|---|---|---|---|
| rs7879330 | 23 | 14395566 | A | 0.4 | 0.0678 | G | 0.0002016 | 9.167 | 3.6955095 | |
| rs2814734 | 9 | 87182609 | A | 0.02273 | 0.2821 | C | 0.0002097 | 0.0592 | 3.6784016 | |
| rs10089613 | 8 | 122595227 | C | 0.4545 | 0.141 | T | 0.0002118 | 5.076 | 3.674074 | |
| rs10520308 | 2 | 82003125 | C | 0.3864 | 0.08974 | A | 0.0002196 | 6.386 | 3.6583677 | |
| rs1032719 | 5 | 7536911 | G | 0.04545 | 0.3333 | A | 0.000223 | 0.09524 | 3.6516951 | ADCY2 |
| rs16953945 | 17 | 4319847 | A | 0.1818 | 0.5256 | G | 0.0002246 | 0.2005 | 3.6485902 | SPNS3 |
| rs10953428 | 7 | 103814099 | T | 0.1136 | 0.4359 | C | 0.0002269 | 0.1659 | 3.6441655 | LHFPL3 |
| rs1989823 | 7 | 103823052 | C | 0.1136 | 0.4359 | T | 0.0002269 | 0.1659 | 3.6441655 | LHFPL3 |
| rs1865651 | 2 | 174015846 | C | 0.6364 | 0.2821 | T | 0.0002278 | 4.455 | 3.6424463 | |
| rs6501658 | 17 | 69173224 | C | 0.5 | 0.1667 | T | 0.0002281 | 5 | 3.6418747 | LOC728102 |
| rs11890028 | 2 | 166651523 | G | 0.4773 | 0.1538 | T | 0.0002288 | 5.022 | 3.640544 | |
| rs2938033 | 18 | 43510320 | G | 0.4773 | 0.1538 | A | 0.0002288 | 5.022 | 3.640544 | |
| rs12186252 | 4 | 6166295 | T | 0.5227 | 0.1923 | C | 0.0002313 | 4.6 | 3.6358244 | JAKMIP1 |
| rs2808067 | 10 | 32085938 | A | 0.5227 | 0.1923 | G | 0.0002313 | 4.6 | 3.6358244 | |
| rs3934812 | 16 | 87674956 | C | 0.5227 | 0.1923 | T | 0.0002313 | 4.6 | 3.6358244 | |
| rs2204630 | 7 | 94409268 | T | 0.6136 | 0.2692 | G | 0.0002445 | 4.311 | 3.6117211 | PPP1R9A |
| rs2056862 | 8 | 88643449 | C | 0.6136 | 0.2692 | A | 0.0002445 | 4.311 | 3.6117211 | |
| rs1801783 | 1 | 225247481 | G | 0.04545 | 0.3205 | A | 0.0002458 | 0.101 | 3.6094181 | CDC42BPA |
| rs1878059 | 18 | 42488544 | A | 0.04545 | 0.3205 | G | 0.0002458 | 0.101 | 3.6094181 | LOC647011 |
| rs5999636 | 22 | 33661041 | T | 0.04545 | 0.3205 | C | 0.0002458 | 0.101 | 3.6094181 | |
| rs2033860 | 3 | 166372514 | G | 0.2045 | 0.5513 | A | 0.0002523 | 0.2093 | 3.5980827 | |
| rs3792426 | 3 | 166392889 | T | 0.2045 | 0.5513 | C | 0.0002523 | 0.2093 | 3.5980827 | SLITRK3 |
| rs261861 | 1 | 239162199 | A | 0.6591 | 0.3077 | G | 0.0002631 | 4.35 | 3.5798792 | RGS7 |
| rs17503919 | 6 | 89622456 | G | 0 | 0.2308 | A | 0.000264 | 0 | 3.5783961 | RNGTT |
| rs940522 | 3 | 181194826 | T | 0 | 0.2179 | G | 0.0002812 | 0 | 3.5509847 | PEX5L |
| rs10013819 | 4 | 25186282 | A | 0 | 0.2179 | G | 0.0002812 | 0 | 3.5509847 | |
| rs1535678 | 9 | 8499378 | C | 0.2727 | 0.03846 | A | 0.0002874 | 9.375 | 3.5415132 | PTPRD |
| rs233557 | 16 | 64918319 | T | 0.2727 | 0.03846 | C | 0.0002874 | 9.375 | 3.5415132 | |
| rs7974562 | 12 | 114502535 | T | 0.2727 | 0.6282 | C | 0.0002907 | 0.2219 | 3.536555 | |
| rs10198974 | 2 | 41350234 | C | 0.6818 | 0.3333 | T | 0.0002929 | 4.286 | 3.5332806 | |
| rs6085283 | 20 | 580959 | T | 0.6818 | 0.3333 | C | 0.0002929 | 4.286 | 3.5332806 | SRXN1 |
| rs2066593 | 13 | 49619118 | C | 0.6364 | 0.2949 | T | 0.0002971 | 4.185 | 3.5270973 | |
| rs12904249 | 15 | 23622445 | A | 0.6364 | 0.2949 | G | 0.0002971 | 4.185 | 3.5270973 | ATP10A |
| rs4688381 | 3 | 63202226 | A | 0.1364 | 0.4615 | G | 0.0002986 | 0.1842 | 3.5249102 | |
| rs2894401 | 6 | 35516937 | A | 0.1364 | 0.4615 | G | 0.0002986 | 0.1842 | 3.5249102 | |
| rs13274046 | 8 | 116082698 | T | 0.1364 | 0.4615 | C | 0.0002986 | 0.1842 | 3.5249102 | |
| rs33053 | 3 | 161084457 | T | 0.09091 | 0.3974 | C | 0.0003098 | 0.1516 | 3.5089186 | SCHIP1 |
| rs1596860 | 13 | 24293067 | G | 0.09091 | 0.3974 | A | 0.0003098 | 0.1516 | 3.5089186 | RNF17 |
| rs9507425 | 13 | 24338318 | A | 0.09091 | 0.3974 | G | 0.0003098 | 0.1516 | 3.5089186 | RNF17 |
| rs12622579 | 2 | 41352004 | C | 0.7045 | 0.359 | T | 0.0003155 | 4.258 | 3.5010006 | |
| rs10506125 | 12 | 37406554 | T | 0.2955 | 0.641 | C | 0.0003155 | 0.2348 | 3.5010006 | CPNE8 |
| rs11672145 | 19 | 12361149 | G | 0.5682 | 0.2308 | T | 0.0003199 | 4.386 | 3.4949858 | ZNF799 |
| rs6747268 | 2 | 209355227 | G | 0.7727 | 0.4359 | T | 0.0003268 | 4.4 | 3.485718 | |
| rs11770288 | 7 | 94355331 | T | 0.5455 | 0.2179 | C | 0.0003284 | 4.306 | 3.4835969 | |
| rs10839595 | 11 | 6676762 | A | 0.7273 | 0.3846 | G | 0.0003292 | 4.267 | 3.4825402 | |
| rs6632863 | 23 | 16592583 | C | 0.6286 | 0.2373 | T | 0.0003563 | 5.44 | 3.4481842 | CTPS2 |
| rs6875512 | 5 | 31367532 | C | 0.5 | 0.1795 | A | 0.0003566 | 4.571 | 3.4478187 | |
| rs3098360 | 10 | 58495356 | C | 0.5 | 0.1795 | T | 0.0003566 | 4.571 | 3.4478187 | |
| rs12918939 | 16 | 64698060 | G | 0.3409 | 0.07692 | A | 0.0003627 | 6.207 | 3.4404524 | |
| rs4746004 | 10 | 71228236 | G | 0.02273 | 0.2692 | A | 0.0004014 | 0.06312 | 3.3964226 | |
| rs1275828 | 14 | 69271895 | G | 0.02273 | 0.2692 | A | 0.0004014 | 0.06312 | 3.3964226 | |
| rs4704050 | 5 | 70829327 | G | 0.5909 | 0.2564 | A | 0.0004061 | 4.189 | 3.391367 | BDP1 |

FIG. 3B

| | | | | | | | | | |
|---|---|---|---|---|---|---|---|---|---|
| rs11246756 | 12 | 130743401 | G | 0.5909 | 0.2564 | T | 0.0004061 | 4.189 | 3.391367 |
| rs4813023 | 20 | 10142246 | T | 0.5909 | 0.2564 | C | 0.0004061 | 4.189 | 3.391367 |
| rs7920439 | 10 | 13332410 | T | 0.2045 | 0.01282 | G | 0.0004192 | 19.8 | 3.3775787 |
| rs12418369 | 11 | 4621018 | A | 0.2045 | 0.01282 | G | 0.0004192 | 19.8 | 3.3775787 |
| rs7326004 | 13 | 107155619 | T | 0.2045 | 0.01282 | C | 0.0004192 | 19.8 | 3.3775787 LOC728215 |
| rs2034127 | 3 | 59343114 | A | 0.3182 | 0.0641 | G | 0.0004221 | 6.813 | 3.3745846 |
| rs7628370 | 3 | 59345640 | C | 0.3182 | 0.0641 | A | 0.0004221 | 6.813 | 3.3745846 |
| rs7581 | 9 | 110819068 | G | 0.3182 | 0.0641 | A | 0.0004221 | 6.813 | 3.3745846 C9orf5 |
| rs627432 | 13 | 28430501 | T | 0.3182 | 0.0641 | C | 0.0004221 | 6.813 | 3.3745846 |
| rs799467 | 14 | 34571253 | C | 0.3182 | 0.0641 | T | 0.0004221 | 6.813 | 3.3745846 |
| rs9924119 | 16 | 69900898 | C | 0.3182 | 0.0641 | A | 0.0004221 | 6.813 | 3.3745846 |
| rs11653735 | 17 | 77802222 | T | 0.3182 | 0.0641 | C | 0.0004221 | 6.813 | 3.3745846 CSNK1D |
| rs13269936 | 8 | 25994155 | G | 0.06818 | 0.3462 | T | 0.0004266 | 0.1382 | 3.3699791 |
| rs9553435 | 13 | 24235300 | A | 0.06818 | 0.3462 | C | 0.0004266 | 0.1382 | 3.3699791 RNF17 |
| rs642407 | 5 | 32542605 | A | 0.1591 | 0.4744 | G | 0.000437 | 0.2096 | 3.3595186 |
| rs495487 | 11 | 78709319 | G | 0.1591 | 0.4744 | A | 0.000437 | 0.2096 | 3.3595186 |
| rs625061 | 11 | 102537638 | G | 0.1136 | 0.4231 | T | 0.0004391 | 0.1748 | 3.3574366 DYNC2H1 |
| rs4600965 | 4 | 157364111 | G | 0.1818 | 0.5128 | A | 0.00044 | 0.2111 | 3.3565473 |
| rs2795492 | 9 | 99953197 | A | 0.1818 | 0.5128 | G | 0.00044 | 0.2111 | 3.3565473 CORO2A |
| rs2680700 | 17 | 53795541 | A | 0.6136 | 0.2778 | C | 0.0004546 | 4.129 | 3.3423706 RNF43 |
| rs7823558 | 8 | 101948774 | G | 0.4091 | 0.1154 | A | 0.0004597 | 5.308 | 3.3375255 |
| rs6481254 | 10 | 58586765 | A | 0.4091 | 0.1154 | C | 0.0004597 | 5.308 | 3.3375255 |
| rs7089692 | 10 | 58603555 | C | 0.4091 | 0.1154 | T | 0.0004597 | 5.308 | 3.3375255 |
| rs5980319 | 23 | 16611686 | G | 0.6286 | 0.2542 | A | 0.0004612 | 4.964 | 3.3361107 CTPS2 |
| rs1432180 | 2 | 81933368 | A | 0.3636 | 0.08974 | G | 0.0004786 | 5.796 | 3.3200273 |
| rs13144587 | 4 | 67295867 | C | 0.3636 | 0.08974 | A | 0.0004786 | 5.796 | 3.3200273 |
| rs4945442 | 11 | 80244906 | A | 0.5455 | 0.2143 | G | 0.000486 | 4.4 | 3.3133637 |
| rs4920935 | 5 | 116134125 | G | 0.4091 | 0.1184 | A | 0.0004872 | 5.154 | 3.3122927 |
| rs391224 | 3 | 37498640 | T | 0.6136 | 0.2821 | C | 0.0004924 | 4.043 | 3.307682 ITGA9 |
| rs191649 | 18 | 31332044 | G | 0.6136 | 0.2821 | A | 0.0004924 | 4.043 | 3.307682 C18orf37 |
| rs10082587 | 11 | 132762982 | A | 0.1136 | 0.4103 | G | 0.0004987 | 0.1843 | 3.3021606 OPCML |
| rs2760912 | 13 | 49630676 | A | 0.1136 | 0.4103 | G | 0.0004987 | 0.1843 | 3.3021606 |
| rs4949509 | 1 | 30124116 | C | 0.4545 | 0.1538 | T | 0.0005011 | 4.583 | 3.3000756 |
| rs172823 | 3 | 25331332 | T | 0.4545 | 0.1538 | C | 0.0005011 | 4.583 | 3.3000756 |
| rs10499030 | 6 | 100851002 | T | 0.4545 | 0.1538 | C | 0.0005011 | 4.583 | 3.3000756 |
| rs7122962 | 11 | 123818932 | A | 0.4545 | 0.1538 | G | 0.0005011 | 4.583 | 3.3000756 |
| rs876144 | 14 | 34536335 | C | 0.4545 | 0.1538 | A | 0.0005011 | 4.583 | 3.3000756 SRP54 |
| rs4765821 | 12 | 1482107 | T | 0.2045 | 0.5385 | G | 0.0005023 | 0.2204 | 3.2990368 |
| rs2066910 | 22 | 41859461 | C | 0.2045 | 0.5385 | T | 0.0005023 | 0.2204 | 3.2990368 MCAT |
| rs4140754 | 2 | 41372882 | A | 0.1818 | 0.5 | G | 0.0005027 | 0.2222 | 3.2986911 |
| rs2927633 | 5 | 73816540 | A | 0.1818 | 0.5 | G | 0.0005027 | 0.2222 | 3.2986911 |
| rs10764851 | 10 | 130807814 | C | 0.1818 | 0.5 | T | 0.0005027 | 0.2222 | 3.2986911 |
| rs1173179 | 5 | 4856549 | T | 0.2857 | 0.6282 | G | 0.0005065 | 0.2367 | 3.2954206 |
| rs2893721 | 10 | 58623966 | G | 0.5227 | 0.2051 | A | 0.000509 | 4.244 | 3.2932822 |
| rs4713842 | 6 | 35302610 | G | 0 | 0.2051 | A | 0.0005225 | 0 | 3.2819137 SCUBE3 |
| rs4713843 | 6 | 35311723 | T | 0 | 0.2051 | C | 0.0005225 | 0 | 3.2819137 SCUBE3 |
| rs707969 | 6 | 35397424 | A | 0 | 0.2051 | G | 0.0005225 | 0 | 3.2819137 DEF6 |
| rs16913276 | 11 | 13838859 | A | 0 | 0.2051 | G | 0.0005225 | 0 | 3.2819137 LOC729147 |
| rs4303985 | 4 | 99618771 | T | 0.6591 | 0.3205 | G | 0.0005545 | 4.099 | 3.2560984 TSPAN5 |
| rs10506126 | 12 | 37409511 | A | 0.6591 | 0.3205 | G | 0.0005545 | 4.099 | 3.2560984 CPNE8 |
| rs2073835 | 9 | 135522004 | T | 0.2045 | 0.5256 | C | 0.0005567 | 0.2321 | 3.2543788 SARDH |
| rs16943741 | 15 | 84079483 | G | 0.2045 | 0.5256 | A | 0.0005567 | 0.2321 | 3.2543788 AKAP13 |

FIG. 3C

| | | | | | | | | | |
|---|---|---|---|---|---|---|---|---|---|
| rs8091335 | 18 | 31282121 | C | 0.6667 | 0.3333 | A | 0.0005589 | 4 | 3.2526659 | |
| rs2373001 | 2 | 37451925 | C | 0.1591 | 0 | T | 0.0005721 | | 3.2425281 | QPCT |
| rs6758414 | 2 | 121012955 | A | 0.1591 | 0 | G | 0.0005721 | | 3.2425281 | |
| rs2361323 | 12 | 51201099 | A | 0.1591 | 0 | G | 0.0005721 | | 3.2425281 | |
| rs9520550 | 13 | 107135055 | A | 0.1591 | 0 | G | 0.0005721 | | 3.2425281 | LOC728215 |
| rs7320808 | 13 | 107138864 | T | 0.1591 | 0 | C | 0.0005721 | | 3.2425281 | LOC728215 |
| rs4113420 | 13 | 107154330 | T | 0.1591 | 0 | C | 0.0005721 | | 3.2425281 | LOC728215 |
| rs10520223 | 2 | 79081765 | A | 0.6364 | 0.3077 | G | 0.0005747 | 3.938 | 3.2405588 | |
| rs12614588 | 2 | 79082779 | C | 0.6364 | 0.3077 | T | 0.0005747 | 3.938 | 3.2405588 | |
| rs12510203 | 4 | 129696979 | C | 0.6364 | 0.3077 | T | 0.0005747 | 3.938 | 3.2405588 | |
| rs1405842 | 7 | 94356931 | G | 0.3636 | 0.6923 | A | 0.0005747 | 0.254 | 3.2405588 | |
| rs1527676 | 7 | 94403058 | A | 0.6364 | 0.3077 | G | 0.0005747 | 3.938 | 3.2405588 | PPP1R9A |
| rs870431 | 12 | 37239340 | G | 0.6364 | 0.3077 | A | 0.0005747 | 3.938 | 3.2405588 | |
| rs11376 | 14 | 50274746 | G | 0.2273 | 0.5526 | A | 0.0005778 | 0.2381 | 3.2382225 | NIN |
| rs1021813 | 3 | 59388100 | C | 0.1364 | 0.4487 | T | 0.0005799 | 0.194 | 3.2366469 | |
| rs6536157 | 4 | 157340270 | T | 0.1364 | 0.4487 | C | 0.0005799 | 0.194 | 3.2366469 | |
| rs6469563 | 8 | 116079356 | T | 0.1364 | 0.4487 | C | 0.0005799 | 0.194 | 3.2366469 | |
| rs547043 | 23 | 150087901 | A | 0.6571 | 0.2881 | G | 0.0005936 | 4.735 | 3.2265061 | |
| rs10495026 | 1 | 214767553 | C | 0.6818 | 0.3462 | T | 0.0005941 | 4.048 | 3.2261404 | ESRRG |
| rs12696221 | 3 | 166354274 | G | 0.6818 | 0.3462 | A | 0.0005941 | 4.048 | 3.2261404 | |
| rs809845 | 13 | 49622056 | T | 0.3182 | 0.6538 | C | 0.0005941 | 0.2471 | 3.2261404 | |
| rs738118 | 2 | 41376902 | G | 0.2273 | 0.5513 | A | 0.0005965 | 0.2394 | 3.2243896 | |
| rs2858 | 5 | 173889562 | G | 0.2273 | 0.5513 | T | 0.0005965 | 0.2394 | 3.2243896 | |
| rs4346964 | 8 | 99421813 | G | 0.09091 | 0.3846 | A | 0.0006092 | 0.16 | 3.2152401 | |
| rs1865874 | 8 | 116106295 | G | 0.09091 | 0.3846 | A | 0.0006092 | 0.16 | 3.2152401 | |
| rs2511887 | 11 | 86275132 | A | 0.2955 | 0.6282 | G | 0.0006191 | 0.2482 | 3.2082392 | |
| rs712306 | 14 | 34465568 | G | 0.7045 | 0.3718 | T | 0.0006191 | 4.029 | 3.2082392 | |
| rs672856 | 18 | 210658 | G | 0.25 | 0.5769 | A | 0.0006206 | 0.2444 | 3.2071882 | THOC1 |
| rs16864725 | 3 | 190890138 | A | 0.2273 | 0.02564 | G | 0.0006218 | 11.18 | 3.2063493 | TP63 |
| rs883073 | 7 | 22150784 | A | 0.2273 | 0.02564 | G | 0.0006218 | 11.18 | 3.2063493 | RAPGEF5 |
| rs4500599 | 13 | 57753504 | C | 0.2273 | 0.02564 | A | 0.0006218 | 11.18 | 3.2063493 | |
| rs6451438 | 5 | 39673322 | C | 0.2727 | 0.6026 | T | 0.0006282 | 0.2473 | 3.2019021 | |
| rs7281481 | 21 | 45621434 | G | 0.2727 | 0.6026 | A | 0.0006282 | 0.2473 | 3.2019021 | |
| rs2466066 | 8 | 32557958 | T | 0.4773 | 0.1711 | C | 0.0006304 | 4.425 | 3.2003838 | NRG1 |
| rs10972619 | 9 | 35898488 | G | 0.1364 | 0.4359 | A | 0.0006383 | 0.2043 | 3.1949752 | LOC158376 |
| rs9309717 | 2 | 3474085 | G | 0.09091 | 0.3718 | A | 0.0006437 | 0.169 | 3.1913165 | |
| rs721250 | 2 | 59630520 | G | 0.6591 | 0.3333 | A | 0.0006486 | 3.867 | 3.1880231 | |
| rs6853651 | 4 | 157343816 | A | 0.6591 | 0.3333 | C | 0.0006486 | 3.867 | 3.1880231 | |
| rs2340252 | 4 | 157348668 | A | 0.6591 | 0.3333 | C | 0.0006486 | 3.867 | 3.1880231 | |
| rs5944265 | 23 | 25937892 | A | 0.2 | 0 | C | 0.000657 | | 3.1824346 | |
| rs563002 | 1 | 112118658 | C | 0.4091 | 0.1282 | T | 0.0006579 | 4.708 | 3.1818401 | KCND3 |
| rs13639 | 2 | 41957833 | T | 0.4091 | 0.1282 | G | 0.0006579 | 4.708 | 3.1818401 | |
| rs2141599 | 3 | 178325169 | T | 0.5455 | 0.2308 | C | 0.0006797 | 4 | 3.1676827 | TBL1XR1 |
| rs11953826 | 5 | 174410242 | C | 0.5455 | 0.2308 | A | 0.0006797 | 4 | 3.1676827 | |
| rs1441234 | 2 | 41341895 | G | 0.6818 | 0.359 | A | 0.0007103 | 3.827 | 3.1485582 | |
| rs6472054 | 8 | 49881005 | C | 0.6818 | 0.359 | T | 0.0007103 | 3.827 | 3.1485582 | |
| rs2094394 | 9 | 36692096 | C | 0.6818 | 0.359 | T | 0.0007103 | 3.827 | 3.1485582 | |
| rs197419 | 1 | 112116973 | C | 0.5682 | 0.2436 | A | 0.0007253 | 4.086 | 3.1394823 | |
| rs777354 | 2 | 166260054 | A | 0.5682 | 0.2436 | G | 0.0007253 | 4.086 | 3.1394823 | TTC21B |
| rs11067819 | 12 | 114810647 | G | 0.5682 | 0.2436 | A | 0.0007253 | 4.086 | 3.1394823 | |
| rs2075379 | 12 | 29707647 | G | 0.25 | 0.03846 | A | 0.0007612 | 8.333 | 3.1185012 | TMTC1 |
| rs12957214 | 18 | 35189538 | C | 0.25 | 0.03846 | A | 0.0007612 | 8.333 | 3.1185012 | |

FIG. 3D

| | | | | | | | | | |
|---|---|---|---|---|---|---|---|---|---|
| rs5752585 | 22 | 26266871 | A | 0.25 | 0.03846 | C | 0.0007612 | 8.333 | 3.1185012 | |
| rs4949503 | 1 | 30102287 | C | 0.4773 | 0.1795 | T | 0.0007642 | 4.174 | 3.116793 | |
| rs4949507 | 1 | 30110659 | A | 0.4773 | 0.1795 | C | 0.0007642 | 4.174 | 3.116793 | |
| rs4504262 | 4 | 96428827 | T | 0.4773 | 0.1795 | G | 0.0007642 | 4.174 | 3.116793 | UNC5C |
| rs2767001 | 9 | 112623833 | A | 0.4773 | 0.1795 | G | 0.0007642 | 4.174 | 3.116793 | |
| rs5970533 | 23 | 150005809 | T | 0.1429 | 0.4915 | C | 0.0007679 | 0.1724 | 3.1146953 | |
| rs7711344 | 5 | 117758026 | A | 0.06818 | 0.3333 | C | 0.0007714 | 0.1463 | 3.1127204 | |
| rs10454357 | 8 | 26008080 | G | 0.06818 | 0.3333 | A | 0.0007714 | 0.1463 | 3.1127204 | |
| rs16932803 | 9 | 35951087 | T | 0.06818 | 0.3333 | G | 0.0007714 | 0.1463 | 3.1127204 | |
| rs1430475 | 14 | 81710262 | A | 0.02273 | 0.25 | G | 0.0007722 | 0.06977 | 3.1122702 | |
| rs7316843 | 12 | 69736078 | C | 0.1591 | 0.4615 | T | 0.0007743 | 0.2207 | 3.1110907 | |
| rs9814318 | 3 | 63136521 | T | 0.1591 | 0.4605 | C | 0.0007813 | 0.2216 | 3.1071822 | |
| rs17528049 | 1 | 225258279 | C | 0.02273 | 0.2564 | A | 0.0007876 | 0.06744 | 3.1036943 | CDC42BPA |
| rs13132933 | 4 | 123230037 | C | 0.02273 | 0.2564 | T | 0.0007876 | 0.06744 | 3.1036943 | |
| rs1490819 | 5 | 67135554 | T | 0.02273 | 0.2564 | C | 0.0007876 | 0.06744 | 3.1036943 | |
| rs1388122 | 5 | 67136012 | G | 0.02273 | 0.2564 | A | 0.0007876 | 0.06744 | 3.1036943 | |
| rs1490822 | 5 | 67137077 | G | 0.02273 | 0.2564 | A | 0.0007876 | 0.06744 | 3.1036943 | |
| rs991264 | 15 | 52063843 | T | 0.1905 | 0.5128 | C | 0.0007898 | 0.2235 | 3.1024829 | |
| rs1864551 | 2 | 79620045 | A | 0.3636 | 0.1026 | G | 0.0007983 | 5 | 3.0978339 | CTNNA2 |
| rs12186253 | 4 | 6166347 | T | 0.3636 | 0.1026 | C | 0.0007983 | 5 | 3.0978339 | JAKMIP1 |
| rs10764855 | 10 | 130809932 | A | 0.3636 | 0.1026 | G | 0.0007983 | 5 | 3.0978339 | |
| rs2068099 | 3 | 46524308 | T | 0.04545 | 0.2949 | C | 0.0008386 | 0.1139 | 3.0764451 | |
| rs10078211 | 5 | 57999775 | T | 0.04545 | 0.2949 | C | 0.0008386 | 0.1139 | 3.0764451 | RAB3C |
| rs17435904 | 8 | 71017763 | T | 0.04545 | 0.2949 | C | 0.0008386 | 0.1139 | 3.0764451 | |
| rs10742158 | 11 | 26714051 | A | 0.04545 | 0.2949 | C | 0.0008386 | 0.1139 | 3.0764451 | |
| rs11656239 | 17 | 9891392 | T | 0.04545 | 0.2949 | C | 0.0008386 | 0.1139 | 3.0764451 | GAS7 |
| rs1997810 | 20 | 11972709 | T | 0.04545 | 0.2949 | C | 0.0008386 | 0.1139 | 3.0764451 | |
| rs2356417 | 16 | 69913636 | C | 0.3095 | 0.06579 | T | 0.0008571 | 6.366 | 3.0669685 | |
| rs449095 | 4 | 103332760 | A | 0.5 | 0.1923 | G | 0.0008596 | 4.2 | 3.0657036 | |
| rs823922 | 9 | 103697095 | A | 0.5 | 0.1923 | C | 0.0008596 | 4.2 | 3.0657036 | |
| rs3761966 | 5 | 70836231 | T | 0.5682 | 0.2564 | C | 0.0008616 | 3.816 | 3.0646943 | BDP1 |
| rs3808899 | 9 | 124032645 | T | 0.5682 | 0.2564 | C | 0.0008616 | 3.816 | 3.0646943 | |
| rs1946977 | 4 | 187686129 | G | 0.04762 | 0.3077 | T | 0.0008631 | 0.1125 | 3.0639389 | |
| rs1323690 | 11 | 34457263 | T | 0.5909 | 0.2692 | C | 0.0008685 | 3.921 | 3.0612302 | ELF5 |
| rs1886714 | 16 | 19970009 | C | 0.5909 | 0.2692 | T | 0.0008685 | 3.921 | 3.0612302 | GPR139 |
| rs6092527 | 20 | 55746462 | A | 0.5909 | 0.2692 | G | 0.0008685 | 3.921 | 3.0612302 | |
| rs1538389 | 1 | 112128667 | A | 0.3182 | 0.07692 | G | 0.0008767 | 5.6 | 3.057149 | KCND3 |
| rs4839168 | 1 | 112144032 | T | 0.3182 | 0.07692 | C | 0.0008767 | 5.6 | 3.057149 | KCND3 |
| rs631037 | 1 | 112145890 | A | 0.3182 | 0.07692 | G | 0.0008767 | 5.6 | 3.057149 | KCND3 |
| rs10979638 | 9 | 110784592 | C | 0.3182 | 0.07692 | A | 0.0008767 | 5.6 | 3.057149 | CTNNAL1 |
| rs2039372 | 10 | 130790379 | C | 0.3182 | 0.07692 | T | 0.0008767 | 5.6 | 3.057149 | |
| rs12778834 | 10 | 130792327 | A | 0.3182 | 0.07692 | C | 0.0008767 | 5.6 | 3.057149 | |
| rs726207 | 20 | 15962926 | T | 0.3182 | 0.07692 | G | 0.0008767 | 5.6 | 3.057149 | MACROD2 |
| rs9570815 | 13 | 62759990 | C | 0.1136 | 0.3974 | A | 0.0008844 | 0.1944 | 3.0533513 | |
| rs1886779 | 14 | 32728645 | C | 0.1136 | 0.3974 | T | 0.0008844 | 0.1944 | 3.0533513 | NPAS3 |
| rs7049850 | 23 | 16607104 | C | 0.6286 | 0.2586 | T | 0.0008857 | 4.851 | 3.0527134 | CTPS2 |
| rs10112994 | 8 | 116016470 | C | 0.1818 | 0.4872 | T | 0.0009002 | 0.2339 | 3.045661 | |
| rs10846577 | 12 | 122966214 | C | 0.1818 | 0.4872 | T | 0.0009002 | 0.2339 | 3.045661 | |
| rs2423413 | 20 | 9606534 | C | 0.1818 | 0.4872 | T | 0.0009002 | 0.2339 | 3.045661 | PAK7 |
| rs12451131 | 17 | 3365426 | T | 0.619 | 0.2973 | C | 0.0009006 | 3.841 | 3.0454681 | TRPV3 |
| rs5936422 | 23 | 147619197 | A | 0.4286 | 0.1186 | G | 0.0009536 | 5.571 | 3.0206338 | AFF2 |
| rs930516 | 13 | 70225002 | T | 0.3864 | 0.1154 | C | 0.0009565 | 4.827 | 3.019315 | |

FIG. 3E

| | | | | | | | | | | |
|---|---|---|---|---|---|---|---|---|---|---|
| rs6063739 | 20 | 50065209 | C | 0.3864 | 0.1154 | A | 0.0009565 | 4.827 | 3.019315 | |
| rs12776148 | 10 | 130803689 | C | 0.3095 | 0.06757 | T | 0.0009808 | 6.186 | 3.0084195 | |
| rs4957661 | 5 | 105922009 | T | 0.2045 | 0.5132 | C | 0.0009842 | 0.244 | 3.0069166 | |
| rs1980977 | 21 | 45640447 | A | 0.2045 | 0.5132 | G | 0.0009842 | 0.244 | 3.0069166 | |
| rs12540943 | 7 | 151141463 | A | 0.2955 | 0.0641 | G | 0.0009958 | 6.123 | 3.0018279 | PRKAG2 |
| rs12155715 | 8 | 19270615 | C | 0.2955 | 0.0641 | T | 0.0009958 | 6.123 | 3.0018279 | SH2D4A |
| rs725076 | 10 | 105571255 | C | 0.2955 | 0.0641 | A | 0.0009958 | 6.123 | 3.0018279 | SH3PXD2A |
| rs11111712 | 12 | 102605853 | T | 0.2955 | 0.0641 | C | 0.0009958 | 6.123 | 3.0018279 | STAB2 |
| rs906363 | 1 | 210925420 | G | 0 | 0.1923 | A | 0.0009968 | 0 | 3.001392 | SNFT |
| rs4692399 | 4 | 25760155 | A | 0 | 0.1923 | G | 0.0009968 | 0 | 3.001392 | |
| rs16871870 | 5 | 73778817 | C | 0 | 0.1923 | A | 0.0009968 | 0 | 3.001392 | |
| rs6581016 | 12 | 53744697 | A | 0 | 0.1923 | C | 0.0009968 | 0 | 3.001392 | |
| rs7146578 | 14 | 69237392 | G | 0 | 0.1923 | A | 0.0009968 | 0 | 3.001392 | KIAA0247 |
| rs3784556 | 15 | 72119241 | T | 0 | 0.1923 | G | 0.0009968 | 0 | 3.001392 | PML |

FIG. 3F

SEQUENCE LISTING

```
<160> NUMBER OF SEQ ID NOS: 19

<210> SEQ ID NO 1
<211> LENGTH: 601
<212> TYPE: DNA
<213> ORGANISM: Homo sapiens

<400> SEQUENCE: 1
ccctcatgct agcaatcctt tctcagtcag ctctgccatt acagaggatg gttgtaacaa     60
attttgtcct ctgaaactaa gcaaatata tcaatttctc acagctgaca gagccaaaag    120
gtggaaaggc ttgatataag taaacaatg gaatgcttag ctgcaggcct agaaaggacc    180
ctttaattgc caggctctgt caccatatca agcgtggtag ggttcgggc tgaagcatac    240 ttacgaagac acacaaggca gtagctggta ccctcacttc tttaccagaa ccaggatgag    300
yatccacatt gtcctggggg actgggaagg aagagacaga gcgtctccta agaaataaca    360
taaagacaaa tattagacag gattgcagag gtttactgct catcaaattg ttagaaagga    420
ctccaagacg accttgctta agcagactgc ctctgttgat agcctgtcct tctagattct    480
tcaaactaca gaacaattca caaaaaaatc aaaagcaccc tcactcaaat gagaaagaga    540
gccagcacat gccttactct cctgcacact aacctgtgga ctccaaaacc caacaatgaa    600
a                                                                    601

<210> SEQ ID NO 2
<211> LENGTH: 646
<212> TYPE: DNA
<213> ORGANISM: Homo sapiens

<400> SEQUENCE: 2
aagatttatt gggggtaaga agagctaatg cctatgaaag ataaaggaga aaggagcaga     60
agtacggaga gaaaagacag ctttcagact gcagtccaga tctaactctg ggacgcaaga    120
gagggaagga taattctgtt gaaagagcat cagactgtga tgcggctgta agagtgtctc    180
aacgagccca gtgggagtt ccagccaaag attgcccagg agaagagtcg cactttgggc    240
agaaatggac aggcccgagc aaccctgcca tgttctgtca ttggctgggg gccacccagg    300
aggcaacatg gtctgacttg aatggtgtgg atccgaggct gcagcctgtc agctgtctgc    360
actccatgca acaggtcctt tgaatggcat gtgttcgtgg ctgccataaa ctgcagcctg    420
ccttttagcc ttacctcctt tgctcttgct ctctgacccy gtgttctggc aacactggcc    480
tgactacacg ccgtatcaca tacaaccaac tgcccatacc aaccccaacc ctgaccttg    540
```

```
ctcactcagt tctttctgcc tggaatgcca ctccttccca gttataccca gcaaaatcct    600
aatgtgcttt caaggcccaa cttaaaaatc atcttctctg gttgac                    646

<210> SEQ ID NO 3
<211> LENGTH: 601
<212> TYPE: DNA
<213> ORGANISM: Homo sapiens

<400> SEQUENCE: 3
atctttatgg aaagatgttc attattcact atattgaatt ttataatgtt aaactctgct     60
tttctttgca taaactatca gagattataa tactaaaatc ttaaatagtt aaattataag    120
taaattttgt gttttcccat atataaagt gatatattta atgaatgcta gtaatcttaa    180
actggttata aattttata ctacaatgag taccttcgag aaagcttatg gtataagaaa     240
tactatttcc aaaacatttt tgttgcacat ttttggtatt agactcatca ttccaatgac    300
rtctggatta tgggaagaaa ggagcctgac tcttatgatg gaataaccac aaatcagaga    360
ggagtcacaa tagcagctct tggtgcagac tgtataccga tagttttgc agatccagtc     420 aaaaaagcat gtggggttgc tcacgctggt aagtatactt aattaaacat ttagaatttt    480
actcattttg ttgtgcagga aaaattgtaa tttctttctg atggacatgg caaacagtta    540
attacattac actgtggtaa gtgtaatgat gggagaggcg gcatagtttt attatatggga   600 c                                                                    601

<210> SEQ ID NO 4
<211> LENGTH: 634
<212> TYPE: DNA
<213> ORGANISM: Homo sapiens

<400> SEQUENCE: 4
cccgccctgc caaggaatgt cacgagcctc aagcagattt gctcttagat atttcttttt     60
aatcgagtct aacagtgatt gttgagccgt ccttcatttt ttttttttt tgtaagatgc     120 ctctgtcaag aaggagccac gagttggctt tcatggaatg ggtgctcttg gtggccaaat    180
agaaataaaa cctggctgtc tggtcctgat ccactcacag aagtggcgta acacccttat    240
ttatgatctg gacattcaa caccatctta taaaagattc atagaataca cattcacaca    300
cccacaaaaa tcaaragagc agattttcca aaaataggtg caagaaagat ccaacttcca    360
ggataaaatt ttagaaccaa catttccatt agcaaaagcg gtcttgtcta aaactctacc    420
gaccgcgcta aaatcccatt caaaacagag ctctggttac gtagatcgtg atcaataatg    480
agaaactgtg aggcgtcccc gtgggatctg acacttccta ggggagcttc tctccactgg    540
taataaagat ataattagga atttcaacta cctgtgattt tgccaactta cggcatttgt    600
tgagaatttc ggtccctgtg tttatgcaca cacc                                634

<210> SEQ ID NO 5
<211> LENGTH: 801
<212> TYPE: DNA
<213> ORGANISM: Homo sapiens

<400> SEQUENCE: 5
ctagaacata tatgccaatg ggtagtgata cacaactgtc actggtaaag ttgcatacca     60
attcacaatc ctattctcat acccaagtta ctactacaca ttgctcttga gtcagtagct    120
gcatttgcca ccctggctca aaatatcagc catcacattt agtaaattct aacatacaaa    180
gcaaattagc actgatttat cagatttacc attgggtggg gtgaggagga ggaggatgct    240
```

```
ggctgactta gcccagtccc ttaagagctc tgttccagag aatatacttg tgctcttcct    300
ccatggccca gcatatgcac agggctccag tcatttgcct ccagcagggg gctcttccac    360
actcattcac agtcagctgg attccaatct ctgctcaagt rtgagcaatg tagatccagc    420
cccctggtta atgtattcat cactgttcaa gcccagtctc tttcagatgt tgagacagtg    480
gccctaactc tgtgtggctg gcccagagct gtgcacctac cctcactttc ataccacatt    540
aatttcagat ccttattgtc atgggtttcc caactacttt ttttcttca ggggaaacct     600 ccacaatgta gtttctaata tgttgaattc atactccaga aagtgtcctg tagaataatg    660
tcttactgaa aacggccatc acagccagga gtccttaact atgttctttg ataccttag     720 ttacagtttg ttgtcatgtt cttcacatct tgtgtgaaga ttgttcaagt attggccaaa    780
ggatatgtca ctatctaaaa t                                              801

<210> SEQ ID NO 6
<211> LENGTH: 401
<212> TYPE: DNA
<213> ORGANISM: Homo sapiens

<400> SEQUENCE: 6
atagctgtaa cactgtgtgc aggtatctgg ggtttctgtc gtgaccacgt ggcaggagct    60
gctgccactg ctgtctgatg ctcgccccac agtggaagga gatgctaaat tccgttacgc    120
attagaggtc agtgaaaagg aagatgcagt ttgttcccgt ccaggcacaa ggactcttga    180
atttgtccat agttaagaac rgctcatcca ggagcagagc gagaggccgg gctgcgcgtc    240
ctcatctcct ctcccagcct tcgcatcctc ctggctgcct cgcgtttcct ccacgggcct    300
ggctgaacgc acacacaggc ctgggggaga ctgcagagac acatcttcag ccacatcttc    360
tgtaaaacag tcactatggg atgacggtga ctggacagtg g                       401

<210> SEQ ID NO 7
<211> LENGTH: 601
<212> TYPE: DNA
<213> ORGANISM: Homo sapiens

<400> SEQUENCE: 7
acaatccaaa cagggtagtg gttacccctg aggagaaaac taggtaggag catggcggga    60
gaggaagatt gagaggtcta aggcaacttt atctactttc caaaatgttt taaaataaga    120
atgctttatt atttgtgtca tttttaaatt aataaagtag gcatgccatt ctgaaattcc    180
acgtctaaat ggcacaaaag tgtaagatag gcaccacagt tgcttataca acattactct    240
ccaaagatta tattcccaaa cgctttacct attccctctt agaaaagact tccagagtct    300
ytcagtcttc atcttggcct gtatttttaa cccattaggc atcctcttgg ggtaacttca    360
gcaggctcca taggtacaac aaccttcacg tgatctttaa attagctcca taatagtgat    420
aatgaggcag gaaccttgag ataaaaagca gatattacag gttccacttt cgcttctagc    480
actaatgatt acatggaaag tcgctcaacc caagttatag cttccacatt catatggaag    540
gaataacaac aagaattata cctcactcct actcagggac atgcaggtag gaaccacaac    600
a                                                                    601

<210> SEQ ID NO 8
<211> LENGTH: 401
<212> TYPE: DNA
<213> ORGANISM: Homo sapiens
```

```
<400> SEQUENCE: 8
aacggatcat caactccagg atactcactt ttgctaaatt ctcaatactt tgtaaagata      60
tcatgtccag gtgaacgtta aaataatctt accttgggga cctcataaga tgtggttcta     120
gtcaaacaca cttattccag gatatatttc agagtgactc caaattccca tctgttgcta    180
gaaccaatca tttctgccgt kccaaaaaat tatcgtagct cagaagacct atgttaaaaa    240
ggccaaaaaa aaaaaggaa tcaattagca ttttaatgtt aaaatgaaac taatttccag     300
tagcaaaata atggttttta accatgacac ctgcagtttc aggcaagtgg cagacagcca    360
aacatatcca tagttgtaag gtgtcctact attagggagg a                         401

<210> SEQ ID NO 9
<211> LENGTH: 201
<212> TYPE: DNA
<213> ORGANISM: Homo sapiens

<400> SEQUENCE: 9
agctgatgtc tgtctcatgg gcaaatacaa caaatactga catagatggc ctcaagagaa     60
gaaaaagtgg caaaacacct tattgactgc ttgttcgcag rctaaggttg tgacgagaag    120
tacaagagaa tgaatttggc cagctatctg gagagtaggg tacctgtgaa gcccaggcct    180
ctaaatgggg tcctctcaca t                                               201

<210> SEQ ID NO 10
<211> LENGTH: 401
<212> TYPE: DNA
<213> ORGANISM: Homo sapiens

<400> SEQUENCE: 10
cttcatttca aaaaagtttt tggcatttac ggaaggcttc ttaaacttct tccatggttt      60
gacatcattg actcagataa aggcctagga agccattcct cctattcagg atctaaaaaa    120
gcagcagttc acatttataa cgcattacaa ccagaacttg aggcctaaga aatttctatg    180
tcgagtccac agtttcaaac rcaaattcac tcatcaaggc tttgttcagg catcagggaa    240
acatcctggc agcaagtata cctatataag gaaatattag gtcacgatcc cataactcca    300
acacacaaga gatgcaccac acactttagg agacttccaa agcagaaaaa cacaagagac    360
tagggagaat gacctctctt cctagtttat gccttcaagg t                         401

<210> SEQ ID NO 11
<211> LENGTH: 401
<212> TYPE: DNA
<213> ORGANISM: Homo sapiens

<400> SEQUENCE: 11
accataaatc aataagaaaa aacaaatgat gaacaattca gtatgagaat aagcaaagaa      60
tataaacaaa tcattcaaaa aggaggaaat taagcttca gagaagcatg taaaggtaat      120
atccaactcc actaacaaga agggaaaaat tgaaatgaaa attaaaactg taatacagca    180
gtattcttat gagaaagaac rtagaatttc tgtgatacac tgtgctttca aaggcatata    240
gacaaagtac tcatgcattg ttagaagaag ggtaatttaa caatatctat caatgttaaa    300
aattgcttac atcttttgat gcagcaaatt gatgtatata tgtttcccta taaacatata    360
tacaaaggta ttcttcccat cattgtttgg aatagcccca a                         401

<210> SEQ ID NO 12
<211> LENGTH: 1001
```

<212> TYPE: DNA
<213> ORGANISM: Homo sapiens

<400> SEQUENCE: 12

```
agactcaatc acatgaggac tctaacttca gcagctattc caaatttgac cttataacta      60
aagaaaatca acacattatt ttgcacctga aatgcagttc ttgacgcggt gaattccccc     120
tccacccatc ccccgcatac ctggtaatga acatcatcag aagaagttga ttttaagcta     180
ggtagtcaag tacacatctt cattgtttaa ttgcagaact ctatcaaatc tccaactcaa     240
actatcctat gtgggctttc cacaaatgac agcatcattc tggctcattc gattcatcaa     300
caatttgctg atcagaccaa ctcaaggta aatagcaatt attttagaaa ttgtaataag     360
ggacacgttg cagagagcag gaaataaatc tcaccaaaaa gtgagggcct gctaccttgg     420
tgaagtttct acatatggtt tggaagatat cctggtccca tctgaagttg ctagttgcgt     480
tgccacagct ccatgcagga rtgcctatga tggacaaaag tgaagaaaaa tcttcccggt     540
gggcagagtt ttgagcagag caccaagtaa ttcattttttt aatggaggta gaaattgatc     600
aatacataga tctatgttga ctgatgagca gtaacaaatt ggctgcataa tgggtaactt     660
ggaaaggata tagctaagag attttaggta agaaattttg ctgaataaat ctaaggataa     720
acttctttca gttggcacag aatgtgaaga tatatgtgcc caacataaat gttaacctag     780
gaaaaccta ttagtaatta ggcggataag atactctgtt ctctagacat aattcccct     840
tttccccaac cactctgtcc ttgcaaatgt ggttcatgag caacatggct atgacagcag     900
agattaagtt atgcatggac tcactaaata atacctattg ctgagtgcct aacttgccaa     960
cagcaggttg gtactcactg ggtgcacact cagctggcac a                       1001
```

<210> SEQ ID NO 13
<211> LENGTH: 809
<212> TYPE: DNA
<213> ORGANISM: Homo sapiens

<400> SEQUENCE: 13

```
tggaaatctt gggaaaattt gcatgtaatt agtactccct tccagctctc cgaagtataa      60
aatacaatac attagggctt gtaacactaa tatcgctgag aacacagcta atgtgggaag     120
tctaattcgc cactaatatg cagatgccaa gctagttggt gcttgctttc acytgttttg     180
gctaattgtt ttcggtgtga tttagaaact ccataccta tgatgcagtt gtacctgatg     240
caacaactca ccagtgctgg actgtgggag gtcacatcat ttagactgca aattcagaag     300
tgactttcga ggaaatttgg tcccgttccc aagcaataaa gccgtcgcat cataatcagc     360
ttagaacaat tgccaatga tagttttctg tgttgcgcca tcagagattc tgattcagca     420
agtcctcgtt ggatctcata catctcaatt aaaaatcaac aatagatcgg gcgtggtggc     480
tcacgcctgt ctgtcatccc agcactttga gaggccaagc caggtggatc aggagttcca     540
gaccagcctg gccaacatgg tgaaacccca tctctgctaa aagtacaaaa attagccagg     600
cgtggtggtg catgcctgta gtcccagcta ctggggaggc tgaggcagga gaataacttg     660
agtccgggag gcggaggttg caatgagcca agatcgtgca actgtactcc agccctgggt     720
gacagagcaa gaatctgttc tcaaataatt aaataactaa gatattgatt aattaacaat     780
tcatgtcttt ttgaatgcga ccagaaaat                                     809
```

<210> SEQ ID NO 14
<211> LENGTH: 1008
<212> TYPE: DNA

<213> ORGANISM: Homo sapiens

<400> SEQUENCE: 14

| | | | | | |
|---|---|---|---|---|---|
| aaaaaaaaaa | aaaaaaaaag | aaagaaagaa | agaaagaaag | gtaggaagga | caaaggaact | 60 |
| cctgcctcct | gtgtcctccc | acagcatatc | actgggggc | cctgtcaaat | gaggggcact | 120 |
| aggttgagaa | ctataaaaca | atctgttgat | ttatgcattt | aaaacctcaa | gactttttt | 180 |
| ttttttttt | tctggagatg | gagtttcgct | cttgttgccc | aggctggagt | gcaatggtgt | 240 |
| gatctcggct | cactgtaacc | tccaccttcc | gggttcaagc | cattcttttg | cctcagcctc | 300 |
| cccagtagct | ggaattataa | gtaagcacca | ccatgcccgg | ctaattttt | atattttag | 360 |
| tagagacgag | gtttttccat | gttagtcagg | ctggtctcga | actcccgacc | tcaggtggtc | 420 |
| ctcccacctc | agcctcccaa | agtgctgaa | ttacaggcat | gagccaccac | gcctggttgg | 480 |
| acttttgtct | caaatgaaat | tgttaaagga | acccacattt | tacaaaatat | gtggtatgtg | 540 |
| gtggaaaaaa | cttccttcca | tgagtctctt | ttccagggta | tatgggagat | aaggagggga | 600 |
| agaccagggc | ttttaggccc | ggctcttcct | ggtgctgaga | tactggaaga | ctgccttgta | 660 |
| aagcatctag | ggatgtaaat | tcaggaaaag | ttctttaagc | attagaccaa | agctgagtga | 720 |
| gctgggagat | tatggatctc | gcatgtagac | ctgataacgg | gcatcggtag | gatcttaatc | 780 |
| cttggagagc | caggtgcctc | cctctgccca | catgatgtgc | atgcaagtaa | aaagaaaca | 840 |
| tggaactaaa | ttatctccca | gttttcctc | ctccgcagtc | ccctccagct | ctatccttcc | 900 |
| tttctaccaa | gagcagagcc | acttagagga | caaggtactc | aycacgtctg | gctcaggtcc | 960 |
| aatgctgtga | agaggtacca | gatacaagag | acaggtggga | ctggctca | | 1008 |

<210> SEQ ID NO 15
<211> LENGTH: 601
<212> TYPE: DNA
<213> ORGANISM: Homo sapiens

<400> SEQUENCE: 15

| | | | | | |
|---|---|---|---|---|---|
| agatgcggta | ttttatgaaa | tacaagaaga | aaaatgctct | aaaacccata | atcataaaca | 60 |
| cagcatatgg | aaaaatgaaa | gcgctagttt | tgagttagaa | gcatctttta | tctacttcca | 120 |
| ctccctccac | tttctggtca | atattagata | cataatcaga | gaaatgctta | aatttcacca | 180 |
| aaggcttgct | tgagttggaa | gcttgatttt | tttttagaa | gaaattcccc | accatccatt | 240 |
| ctactgcaaa | gattttcttt | tcaagtgct | ttcacctgtc | aaaagccctc | tgtccagata | 300 |
| yttagcagat | ccctccactc | tctcattctg | caaggcagag | ggaagaggag | gctacattga | 360 |
| gtgagtgtct | accatgaacc | aggctcagac | acagacatct | ggcatctcat | gccggcctct | 420 |
| cagaggggct | gcgaggacag | tgggctgccc | acgggctctc | gggttcagag | aggcagtgag | 480 |
| cctggctgaa | gggcaccagc | taggaaatgg | cagagccaga | ttctgcacat | ccccaaagcc | 540 |
| caagacacct | ccctacctcc | cagacttctc | catttgagta | tatgcgccct | gacgaaaagc | 600 |
| a | | | | | | 601 |

<210> SEQ ID NO 16
<211> LENGTH: 501
<212> TYPE: DNA
<213> ORGANISM: Homo sapiens

<400> SEQUENCE: 16

| | | | | | |
|---|---|---|---|---|---|
| ctatctgcat | ttcagagagg | gcttttcagt | tttgttataa | aacctcatta | cttttttatt | 60 |
| acagacttag | tggagccttc | tctgttgaat | tgaatcatat | gattcactat | tagctggaca | 120 |

```
tttaatacta tatcgtcttt atattgttca ggattcttct cagttctttt atttgcactt    180
tggaaatgtc tcaggagaag aaattgaaag atgatagttc tttcaaataa ttattccctg    240
tcccaggaag rtagtgtttt aaagacaatt atttaaacaa aatatactac cattttctaa    300 ttcttttga  tttaagctcc ctacaataat gaatgagaag aatgagaatt aagcggttta    360
gaaaacaatg tggttttgg  caaaatcaaa atattttaa  aaatccttta agatcatcag    420
tgcataccac atgttttgtg aagcttttgt agaatctctg aggtgtccac ctctcttatt    480
gtacttattc acatctcttc c                                              501

<210> SEQ ID NO 17
<211> LENGTH: 601
<212> TYPE: DNA
<213> ORGANISM: Homo sapiens

<400> SEQUENCE: 17
aaaccgcttt acaacactta caactttatt taacagcaga aagctcaaag ctgccatgca     60
gagggaagct atgtagactc tggaagcctt gaagcttagg agcataggaa ttacagctct    120
gtctggttgg cttaaccaca tccaggcatg gaggcaagga aaaaaaaaaa aactcaaagc    180
tttgtttgga ggatggtact aggaaagaac taggaaacta gtgagagaag gtaccaagct    240
atgcctttgt ccacccacta ttcaatttac aaatatttct tggtcctata tcaggcactc    300
yattgggtac taggaataaa tacgcagatg aatgaggcat ggctctttcc ccaaaaagga    360
cttatatgtg ctcaaaatgt gttacagaaa tcccatgagg attcttggat attccaagag    420
ggtcaaattt cattgctctg ttttcatac  ctgggactgg gctttagtag actctctctg    480
gtttcctgaa gcttcatacc ccacatctgc cctactgtga gagtccaacc ccagggctct    540
agctggcttc tctcaactgt tctacagttt tctaggccac agcttgagat gtgacagaaa    600
g                                                                    601

<210> SEQ ID NO 18
<211> LENGTH: 801
<212> TYPE: DNA
<213> ORGANISM: Homo sapiens

<400> SEQUENCE: 18
tttgataagg aagtgagtgg tgtgaaatcc aggctcaaga acaaaagccc tacaagcctg     60
tacccaacgg ggccactggc ctagaatggt aataaataga attgggtgac aaccttgaag    120 gtcaccgtg  gttcagctct ggaggtgtcc ttgtttgtac tcactttgag taaccatcaa    180
cttataaata gcctcaggcc aattgcccag tgatgatttt gactgtcgct tgccaggggc    240
ctgggcttgt ggtttggttg tgagtctgtc atggtctctg tgacctcaga ggaggaggaa    300
ggaagatgat gatggatgct tctagtgatg caagcaacaa acattttgg  acaatgtgcc    360 caataccatt ctctgtactc tgcatgagtt aacccttcag kcttcaaaca acgctttgag    420
gtaggtgagg agactgagca ctaaaaaggt gaatgcggag ccagtgtgag cacaaaaggc    480
ctggttccct gctagaccgt gcctcctctt ggctggagct ctatggaaag agttggaacc    540
agggagcctt ggttaaaata tcagctccat cccttatgac cttgggcaac ttacaaatct    600
ccaaatctgt attttcacct tttaactaga ataatgtatg tcaattatag ggtgttagga    660
ttaaatgaga aaatgtacat aaaactttg  gggcattgtc tggcactggg taagtactca    720
atgaaaaaag gtaatggttt tttaacttgt ttaatgtttc taagccttag gttttccact    780
```

```
tataaaatga aagcgtcatt a                                              801
```

<210> SEQ ID NO 19
<211> LENGTH: 1001
<212> TYPE: DNA
<213> ORGANISM: Homo sapiens

<400> SEQUENCE: 19

```
ctggttgaca gcgcaagact cccttccccc cccaaaaaaa tctcctaatc ttctgtgtct      60
gtgtggcaag ccatgaactc cttctcagaa gaatgttttt aaatgcatta aataaagcat     120
gaggtgggga gagttccaaa ggaagccagt gatactaaaa catacagaat tatcaaacag     180
tgtttatgct tctgttataa gaatagatgg gctactttca catattaaac agcaagagct     240
agcagcaagt ctagtgaact gggcacttgg aagcagtgat gagcatagca gtatctctgg     300
atagctgtaa cactgtgtgc aggtatctgg ggtttctgtc gtgaccacgt ggcaggagct     360
gctgccactg ctgtctgatg ctcgccccac agtggaagga gatgctaaat tccgttacgc     420
attagaggtc agtgaaaagg aagatgcagt ttgttcccgt ccaggcacaa ggactcttga     480
atttgtccat agttaagaac rgctcatcca ggagcagagc gagaggccgg gctgcgcgtc     540
ctcatctcct ctcccagcct tcgcatcctc ctggctgcct cgcgtttcct ccacgggcct     600
ggctgaacgc acacacaggc ctgggggaga ctgcagagac acatcttcag ccacatcttc     660
tgtaaaacag tcactatggg atgacggtga ctggacagtg gctccgtgca gtcggtgtct     720
tttgcaaagt tttccaccgt gtgcatcctc tgcagccaac tccagctgag ggagaacgga     780
ccctcggtga gttggggctg cacagcaggt atggcctgct gccttcaccc cacacctgct     840
atcaaatgaa tcagcccct ttccctacaa ccccaagaaa agcctcagga cccatcaggg     900
gaagaagaag ctgccatat agagagaggg aagggatact gctcctcatt ccccacacgg     960
catagcccag gtgtagaaag tggccaacat ccatttagga a                       1001
```

METHODS OF DETERMINING RESPONSIVENESS TO ANTI-TNFα THERAPY IN INFLAMMATORY BOWEL DISEASE

CROSS-REFERENCE TO RELATED APPLICATIONS

This application is a continuation of U.S. application Ser. No. 16/025,769 filed Jul. 2, 2018 which is a continuation of U.S. application Ser. No. 13/130,998 filed May 24, 2011, which is a National Phase of International Application PCT/US09/65928, filed Nov. 25, 2009, which claims the benefit of U.S. Provisional Application No. 61/118,290, filed Nov. 26, 2008, U.S. Provisional Application No. 61/142,307, filed Jan. 2, 2009, and U.S. Provisional Application No. 61/182,552, filed May 29, 2009.

GOVERNMENT RIGHTS

This invention was made with government support under Contract Nos. DK046763, and DK56928 awarded by the National Institutes of Health. The government has certain rights in the invention.

SEQUENCE LISTING

The instant application contains a Sequence Listing which has been submitted electronically in ASCII format and hereby incorporated by reference in its entirety. Said ASCII copy, created Dec. 14, 2021 is named 56884-707_302_SL.txt_and is 18,360 bytes in size.

FIELD OF THE INVENTION

The invention relates generally to the field of inflammatory bowel disease and, more specifically, to genetic methods for diagnosing, prognosing, and treating inflammatory bowel disease.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Natural history observations in both early and later onset inflammatory bowel disease (IBD) have prompted the increasing use of anti-TNFα therapy for IBD patients. Various past studies have demonstrated that infliximab has the potential to be effective for the induction and maintenance response and remission in some CD patients. However, the clinical trial data for all anti-TNFα therapies among adult CD patients report that 40% of patients do not respond to the induction phase (primary non-responder) and that approximately 40% of those patients who do enter the maintenance phase of the trial lose response over time. The pediatric REACH trial, for example, reported that close to 90% of children responded to induction, suggesting a more robust acute response to anti-TNFα therapy in children as compared to adults with CD. This primary response outcome did not, however, require children to have weaned corticosteroids to meet response criteria. This would be a more clinically robust outcome definition given that the importance of steroid sparing in the induction and maintenance phase of these therapies. Moreover, approximately 40% of children, like their adult counterparts, who entered the maintenance phase lost response and were no longer in remission and off steroids at 12 months. More studies are needed to assess the true incidence of primary non-response in children in a non clinical trial setting. The adult UC trials (ACT 1 and ACT 2) reported similar response rates among adult UC patients receiving infliximab as the CD trials. Infliximab is being used off label in children with UC and the official clinical trial for indication is currently underway. There are many differences in the patient population and outcome measures making a comparison across trials difficult and hard to interpret.

Inter-individual variability in therapeutic response may be best explained by genetic variability as it relates to disease pathogenesis and mechanism of action of this class of therapies. Other than NOD2 and IBD5, IBD susceptibility genes identified via genome wide linkage approach or Genome Wide Association Studies (GWAS) have not been evaluated as predictors of response to anti-TNFα therapies. NOD2 was not found to be associated with therapeutic response to infliximab in these limited studies. It is conceivable that disease susceptibility genes do not influence the ultimate response to therapeutic targets given the multifactorial influences on disease and the relatively unknown functionality of these susceptibility genes. However, the GWAS approach, which identifies portions of the genome that contain genetic variants associated with specific phenotypes, can also identity novel variants that contribute to therapeutic outcome i.e. discovery of genetic loci that are responsible for the mechanism of altered drug response, such as to anti-TNFα. There may also be important non genetic factors that influence or modify primary response to anti-TNFα. Among the serologic immune responses, pANCA has been shown to be negatively associated with primary response in both CD and UC patients. PANCA is present in both CD and UC and defines a specific colitis phenotype suggesting a degree of overlap in the underlying pathway biology of these two disease subtypes. Other than duration of disease at initiation of therapy, there are likely important clinical and demographic variables that also influence therapeutic outcomes. To date, however, it remains unknown whether these are independent of genetic variability. Thus, there is a need in the art to study associations of known IBD susceptibility loci as well as novel loci identified by pharmacogenetic GWAS with anti-TNFα response in pediatric IBD patients, and to develop predictive models of anti-TNFα primary non-response using clinical phenotype, serologic and genetic variables.

BRIEF DESCRIPTION OF THE FIGURES

Exemplary embodiments are illustrated in referenced figures. It is intended that the embodiments and figures disclosed herein are to be considered illustrative rather than restrictive.

FIG. 1A-1F depicts, in accordance with embodiments herein, associations of genetic variants with primary non-response to anti-TNFα therapy as the outcome in patients with IBD. Results of SNPs with significance >$10^{-3}$. FIG. 1A depicts, in accordance with embodiments herein, associations of genetic variants with primary non-response to anti-TNFα therapy as the outcome in patients with IBD. Results of SNPs with significance >$10^{-3}$. FIG. 1B depicts, in accordance with embodiments herein, associations of genetic variants with primary non-response to anti-TNFα therapy as the outcome in patients with IBD. Results of SNPs with significance >10⁻³. FIG. 1C depicts, in accordance with embodiments herein, associations of genetic variants with primary non-response to anti-TNFα therapy as the outcome in patients with IBD. Results of SNPs with significance >10⁻³. FIG. 1D depicts, in accordance with embodiments herein, associations of genetic variants with primary non-response to anti-TNFα therapy as the outcome in patients with IBD. Results of SNPs with significance >10⁻³. FIG. 1E depicts, in accordance with embodiments herein, associations of genetic variants with primary non-response to anti-TNFα therapy as the outcome in patients with IBD. Results of SNPs with significance >10⁻³. FIG. 1F depicts, in accordance with embodiments herein, associations of genetic variants with primary non-response to anti-TNFα therapy as the outcome in patients with IBD. Results of SNPs with significance >10⁻³.

FIG. 2A-2F depicts, in accordance with embodiments herein, associations of genetic variants with secondary loss of response to anti-TNFα therapy as the outcome in patients with IBD. FIG. 2A depicts, in accordance with embodiments herein, associations of genetic variants with secondary loss of response to anti-TNFα therapy as the outcome in patients with IBD. FIG. 2B depicts, in accordance with embodiments herein, associations of genetic variants with secondary loss of response to anti-TNFα therapy as the outcome in patients with IBD. FIG. 2C depicts, in accordance with embodiments herein, associations of genetic variants with secondary loss of response to anti-TNFα therapy as the outcome in patients with IBD. FIG. 2D depicts, in accordance with embodiments herein, associations of genetic variants with secondary loss of response to anti-TNFα therapy as the outcome in patients with IBD. FIG. 2E depicts, in accordance with embodiments herein, associations of genetic variants with secondary loss of response to anti-TNFα therapy as the outcome in patients with IBD. FIG. 2F depicts, in accordance with embodiments herein, associations of genetic variants with secondary loss of response to anti-TNFα therapy as the outcome in patients with IBD.

FIG. 3A-3F depicts, in accordance with embodiments herein, associations of genetic variants with failure for any reason to anti-TNFα therapy as the outcome in patients with IBD. FIG. 3A depicts in accordance with embodiments herein, associations of genetic variants with failure for any reason to anti-TNFα therapy as the outcome in patients with IBD. FIG. 3B depicts in accordance with embodiments herein, associations of genetic variants with failure for any reason to anti-TNFα therapy as the outcome in patients with IBD. FIG. 3C depicts in accordance with embodiments herein, associations of genetic variants with failure for any reason to anti-TNFα therapy as the outcome in patients with IBD. FIG. 3D depicts in accordance with embodiments herein, associations of genetic variants with failure for any reason to anti-TNFα therapy as the outcome in patients with IBD. FIG. 3E depicts in accordance with embodiments herein, associations of genetic variants with failure for any reason to anti-TNFα therapy as the outcome in patients with IBD. FIG. 3F depicts in accordance with embodiments herein, associations of genetic variants with failure for any reason to anti-TNFα therapy as the outcome in patients with IBD.

SUMMARY OF THE INVENTION

Figure 4:
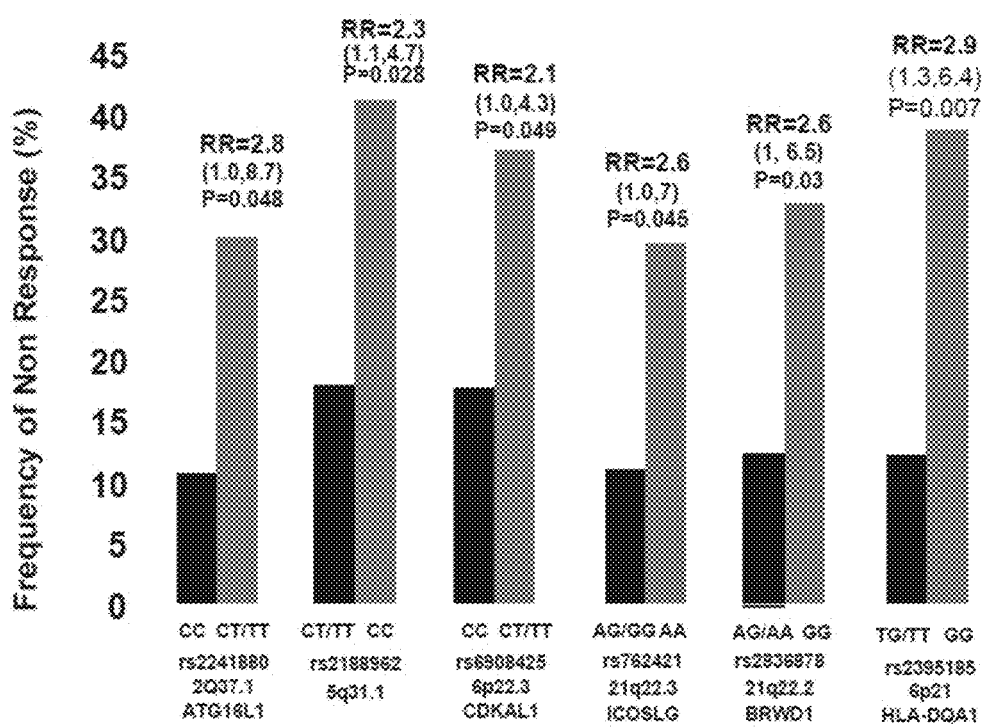
FIG. 4 depicts, in accordance with embodiments herein, genotype associations of known IBD susceptibility loci with primary non-response. The dominant rare allele model (i.e. presence of the rare allele) was assumed for the statistical analyses. The relative risk (RR) and frequency of non-response are shown for the genotypes for each locus that met p value significance in univariate analysis.

Various embodiments include a method of determining a high risk relative to a normal subject of non-responsiveness to treatment with an anti tumor necrosis actor alpha (TNFα) therapy in an individual, comprising obtaining a sample from the individual, assaying the sample for the presence or absence of one or more genetic and/or serological risk factors, and determining the high risk relative to a normal subject of non-responsiveness to the anti TNFα therapy based on the presence of one or more risk factors carried by the individual. In another embodiment, the presence of each genetic and/or serological risk factor has an additive effect on increasing the risk of non-responsiveness in the individual. In another embodiment, the individual is diagnosed with inflammatory bowel disease (IBD). In another embodiment, the individual is diagnosed with ulcerative colitis (UC). In another embodiment, the individual is a child. In another embodiment, the one or more genetic risk factors comprise genetic variants at the loci of tachykinin receptor 1 (TACR1), family with sequence similarity 19 member A4 (FAM19A4), phosphatase and actin regulator 3 (PHACTR3) and/or bromodomain and WD repeat domain containing 1 (BRWD1). In another embodiment, the one or more genetic risk factors comprise SEQ. ID. NO.: 1, SEQ. ID. NO.: 2, SEQ. ID. NO.: 3, SEQ. ID NO.: 4, SEQ. ID. NO.: 5 and/or SEQ. ID. NO.: 6. In another embodiment, the one or more genetic risk factors comprise SEQ. ID. NO.: 7, SEQ. ID. NO.: 8, SEQ. ID. NO.: 9, SEQ. ID. NO.: 10, SEQ. ID. NO.: 11, SEQ. ID. NO.: 12, SEQ. ID. NO.: 13, SEQ. ID. NO.: 14, SEQ. ID. NO.: 15, and/or SEQ. ID. NO.: 16. In another embodiment, the one or more genetic risk factors comprise SEQ. ID. NO.: 17, SEQ. ID. NO.: 8, SEQ. ID. NO.: 19, and/or SEQ. ID. NO.: 6. In another embodiment, the one or more genetic risk factors comprise genetic variants at the loci of ATG16, Orf13, inducible T-cell co-stimulator ligand (ICOSLG) and/or major histocompatibility complex class II DQ alpha 1 (HLADQA1). In another embodiment, one of the one or more serological risk factors comprise perinuclear anti-neutrophil cytoplasmic antibody (pANCA). In another embodiment, the anti TNFα therapy comprises infliximab. In another embodiment, the anti TNFα therapy comprises cyclosporin.

Other embodiments include a method of determining a significant likelihood of responsiveness to treatment with anti tumor necrosis factor alpha (TNF-α) therapy in an individual, comprising obtaining a sample from the individual, assaying the sample for the presence of one or more serological markers associated with responsiveness to anti TNFα therapy, and determining a significant likelihood of responsiveness based on the presence of one or more serological markers associated with responsiveness to anti TNFα therapy. In another embodiment, the individual is diagnosed with inflammatory bowel disease (IBD). In another embodiment, the individual is diagnosed with ulcerative colitis (UC). In another embodiment, the individual is a child. In another embodiment, one of the one or more serological markers comprises anti-*Saccharomyces cerevisiae* antibodies (ASCA).

Other embodiments include a method of predicting a high risk relative to a normal subject of non-responsiveness to anti tumor necrosis factor alpha (TNF-α) therapy in an individual with inflammatory bowel disease (IBD), comprising determining the presence or absence of one or more nonresponsive genetic risk variants, determining the presence or absence of positive expression of perinuclear anti-neutrophil cytoplasmic antibody (pANCA), determining the presence or absence of an ulcerative colitis phenotype, and predicting a high risk relative to a normal subject of non responsiveness to anti TNF-α therapy based on the presence of one or more responsive risk variants, the presence of positive expression of pANCA, and/or the presence of the ulcerative colitis phenotype. In another embodiment, one of the one or more nonresponsive genetic risk variants comprise variants at the genetic loci of tachykinin receptor 1 (TACR1), family with sequence similarity 19 member A4 (FAM19A4), phosphatase and actin regulator 3 (PHACTR3) and/or bromodomain and WD repeat domain containing 1 (BRWD1). In another embodiment, the high risk relative to a normal subject of non-responsiveness comprises a range of 7 to 10 fold increase in risk of non-responsiveness to treatment with anti TNFα therapy.

Various embodiments include a method of diagnosing an inflammatory bowel disease (IBD) subtype in an individual, comprising obtaining a sample from the individual, assaying the sample for the presence or absence of one or more genetic and/or serological risk factors of nonresponsiveness to anti TNFα therapy, and diagnosing the IBD subtype based upon the presence of one or more genetic and/or serological risk factors of nonresponsiveness to anti TNFα therapy. In another embodiment, the individual is a child. In another embodiment, the one or more genetic risk factors comprise genetic variants at the loci of tachykinin receptor 1 (TACR1), family with sequence similarity 19 member A4 (FAM19A4), phosphatase and actin regulator 3 (PHACTR3) and/or bromodomain and WD repeat domain containing 1 (BRWD1). In another embodiment, the one or more genetic risk factors comprise SEQ. ID. NO.: 1, SEQ. ID. NO.: 2, SEQ. ID. NO.: 3, SEQ. ID NO.: 4, SEQ. ID. NO.: 5 and/or SEQ. ID. NO.: 6. In another embodiment, the one or more genetic risk factors comprise SEQ. ID. NO.: 7, SEQ. ID. NO.: 8, SEQ. ID. NO.: 9, SEQ. ID. NO.: 10, SEQ. ID. NO.: 11, SEQ. ID. NO.: 12, SEQ. ID. NO.: 13, SEQ. ID. NO.: 14, SEQ. ID. NO.: 15, and/or SEQ. ID. NO.: 16. In another embodiment, the one or more genetic risk factors comprise SEQ. ID. NO.: 17, SEQ. ID. NO.: 8, SEQ. ID. NO.: 19, and/or SEQ. ID. NO.: 6. In another embodiment, one of the one or more serological risk factors comprise perinuclear anti-neutrophil cytoplasmic antibody (pANCA).

Other embodiments include a method of treating an individual, comprising diagnosing the individual as susceptible to non-responsiveness to anti tumor necrosis factor alpha (TNF-α) therapy, and treating the individual. In another embodiment, treating the individual comprises administering a therapeutically effective dosage of natalizumab. In another embodiment, the individual has inflammatory bowel disease (IBD).

Other features and advantages of the invention will become apparent from the following detailed description, taken in conjunction with the accompanying drawings, which illustrate, by way of example, various embodiments of the invention.

DESCRIPTION OF INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, NY 1994); March, *Advanced Organic Chemistry Reactions, Mechanisms and Structure* 4th ed., J. Wiley & Sons (New York, NY 1992); and Sambrook and Russel, *Molecular Cloning: A Laboratory Manual* 3rd ed., Cold Spring Harbor Laboratory Press (Cold Spring Harbor, NY 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

One skilled in the art will recognize many methods and materials similar or equivalent to those described herein, which could be used in the practice of the present invention. Indeed, the present invention is in no way limited to the methods and materials described.

"IBD" as used herein is an abbreviation of inflammatory bowel disease.

"CD" as used herein is an abbreviation of Crohn's Disease.

"U C" as used herein is an abbreviation of ulcerative colitis.

"GWA" as used herein is an abbreviation of genome wide associations.

"IFX" as used herein is an abbreviation of infliximab.

"TNFα" as used herein is an abbreviation of tumor necrosis factor alpha.

"SNP" as used herein is an abbreviation of single-nucleotide polymorphism

"ATI" as used herein is an abbreviation of anti infliximab antibodies.

"CDAI" as used herein is an abbreviation of Crohn's Disease activity index.

"PCDAI" as used herein is an abbreviation of pediatric Crohn's Disease activity index.

"pANCA" as used herein is an abbreviation of perinuclear anti-neutrophil cytoplasmic antibodies.

"ASCA" as used herein is an abbreviation of Anti-*Saccharomyces cerevisiae* antibodies.

As used herein, the term "biological sample" means any biological material from which nucleic acid molecules can be prepared. As non-limiting examples, the term material encompasses whole blood, plasma, saliva, cheek swab, or other bodily fluid or tissue that contains nucleic acid.

As used herein, the term "normal subject" means an individual who has an average likelihood of successful treatment.

As used herein, the term "positive likelihood ratio of non-response" means the value that when multiplied by the odds of non-responsiveness in a normal subject yields the total odds of non-responsiveness in an individual.

As readily apparent to one of skill in the art, any number of examples may be used for various genetic loci and variants described herein and the invention is in no way limited to specific examples of sequences used and described herein. For example, SNPs rs2241880, rs2188962, rs3764147, rs762421, rs9271568, rs2836878, described herein as SEQ. ID. NO.: 1, SEQ. ID. NO.: 2, SEQ. ID. NO.: 3, SEQ. ID NO.: 4, SEQ. ID. NO.: 5, and SEQ. ID. NO.: 6, respectively, are not limited to the specific sequences described and various additional genetic sequences may also be used while still containing the relevant allele. Similarly, as apparent to one of skill in the art, various examples of sequences may be used to represent SNPs rs13079040, rs4855535, rs17048128, rs17048129, rs17039556, rs12640159, rs880330, rs2057917, rs2983478, rs4776127, rs975664, rs6100556, and rs2836878, and thus the aforementioned genetic variants are not specifically limited to the sequences described herein as SEQ. ID. NO.: 7, SEQ. ID. NO.: 8, SEQ. ID. NO.: 9, SEQ. ID. NO.: 10, SEQ. ID. NO.: 11, SEQ. ID. NO.: 12, SEQ. ID. NO.: 13, SEQ. ID. NO.: 14, SEQ. ID. NO.: 15, and SEQ. ID. NO.: 16, SEQ. ID. NO.: 17, SEQ. ID. NO. 18, and SEQ. ID. NO.: 19, respectively.

As further described herein, inter-individual variation in response to anti-TNFα therapy may be explained by genetic variability in disease pathogenesis or mechanism of action. Recent genome wide association studies (GWAS) in IBD have increased understanding of the genetic susceptibility to IBD.

As described herein, the inventors have developed various predictive models, including a predicted model of primary response by testing associations of known IBD susceptibility loci and novel "pharmacogenetic" GWAS identified loci with primary non-response to anti-TNFα in pediatric IBD patients. Primary non response was defined using the HBI for CD and partial Mayo score for UC. Genotyping was performed using the Illumina Infinium platform. Chi square analysis tested associations of phenotype and genotype with primary non-response. Genetic associations were identified by testing known IBD susceptibility loci and by performing a GWAS for primary non-response. Step-wise multiple logistic regression was performed to build predictive models.

As further described herein, non-response occurred in 22 of 94 subjects. Six known susceptibility loci were associated with primary non-response (p<0.05). The 21q22.2/BRWDI loci remained significant in the predictive model. The most predictive model included 3 novel "pharmacogenetic" GWAS loci, previously identified BRWD1, pANCA and a UC diagnosis ($R^2$=0.82 and AUC=0.98%). The relative risk of non-response increased 15 fold when number of risk factors increased from 0-2 to ≥3.

As further disclosed herein, the inventors have described the combination of phenotype and genotype as most predictive of primary non response to anti-TNFα in pediatric IBD. Defining predictors of response to anti-TNFα allows the identification of patients who will not benefit from this class of therapy.

In one embodiment, the present invention provides a method of evaluating the prognosis of anti-TNFα therapy in an individual undergoing inflammatory bowel disease treatment by determining the presence or absence of a non-response genetic variant and/or non-response serological marker, where the presence of the non-response genetic variant and/or non-response serological marker is indicative of inflammatory bowel disease that is non-responsive to anti-TNFα therapy. In another embodiment, the non-response genetic variant and/or non response serological marker is described in Tables 1, 2 and/or 3(A)-(D). In another embodiment, the non-response genetic variant is at the genetic loci of ATG16, Orf13, ICOSLG, HLADQA1 and/or BRWD1. In another embodiment, the non-response serological marker is pANCA. In another embodiment, the anti-TNFα therapy includes the use of Infliximab. In another embodiment, the individual is a child.

In one embodiment, the present invention provides a method of evaluating the prognosis of anti-TNFα therapy in an individual undergoing inflammatory bowel disease treatment by determining the presence or absence of a non-response genetic variant and/or a response serological marker, where the absence of the non-response genetic variant and/or the presence of the response serological marker is indicative of inflammatory bowel disease responsive to anti-TNFα therapy. In another embodiment, the non-response genetic variant and/or response serological marker is described in Tables 1, 2 and/or 3(A)-(D). In another embodiment, the non-response genetic variant is at the genetic loci of ATG16, Orf13, ICOSLG, HLADQA1 and/or BRWD1. In another embodiment, the response serological marker is ASCA. In another embodiment, the anti-TNFα therapy includes the use of Infliximab. In another embodiment, the individual is a child.

In one embodiment, the present invention provides a method of diagnosing an inflammatory bowel subtype in an individual by determining the presence or absence of a non-response genetic variant and/or non-response serological marker, where the presence of the non-response genetic variant and/or non-response serological marker is indicative of the inflammatory bowel disease subtype in the individual. In another embodiment, the individual is a child.

In one embodiment, the present invention provides a method of treating inflammatory bowel disease in an individual by determining the presence of a non-response genetic variant and/or non-response serological marker, and treating the individual. In another embodiment, the individual is a child. In another embodiment, the treatment includes the use of anti-TNFα therapy.

As disclosed herein, the inventors conducted association studies of anti-TNFα responsiveness against the whole genome. Three (3) outcomes were evaluated (primary non-response, loss of response, and failure for any reason), with the analysis of such outcomes described in Table 4 and FIGS. 1-3 herein, including novel findings in the FAM19 genetic locus.

In one embodiment, the present invention provides a method of evaluating the prognosis of anti-TNFα therapy in an individual undergoing inflammatory bowel disease treatment by determining the presence or absence of a non-response genetic variant, where the presence of the non-response genetic variant is indicative of inflammatory bowel disease that is non-responsive to anti-TNFα therapy. In another embodiment, the non-response genetic variant is described in Table 4 and/or FIGS. 1-3 herein. In another embodiment, the anti-TNFα therapy includes the use of Infliximab. In another embodiment, the individual is a child.

In one embodiment, the present invention provides a method of evaluating the prognosis of anti-TNFα therapy in an individual undergoing inflammatory bowel disease treatment by determining the absence of a non-response genetic variant, where the absence of the non-response genetic variant is indicative of inflammatory bowel disease responsive to anti-TNFα therapy. In another embodiment, the non-response genetic variant is described in Table 4 and/or FIGS. 1-3. In another embodiment, the response genetic variant is at the FAM19A4 genetic locus. In another embodiment, the anti-TNFα therapy includes the use of Infliximab. In another embodiment, the individual is a child.

As disclosed herein, the inventors tested associations of genetic loci with anti-TNFα response in pediatric IBD patients by pursing a variety of strategies. The result was the development of various predictive models of anti-TNFα response using phenotype, serologic and genetic variables.

In one embodiment, the present invention provides a method of evaluating the prognosis and/or predicting responsiveness of anti-TNFα therapy in an individual undergoing inflammatory bowel disease treatment by determining the presence or absence of a non-response genetic variant, where the presence of the non-response genetic variant is indicative of inflammatory bowel disease that is non-responsive to anti-TNFα therapy. In another embodiment, the non-response genetic variant is a known IBD susceptibility locus. In another embodiment, the non-response genetic variant is described in Tables 6-10 herein. In another embodiment, the anti-TNFα therapy includes the use of Infliximab. In another embodiment, the individual is a child.

In another embodiment, the present invention provides a method of evaluating the prognosis and/or predicting responsiveness of anti-TNFα therapy in an individual undergoing inflammatory bowel disease treatment by determining the presence or absence of one or more risk factors, where the presence of each risk factor has an additive effect for an increased risk of non-responsiveness to anti-TNFα therapy. In another embodiment, one of the risk factors is a non-response genetic variant. In another embodiment, the non-response genetic variant is described in Tables 6-10 herein. In another embodiment, one of the risk factors is positive expression of a serological marker. In another embodiment, the serological marker is pANCA. In another embodiment, one of the risk factors is the diagnosis of the individual, where a diagnosis of ulcerative colitis predicts non-responsiveness to anti-TNFα therapy. In another embodiment, the anti-TNFα therapy includes the use of Infliximab. In another embodiment, the individual is a child.

In one embodiment, the present invention provides a method of treating inflammatory bowel disease in an individual by determining the presence of one or more risk factors and treating the individual. In another embodiment, one of the risk factors is a non-response genetic variant. In another embodiment, the non-response genetic variant is described in Tables 6-10 herein. In another embodiment, one of the risk factors is positive expression of a serological marker. In another embodiment, the serological marker is pANCA. In another embodiment, one of the risk factors is the diagnosis of the individual, where a diagnosis of ulcerative colitis predicts non-responsiveness to anti-TNFα therapy. In another embodiment, the individual is a child. In another embodiment, the treatment includes the administration of a therapeutically effective amount of anti-TNFα therapy to the individual.

In one embodiment, the present invention provides a method of diagnosing an inflammatory bowel subtype in an individual by determining the presence or absence of one or more risk factors, where the presence of one or more risk factors is indicative of the inflammatory bowel disease subtype in the individual. In another embodiment, one of the risk factors is a non-response genetic variant. In another embodiment, the non-response genetic variant is described in Tables 6-10 herein. In another embodiment, one of the risk factors is positive expression of a serological marker. In another embodiment, the serological marker is pANCA. In another embodiment, one of the risk factors is the diagnosis of the individual, where a diagnosis of ulcerative colitis predicts non-responsiveness to anti-TNFα therapy. In another embodiment, the individual is a child.

A variety of methods can be used to determine the presence or absence of a variant allele or haplotype. As an example, enzymatic amplification of nucleic acid from an individual may be used to obtain nucleic acid for subsequent analysis. The presence or absence of a variant allele or haplotype may also be determined directly from the individual's nucleic acid without enzymatic amplification.

Analysis of the nucleic acid from an individual, whether amplified or not, may be performed using any of various techniques. Useful techniques include, without limitation, polymerase chain reaction based analysis, sequence analysis and electrophoretic analysis. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

The presence or absence of a variant allele or haplotype may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

A TaqmanB allelic discrimination assay available from Applied Biosystems may be useful for determining the presence or absence of a variant allele. In a TaqmanB allelic discrimination assay, a specific, fluorescent, dye-labeled probe for each allele is constructed. The probes contain different fluorescent reporter dyes such as FAM and VICTM to differentiate the amplification of each allele. In addition, each probe has a quencher dye at one end which quenches fluorescence by fluorescence resonant energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MGB) group to a DNA probe as described, for example, in Kutyavin et al., "3'-minor groove binder-DNA probes increase sequence specificity at PCR extension temperature," Nucleic Acids Research 28:655-661 (2000)). Minor grove binders include, but are not limited to, compounds such as dihydrocyclopyrroloindole tripeptide (DPI).

Sequence analysis also may also be useful for determining the presence or absence of a variant allele or haplotype.

Restriction fragment length polymorphism (RFLP) analysis may also be useful for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization may also be used to detect a disease-predisposing allele. Allele-specific oligonucleotide hybridization is based on the use of a labeled oligonucleotide probe having a sequence perfectly complementary, for example, to the sequence encompassing a disease-predisposing allele. Under appropriate conditions, the allele-specific probe hybridizes to a nucleic acid containing the disease-predisposing allele but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a disease-predisposing allele by using an allele-specific oligonucleotide primer that is perfectly complementary to the nucleotide sequence of the disease-predisposing allele but which has one or more mismatches as compared to other alleles (Mullis et al., supra, (1994)). One skilled in the art understands that the one or more nucleotide mismatches that distinguish between the disease-predisposing allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and other alleles at the 3' end of the primer.

A heteroduplex mobility assay (HMA) is another well known assay that may be used to detect a SNP or a haplotype. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

The technique of single strand conformational, polymorphism (SSCP) also may be used to detect the presence or absence of a SNP and/or a haplotype (see Hayashi, K., Methods Applic. 1:34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect a SNP and/or a haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of a SNP and/or a haplotype are known in the art and useful in the methods of the invention. Other well-known approaches for determining the presence or absence of a SNP and/or a haplotype include automated sequencing and RNAase mismatch techniques (Winter et al., Proc. Natl. Acad. Sci. 82:7575-7579 (1985)). Furthermore, one skilled in the art understands that, where the presence or absence of multiple alleles or haplotype(s) is to be determined, individual alleles can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that multiple alleles can be detected in individual reactions or in a single reaction (a "multiplex" assay). In view of the above, one skilled in the art realizes that the methods of the present invention for diagnosing or predicting susceptibility to or protection against CD in an individual may be practiced using one or any combination of the well known assays described above or another art-recognized genetic assay.

Similarly, there are many techniques readily available in the field for detecting the presence or absence of serotypes, antibodies, polypeptides or other biomarkers, including protein microarrays. For example, some of the detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Similarly, there are any number of techniques that may be employed to isolate and/or fractionate biomarkers. For example, a biomarker may be captured using biospecific capture reagents, such as antibodies, aptamers or antibodies that recognize the biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called "affinity capture mass spectrometry," or "Surface-Enhanced Affinity Capture" or "SEAC," which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer and hybrids of these.

Alternatively, for example, the presence of biomarkers such as polypeptides maybe detected using traditional immunoassay techniques. Immunoassay requires biospecific capture reagents, such as antibodies, to capture the analytes. The assay may also be designed to specifically distinguish protein and modified forms of protein, which can be done by employing a sandwich assay in which one antibody captures more than one form and second, distinctly labeled antibodies, specifically bind, and provide distinct detection of, the various forms. Antibodies can be produced by immunizing animals with the biomolecules. Traditional immunoassays may also include sandwich immunoassays including ELISA or fluorescence-based immunoassays, as well as other enzyme immunoassays.

Prior to detection, biomarkers may also be fractionated to isolate them from other components in a solution or of blood that may interfere with detection. Fractionation may include platelet isolation from other blood components, sub-cellular fractionation of platelet components and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Generally

Genetics, immune responses and environmental factors for disease susceptibility and development, as well as their interactions, are important determinants of inflammatory bowel disease phenotype and disease progression. These factors may also interact in such a way that influences the outcome of therapies used to treat these heterogeneous phenotypes. Recent genomic discoveries from Genome Wide Association (GWA) studies in both Crohn's disease (CD) and ulcerative colitis (UC) have increased understanding of the genetic susceptibility to IBD. This novel genetic information provides important insight regarding the various mechanisms of inflammation involved in disease pathogenesis. Targeting these various pathways with effective therapies is the key to the successful management of the IBD patient. When introduced, the monoclonal antibodies targeting tumor necrosis factor alpha (TNFα) represented the largest advance in decades made in the realm of IBD therapeutics. However there is clear inter-individual variability in both efficacy and safety outcomes to this class of therapy which has yet to be explained. The inventors have demonstrated that therapeutic outcomes to anti-TNFα in children and young adults with IBD are associated with inter-individual genetic variability, and determined that genetic loci identified by Genome Wide Association (GWA) studies alone or in combination with clinical and/or immune markers are associated with and predictive of therapeutic responsiveness to anti-TNFα therapy in pediatric IBD patients.

Example 2

Significance of Defining Predictors of Response to Anti-TNFα

Defining predictors of response to anti-TNFα will allow clinicians to choose the appropriate therapy for the appropriate IBD patient with the goal of maximizing efficacy and minimizing toxicity. Research described herein will allow the individualization of therapy based on who will or perhaps more importantly will not respond to different classes of therapeutic interventions currently available to IBD patients. The development of lymphoma, particularly a rare almost uniformly fatal sub-type of hepatosplenic T cell lymphoma in individuals receiving infliximab along with immunomodulators have resulted in clinicians wanting to carefully select those patients who are appropriate candidates for these therapies. The novel pharmacogenetic information described herein can not only improve the management of patients in the clinic with an existing anti-TNFα agent but also ultimately change the way large scale clinical trials are conducted, such that only patients with a higher probability of response to specific therapies will be enrolled to negate exposure to ineffective therapies and protect patients from treatment related serious and potentially fatal adverse events. The data described herein will aid in the translation of significant genetic findings into the clinical setting for IBD patients and for other patients receiving anti-TNFα for other immune mediated disorders.

Example 3

Pharmacogenetic GWAS and Primary Non-Response

The inventors tested the association of the most significant CD susceptibility loci previously identified with infliximab responsiveness in pediatric IBD patients receiving infliximab from which there was complete clinical follow up. For these preliminary analyses, two (2) outcomes were evaluated:
1) primary non-response: patient did not respond to the induction regimen as defined by patient did not receive a clinical benefit from the first 3 infusions of infliximab and did not receive any further treatment doses. All significant associations are shown in Table 1 below. Remainder of analyses are detailed in Table 3.
2) secondary loss of response: patient responded to the induction regimen and despite dose escalation and/or frequency intensification of infliximab the drug was discontinued as of last follow up. Time to loss of response was also analyzed and data are shown in Table 3.

Example 4

Table 1—Significant Associations Between GWAS Loci and Primary Non-Response

TABLE 1 (A)

| SNP | Chromosome | Primary Non Response (YES = 1, NO = 0) | Genotype 12/22 | Genotype 11 | P value | OR* | Gene of interest |
|---|---|---|---|---|---|---|---|
| rs2241880 | 2q37 | 0 | 30(58.8%) | 21(41.2%) | 0.04 | | ATG16 |
| | | 1 | 7(100.0%) | | | 10.6 | |
| rs2188962 | 5q23 | 0 | 45(83.3%) | 9(16.7%) | 0.03 | 6.7 | unknown |
| | | 1 | 3(42.9%) | 4(57.1%) | | | |

TABLE 1 (A)-continued

| SNP | Chromosome | Primary Non Response (YES = 1, NO = 0) | Genotype 12/22 | Genotype 11 | P value | OR* | Gene of interest |
|---|---|---|---|---|---|---|---|
| rs3764147 | 13q14 | 0 | 31(57.4%) | 23(42.6%) | 0.004 | 20.1 | Orf13 |
|  |  | 1 |  | 7100.0%) |  |  |  |
| rs762421 | 21q22 | 0 | 34(63.0%) | 20(37.0%) | 0.03 | 10.2 | ICOSLG |
|  |  | 1 | 1(14.3%) | 6(85.7%) |  |  |  |
| rs9271568 | 6p21.32 | 0 | 31(58.5%) | 22(41.5%) | 0.004 | 21.0 | HLADQA1 |
|  |  | 1 |  | 7(100.0%) |  |  |  |
| rs2836878 | 21q22.2 | 0 | 29(53.7%) | 25(46.3%) | 0.01 | 17.4 | BRWD1 |
|  |  | 1 |  | 7(100.0%) |  |  |  |

*If there is any zero cell, 0.5 is added to each cell count to calculate OR.

As described in Table 1(A), there were 6 SNPs that were found to be significantly associated with primary non-response. Interestingly there was no overlap with any SNP found to be associated with secondary loss of response and time to loss of response. This shows that there may be different genetic predictors and biological explanations for the 2 therapeutic response outcomes.

In conjunction with the various genotypes and SNPs listed in Table 1(A) above, the alleles are listed in Table 1(B) below:

TABLE 1(B)

| SNP | Alleles Corresponding to Genotype |
|---|---|
| rs2241880 | 11 = CC, 12 = CT, 22 = TT |
| rs2188962 | 11 = CC, 12 = CT, 22 = TT |
| rs3764147 | 11 = AA, 12 = AG, 22 = GG |
| rs762421 | 11 = AA, 12 = AG, 22 = GG |
| rs9271568 | 11 = GG, 12 = GA, 22 = AA |
| rs2836878 | 11 = GG, 12 = GA, 22 = AA |

Example 5

Serological Immune Responses and Therapeutic Response

The associations between ASCA, pANCA, OmpC, I2 and CBIr-1 antibodies and therapeutic outcome was analyzed. Only significant associations with primary non-response are illustrated in Table 2. pANCA positivity was associated with primary non-response and ASCA positivity was protective against primary non-response. There was no association found anti-OmpC, anti-I2 and anti-CBir-1 for primary non-response and none of the serologies were associated with loss of response.

Example 6

Table 2—Significant Associations Between Serological Immune Responses and Therapeutic Outcome

TABLE 2

| Immune Responses | Positive = 1, Negative = 0 | Primary non response yes | Primary non response no | P | OR* | 95% CI |
|---|---|---|---|---|---|---|
| pANCA | 0 | 3(30.0%) | 44(69.8%) |  |  |  |
|  | 1 | 6(85.7%) | 12(25.5%) | 0.002 | 17.5 | 1.9-160.6 |
| ASCA IgA ancifor IgG | 0 | 1(14.3%) | 35(74.5%) |  |  |  |
|  | 1 |  | 30(47.6%) | 0.004 | 0.05 |  |

*If there is any zero cell, 0.5 is added to each cell count to calculate OR.

Example 7

Table 3 (A)-(D)—Details of SNPs Analyzed and Includes Outcomes: Primary Non-Response, Secondary Loss of Response, and Time to Loss of Response

TABLE 3(A)

Table 3(A) depicts top IBD risk loci from GWA studies and primary non-response.

| SNP | Primary non response Yes = 1 No = 0 | Genotype 12/22 | Genotype 11 | P Value |
|---|---|---|---|---|
| rs2476601 | 0 | 7 (12.96) | 47 (87.04) | 0.311 |
|  | 1 |  | 7 (100.00) |  |
| rs2274910 | 0 | 23 (42.59) | 31 (57.41) | 0.150 |
|  | 1 | 5 (71.43) | 2 (28.57) |  |
| rs9286879 | 0 | 28 (51.85) | 26 (48.15) | 0.654 |
|  | 1 | 3 (42.86) | 4 (57.14) |  |
| rs2241880 | 0 | 30 (56.82) | 21 (41.18) | 0.04 |
|  | 1 | 7 (100.00) |  |  |
| rs3197999 | 0 | 34 (62.96) | 20 (37.04) | 0.082 |
|  | 1 | 2 (28.57) | 5 (71.43) |  |

TABLE 3(A)-continued

Table 3(A) depicts top IBD risk loci from GWA studies and primary non-response.

| SNP | Primary non response Yes = 1 No = 0 | Genotype 12/22 | Genotype 11 | P Value |
|---|---|---|---|---|
| rs4613763 | 0 | 4 (7.41) | 50 (92.59) | 0.533 |
|  | 1 | 1 (14.29) | 6 (85.71) |  |
| rs10044354 | 0 | 38 (70.37) | 16 (29.63) | 0.477 |
|  | 1 | 4 (57.14) | 3 (42.86) |  |
| rs2188962 | 0 | 45 (63.33) | 9 (16.67) | 0.03 |
|  | 1 | 3 (42.86) | 4 (57.14) |  |
| rs10045431 | 0 | 22 (40.74) | 32 (59.26) | 0.535 |
|  | 1 | 2 (28.57) | 5 (71.43) |  |
| rs6908425 | 0 | 13 (24.07) | 41 (75.93) | 0.066 |
|  | 1 | 4 (57.14) | 3 (42.86) |  |
| rs2844480 | 0 | 22 (40.74) | 32 (59.26) | 0.535 |
|  | 1 | 2 (28.57) | 5 (71.43) |  |
| rs2301436 | 0 | 36 (66.67) | 18 (33.33) | 0.618 |
|  | 1 | 4 (57.14) | 3 (42.86) |  |
| rs1456893 | 0 | 29 (53.70) | 25 (46.30) | 0.211 |
|  | 1 | 2 (28.57) | 5 (71.43) |  |
| rs1551398 | 0 | 32 (59.26) | 22 (40.74) | 0.535 |
|  | 1 | 5 (71.43) | 2 (28.57) |  |
| rs2456449 | 0 | 31 (57.41) | 23 (42.59) | 0.466 |
|  | 1 | 3 (42.86) | 4 (57.14) |  |
| rs10758669 | 0 | 43 (79.63) | 11 (20.37) | 0.618 |
|  | 1 | 5 (71.43) | 2 (28.57) |  |
| rs4574921 | 0 | 21 (38.89) | 33 (61.11) | 0.202 |
|  | 1 | 1 (14.29) | 6 (85.71) |  |
| rs10995239 | 0 | 35 (64.81) | 19 (35.19) | 0.259 |
|  | 1 | 3 (42.86) | 4 (57.14) |  |
| rs11190140 | 0 | 39 (72.22) | 15 (27.78) | 0.445 |
|  | 1 | 6 (85.71) | 1 (14.29) |  |
| rs3764147 | 0 | 31 (57.41) | 23 (42.59) | 0.004 |
|  | 1 |  | 7 (100.00) |  |
| rs1968752 | 0 | 26 (51.65) | 26 (48.15) | 0.654 |
|  | 1 | 3 (42.86) | 4 (57.14) |  |
| rs8049439 | 0 | 25 (46.30) | 29 (53.70) | 0.864 |
|  | 1 | 3 (42.86) | 4 (57.14) |  |
| rs2076756 | 0 | 32 (59.26) | 22 (40.74) | 0.409 |
|  | 1 | 3 (42.86) | 4 (57.14) |  |
| rs2872507 | 0 | 41 (75.93) | 13 (24.07) | 0.143 |
|  | 1 | 7 (100.00) |  |  |
| rs744166 | 0 | 27 (50.00) | 27 (50.00) | 0.285 |
|  | 1 | 5 (71.43) | 2 (28.57) |  |
| rs762421 | 0 | 34 (62.96) | 20 (37.04) | 0.03 |
|  | 1 | 1 (14.29) | 6 (85.71) |  |
| rs10489630 | 0 | 36 (66.67) | 18 (33.33) | 0.050 |
|  | 1 | 2 (28.57) | 5 (71.43) |  |
| rs917997 | 0 | 26 (46.15) | 28 (51.85) | 0.792 |
|  | 1 | 3 (42.86) | 4 (57.14) |  |
| rs9271568 | 0 | 31 (58.49) | 22 (41.51) | 0.004 |
|  | 1 |  | 7 (100.00) |  |
| rs11174631 | 0 | 9 (16.67) | 45 (83.33) | 0.242 |
|  | 1 |  | 7 (100.00) |  |
| rs991804 | 0 | 24 (44.44) | 30 (55.56) | 0.424 |
|  | 1 | 2 (28.57) | 5 (71.43) |  |
| rs2836878 | 0 | 29 (53.70) | 25 (46.30) | 0.01 |
|  | 1 |  | 7 (100.00) |  |
| rs3749946 | 0 | 36 (66.67) | 18 (33.33) | 0.050 |
|  | 1 | 2 (28.57) | 5 (71.43) |  |
| rs7228236 | 0 | 26 (48.15) | 28 (51.85) | 0.792 |
|  | 1 | 3 (42.86) | 4 (57.14) |  |

TABLE 3(B)

Table 3(B) depicts top IBD loci from GWA studies and secondary loss of response.

| SNP | Secondary Loss of response YES = 1, NO = 0 | genotype 12/22 | genotype 11 | P value |
|---|---|---|---|---|
| rs2476601 | 0 | 7 (18.42) | 31 (81.58) | 0.066 |
|  | 1 |  | 16 (100.00) |  |
| rs2274910 | 0 | 16 (42.11) | 22 (57.89) | 0.911 |
|  | 1 | 7 (43.75) | 9 (56.25) |  |
| rs9266879 | 0 | 19 (50.00) | 19 (50.00) | 0.675 |
|  | 1 | 9 (56.25) | 7 (43.75) |  |
| rs2241880 | 0 | 22 (57.89) | 16 (42.11) | 0.818 |
|  | 1 | 8 (61.54) | 5 (38.46) |  |
| rs3197999 | 0 | 23 (60.53) | 15 (39.47) | 0.568 |
|  | 1 | 11 (68.75) | 5 (31.25) |  |
| rs4613763 | 0 | 4 (10.53) | 34 (89.47) | 0.177 |
|  | 1 |  | 16 (100.00) |  |
| rs10044354 | 0 | 30 (78.95) | 8 (21.05) | 0.033 |
|  | 1 | 8 (50.00) | 8 (50.00) |  |
| rs2188962 | 0 | 31 (81.58) | 7 (18.42) | 0.594 |
|  | 1 | 14 (87.50) | 2 (12.50) |  |
| rs10045431 | 0 | 16 (42.11) | 22 (57.89) | 0.753 |
|  | 1 | 6 (37.50) | 10 (62.50) |  |
| rs6908425 | 0 | 6 (15.79) | 32 (84.21) | 0.028 |
|  | 1 | 7 (43.75) | 9 (56.25) |  |
| rs2844480 | 0 | 15 (39.47) | 23 (60.53) | 0.770 |
|  | 1 | 7 (43.75) | 9 (56.25) |  |
| rs2301436 | 0 | 26 (68.42) | 12 (31.58) | 0.673 |
|  | 1 | 10 (62.50) | 6 (37.50) |  |
| rs1456893 | 0 | 20 (52.63) | 18 (47.37) | 0.808 |
|  | 1 | 9 (56.25) | 7 (43.75) |  |
| rs1551398 | 0 | 23 (60.53) | 15 (39.47) | 0.770 |
|  | 1 | 9 (56.25) | 7 (43.75) |  |
| rs2456449 | 0 | 18 (47.37) | 20 (52.63) | 0.021 |
|  | 1 | 13 (81.25) | 3 (18.75) |  |
| rs10758669 | 0 | 31 (61.58) | 7 (18.42) | 0.584 |
|  | 1 | 12 (75.00) | 4 (25.00) |  |
| rs4674921 | 0 | 16 (42.11) | 22 (57.89) | 0.455 |
|  | 1 | 5 (31.25) | 11 (68.75) |  |
| rs10995239 | 0 | 27 (71.05) | 11 (28.95) | 0.139 |
|  | 1 | 8 (50.00) | 8 (50.00) |  |
| rs11190140 | 0 | 26 (68.42) | 12 (31.58) | 0.337 |
|  | 1 | 13 (81.25) | 3 (18.75) |  |
| rs3764147 | 0 | 22 (57.89) | 16 (42.11) | 0.911 |
|  | 1 | 9 (56.25) | 7 (43.75) |  |
| rs1968752 | 0 | 19 (50.00) | 19 (50.00) | 0.675 |
|  | 1 | 9 (56.25) | 7 (43.75) |  |
| rs8049439 | 0 | 14 (36.84) | 24 (63.16) | 0.032 |
|  | 1 | 11 (68.75) | 5 (31.25) |  |
| rs2076756 | 0 | 23 (60.53) | 15 (39.47) | 0.770 |
|  | 1 | 9 (56.25) | 7 (43.75) |  |
| rs2872507 | 0 | 30 (78.95) | 8 (21.05) | 0.424 |
|  | 1 | 11 (68.75) | 5 (31.25) |  |
| rs744166 | 0 | 19 (50.00) | 19 (50.00) | 1.000 |
|  | 1 | 8 (50.00) | 8 (50.00) |  |
| rs762421 | 0 | 24 (63.16) | 14 (36.84) | 0.964 |
|  | 1 | 10 (62.50) | 6 (37.50) |  |
| rs10489630 | 0 | 24 (63.16) | 14 (36.84) | 0.399 |
|  | 1 | 12 (75.00) | 4 (25.00) |  |
| rs917997 | 0 | 19 (50.00) | 19 (50.00) | 0.675 |
|  | 1 | 7 (43.75) | 9 (56.25) |  |
| rs9271568 | 0 | 22 (59.46) | 15 (40.54) | 0.828 |
|  | 1 | 9 (56.25) | 7 (43.75) |  |
| rs11174631 | 0 | 9 (23.68) | 29 (76.32) | 0.033 |
|  | 1 |  | 16 (100.00) |  |
| rs991804 | 0 | 15 (39.47) | 23 (60.53) | 0.257 |
|  | 1 | 9 (86.25) | 7 (43.75) |  |
| rs2836878 | 0 | 19 (50.00) | 19 (50.00) | 0.400 |
|  | 1 | 10 (62.50) | 6 (37.50) |  |
| rs3749946 | 0 | 24 (63.16) | 14 (36.84) | 0.399 |
|  | 1 | 12 (75.00) | 4 (25.00) |  |
| rs7228236 | 0 | 19 (50.00) | 19 (50.00) | 0.675 |
|  | 1 | 7 (43.75) | 9 (56.25) |  |

TABLE 3(C)

Table 3(C) depicts time of loss of response: Kaplan Meier Survival Analysis (time to loss of response).

| SNP | genotype | number | mean duration | P | % censored | P |
|---|---|---|---|---|---|---|
| rs2476601 | 11 | 47 | 26.234 | 0.893 | 67% | 0.12 |
|  | 12/22 | 7 | 25.000 |  | 100% |  |
| rs2274910 | 11 | 31 | 24.613 | 0.582 | 71% | 0.94 |
|  | 12/22 | 23 | 28.043 |  | 69.60% |  |
| rs9286879 | 11 | 26 | 23.808 | 0.478 | 73.10% | 0.94 |
|  | 12/22 | 28 | 28.179 |  | 67.90% |  |
| rs2241880 | 11 | 21 | 33.238 | 0.098 | 76.20% | 0.48 |
|  | 12/22 | 30 | 22.567 |  | 73.30% |  |
| rs3197999 | 11 | 20 | 28.550 | 0.537 | 75% | 0.62 |
|  | 12/22 | 34 | 24.618 |  | 67.70% |  |
| rs4613763 | 11 | 50 | 25.840 | 0.788 | 68% | 0.21 |
|  | 12/22 | 4 | 29.000 |  | 100% |  |
| rs10044354 | 11 | 16 | 20.938 | 0.277 | 50% | 0.02 |
|  | 12/22 | 38 | 28.237 |  | 78.90% |  |
| rs2188962 | 11 | 9 | 21.556 | 0.511 | 77.80% | 0.67 |
|  | 12/22 | 45 | 26.978 |  | 68.90% |  |
| rs10045431 | 11 | 32 | 25.031 | 0.683 | 68.80% | 0.66 |
|  | 12/22 | 22 | 27.591 |  | 72.70% |  |
| rs6908425 | 11 | 41 | 27.122 | 0.545 | 78.10% | 0.04 |
|  | 12/22 | 13 | 22.769 |  | 46.20% |  |
| rs2844480 | 11 | 32 | 23.625 | 0.336 | 71.90% | 0.95 |
|  | 12/22 | 22 | 29.636 |  | 68.20% |  |
| rs2301436 | 11 | 18 | 24.222 | 0.671 | 66.70% | 0.62 |
|  | 12/22 | 36 | 27.000 |  | 72.20% |  |
| rs1456893 | 11 | 25 | 27.200 | 0.734 | 72% | 0.94 |
|  | 12/22 | 29 | 25.103 |  | 69% |  |
| rs1551398 | 11 | 22 | 28.818 | 0.459 | 68.20% | 0.99 |
|  | 12/22 | 32 | 24.188 |  | 71.90% |  |
| rs2456449 | 11 | 23 | 26.913 | 0.815 | 87% | 0.03 |
|  | 12/22 | 31 | 25.452 |  | 58.10% |  |
| rs10758669 | 11 | 11 | 20.455 | 0.355 | 64.60% | 0.28 |
|  | 12/22 | 43 | 27.512 |  | 72.10% |  |
| rs4574921 | 11 | 33 | 25.061 | 0.680 | 66.70% | 0.49 |
|  | 12/22 | 21 | 27.667 |  | 76.20% |  |
| rs10995239 | 11 | 19 | 24.105 | 0.638 | 57.90% | 0.16 |
|  | 12/22 | 35 | 27.143 |  | 77.10% |  |
| rs11190140 | 11 | 15 | 31.267 | 0.294 | 80% | 0.25 |
|  | 12/22 | 39 | 24.077 |  | 66.70% |  |
| rs3764147 | 11 | 23 | 26.522 | 0.900 | 69.60% | 0.93 |
|  | 12/22 | 31 | 25.742 |  | 71% |  |
| rs1968752 | 11 | 26 | 19.231 | 0.029 | 73.10% | 0.86 |
|  | 12/22 | 28 | 32.429 |  | 67.90% |  |
| rs8049439 | 11 | 29 | 27.000 | 0.746 | 82.80% | 0.07 |
|  | 12/22 | 25 | 25.000 |  | 56% |  |
| rs2076756 | 11 | 22 | 26.909 | 0.822 | 68.20% | 0.89 |
|  | 12/22 | 32 | 25.500 |  | 71.90% |  |
| rs2872507 | 11 | 13 | 31.462 | 0.323 | 61.50% | 0.63 |
|  | 12/22 | 41 | 24.366 |  | 73.20% |  |
| rs744166 | 11 | 27 | 21.519 | 0.135 | 70.40% | 0.68 |
|  | 12/22 | 27 | 30.630 |  | 70.40% |  |
| rs762421 | 11 | 20 | 22.900 | 0.428 | 70% | 0.89 |
|  | 12/22 | 34 | 27.941 |  | 70.60% |  |
| rs10489630 | 11 | 18 | 31.556 | 0.205 | 77.90% | 0.42 |
|  | 12/22 | 36 | 23.333 |  | 66.70% |  |
| rs917997 | 11 | 28 | 27.571 | 0.614 | 67.90% | 0.57 |
|  | 12/22 | 26 | 24.462 |  | 73.10% |  |
| rs9271568 | 11 | 22 | 30.045 | 0.340 | 68.20% | 0.99 |
|  | 12/22 | 31 | 24.065 |  | 71% |  |
| rs11174631 | 11 | 45 | 22.622 | 0.010 | 64.40% | 0.03 |
|  | 12/22 | 9 | 43.333 |  | 100% |  |
| rs991804 | 11 | 30 | 27.500 | 0.605 | 76.70% | 0.24 |
|  | 12/22 | 24 | 24.292 |  | 62.50% |  |
| rs2836878 | 11 | 25 | 29.000 | 0.376 | 76% | 0.42 |
|  | 12/22 | 29 | 23.552 |  | 65.50% |  |
| rs3749946 | 11 | 18 | 31.556 | 0.205 | 77.80% | 0.42 |
|  | 12/22 | 36 | 23.333 |  | 66.70% |  |
| rs7228236 | 11 | 28 | 27.571 | 0.614 | 67.90% | 0.57 |
|  | 12/22 | 26 | 24.462 |  | 73.10% |  |

TABLE 3(D)

Table 3(D) depicts serological immune markers and anti-TNFα responsiveness (n = 63).

| Immune Response | Positive = 1 Negative = 0 | yes | no | P | OR | 95 % CI |
|---|---|---|---|---|---|---|
| *Primary non response* | | | | | | |
| pANCA | 1 | 6(85.71) | 12(25.53) | 0.002 | 17.5 | 1.91-160.5 |
|  | 0 | 1(14.29) | 35(74.47) | | | |
| ASCA IgA and/or IgG | 1 |  | 30(47.62) | 0.004 | 0.05 | |
|  | 0 | 10(100.00) | 33(52.38) | | | |
| OmpC | 1 | 1(10.00) | 16(25.40) | 0.29 | 0.33 | 0.04-2.78 |
|  | 0 | 9(90.00) | 47(74.60) | | | |
| I2 | 1 | 3(30.00) | 19(30.65) | 0.97 | 0.97 | 0.23-4.16 |
|  | 0 | 7(70.00) | 43(69.35) | | | |
| CBir1 | 1 | 5(50.00) | 28(45.16) | 0.78 | 1.20 | 0.32-4.62 |
|  | 0 | 5(50.00) | 34(54.84) | | | |
| *Secondary Loss of response* | | | | | | |
| pANCA | 1 | 4(36.36) | 8(22.22) | 0.35 | 2.000 | 0.47-8.60 |
|  | 0 | 7(63.64) | 28(77.78) | | | |
| ASCA IgA and/or IgG | 1 | 6(33.33) | 24(53.33) | 0.15 | 0.438 | 0.14-1.37 |
|  | 0 | 12(66.67) | 21(46.67) | | | |
| OmpC | 1 | 6(33.33) | 10(22.22) | 0.36 | 1.750 | 0.52-5.85 |
|  | 0 | 12(66.67) | 35(77.78) | | | |
| I2 | 1 | 8(44.44) | 11(25.00) | 0.13 | 2.400 | 0.76-7.60 |
|  | 0 | 10(55.56) | 33(75.00) | | | |
| CBir1 | 1 | 7(38.89) | 21(47.73) | 0.53 | 0.697 | 0.23-2.13 |
|  | 0 | 11(61.11) | 23(52.27) | | | |

Example 8

Enrollment Criteria

Inclusion Criteria:
1. IBD patients <21 years of age
2. Active CD or UC patients initiating infliximab therapy as prescribed by the treating physician.
3. No predetermined minimum Crohn's Disease Activity Index (CDAI) or Pediatric Crohn's Disease Activity Index (PCDAI) or Partial Mayo score will be necessary for inclusion (see justification below)
4. Willingness to participate
5. Able to give consent by patient or legal guardian
6. Willing to provide blood Exclusion Criteria:
1. IBD Patients not receiving infliximab
2. Patients in remission at time of initiating infliximab
3. IBD patients who are on low dose prednisone for adrenal insufficiency and unable to wean in designated time frame.
4. CD patients with exclusive perianal fistulizing disease (see justification below)

Example 9

Association of Anti-TNF Responsiveness Against the Whole Genome

Three (3) outcomes were evaluated:
1) primary non-response: patient did not respond to the induction regimen as defined by patient did not receive a clinical benefit from the first 3 infusions of infliximab and did not receive any further treatment doses.
2) secondary loss of response: patient responded to the induction regimen and despite dose escalation and/or frequency intensification of infliximab the drug was discontinued as of last follow up.
3) failure for any reason.

The results and analysis of the three outcomes are further described in Tables 1(A-C) and 2 (A-C) below.

Example 10

TABLE 4(A-C)

Results of top ten (10) most significant associations
Analysis of top ten (10) most significant associations for
primary non-response as an outcome.

| snp | CHR | BP | A1 | F_A | F_U | A2 | fisher_p | OR | l_p | loci |
|---|---|---|---|---|---|---|---|---|---|---|
| rs13079040 | 3 | 68988334 | C | 0.7143 | 0.1574 | T | 0.00003361 | 13.38 | 4.47353149 | FAM19A4 |
| rs4855535 | 3 | 69017124 | G | 0.5714 | 0.05556 | T | 6.987E−06 | 22.67 | 5.15570926 | FAM19A4 |
| rs17048128 | 3 | 69028502 | A | 0.5714 | 0.05556 | G | 6.987E−06 | 22.67 | 5.15570926 | FAM19A4 |
| rs17048129 | 3 | 69031452 | A | 0.5714 | 0.05556 | G | 6.987E−06 | 22.67 | 5.15570926 | FAM19A4 |
| rs17039556 | 4 | 161545059 | A | 0.7143 | 0.1296 | G | 8.744E−06 | 16.79 | 5.05828985 | |
| rs12640159 | 4 | 161586073 | A | 0.7857 | 0.1944 | G | 0.00001882 | 15.19 | 4.72538038 | |
| rs880330 | 7 | 67842575 | T | 0.7857 | 0.213 | C | 0.00003927 | 13.55 | 4.4059391 | |

TABLE 4(A-C)-continued

Results of top ten (10) most significant associations
Analysis of top ten (10) most significant associations for
primary non-response as an outcome.

| snp | CHR | BP | A1 | F_A | F_U | A2 | fisher_p | OR | l_p | loci |
|---|---|---|---|---|---|---|---|---|---|---|
| rs2057917 | 7 | 67867804 | C | 0.8571 | 0.2778 | T | 0.00004331 | 15.6 | 4.36341182 | |
| rs2983478 | 14 | 94433843 | C | 1 | 0.4167 | T | 0.00001555 | | 4.80826961 | |
| rs4776127 | 15 | 51373815 | G | 0.7857 | 0.213 | A | 0.00003927 | 13.55 | 4.4059391 | |

TABLE 4(B)

Analysis of top ten (10) most significant associations for secondary loss of response as an outcome.

| snp | CHR | BP | A1 | F_A | F_U | A2 | fisher_p | OR | l_p | loci |
|---|---|---|---|---|---|---|---|---|---|---|
| rs1838990 | 3 | 63142891 | C | 0.09375 | 0.5132 | T | 0.00002815 | 0.09814 | 4.5505216 | |
| rs11713998 | 3 | 168613099 | T | 0.4375 | 0.06579 | C | 0.00001437 | 11.04 | 4.84254323 | |
| rs13144587 | 4 | 67295867 | C | 0.4375 | 0.07895 | A | 0.00003895 | 9.074 | 4.40949254 | |
| rs6928719 | 6 | 166117879 | C | 0.1875 | 0.6711 | A | 5.292E−06 | 0.1131 | 5.27638016 | |
| rs6928737 | 6 | 166118611 | G | 0.1875 | 0.6579 | A | 7.617E−06 | 0.12 | 5.11821604 | |
| rs6904237 | 6 | 166121014 | C | 0.1875 | 0.6316 | T | 0.00004141 | 0.1346 | 4.38289477 | |
| rs4762507 | 12 | 97659769 | T | 0 | 0.3553 | C | 0.0000171 | 0 | 4.76700389 | ANKS1B |
| rs12857230 | 13 | 42654650 | G | 0.7188 | 0.25 | T | 8.917E−06 | 7.667 | 5.04978123 | |
| rs12918939 | 16 | 64698060 | G | 0.4375 | 0.07895 | A | 0.00003895 | 9.074 | 4.40949254 | |
| rs5999636 | 22 | 33661041 | T | 0 | 0.3289 | C | 0.00004165 | 0 | 4.38038499 | |

TABLE 4(C)

Analysis of top ten (10) most significant associations for failure for any reason as an outcome.

| snp | CHR | BP | A1 | F_A | F_U | A2 | fisher_p | OR | l_p | loci |
|---|---|---|---|---|---|---|---|---|---|---|
| rs11695174 | 2 | 9705766 | T | 0.2955 | 0.02564 | C | 0.00002682 | 15.94 | 4.57154123 | |
| rs17020744 | 2 | 81845572 | A | 0.25 | 0.01282 | G | 0.00004771 | 25.67 | 4.32139058 | |
| rs1549599 | 3 | 37506369 | G | 0.6818 | 0.2692 | A | 0.00001852 | 5.816 | 4.73235902 | ITGA9 |
| rs1569091 | 7 | 94356064 | A | 0.6136 | 0.2308 | G | 0.00003676 | 5.294 | 4.4346245 | |
| rs7335910 | 13 | 24220725 | G | 0.09091 | 0.4615 | A | 0.00001775 | 0.1167 | 4.75080164 | |
| rs4326996 | 15 | 61567335 | G | 0.25 | 0.01282 | T | 0.00004771 | 25.67 | 4.32139058 | |
| rs1554983 | 16 | 77425340 | A | 0.3182 | 0.7179 | G | 0.00002387 | 0.1833 | 4.62214758 | |
| rs9915945 | 17 | 6089542 | A | 0.3636 | 0.05128 | G | 0.00001539 | 10.57 | 4.81276138 | |
| rs4794558 | 17 | 50702952 | A | 0.5682 | 0.1923 | G | 0.00004192 | 5.526 | 4.37757873 | HLF |
| rs323391 | 17 | 69199193 | A | 0.4773 | 0.1154 | C | 0.00001732 | 7 | 4.76145211 | |

Example 11

Methods—Patient Population 94 pediatric CD and UC patients (age <21 years), followed at CSMC. Each received at least 2 doses (week 0 and 2) of infliximab. Clinical data was collected and stored in a secure database at CSMC. Serological immune responses (ELISA EU/ml) collected and analyzed at CSMC. Specifically, ASCA (IgG and IgA), anti-Cbir1 (IgG), pANCA (IgG) 12 (IgA), OmpC (IgA). Genotype data was also obtained.

Example 12

Methods—Primary Outcome Definitions

Primary non-response was evaluated for patients. For Crohn's Disease, primary non response was defined by no change or increase in HBI from baseline at week 10 or earlier if drug discontinued before week 6 infusion. For ulcerative colitis, primary non response was defined by no change or increase from baseline in the sum of stool frequency and rectal bleeding subscores of the partial Mayo score and no improvement in the physician's global assessment subscore.

Example 13

Methods—Association Variables

SNP selection of known IBD susceptibility SNPs (GWA significance) were taken from previous adult CD meta GWAS (32 loci), adult UC GWAS (5 loci), and pediatric IBD GWAS (2 loci). SNP selection was also taken of top 10 significant SNPs from pharmacogenetic GWAS, using chi square test. Serology status, of positive or negative, was determined with chi square test. Finally, demographic and phenotype data was taken with t-test for continuous variables and chi-square test for categorical variables.

Example 14

Methods—Predictive Models

Predictive models of non-response were created using Strategy A, B and C. Strategy A utilizes known susceptibility IBD SNPs, using logistic multiple regression, and stepwise selection of phenotype, serologic and genetic variables with univariate association p<0.1. Strategy B utilizes the top 10 SNPs from pharmacogenetics GWAS ($p<2*10^{-5}$), using logistic multiple regression, and stepwise selection of phenotype, serologic and genetic variables with univariate association p<0.1. Strategy C is the combination of Strategy A and B (also known as Final Model).

With regard to clinical utility, the sensitivity, specificity, accuracy, ROC, positive likelihood ratio calculated for the models.

Example 15

Table 5—Results of Demographic and Phenotype Associations with Primary Non Response From 94 patients meeting inclusion criteria, 22 exhibited primary non response, and 72 exhibited primary response.

TABLE 5

| CLINICAL VARIABLE | NON RESPONSE | RESPONSE | P Value |
|---|---|---|---|
| UC vs. CD | 14:8 | 6:66 | <0.0001 |
| Mean age at diagnosis (years) | 10.1 | 10.5 | 0.71 |
| Gender M:F | 8:14 | 40:32 | 0.12 |
| Disease duration at start of IFX (months) | 26 | 25 | 0.96 |
| IMM use at start of IFX (%) | 79% | 92.8% | 0.1 |
| Duration of IMM at start of IFX (months) | 12.7 | 15.3 | 0.57 |
| pANCA+ | 76.2% | 29% | 0.0001 |
| ASCA+ | 0% | 46.9% | 0.0003 |

Example 16

Table 6—Results of Strategy A: Models of Primary Non-Response with Known Susceptibility Loci

TABLE 6

| Model | Variable | Description | P value | OR (95% CI) | R-square |
|---|---|---|---|---|---|
| I | Diagnosis | UC vs. CD | 0.0001 | 15.0 (4.1, 55.8) | 0.48 |
| | pANCA | Pos vs. Neg | 0.01 | 5.4 (1.5, 19.9) | |
| II (known IBD susceptibility SNPs only) | rs2188962 5q31.1 | CC vs. CT/TT | 0.04 | 3.3 (1.03, 10.9) | 0.30 |
| | rs6908425 6p22.3 CDKA1 | CT/TT vs. CC | 0.04 | 3.2 (1.01, 10.4) | |
| | rs2836878 21q22.2/ BRWD1 | GG vs AG/AA | 0.05 | 3.3 (0.98, 11.2) | |
| | rs2395185 6p21/HLA-DQA1 | GG vs. TG/TT | 0.01 | 4.6 (1.4, 14.9) | |

Example 17

Table 7—Results of Strategy A: Models of Primary Non-Response with Known Susceptibility Loci

TABLE 7

| Model | Variable | Description | P value | OR (95% CI) | R-square |
|---|---|---|---|---|---|
| III: I & II (Combined) | Diagnosis | UC vs. CD | 0.0008 | 14.7 (3.1, 70.4) | 0.59 |
| | pANCA | Pos vs. Neg | 0.004 | 15.3 (2.4, 96.2) | |
| | rs6908425 6p22.3 CDKA1 | CT/TT vs. CC | 0.05 | 4.6 (1.0, 21.0) | |

TABLE 7-continued

| Model | Variable | Description | P value | OR (95% CI) | R-square |
|---|---|---|---|---|---|
| | rs2836878 21q22.2/ BRWD1 | GG vs. AG/AA | 0.02 | 9.8 (1.5, 64.0) | |
| | rs2395185 6p21/HLA-DQA1 | GG vs. TG/TT | 0.047 | 5.4 (1.0, 28.6) | |

Example 18

Table 8—Results of Strategy B: Model of Primary Non-Response with Pharmacogenetic GWAS Loci

TABLE 8

| Model | Variable | Description | P Value | R square |
|---|---|---|---|---|
| IV (pharmacogenetic GWAS genes only) | rs975664 2p12 TACR1 | TT vs. CT/CC | 0.0006 | 0.67 |
| | rs4855535 3p14 FAM19A4 | GG/GT vs. TT | 0.006 | |
| | Rs4796606 17q21 KRT35, 32, 36, 13 Keratin gene cluster | CC/CT vs. TT | 0.01 | |
| | Rs765132 Xq26 | TT/TC vs. CC | 0.03 | |

Example 19

Results—Strategy C: Final Model of Primary Non-Response with Pharmacogenetic GWA and Known Susceptibility SNPs and Clinical Phenotype and Serology Status

TABLE 9

| Model | Variable | Description | P value | R-square |
|---|---|---|---|---|
| V: III & IV | Dx | UC vs. CD | 0.008 | 0.82 |
| | pANCA | Pos vs. Neg | 0.03 | |
| | rs975664 2p12/TACR1 | TT vs. CT/CC | 0.01 | |
| | rs4855535 3p14/FAM19A4 | GG/GT vs. TT | 0.02 | |
| | rs6100556 20q13/PHACTR3 | TG/TT vs. GG | 0.02 | |
| | rs2836878 21q22/BRWD1 | GG vs. AG/AA | 0.07 | |

Example 20

Table 10—Results Demonstrating Diagnostic Utility of Final Model for Non-Response to Anti-TNFα

TABLE 10

| Model | Variable | Description | ROC | SN | SP | ACC | Positive Likelihood Ratio of NR |
|---|---|---|---|---|---|---|---|
| V: III & IV | Dx | UC vs. CD | 0.98 | 0.95 (cut-off: ≥ 3 risk factors) | 0.88 | 0.92 | 8 |
| | pANCA | Pos vs. Neg | | | | | |
| | rs975664 2p12/ TACR1 | TT vs CT/CC | | | | | |
| | rs4855535 3p14/ FAM19A4 | GG/GT vs TT | | | | | |
| | rs6100556 20q13/ PHACTR3 | TG/TT vs GG | | | | | |
| | rs2836878 21q22/ BRWD1 | GG vs AG/AA | | | | | |

SN = sensitivity;

SP = specificity;

ACC = accuracy.

Example 21

Conclusions 4 known IBD susceptiblity genes were associated with non-response to infliximab.
UC-independent predictor of non-response to infliximab and may be the most important predictor.
pANCA positive independently predicts non-response to infliximab.
Pharmacogenetic GWAS top loci improved prediction of non-response compared to known susceptibility loci.
The combination of genotype, phenotype and serotype was best predictor of non-response to anti-TNFα.
Defining predictors of response to anti-TNFα aid clinicians in choosing the right therapy for the right patient.
Trial design may be enhanced using genetic markers.

Example 22

Genotyping

Genotyping may be performed at Cedars-Sinai Medical Center in the GCRC phenotyping/genotyping Core Facility. Genotyping for single nucleotide polymorphisms (SNPs) is performed using ABI TaqMan MGB chemistry with an ABI 7900 instrument in 384 well format. A robotic workstation (Tecan Genesis) is used to set up the PCR plates and the current throughput is 6×384 assays per day. TaqMan chemistry results in the release of dye as the 5'-nuclease activity of Taq polymerase degrades a probe/quencher bound to a particular allele. The use of two dyes, one for each allele, allows the SNP genotyping in a single PCR reaction. The "MGB" system has several advantages over earlier version of this chemistry for SNP genotyping and is therefore a "second generation" technology that includes: 1) a more sensitive VIC dye rather than TET, 2) an improved optical system in the ABI7900 instrument eliminates missed reads due to scratches in the caps, 3) primer and probe design software that considerably lowers the amount of troubleshooting 4) 384-well format for high throughput, and 5) use of a minor groove binder (MGB) shortens the length of the probe and thus increases discrimination between the two alleles of the SNP. This technology has been used extensively in the CSMC genotyping core.

Example 23

Definitions of Therapeutic Responsiveness

Response criteria described below have been employed in phase 3 clinical trials in both pediatric and adult IBD patients receiving infliximab. It is important to determine whether a patient is responding to their induction regimen. This will negate any non responders from continuing to receive ineffective therapy. The primary goal of using anti-TNFα is to induce and maintain a steroid free remission. The side effect profile and the potential growth stunting effects of corticosteroids make this steroid sparing agent very important in IBD patients, especially children. Having a strict corticosteroid specification for response makes for a more robust end point and potentially more clinically meaningful.

Primary Non-Response:
CD: Inability to achieve a drop in PCDAI of >15 points from baseline or CDAI drop of >70 points and >75% reduction in corticosteroid dose at week 10 if on steroids at initiation of infliximab.

UC: Inability to achieve an improvement of at least 2 points in the sum of stool frequency and rectal bleeding subscores of the partial Mayo score, and no worsening in the physician's global assessment subscore OR the sum of the subject's stool frequency and rectal bleeding subscores is less than or equal to 1, and no worsening in the physician's global assessment subscore and >75% reduction in corticosteroid dose at week 10 if on corticosteroids at initiation of infliximab.

Response:
CD: Drop in PCDAI of >15 points from baseline or CDAI drop of >70 points from baseline for CD and >75% reduction in corticosteroid dose at week 10 if on corticosteroids at initiation of infliximab. For example a patient started on 40 mg/day will need to be weaned to <10 mg/day.

UC: An improvement of at least 2 points in the sum of stool frequency and rectal bleeding subscores of the partial Mayo score, and no worsening in the physician's global assessment subscore OR the sum of the subject's stool frequency and rectal bleeding subscores is less than or equal to 1, and no worsening in the physician's global assessment subscore and >75% reduction in corticosteroid dose at week 10 if on corticosteroids at initiation of infliximab.

Forced Corticosteroid Taper: (Standard Corticosteroid Wean Based on Clinical Trials and Routine Clinical Care):
Subjects on oral prednisone or equivalent will keep their enrollment dose stable for 2 weeks as anti-TNFα may take 10-14 days to have a clinical effect. Starting at week 2, corticosteroids will be tapered at the following rate:
Prednisone or equivalent: >20 mg/day 5 mg/q 5 days
>10-<20 mg/day 5 mg/week
<10 mg/day 2.5 mg/week Sustained Remission:
CD: PCDAI<10 or CDAI<150 for CD and off corticosteroids at week 10 and week 54 without rescue therapy with steroids or infliximab dose increase or frequency escalation in between.

UC: partial mayo score ≤2 points, with no individual subscore >1 and off corticosteroids at week 10 and week 54 without rescue therapy with steroids or infliximab dose increase or frequency escalation in between.

Loss of Response:
Recurrence of symptoms as determined by the treating physician necessitating rescue therapy with corticosteroids or an increase dose of infliximab from 5 mg/kg to 10 mg/kg or the patient requires infliximab more frequent then every 8 weeks. Physician Global Assessment Score will be used to document the condition of the patient at time of the visit determining loss of response and change in clinical condition from week 10 assessment. The physician global assessment of change is a 5-point scale used to assess the change from baseline (week 10) in the subject's disease activity from the perspective of the physician.

Immunogenicity and Infliximab Trough Drug Levels:
Immunogenicity may be determined based on the development of antibodies to infliximab. Antibody levels will be measured as detectable vs. non detectable. Levels >8 ug/dl have been shown to be associated with loss of response and will be chosen as cut point for detectable vs. non detectable.

Trough drug levels: levels of infliximab in the blood at the time of the infliximab infusion. Levels <12 ug/ml have been shown to be associated with loss of response and will be chosen as threshold for detectable vs. non detectable.

mRNA Expression:

Subject's mRNA expression may be classified as respondents or non-respondents. Respondents will be determined by a more than 2-fold increase in mRNA expression after induction.

Clinical Phenotype:

The baseline clinical features to be analyzed include: age at diagnosis, gender, disease location (upper tract, small bowel, large bowel, perianal), disease behavior (fistulizing and or stricturing disease), duration of disease at baseline, disease activity at baseline, smoking (active or passive) history and use of concomitant immunomodulators.

Example 24

Serological Immune Response Processing

ASCA/ANCA ELISA:

ASCA: the samples will be analyzed by ELISA with phosphopeptidomannan extracted from *Saccharomyces cerevisiae* serving as the antigen. Briefly, plasma diluted 1:80 (for IgA detection) or 1:800 (for IgG detection) will be added to plates previously coated with mannan at 100 ug/ml. After incubation and washing, alkaline phosphatase labeled goat anti-human IgA and IgG are added to their respective plates. Finally, after another incubation and wash, substrate (p-nitrophenyl phosphate) is added and color change is detected at 405 nm. All samples are compared to standard positive control samples and expressed as ELISA units (EU).

ANCA/pANCA: the samples will be quantitatively analyzed by ELISA and ELISA positive samples will be further characterized qualitatively by immunofluorescence binding pattern including DNase treatment of samples with pANCA binding. For ELISA analysis, microtiter plates are coated with a monolayer of neutrophils (25,000/well) and air-dried, fixed with 100% methanol, dried again and stored at −20° C. For use, the plates are blocked for non specific binding by 0.5% bovine serum albumin in phosphate buffered saline (BSA/PBS), the blocking material is discarded and samples at a 1:100 dilution in BSA/PBS are added. After incubation and washing, alkaline phosphatase labeled goat anti-human IgG (gamma chain specific) is added. Finally, after another incubation and wash, substrate (p-nitrophenyl phosphate) is added and color change is detected at 405 nm. All samples are compared to standard positive control samples and expressed as ELISA units (EU). For indirect immunofluorescence analysis of ANCA, slides are prepared by cytocentrifugation of 100,000 neutrophils. The slides are air-dried and fixed in 100% methanol, then air-dried and stored at −20° C. For use, the slides are rehydrated in PBS and samples diluted 1:20 in BSA/PBS are added. After washing, fluoroscein labeled goat F (ab)'2 anti human IgG (gamma chain specific) is added. The slides are washed again and evaluated by fluorescence microscopy. For evaluation of DNase sensitivity of pANCA patterns, slides are pretreated with 100 U/ml of RNase free DNase for 30 minutes. Slides are stained as above with a pair of DNase-treated and untreated slides used for each sample.

CBir1 ELISA:

ELISA analysis of anti-CBir1 was performed as previously described 21 but using NH2-terminal fragment of CBir1 (147 aa) without knowledge of diagnosis or other serology results. Briefly, ELISA plates were coated overnight with 100 ng/well of CBir1, then blocked with 1% BSA in PBS for 2 hours. Plates were washed and serum was added at a 1:200 dilution in 1% BSA-PBS for a 30 minute incubation. After washing, horseradish peroxidase conjugated anti-human IgG at a 1:10,000 dilution was added and incubated for 30 minutes. After another wash, the plates were incubated with tetramethylbenzidine substrate for 15 minutes. The reaction was stopped with 1 N sulfuric acid and read at 450 nm. Positive was defined as the mean+2 SD of the healthy controls. For Cohort 2 and the longitudinal cohorts and phenotype cohorts, this assay was modified to be more similar to the ANCA, OmpC and I2 protocols: alkaline phosphatase was substituted as the secondary conjugate and incubated for 1 hour followed by paranitrophenyl phosphate as substrate for 30 minutes.

OmpC/I2 Purification

Trimeric OmpC is biochemically purified from an OmpF−/−/OmpA−/− disruptive insertion mutant *E. coli* K12 (provided by R. Misra). Mutant *E. coli* glycerol stocks are inoculated into 10-20 ml of Luria Bertani broth supplemented with 100 ug/ml Streptomycin (LB-Strep), and culture vigorously at 37° C. for ~8 hours to log phase followed by expansion to 1 liter in LB-Strep over 15 hours at 25° C. Cells are harvested by centrifugation, washed twice with 100 ml of ice cold 20 mM Tris-Cl pH 7.5, and resuspend in cold spheroplast forming buffer (20 mM Tris-Cl pH 7.5, 20% Sucrose, 0.1M EDTA pH 8.0, 1 mg/ml Lysozyme). Spheroplasts are allowed to form for 1 hour on ice with occasional mixing, and then lysed by 14 fold dilution into ice cold 10 mM Tris-Cl pH 7.5, 1 mg/ml DNase-I, and vigorous vortexing followed by pulse sonication (4×30 seconds, On time=1 second at high power). Cell debris is by low speed centrifugation, and membrane preparation collected by ultra centrifugation at 100,000 g in a swing bucket rotor. Membrane pellet is resuspended by homogenizing into 20 mM Tris-Cl pH 7.5, and extracted for 1 hour in 20 mM Tris-Cl pH 7.5+1% SDS by rotating at 37° C. Pre-extracted membrane preparation is then pelleted by ultracentrifugation and resuspended by homogenizing into 20 mM Tris-Cl pH 7.5 as above, and OmpC is extracted for 1 hour rotating at 37° C. with 20 mM Tris-Cl pH 7.5, 3% SDS, and 0.5M NaCl. Membrane is then pelleted by ultracentrifugation and the supernatant containing trimeric OmpC is collected. SDS is removed from OmpC preparations by detergent exchange dialysis against >10,000 volumes of 0.2% triton x100 followed by dialysis against >10,000 volumes Tris-Cl pH 7.5. Purified OmpC is quantified using the Bradford reagent (Biorad, Hercules, CA) and purity of >95% is validated by SDS-PAGE and Silver staining (Biorad). Purified protein is aliquoted and stored at −20° C. until used.

The 100 amino acid open reading frame (ORF) of I2 is subcloned into pGEX-KG and expressed in *E. coli* XL-1 blue (Stratagene, La Jolla, CA). I2-GST fusion protein is present as an inclusion body, and purified according to manufacturer's instructions by differential solubilization in 0.1% sodium dodecyl sulfate (SDS). The glutathione-S-transferase (GST) control is produced with unmodified pGEX-KG and XL-1 blue cells, and is present about 50% in the soluble and inclusion body fractions. The latter is purified exactly as I2-GST, and the former is purified by G-Sepharose affinity chromatography. All protein preparations are >90% pure by SDS polyacrylamide gel electrophoresis (PAGE) and Coomassie blue protein staining.

Determination and Characterization of the OmpC/I2 Response:

Human IgA antibodies that bind I2 or OmpC will be detected by direct ELISA assays. Plates (Greiner, USA Scientific, Ocala, FL) will be coated overnight at 4 C with 100 μl/well of GST alone and I2-GST (5 μg/ml) or OmpC (0.25 μg/ml) in borate buffered saline, pH 8.5. After three washes in 0.05% Tween 20 in phosphate buffered saline (PBS), the plates will be blocked with 150 μl/well of 0.5% bovine serum albumin in PBS, pH 7.4 (BSA-PBS) for 30 minutes at room temperature (RT). The blocking solution will then be discarded and 100 μl/well of sera diluted 1:100 will be added and incubated for 2 hours at RT. The plates will be washed as before and alkaline phosphatase conjugated goat anti-human IgA (_-chain specific, Jackson ImmunoResearch, West Grove, PA) at a dilution of 1:1000 in BSA-PBS will be added for 2 hours at RT. The plates will be washed three times with 0.05% Tween 20 in phosphate buffered saline followed by another three washes with Tris buffered normal saline, pH7.5. Substrate solution (1.5 mg/ml disodium P-nitrophenol phosphate (Amresco, Solon, OH), 2.5 mM MgCl2, 0.01M Tris, pH 8.6) will be added at 100_I/well and color will be allowed to develop for one hour at which time the plates will be read at 405 nm. Nonspecific binding of sera to GST alone (typically <0.1) will be subtracted from raw values of I2-GST binding to obtain I2 specific absorbances. Levels will be determined relative to a standard consisting of serum obtained from a well-characterized CD patient. Results will be expressed as ELISA units (EU/ml). Sera with antibody levels exceeding the normal reference range value will be termed positive.

Example 25

Blood Stimulation

Anti-TCR antibody (IgG1) or controls (control IgG1 BioLegend, San Diego, CA) may be stored at −20° C. in 6-well strip microtubes until use. Sixty microliters of whole blood will be added into 6 wells of microwell strip (3 wells for control IgG and 3 wells for anti-TCR antibody) and incubated at 37° C. for 4 hours with the cap closed. Following each treatment, blood samples were stored frozen at_80° C.

Example 26

Final Predictive Model—Overall

Inter-individual variation in response to anti-TNFα therapy may be explained by genetic variability in disease pathogenesis or mechanism of action. Recent genome wide association studies (GWAS) in IBD have increased understanding of the genetic susceptibility to IBD.

As disclosed herein, the inventors tested associations of known IBD susceptibility loci and novel "pharmacogenetic" GWAS identified loci with primary non-response to anti-TNFα in pediatric IBD patients and developed a predictive model of primary non-response. Primary non response was defined using the HBI for CD and partial Mayo score for UC. Genotyping was performed using the Illumina Infinium platform. Chi square analysis tested associations of phenotype and genotype with primary non-response. Genetic associations were identified by testing known IBD susceptibility loci and by performing a GWAS for primary non-response. Step-wise multiple logistic regression was performed to build predictive models.

As further disclosed herein, non-response occurred in 22 of 94 subjects. Six known susceptibility loci were associated with primary non-response (p<0.05). The 21q22.2/BRWDI loci remained significant in the predictive model. The most predictive model included 3 novel "pharmacogenetic" GWAS loci, the previously identified BRWD1, pANCA and a UC diagnosis ($R^2$=0.82 and AUC=0.98%). The relative risk of non-response increased 15 fold when number of risk factors increased from 0-2 to 3. The combination of phenotype and genotype is most predictive of primary non response to anti-TNFα in pediatric IBD. Defining predictors of response to anti-TNFα will allow the identification of patients who will not benefit from this class of therapy.

Example 27

Final Predictive Model—Patient Population

A total of 94 pediatric CD and UC patients (age at diagnosis <21 years) followed at Cedars-Sinai Medical Center (CSMC) by one clinician (MD) were enrolled in this study. All subjects must have received at least 2 doses of (weeks 0 and 2) of infliximab to be eligible. Infliximab was chosen as the first line anti-TNFα used in both CD and UC for children. This study was approved by the institutional IRB.

Example 28

Final Predictive Model—Phenotyping

All data was collected by chart review and stored in a secured database. For the purpose of this study phenotype was defined as all variables that were not genetic.

Clinical Phenotype: These included demographic and clinical variables: age, gender, IBD subtype (CD vs. UC), disease duration, age at diagnosis, age at initiation of infliximab, immunomodulator history, steroid history, Harvey Bradshaw Index (HBI) activity scores, Partial Mayo scores and reason for infliximab discontinuation.

Immune Phenotype: Serum was collected on all patients and analyzed at CSMC. Serum immune responses: anti-*Saccharomyces cereviciae* antibodies (ASCA IgG and IgA), perinuclear anti-nuclear cytoplasmic antibody (pANCA), anti-flagellin (antiCBir1), anti-outer membrane porin C (anti-OmpC) and anti-*Pseudomonas fluorescens*-associated sequence 12 (anti-I2) were analyzed blinded to therapeutic responsiveness by ELISA as previously described.

Example 29

Final Predictive Model—Genotype

Genotyping was performed at Children's Hospital of Philadelphia (CHOP) using the Illumina Human550 platform (n=70) and the Medical Genetics Institute at CSMC using the Illumina Human610 platform for CD samples (n=17) and HumanCNV370 platform for UC samples (n=11) (23). First, genotype data were tested for association between previously reported IBD susceptibility SNPs and anti-TNFα response. Table 11 illustrates the 28 SNPs included in this part of the analysis and references the GWAS that first reported these associations with disease. Twenty-one SNPs from a previous CD meta-analysis GWAS, 5 SNPS from various UC GWAS and 2 SNPs from a pediatric IBD GWAS were analyzed. Second, the genome wide data were tested for association with anti-TNFα response ("pharmacogenetic" GWAS, see below).

TABLE 11

Known Genetic Susceptibility Loci

| Chromosome/<br>Loci of interest | GWAS Reference<br>1 = Adult CD (14)<br>2 = Adult UC (15-17)<br>3 = Pediatric IBD (18) |
|---|---|
| 1p13/PTPN22 | 1 |
| 1p36 | 2 |
| 1q23/ITLN1 | 1 |
| 1q24 | 1 |
| 1q21.2/ECM1 | 2 |
| 1q32.1/IL10 | 2 |
| 1p31/IL23R | 1 |
| 2q37/ATG16L1 | 1 |
| 3p21/MST1 | 1 |
| 5p13/PTGER4 | 1 |
| 5q31/IBD5 | 1 |
| 5q33/IL12b | 1 |
| 6p21/HLA-DQA1/TNFα, TNFβ | 2 |
| 6p22/CDKAL1 | 1 |
| 6q27/CCR6 | 1 |
| 8q24.13/TRIB1 | 1 |
| 9p24/JAK2 | 1 |
| 9q32/TNFSF15 | 1 |
| 10q21/ZNF365 | 1 |
| 10q24/NKX2-3 | 1 |
| 12q15 | 2 |
| 13q14/C13orf31 | 1 |
| 16q12/NOD2 | 1 |
| 17q12/CCL2 | 1 |
| 17q21/ORMDL3/STAT3 | 1 |
| 20q13/TNFRSR6B | 3 |
| 21q22/COSLG | 1 |
| 21q22.2/BRWD1 | 3 |

Example 30

Final Predictive Model—Outcomes and Definitions

The primary outcome of this study was to identify genetic loci associated with primary non-response defined as:
- CD: Failure to decrease HBI≥3 points (24) or increase from baseline at week 10 or 4 weeks after their last infusion if they did not receive the $3^{rd}$ induction dose
- UC: Failure to decrease ≥2 points or increase from baseline in the sum of stool frequency and rectal bleeding subscores of the partial Mayo score (7) and no improvement in the physician's global assessment subscore at week 10 or 4 weeks after their last infusion if they did not receive the $3^{rd}$ induction dose

Example 31

Final Predictive Model—Univariate Analysis

Association between clinical and demographic variables and primary non-response: The Chi-square test was used to check the association of primary non-response with the following categorical variables: CD vs. UC, male vs. female, serum immune response positivity, percentage of immunomodulator use at the start of infliximab and primary non-response. The Student t test was used for associations of continuous variables; age of diagnosis, disease duration and duration of immunomodulator use at the start of infliximab.

Association between known IBD susceptibility loci and primary non-response: The Chi-square test was applied to test the association between each SNP (Table 11) and primary non-response. A dominant model based on the presence of the rare allele was assumed. Relative risk was calculated by comparing the risk of non-response in the patients with a specific genotype versus those without the genotype.

Pharmacogenetic Genome Wide Association Study (GWAS):
- a. Principal components (PC) analysis (using Eigenstrat) was conducted to examine population stratification (25). All the subjects formed one cluster with no significant outliers. There was no need to correct for population stratification during the association analysis, as the first ten PC evaluated were not significantly associated with primary non-response.
- b. For the purpose of quality control, SNPs with a minor allele frequency (MAF)<0.01, genotype failure rate >0.10, HWE P value <0.001 were excluded from the analysis. Allelic association between an individual SNP and primary non-response was carried out by chi-square test in PLINK (26). The first 10 SNPs with the most significant results were then retained for modeling. Following quality control, 301,742 SNPs were available in all data sets for analysis.

Example 32

Final Predictive Model—Multivariate Analysis

Predictive models of primary non-response: Models to predict non-response were built using step-wise multiple logistic regression, combining a) IBD susceptibility SNPs, b) the top 10 hits from the pharmacogenetic GWAS analysis, c) serology status and d) IBD subtypes. Since rs5975493 and rs7059861 are in high linkage disequilibrium, only rs7059861 was kept in the model. Exact logistic regression was used if the estimate from a regular regression model was not available. The significance level for a variable to enter and stay in the model was 10%. The likelihood based pseudo-R squared from the logistic regression model was used to measure the strength of association as well as the proportion of variance of the outcome accounted by the model's independent variables.

Models were built at five different levels:
- I. demographic variables, serology status and IBD subtype only
- II. known IBD susceptibility SNPs only
- III. model I and II combined
- IV. pharmacogenetic GWAS SNPs (dominant model assumed) only
- V. model III and IV combined (final model). (known IBD susceptibility SNPs, pharmacogenetic GWAS top hits, serologic status and clinical variables)

Clinical Utility Measures: The area under the Receiver Operating Characteristic (ROC) curve (AUC) was used as a measure of the predictive performance of the final model. The risk score was calculated based on the final model by assigning each risk phenotype or genotype as 1 point. Sensitivity [# true positives/(# of true positives+# of false negatives)], specificity [# of true negatives/(# of true negatives+# of false positives)], accuracy [(sensitivity+specificity)/2] and positive likelihood ratio test (sensitivity/(1−specificity)) for primary non response were also calculated for the final model (28). All statistical analysis was conducted by SAS software v9.1 (SAS Institute; Cary, NC).

Example 33

Final Predictive Model—Results of Patient Population and Phenotype Associations

Of the 94 patients evaluated, 22 patients (23%) met the criteria of primary non-response. Table 12 illustrates the key demographic data for both responders and non responders. A diagnosis of UC (p<0.0001) and pANCA positivity (p=0.0001) were associated with primary non-response. Gender, mean age at diagnosis, disease duration at initiation of infliximab, percentage of immunomodulator use and duration of use at start of infliximab did not differ between the two groups.

TABLE 12

Phenotype Associations with Therapeutic Outcomes to Anti-TNFα

| CLINICAL VARIABLE | NON-RESPONSE | RESPONSE | P Value |
|---|---|---|---|
| UC vs. CD | 14:8 | 6:66 | <0.0001 |
| Mean age at diagnosis (years) | 10.1 | 10.5 | 0.71 |
| Gender M:F | 8:14 | 40:32 | 0.12 |
| Disease duration at start of IFX (months) | 26 | 25 | 0.96 |
| IMM use at start of IFX (%) | 79% | 92.8% | 0.1 |
| Duration of IMM at start of IFX (months) | 12.7 | 15.3 | 0.57 |
| pANCA+ | 76.2% | 29% | 0.0001 |
| ASCA+ | 0% | 46.9% | 0.0003 |

Example 34

Final Predictive Model—Results of Genetic Associations: Univariate Analysis

Known IBD Susceptibility Loci: Of the 28 previously identified genetic loci (Table 11), 6 were found to be significantly associated with primary non-response. FIG. 4 herein illustrates the frequency of primary non-response for the different genotypes of these 6 SNPs. Four of the 6 SNPs are from the CD meta-analysis, 1 from the UC GWAS and 1 from pediatric IBD GWAS. For this analysis, the dominant model of the rare allele was assumed. The common allelic variant was associated with non-response in 4 of the 6 SNPs. Table 13 compares the reported IBD risk allele with the allele found to be associated with non-response in this study for all 6 SNPs. In only 2 of the SNPs was the disease risk allele the same as that found to be associated with non response to anti-TNFα.

TABLE 13

Allelic Variants

| SNP and Gene/Locus | GWAS Reference 1 = Adult CD (14) 2 = Adult UC (15-17) 3 = Pediatric IBD (18 | IBD Risk Allele | Non-Response Allele |
|---|---|---|---|
| rs2241880 2q37/ATG16L1 | 1 | C | T |
| rs2188962 5q31 | 1 | T | C |
| rs6908425 6p22/CDKAL1 | 1 | C | T |
| rs762421 21q22/ICOSLG | 1 | G | A |
| rs2395185 6p21/HLA-DAQ1 | 2 | G | G |
| rs2836878 21q22/BRWD1 | 3 | G | G |

Pharmacogenetic GWAS: Table 14 lists the results of the chi square analyses for the pharmacogenetic GWAS. Only those SNPs with a p value $<10^{-4}$ are listed.

TABLE 14

Pharmacocienetic GWAS: p < 0.0001

| Chromosome | SNP | Position* | Gene db129*, | Other loci**, | OR | P |
|---|---|---|---|---|---|---|
| 13 | rs1155848 | 78786477 | | RBM26 | 35.73 | 5.35E−07 |
| 5 | rs1592749 | 159904599 | | | 5.949 | 1.09E−06 |
| X | rs765132 | 133150270 | | 347475 \|402425 \|644403 | 35 | 1.09E−06 |
| 6 | rs4707930 | 72463040 | | | 6.603 | 5.55E−06 |
| 10 | rs7905482 | 81853944 | | PLAC9 \|389988 642506 \|642521 \|642538 \|727879 | 4.875 | 1.08E−05 |
| 20 | rs6100556 | 57701043 | PHACTR3 | PHACTR3 | 4.951 | 1.23E−05 |
| X | rs7059861 | 133191565 | | 347475 \|402425 | 8.333 | 1.62E−05 |
| X | rs5975453 | 133212999 | | 347475 402425 | 8.333 | 1.62E−05 |
| 10 | rs4077511 | 5568172 | | CALML3 CALML5 100132159 | 8.214 | 1.74E−05 |
| 2 | rs975664 | 75222305 | TACR1 | TACR1 | 0.1667 | 1.75E−05 |
| 3 | rs4855535 | 69017124 | FAM19A4 | FAM19A4 | 5.619 | 1.77E−05 |
| 17 | rs4796606 | 36917613 | | KRT13 \|KRT15 \|KRT32 \|KRT35 \|KRT38 \|KRT37 \|KRT36 | 11.73 | 1.98E−05 |
| 8 | rs2943177 | 88121513 | CNBD1 | CNBD1 | 6.412 | 2.06E−05 |
| 8 | rs11991611 | 139676572 | COL22A1 | FAM135B COL22A1 | 15.29 | 2.12E−05 |

TABLE 14-continued

| Pharmacocienetic GWAS: p < 0.0001 | | | | | | |
|---|---|---|---|---|---|---|
| Chromosome | SNP | Position* | Gene db129*, | Other loci**, | OR | P |
| 10 | rs3740543 | 129140065 | DOCK1 | DOCK1 \| NPS | 4.932 | 2.18E−05 |
| 21 | rs2825673 | 19888587 | | 100128057 | 6.438 | 2.28E−05 |
| 1 | rs7521532 | 70351206 | LRRC7 | SFRS11 \|LRRC7 | 7.143 | 2.54E−05 |
| 3 | rs4605505 | 141323576 | CLSTN2 | CLSTN2 | 7.143 | 2.54E−05 |
| 8 | rs7003556 | 5213929 | | | 7.143 | 2.54E−05 |
| 14 | rs1243519 | 94370110 | | GSC | 6 | 3.06E−05 |
| 5 | rs2044111 | 22897160 | | CDH12 | 4.444 | 3.54E−05 |
| 6 | rs2103867 | 47374655 | TNFRSF21 | TNFRSF21 | 12.07 | 3.6E−05 |
| 7 | rs17168564 | 14977349 | | | 8.286 | 3.68E−05 |
| 6 | rs10485363 | 13245751 | PHACTR1 | PHACTR1 | 5.182 | 3.87E−05 |
| 5 | rs7726515 | 129736249 | | | 5.187 | 4E−05 |
| 11 | rs835780 | 44816947 | | TSPAN18 | 5.187 | 4E−05 |
| 11 | rs835791 | 44823513 | | TSPAN18 | 5.187 | 4E−05 |
| 1 | rs3795727 | 154856074 | HAPLN2 | GPATCH4 \|HAPLN2 BCAN IQGAP3 646129 | 4.5 | 4.1E−05 |
| 6 | rs6906890 | 13069206 | PHACTR1 | PHACTR1 | 5.899 | 4.31E−05 |
| 11 | rs7124825 | 44812803 | | TSPAN18 | 0.1263 | 4.31E−05 |
| 19 | rs302827 | 61102034 | NLRP13 | NLRP13 NLRP8 NLRP1 | 4.545 | 4.45E−05 |
| 12 | rs2723829 | 11819364 | ETV6 | ETV6 | 4.333 | 4.47E−05 |
| 2 | rs1372256 | 141070866 | LRP1B | LRP1B | 4.626 | 4.65E−05 |
| 4 | rs13138970 | 155494510 | DCHS2 | DCHS2 | 5.297 | 4.75E−05 |
| 20 | rs1205434 | 36302930 | KIAA1755 | BPI \| TGM2 KIAA1755 | 0.1526 | 4.75E−05 |
| 13 | rs9556658 | 96476252 | | OXGR1 | 6.111 | 4.92E−05 |
| 2 | rs7588326 | 75202554 | TACR1 | TACR1 | 0.1826 | 5.07E−05 |
| 2 | rs3771823 | 75205456 | TACR1 | TACR1 | 0.1826 | 5.07E−05 |
| 20 | rs1555901 | 20762132 | | | 0.1826 | 5.07E−05 |
| X | rs4465121 | 133249071 | | PHF6 | 7 | 5.26E−05 |
| 6 | rs12527937 | 16652564 | ATXN1 | ATXN1 | 5.5 | 5.74E−05 |
| 7 | rs10269232 | 10442565 | | 100128638 | 6.368 | 6.33E−05 |
| 6 | rs3757105 | 73950398 | KCNQ5 | KCNQ5 | 24.2 | 6.51E−05 |
| 18 | rs1667216 | 27383929 | | DSG2 \| TTR | 4.952 | 6.75E−05 |
| 12 | rs278917 | 39666755 | CNTN1 | CNTN1 | 4.172 | 6.93E−05 |
| 6 | rs9404502 | 104605814 | | 100129694 | 5.409 | 7.01E−05 |
| X | rs5977968 | 133151511 | | 347475 402425 644403 | 7.333 | 7.03E−05 |
| 1 | rs12567958 | 154861280 | HAPLN2 | GPATCH4 HAPLN2 BCAN IQGAP3 646129 | 4.167 | 7.03E−05 |
| 8 | rs1880473 | 88079222 | CNBD1 | CNBD1 | 5.085 | 7.09E−05 |
| 4 | rs7689941 | 182246739 | hCG_2025798 | 728081 | 4.244 | 7.3E−05 |
| 17 | rs12937472 | 15194290 | | PMP22 TEKT3 | 8.509 | 7.5E−05 |
| 5 | rs4301261 | 159902033 | | | 5.433 | 7.59E−05 |
| X | rs1264379 | 132893432 | GPC3 | GPC3 | 6.092 | 7.59E−05 |
| X | rs6529954 | 4194349 | | | 0.1781 | 7.69E−05 |
| 22 | rs3088103 | 25250048 | TPST2 | CRYBA4 \|TPST2 TFIP11 HPS4 644380 653715 729905 100128401 HMGB1L10 | 4.308 | 7.77E−05 |
| 6 | rs4711716 | 42375201 | TRERF1 | TRERF1 387535 653802 | 8.727 | 7.82E−05 |
| 7 | rs10464448 | 141433796 | MGAM | MGAM | 0.134 | 8.32E−05 |
| X | rs12559781 | 4225952 | | | 7.973 | 8.49E−05 |
| 7 | rs2540678 | 36227249 | EEPD1 | EEPD1 | 4.6 | 8.54E−05 |
| 4 | rs7659755 | 182246126 | hCG_2025798 | 728081 | 4.461 | 8.62E−05 |

TABLE 14-continued

| Pharmacocienetic GWAS: $p < 0.0001$ | | | | | | |
|---|---|---|---|---|---|---|
| Chromosome | SNP | Position* | Gene db129*, | Other loci**, | OR | P |
| 13 | rs770389 | 50043157 | LOC730194 | 730194 | 5.1 | 8.96E−05 |
| 21 | rs2825699 | 19934102 | | | 5.1 | 8.96E−05 |
| 12 | rs7309734 | 39564210 | CNTN1 | CNTN1 | 4.171 | 9.7E−05 |
| 2 | rs11903032 | 3840992 | | | 5.469 | 9.78E−05 |
| 8 | rs10808755 | 68679235 | CPA6 | CPA6 | 0.08701 | 9.87E−05 |

*Defined using dbSNP Build 129
**Loci include genes that overlap each SNP within 100 kb of 5' end and 10 kb of 3' end of each gene. Numbers refer to dbGene (NCBI).

Example 36

Final Predictive Model—Results of Multivariate Analysis

Predictive models of non-response: Logistic multiple regression was employed to develop models of primary non-response. Five different models were developed. Model 1 examined the significance of pANCA and IBD subtype (UC vs. CD). Both pANCA (OR 5.4; p=0.01) and the diagnosis of UC (OR 15.0; p=0.0001) remained significant in model I, with an R squared ($R^2$) of 0.48. Model II ($R^2$=0.30) examined the 6 SNPs from the univariate analysis. Four (4) of the 6 IBD susceptibility SNPs remained significant; rs2188962 (5q31) (OR 3.3; p=0.04), rs6908425 (6p22/CDKAL1) (OR 3.2; p=0.04), rs2836878 (21q22/BRWD1) (OR 3.3; p=0.05) and rs2395185 (6p21/HLA-DAQ1) (OR 4.6; p=0.01). Table 15 shows the results of Model III which included serology, IBD subtype and susceptibility SNPs (combining the variables of models I and II). 3 SNPs survived the model when combined with these other independent variables. Model IV analyzed the top 10 SNPs from the pharmacogenetic GWAS and only 4 SNPs remained significant; rs975664 (TACR1) (OR 17.6, p=0.0006), rs4855535 (FAM19A4) (OR 8.8, p=0.006), rs4796606 (KRT32 KRT35 KRT36 KRT13)(OR 13.4, p=0.01) and rs765132 (OR 30.1, p=0.03). The R squared for this particular model was 0.67. The results of the final model (V) are shown in Table 16. Model V ($R^2$=0.82, including all variables) examined the associations of pANCA, diagnosis of UC, the 6 known susceptibility SNPs and the top 10 SNPs from the pharmacogenetic GWAS. UC, pANCA, 3 SNPs from the pharmacogenetic GWAS, and rs2836878 (21q22/BRWD1), a susceptibility SNP remained significant.

TABLE 15

| Model III: susceptibility SNPs and phenotype | | | | |
|---|---|---|---|---|
| Model | Variable | P value | OR | R squared |
| III: | UC vs. CD | 0.0008 | 14.7 | 0.59 |
| | pANCA pos | 0.004 | 15.3 | |

TABLE 15-continued

| Model III: susceptibility SNPs and phenotype | | | | |
|---|---|---|---|---|
| Model | Variable | P value | OR | R squared |
| | rs6908425 6p22.3 CDKA1 | 0.05 | 4.6 | |
| | rs2836878 21q22.2 BRWD1 | 0.02 | 9.8 | |
| | rs2395185 6p21 HLA-DQA1 | 0.047 | 5.4 | |

TABLE 16

| Model V: Final Model | | | | |
|---|---|---|---|---|
| Model | Variable | P value | OR | R squared |
| V: | Diagnosis: UC vs. CD | 0.008 | 28.9 | 0.82 |
| | pANCA pos vs neg | 0.03 | 15.4 | |
| | rs975664 2p12/TACR1 | 0.01 | 26.5 | |
| | rs4855535 3p14/FAM19A4 | 0.02 | 10.8 | |
| | rs6100556 20q13/PHACTR3 | 0.02 | 13.8 | |
| | rs2836878 21q22/BRWD1 | 0.07 | 8.0 | |

Example 37

Final Predictive Model—Results of Clinical Utility Measures

The potential clinical utility of the final model (V) was calculated. Table 17 lists the AUC, sensitivity, specificity, accuracy and positive likelihood ratio of non response in a patient who had at least 3 of the 6 risk factors of non response based on model V. In addition, the negative likelihood ratio, i.e. the likelihood that a patient will not be a non-responder if at least 3 risk factors are absent, was calculated at 0.06.

TABLE 17

| Clinical Utility Measures | | | | | | |
|---|---|---|---|---|---|---|
| Model | Variable | AUC | Sensitivity | Specificity | Accuracy | Positive Likelihood Ratio |
| V: | Diagnosis pANCA rs975664 2p12 TACR1 | 0.98 | 0.95 | 0.88 | 0.92 | 8 |

TABLE 17-continued

Clinical Utility Measures

| Model | Variable | AUC | Sensitivity | Specificity | Accuracy | Positive Likelihood Ratio |
|---|---|---|---|---|---|---|
| | rs4855535 | | | | | |
| | 3p14 FAM19A4 | | | | | |
| | rs6100556 | | | | | |
| | 20q13 PHACTR3 | | | | | |
| | rs2836878 | | | | | |
| | 21q22 BRWD1 | | | | | |

Figure 5:
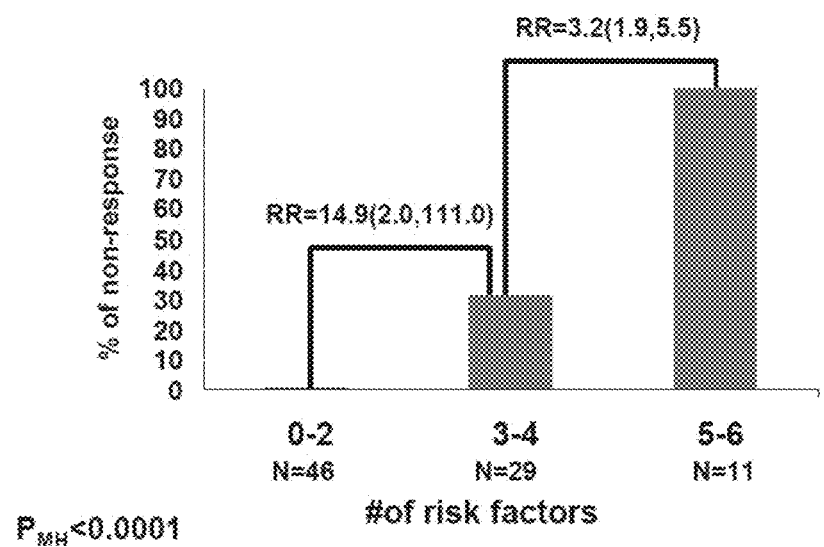
FIG. 5 depicts, in accordance with embodiments herein, relative risk (RR) of non-response based on number of risk factors derived from Model V (the most general model). Risk of non-response was compared between patients with 2 or less risk factors as compared to 3-4 markers and then as compared to at least 5 of the 6 risk factors for non-response.

The relative risk of non-response was calculated based on the number of risk factors (model V) carried by an individual patient. Both the frequency of non-response and the relative risk increase with increasing number of risk factors (p<0.0001) (FIG. 5).

Example 38

Final Predictive Model

TABLE 18

| MODEL | MODEL DESCRIPTOR | R SQUARED | AUC |
|---|---|---|---|
| I | Diagnosis and pANCA | 0.48 | 0.9 |
| II | Known Susceptibility SNPs only | 0.3 | 0.8 |
| III | Diagnosis, pANCA and known susceptibility SNPs | 0.59 | 0.93 |
| IV | Pharmacogenetic GWAS SNPS only | 0.67 | 0.94 |
| V | Diagnosis, pANCA, known susceptibility SNPs AND pharmacogenetic GWAS SNPs | 0.82 | 0.98 |

Anti-TNFα is an important and effective class of therapies for the management of both adult and pediatric IBD patients. Clinical experience suggests inter-individual variation in efficacy, both induction and maintenance, and in the occurrence of side effects. There are likely multiple host factors that influence these variations such as disease and immune phenotype as well as genetic background. The ability to predict which patient would have a lower likelihood of response before treatment is initiated in order to minimize exposure to potentially ineffective therapies may be an important consideration in IBD patients. In the current era of risk/benefit balance, this concept may be very timely.

As described herein, the inventors tested the associations of known and novel genetic loci with primary response outcome and developed a predictive model of primary non response using clinical phenotype, serologic and genetic variables. Six of the 28 known susceptibility loci tested were found to be associated with primary non response in the univariate analysis. The relative risk of primary non response ranged from 2.1-2.9. When tested in the multivariate analysis, 4 of these loci remained significant. However when combined with the novel pharmacogenetic GWAS loci, only 1 loci remained significant. This one locus was initially reported in the pediatric IBD GWAS reported by Kugathasan et al. The functional significance of this locus remains unknown. Of the 10 novel pharmacogenetic GWAS loci tested in the predictive model, 3 remained significant in the final model. TACR1 is a receptor for substance P a known pro-inflammatory molecule. PHACTR3 (phosphatase and actin regulator 3) is associated with the nuclear scaffold in proliferating cells. While there is little known about FAM19A4 it is thought to be structurally related to MIP1α and function as a chemokine. The pharmacogenetic GWAS identified top loci did substantially improve the strength of the prediction of non-response compared to known susceptibility loci. In addition, a diagnosis of UC and pANCA positivity was independently associated with primary non-response. Table 18 compares the r-squared and AUC values for all 5 models. The combination of genotype, phenotype and serotype was the best predictive model of non response to anti-TNFα with an r-squared of 0.82 and an AUC of 0.98, and substantially better than the models that included only known IBD SNPs. (models II or III).

The findings suggest that the majority of the known IBD susceptibility loci do not appear to greatly modify or influence primary response outcomes to anti-TNFα in pediatric IBD patients. This raises the possibility that the majority of genes that are associated with risk of disease may not influence the immune pathways that should be targeted to control or modify disease activity. The results of previously reported candidate gene association studies with anti-TNFα response have not been translated into the clinic and the functional significance of the genes tested remain unknown (8-13). The functionality of the cytokines and/or receptor renders them of interest as it relates to therapeutic outcome. With the GWAS approach, however, no a priori assumptions need to be set, as there is not a prior focus on a particular protein or target or enzyme as it relates to drug response. This hypothesis generating approach allows the identification of genetic variants that are associated with response and non-response and thus potentially identify pathways that are responsible and may well be apparent from a functional and mechanistic perspective. In this study the inventors have analyzed the associations with primary non-response only, as believed this was of the greatest clinical relevance.

As described herein, the inventors have included all pediatric IBD subjects receiving anti-TNFα therapy. Currently clinicians treat both CD and UC with anti-TNF therapy and the clinical trial data suggest similar primary non response and steroid free remission outcomes for both disease subtypes. Moreover there is genetic and serologic evidence that there is pathway biology overlap within the spectrum of CD and UC phenotype. The inventors analyzed UC, CD and shared susceptibility loci and the pharmacogenetic GWAS would identify loci that are independent of disease phenotype.

Defining predictors of response to anti-TNFα will assist clinicians in choosing the appropriate therapy for the appropriate IBD patient, with the goal of maximizing efficacy and minimizing toxicity. As research progresses in defining the characteristics of patients who require biologics, of equal importance will be the research as proposed herein to individualize therapy based on who will or will not respond to different classes of IBD therapeutic interventions. The development of adverse events to anti-TNF therapies such as lymphoma, and sepsis naturally induce caution in clinicians who would like the ability to appropriately select patients who are most likely to respond to these therapies.

As readily apparent to one of skill in the art, after a diagnosis of nonresponsiveness to anti TNFα in an individual, the invention also includes the administration of any number of treatments that may act as an alternative to anti TNFα therapy, such as natalizumab for example. Similarly, after a diagnosis of responsiveness to anti TNFα therapy, any number of examples of anti TNFα therapy may be used, such as infliximab or cyclosporin. Additionally, as apparent to one of skill in the art, the various embodiments described herein may be used in conjunction with any number of additional inflammatory bowel disease treatments, therapies and methods of diagnosis and prognosis. Finally, as apparent to one of skill in the art, the invention may be applied to any number of conditions and diseases related to or potentially affected by anti TNFα therapy and the invention is not limited to inflammatory bowel disease. While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended to be "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

REFERENCES

1. Beaugerie L, Seksik P, Nion-Larmurier I, Gendre J P, Cosnes J. Predictors of Crohn's disease. *Gastroenterology.* 2006; 130:650-656
2. Van Limbergen J. Russell R K. Drummond H E. Aldhous M C. Round N K. Nimmo E R. Smith L. Gillett P M. McGrogan P. Weaver L T. Bisset W M. Mandi G. Arnott I D. Satsangi J. Wilson D C. Definition of phenotypic characteristics of childhood-onset inflammatory bowel disease. Gastroenterology 2008; 135:1114-22
3. Hyams J. Crandall W. Kugathasan S. Griffiths A. Olson A. Johanns J. Liu G. Travers S. Heuschkel R. Markowitz J. Cohen S. Winter H. Veereman-Wauters G. Ferry G. Baldassano R. REACH Study Group. Induction and maintenance infliximab therapy for the treatment of moderate-to-severe Crohn's disease in children. Gastroenterology 2007; 132:863-73
4. Hanauer S B, Feagan B G, Lichtenstein G R, Mayer L F, Schreiber S, Colombel J F, Rachmilewitz D, Wolf D C, Olson A, Bao W, Rutgeerts P; ACCENT I Study Group. Maintenance infliximab for Crohn's disease: the ACCENT I randomized trial. Lancet 2002; 359:1541-1549.
5. Colombel J F. Sandborn W J. Rutgeerts P. Enns R. Hanauer S B. Panaccione R. Schreiber S. Byczkowski D. Li J. Kent J D. Pollack P F. Adalimumab for maintenance of clinical response and remission in patients with Crohn's disease: the CHARM trial. Gastroenterology 2007; 132:52-65.
6. Schreiber S. Khaliq-Kareemi M. Lawrance I C. Thomsen 00. Hanauer S B. McColm J. Bloomfield R. Sandborn W J. PRECISE 2 Study Investigators. Maintenance therapy with certolizumab pegol for Crohn's disease. N Engl J Med. 2007; 357:239-250.
7. Rutgeerts P. Sandborn W J. Feagan B G. Reinisch W. Olson A. Johanns J. Travers S. Rachmilewitz D. Hanauer S B. Lichtenstein G R. de Villiers W J. Present D. Sands B E. Colombel J F. Infliximab for induction and maintenance therapy for ulcerative colitis. New England Journal of Medicine 2005; 353:2462-76
8. Pierik M. Vermeire S. Steen K V. Joossens S. Claessens G. Vlietinck R. Rutgeerts P. Tumour necrosis factor-a receptor 1 and 2 polymorphisms in inflammatory bowel disease and their association with response to infliximab. Aliment. Pharmacol. Ther 2004; 20:303-310
9. Mascheretti S. Hampe J. Kuhbacher T. Herfarth H. Krawczak M. Folsch U R. Schreiber S. Pharmacogenetic investigation of the TNF/TNF-receptor system in patients with chronic active Crohn's disease treated with infliximab. Pharmacogenomics 2002; J. 2:127-136
10. Louis E. Vermeire S. Rutgeerts P. De Vos M. Van Gossum A. Pescatore P. Fiasse R. Pelckmans P. Reynaert H. D'Haens G. Malaise M. Belaiche J. A positive response to infliximab in Crohn disease: association with a higher systemic inflammation before treatment but not with _308 TNF gene polymorphism. Scand. J. Gastroenterol. 2002; 37:818-824
11. Taylor K D. Plevy S E. Yang H. Landers C J. Barry M J. Rotter J I. Targan S R. LTa 1-1-1-1 haplotype is associated with negative response in Crohn's disease ANCA pattern and LTA haplotype relationship to clinical responses to anti-TNF antibody treatment in Crohn's disease. Gastroenterology 2001; 120, 1347-1355.
12. Vermeire S. Louis E. Rutgeerts P. De Vos M. Van Gossum A. Belaiche J. Pescatore P. Fiasse R. Pelckmans P. Vlietinck R. Merlin F. Zouali H. Thomas G. Colombel J F. Hugot J P. NOD2/CARD15 does not influence response to infliximabin Crohn's disease. Gastroenterology 2002; 123, 106-111.
13. Urcelay E. Mendoza J L. Martinez A. Fernandez L. Taxonera C. Diaz-Rubio M. de la Concha E G. IBD 5 (5q31) TT is associated with negative response in Crohn's disease. IBD5 polymorphisms in inflammatory bowel disease: association with response to infliximab. World J. Gastroenterol 2005; 11:1187-1192
14. Barrett J C. Hansoul S. Nicolae D L. Cho J H. Duerr R H. Rioux J D. Brant S R. Silverberg M S. Taylor K D. Barmada M M. Bitton A. Dassopoulos T. Datta L W. Green T. Griffiths A M. Kistner E O. Murtha M T. Regueiro M D. Rotter J I. Schumm L P. Steinhart A H. Targan S R. Xavier R J. NIDDK IBD Genetics Consortium. Libioulle C. Sandor C. Lathrop M. Belaiche J. Dewit O. Gut I. Heath S. Laukens D. Mni M. Rutgeerts P. Van Gossum A. Zelenika D. Franchimont D. Hugot J P. de Vos M. Vermeire S. Louis E. Belgian-French IBD Consortium. Wellcome Trust Case Control Consortium. Cardon L R. Anderson C A. Drummond H. Nimmo E. Ahmad T. Prescott N J. Onnie C M. Fisher S A. Marchini J. Ghori J. Bumpstead S. Gwilliam R. Tremelling M. Deloukas P. Mansfield J. Jewell D. Satsangi J. Mathew C G. Parkes M. Georges M. Daly M J. Genome-wide association defines more than 30 distinct susceptibility loci for Crohn's disease. Nat Genet 2008; 40:955-62
15. Franke A, Balschun T, Karlsen T H, Sventoraityte J, Nikolaus S, Mayr G, Domingues F S, Albrecht M, Nothnagel M, Ellinghaus D, Sina C, Onnie C M, Weersma R K, Stokkers P C, Wijmenga C, Maria Gazouli M, Strachan D, McArdle W L, Vermeire S, Rutgeerts P, Rosenstiel P, Krawczak M, Vatn M H, the IBSEN study group, Mathew C G, Schreiber Sequence variants in IL10, ARPC2 and multiple other loci contribute to ulcerative colitis susceptibility. Nat Genetics 2008; 40:710-712
16. Fisher S A. Tremelling M. Anderson C A. Gwilliam R. Bumpstead S. Prescott N J. Nimmo E R. Massey D. Berzuini C. Johnson C. Barrett J C. Cummings F R. Drummond H. Lees C W. Onnie C M. Hanson C E. Blaszczyk K. Inouye M. Ewels P. Ravindrarajah R. Keniry A. Hunt S. Carter M. Watkins N. Ouwehand W. Lewis C M. Cardon L. Welcome Trust Case Control Consortium. Lobo A. Forbes A. Sanderson J. Jewell D P. Mansfield J C. Deloukas P. Mathew C G. Parkes M. Satsangi J. Genetic determinants of ulcerative colitis include the ECM1 locus and five loci implicated in Crohn's disease. Nat. Genet 2008; 40:710-712.
17. Silverberg M S. Cho J H. Rioux J D. McGovern D P. Wu J. Annese V. Achkar J P. Goyette P. Scott R. Xu W. Barmada M M. Klei L. Daly M J. Abraham C. Bayless $T_M$. Bossa F. Griffiths A M. Ippoliti A F. Lahaie R G. Latiano A. Pare P. Proctor D D. Regueiro M D. Steinhart A H. Targan S R. Schumm L P. Kistner E O. Lee A T. Gregersen P K. Rotter W. Brant S R. Taylor K D. Roeder K. Duerr R H. Ulcerative colitis-risk loci on chromosomes 1p36 and 12q15 found by genome-wide association study. Nat Genetics. 41(2):216-20, 2009
18. Kugathasan S, Baldassano R N, Bradfield J P, Sleiman P M, Imielinski M, Guthery S L, Cucchiara S, Kim C E, Frackelton E C, Annaiah K, Glessner J T, Santa E, Willson T, Eckert A W, Bonkowski E, Shaner J L, Smith R M, Otieno F G, Peterson N, Abrams D J, Chiavacci R M, Grundmeier R, Mamula P, Tomer G, Piccoli D A, Monos D S Annese V, Denson L A, Grant S F, Hakonarson H. Loci on 20q13 and 21q22 are associated with pediatric-onset inflammatory bowel disease. Nat Genetics; 40; 1211-1215.
19. Ferrante M. Vermeire S. Katsanos K H. Noman M. Van Assche G. Schnitzler F. Arijs I. De Hertogh G. Hoffman I. Geboes J K. Rutgeerts P Predictors of early response to infliximab in patients with ulcerative colitis. Inflammatory Bowel Diseases 2007; 13:123-8
20. Vasiliauskas E A, Plevy S E, Landers C J, Binder S W, Ferguson D M, Yang H, Rotter J I, Vidrich A, Targan S R. Perinuclear antineutrophil cytoplasmic antibodies in patients with Crohn's disease define a clinical subgroup. Gastroenterology 1996; 110:1810-1819.
21. Anderson C A. Massey D C. Barrett J C. Prescott N J. Tremelling M. Fisher S A. Gwilliam R. Jacob J. Nimmo E R. Drummond H. Lees C W. Onnie C M. Hanson C. Blaszczyk K. Ravindrarajah R. Hunt S. Varma D. Hammond N. Lewis G. Attlesey H. Watkins N. Ouwehand W. Strachan D. McArdle W. Lewis C M. Wellcome Trust Case Control Consortium. Lobo A. Sanderson J. Jewell D P. Deloukas P. Mansfield J C. Mathew C G. Satsangi J. Parkes M. Investigation of Crohn's disease risk loci in ulcerative colitis further defines their molecular relationship. Gastroenterology 2009; 136:523-9.
22. Dubinsky M C, Kugathasan S, Mei L, Picornell Y, Nebel J, Wrobel I, Quiros A, Silber G, Wahbeh G Katzir L, Vasiliauskas E, Bahar R, Otley A, Mack D, Evans J, Rosh J, Oliva Hemker M, Leleiko L, Crandall W, Langton C, Landers C, Taylor K D, Targan S R, Rotter J I, Markowitz J, Hyams J for the Western Regional Pediatric IBD Research Alliance, Pediatric IBD Collaborative Research Group and the Wisconsin Pediatric IBD Alliance. Increased immune reactivity predicts aggressive complicating Crohn's disease in children. Clinical Gastroenterology and Hepatology 2008:6; 1105-11
23. A genome-wide scalable SNP genotyping assay using microarray technology. Gunderson K L, Steemers F J, Lee G, Mendoza L G, Chee M S. Nat Genet. 2005; 37:549-54
24. Harvey R F, Bradshaw J M. A simple Index of Crohn's disease activity. Lancet 1980; 1:514

25. Price A L, Patterson N J, Plenoe R M, Weinblatt M E, Shadick N A, Reich D. Principal components analysis corrects for stratification in genome-wide association studies. Nat Genet. 2006 August; 38(8):904-9.
26. Purcell S, Neale B, Todd-Brown K, et al. PLINK: a tool set for whole-genome association and population-based linkage analyses. Am J Hum Genet 2007; 81:559-75.
27. Stokes, M E, Davis C S, Koch, G G. Categorical data analysis using the SAS system. 2nd edition. SAS press, 2000, Cary, NC, USA
28. Armitage P, Berry G, Matthews J N S. Statistical Methods in Medical Research. Fourth Edition. Wiley-Blackwell, Malden, M A, 2002
29. Yamazaki K. McGovern D. Ragoussis J. Paolucci M. Butler H. Jewell D. Cardon L. Takazoe M. Tanaka T. Ichimori T. Saito S. Sekine A. Iida A. Takahashi A. Tsunoda T. Lathrop M. Nakamura Y. Single nucleotide polymorphisms in TNFSF15 confer susceptibility to Crohn's disease. Human Molecular Genetics 2005. 14:3499-506
30. SLCO1B1 variants and statin-induced myopathy—a genomewide study. SEARCH Collaborative Group. Link E. Parish S. Armitage J. Bowman L. Heath S. Matsuda F. Gut I. Lathrop M. Collins R. New England Journal of Medicine 2008; 359:789-99
31. Burgner D. Davila S. Breunis W B. Ng S B. Li Y. Bonnard C. Ling L. Wright V J. Thalamuthu A. Odam M. Shimizu C. Burns J C. Levin M. Kuijpers T W. Hibberd M L. International Kawasaki Disease Genetics Consortium. A genome-wide association study identifies novel and functionally related susceptibility Loci for Kawasaki disease PLoS Genetics 2009; 5: e1000319.

The invention claimed is:

1. A method for treating inflammatory bowel disease (IBD) in a subject, the method comprising:
   predicting whether the subject with the inflammatory bowel disease will exhibit non-response to an anti-tumor necrosis factor (TNF) therapy by:
      obtaining or having obtained a biological sample from the subject; and
      performing or having performed a genotyping assay on the biological sample to determine if the subject comprises one or more genetic risk factors comprising a risk allele within rs35693, wherein the risk allele within rs35693 is a T allele at rs35693; and
   if the subject does not comprise the one or more genetic risk factors, then administering an anti-TNF therapy, and
   if the subject comprises the one or more genetic risk factors, then administering an active agent for the treatment of IBD that does not target TNF,
   wherein a risk of non-response to the anti-TNF therapy is higher in the subject if the subject comprises the one or more genetic risk factors than if the subject does not comprise the one or more genetic risk factors.

2. The method of claim 1, wherein the one or more genetic risk factors further comprises a risk allele within rs598672, wherein the risk allele within rs598672 is a C allele at rs598672.

3. The method of claim 1, wherein the non-response to the anti-TNF therapy comprises primary non-response or secondary loss of response.

4. The method of claim 1, wherein the anti-TNF therapy comprises infliximab.

5. The method of claim 1, wherein the inflammatory bowel disease comprises Crohn's disease or ulcerative colitis.

6. The method of claim 1, wherein the one or more genetic risk factors further comprises a risk allele within rs666595, wherein the risk allele within rs666595 is a T allele at rs666595.

7. The method of claim 1, wherein the one or more genetic risk factors further comprises a risk allele that is a T allele at rs666595 and a risk allele that is a C allele at rs598672.

8. The method of claim 4, wherein the anti-TNF therapy is administered to the subject as a combination therapy with cyclosporine.

* * * * *